(12) United States Patent
Tang et al.

(10) Patent No.: US 7,572,924 B2
(45) Date of Patent: *Aug. 11, 2009

(54) PYRROLE SUBSTITUTED 2-INDOLINONE PROTEIN KINASE INHIBITORS

(75) Inventors: Peng Cho Tang, Moraga, CA (US);
Todd Anthony Miller, San Marcos, CA (US); Xiaoyuan Li, Los Altos, CA (US); Connie Li Sun, Palo Alto, CA (US); Chung Chen Wei, Foster City, CA (US); Shahrzad Shirazian, Corte Madera, CA (US); Congxin Liang, Jupiter, FL (US); Tomas Vojkovsky, San Mateo, CA (US); Asaad S. Nematalla, Concord, CA (US); Michael Hawley, Kalamazoo, CA (US)

(73) Assignees: Sugen, Inc., South San Francisco, CA (US); Pharmacia & Upjohn Co., Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/517,529

(22) Filed: Sep. 6, 2006

(65) Prior Publication Data

US 2007/0010569 A1  Jan. 11, 2007

Related U.S. Application Data

(60) Division of application No. 11/028,477, filed on Jan. 4, 2005, now Pat. No. 7,125,905, which is a continuation of application No. 10/412,690, filed on Apr. 14, 2003, now abandoned, which is a division of application No. 09/783,264, filed on Feb. 15, 2001, now Pat. No. 6,573, 293.

(60) Provisional application No. 60/182,710, filed on Feb. 15, 2000, provisional application No. 60/216,422, filed on Jul. 6, 2000, provisional application No. 60/243,532, filed on Oct. 27, 2000.

(51) Int. Cl.
*A61K 31/404* (2006.01)
*C07D 403/06* (2006.01)
(52) U.S. Cl. ..................... 548/468; 514/414
(58) Field of Classification Search .............. 548/468
See application file for complete search history.

(56) References Cited

U.S. PATENT DOCUMENTS

| | | | |
|---|---|---|---|
| 2,622,980 A | 12/1952 | Copeland et al. |
| 2,872,372 A | 2/1959 | Hull |
| 2,968,557 A | 1/1961 | Burgandt et al. |
| 3,140,180 A | 7/1964 | Fritz |
| 3,308,134 A | 3/1967 | Plostneiks |
| 3,551,571 A | 12/1970 | Pachter et al. |
| 3,564,016 A | 2/1971 | Schoen et al. |
| 3,715,364 A | 2/1973 | Hoff |
| 3,880,871 A | 4/1975 | Haugwitz et al. |
| 3,922,163 A | 11/1975 | Church et al. |
| 4,002,643 A | 1/1977 | Carson |
| 4,002,749 A | 1/1977 | Rovnyak |
| 4,053,613 A | 10/1977 | Rovnyak et al. |
| 4,070,366 A | 1/1978 | Gregorovich et al. |
| 4,259,345 A | 3/1981 | Cross et al. |
| 4,259,346 A | 3/1981 | Stähle et al. |
| 4,343,923 A | 8/1982 | Lenox et al. |
| 4,376,110 A | 3/1983 | David et al. |
| 4,436,892 A | 3/1984 | Zondler et al. |
| 4,489,089 A | 12/1984 | Wright, Jr. et al. |
| 4,493,642 A | 1/1985 | Furazawa et al. |
| 4,560,700 A | 12/1985 | Schnettler et al. |
| 4,628,105 A | 12/1986 | Schmid et al. |
| 4,642,309 A | 2/1987 | Michel et al. |
| 4,678,798 A | 7/1987 | Rentzea et al. |
| 4,826,847 A | 5/1989 | Michel et al. |
| 4,853,403 A | 8/1989 | Shiraishi et al. |
| 4,853,404 A | 8/1989 | Takamura et al. |
| 4,868,304 A | 9/1989 | Larok |
| 4,924,000 A | 5/1990 | Rentzea et al. |
| 4,966,849 A | 10/1990 | Vallee et al. |
| 4,971,996 A | 11/1990 | Shiraishi et al. |
| 4,987,146 A | 1/1991 | Rohde et al. |
| 5,043,348 A | 8/1991 | Zoller et al. |
| 5,043,454 A | 8/1991 | Wriede et al. |
| 5,047,554 A | 9/1991 | Ehrgott et al. |
| 5,051,417 A | 9/1991 | Nadler et al. |
| 5,057,538 A | 10/1991 | Shiraishi et al. |
| 5,082,856 A | 1/1992 | Taniguchi et al. |

(Continued)

FOREIGN PATENT DOCUMENTS

AU           286870        5/1967

(Continued)

OTHER PUBLICATIONS

Abramovitch and Hey, "Internuclear cyclisation. Part VIII. Naphth[3:2:1-cd]oxindoles," *J. Chem. Soc.* 1697-1703 (1954), Strand, London.

(Continued)

*Primary Examiner*—Laura L. Stockton
(74) *Attorney, Agent, or Firm*—Bryan C. Zielinski; Stephen D. Prodnuk

(57) ABSTRACT

The present invention relates to pyrrole substituted-2-indolinone compounds and their pharmaceutically acceptable salts which modulate the activity of protein kinases and therefore are expected to be useful in the prevention and treatment of protein kinase related cellular disorders such as cancer.

3 Claims, No Drawings

U.S. PATENT DOCUMENTS

| | | | |
|---|---|---|---|
| 5,089,516 A | 2/1992 | Shiraishi et al. |
| 5,124,347 A | 6/1992 | Connor et al. |
| 5,145,983 A | 9/1992 | West |
| 5,153,217 A | 10/1992 | Taniguchi et al. |
| 5,196,446 A | 3/1993 | Levitzki et al. |
| 5,202,341 A | 4/1993 | Shiraishi et al. |
| 5,206,261 A | 4/1993 | Kawaguchi et al. |
| 5,217,999 A | 6/1993 | Levitzki et al. |
| 5,258,357 A | 11/1993 | Muenster et al. |
| 5,278,184 A | 1/1994 | Artico et al. |
| 5,290,947 A | 3/1994 | Zoller et al. |
| 5,302,606 A | 4/1994 | Spada et al. |
| 5,322,950 A | 6/1994 | Sircar et al. |
| 5,330,992 A | 7/1994 | Eissenstat et al. |
| 5,332,736 A | 7/1994 | Carmosin et al. |
| 5,374,652 A | 12/1994 | Buzzetti et al. |
| 5,382,593 A | 1/1995 | Le Baut et al. |
| 5,389,661 A | 2/1995 | Sircar et al. |
| 5,397,787 A | 3/1995 | Buzzetti et al. |
| 5,409,930 A | 4/1995 | Spada et al. |
| 5,409,949 A | 4/1995 | Buzzetti et al. |
| 5,463,052 A | 10/1995 | Haga et al. |
| RE35,096 E | 11/1995 | Taniguchi et al. |
| 5,565,324 A | 10/1996 | Still et al. |
| 5,610,173 A | 3/1997 | Schwartz et al. |
| 5,723,665 A | 3/1998 | Kato et al. |
| 5,786,488 A | 7/1998 | Tang et al. |
| 5,792,783 A | 8/1998 | Tang et al. |
| 5,834,504 A | 11/1998 | Tang et al. |
| 5,849,710 A | 12/1998 | Battistini et al. |
| 5,880,141 A | 3/1999 | Tang et al. |
| 5,883,113 A | 3/1999 | Tang et al. |
| 5,883,116 A | 3/1999 | Tang et al. |
| 5,886,020 A | 3/1999 | Tang et al. |
| RE36,256 E | 7/1999 | Spada et al. |
| 6,130,239 A | 10/2000 | Chen et al. |
| 6,133,305 A | 10/2000 | Tang et al. |
| 6,248,894 B1 | 6/2001 | Phillion et al. |
| 6,310,217 B1 | 10/2001 | Lehr |
| 6,395,736 B1 | 5/2002 | Parks et al. |
| 6,451,838 B1 | 9/2002 | Moon et al. |
| 6,462,072 B1 | 10/2002 | Hamilton et al. |
| 6,573,293 B2 | 6/2003 | Tang et al. |
| 6,635,640 B2 | 10/2003 | Tang et al. |
| 6,677,368 B2 | 1/2004 | Cui et al. |
| 7,053,086 B2 * | 5/2006 | Tang et al. ............... 514/235.2 |

FOREIGN PATENT DOCUMENTS

| | | |
|---|---|---|
| CA | 2012634 A1 | 9/1991 |
| DE | 878539 | 6/1953 |
| DE | 2159360 A | 6/1973 |
| DE | 2159361 A | 6/1973 |
| DE | 2159362 | 6/1973 |
| DE | 2159363 A | 6/1973 |
| DE | 2321656 A | 11/1973 |
| DE | 3426419 A | 1/1986 |
| EP | 0 252 713 B1 | 1/1988 |
| EP | 0 304 493 B1 | 3/1989 |
| EP | 0 351 213 A2 | 1/1990 |
| EP | 0 525 472 A2 | 2/1993 |
| EP | 0 566 226 B1 | 10/1993 |
| EP | 0 580 502 B1 | 1/1994 |
| EP | 0 626 377 B1 | 11/1994 |
| EP | 0 632 102 A1 | 1/1995 |
| EP | 0 662 473 A1 | 7/1995 |
| EP | 0 769 947 B1 | 5/1997 |
| EP | 0 788 890 A1 | 8/1997 |
| EP | 0 810 217 A1 | 12/1997 |
| EP | 0 934 931 A2 | 8/1999 |
| EP | 1 082 305 A1 | 3/2001 |
| FR | 1398224 | 5/1965 |
| FR | 1.599.772 | 8/1970 |
| FR | 2.689.397 A1 | 10/1993 |
| GB | 809691 | 3/1959 |
| GB | 835473 | 5/1960 |
| JP | 62-29570 A | 2/1987 |
| JP | 62-39564 A | 2/1987 |
| JP | 63-141955 A | 6/1988 |
| JP | 5-58894 A | 3/1993 |
| WO | WO88/07035 A1 | 9/1988 |
| WO | WO91/13055 A2 | 9/1991 |
| WO | WO91/15495 A1 | 10/1991 |
| WO | WO92/03736 A1 | 3/1992 |
| WO | WO92/07830 A2 | 5/1992 |
| WO | WO92/20642 A1 | 11/1992 |
| WO | WO92/21660 A1 | 12/1992 |
| WO | WO93/01182 A1 | 1/1993 |
| WO | WO93/23040 A1 | 11/1993 |
| WO | WO94/03427 A1 | 2/1994 |
| WO | WO94/10202 A1 | 5/1994 |
| WO | WO94/14808 A1 | 7/1994 |
| WO | WO95/01349 A1 | 1/1995 |
| WO | WO95/14667 A1 | 6/1995 |
| WO | WO95/17181 A1 | 6/1995 |
| WO | WO95/24190 A2 | 9/1995 |
| WO | WO96/00226 A1 | 1/1996 |
| WO | WO96/16964 A1 | 6/1996 |
| WO | WO96/22976 A1 | 8/1996 |
| WO | WO96/32380 A1 | 10/1996 |
| WO | WO96/40116 A1 | 12/1996 |
| WO | WO97/25986 A1 | 7/1997 |
| WO | WO97/34920 A1 | 9/1997 |
| WO | WO97/36867 A1 | 10/1997 |
| WO | WO98/07695 A1 | 2/1998 |
| WO | WO98/07835 A2 | 2/1998 |
| WO | WO98/24432 A2 | 6/1998 |
| WO | WO98/38984 A2 | 9/1998 |
| WO | WO98/45708 A1 | 10/1998 |
| WO | WO98/50356 A1 | 11/1998 |
| WO | WO98/56376 A1 | 12/1998 |
| WO | WO99/10325 A1 | 3/1999 |
| WO | WO99/19325 A1 | 4/1999 |
| WO | WO99/48868 A2 | 9/1999 |
| WO | WO99/52869 A1 | 10/1999 |
| WO | WO99/61422 A1 | 12/1999 |
| WO | WO99/65869 A1 | 12/1999 |
| WO | WO00/08202 A2 | 2/2000 |
| WO | WO00/35908 A1 | 6/2000 |
| WO | WO00/38519 A1 | 7/2000 |
| WO | WO00/56709 A1 | 9/2000 |
| WO | WO01/37820 A2 | 5/2001 |
| WO | WO01/60814 A2 | 8/2001 |

OTHER PUBLICATIONS

Abramovitch et al., "A Novel Synthesis of a Cyclic Hydroxamic Acid Involving a Molecular Rearrangement," *Chemistry and Industry* 44:1871 (1967) 8Laporte Industries Limited, Lancashire.

Akbasak and Sunar-Akbasak, "Oncogenes: cause or consequence in the development of glial tumors," *J. Neurol. Sci.* 111:119-133 (1992)8 Elsevier Science Publishers.

Andreani et al., "Potential Antitumor Agents. 25[1]. Synthesis and Cytotoxic Activity of 3-(2-Chloro-3-Indolymethylene)1,3-Dihydroindol-2-Ones," *Anticancer Research* 16:3585-3588 (1996) 8 Elsevier, Paris.

Andreani et al., "Synthesis and cardiotonic activity of 2-indolinones," *Eur. J. Med. Chem.* 25:187-190 (1990).

Andreani et al., "Synthesis and cardiotonic activity of 2-indolinones bearing pyridyl groups," *Eur. J. Med. Chem.* 28:653-657 (1993) 8 Elsevier, Paris.

Andreani et al., "Synthesis and cardiotonic activity of 2-indolinones," *Chemical Abstracts*, vol. 113, abstract No. 78106 (1990).

Andreani et al., "Synthesis and cardiotonic activity of pyridylmethylene-2-indolinones," *Eur. J. Med. Chem.* 27:167-170 (1992) 8 Elsevier, Paris.

Andreani et al., "Synthesis and potential coanthracyclinic activity of substituted 3-(5-imidazo[2,1-b]thiazolylmethylene)-2-indolinones," *Eur. J. Med. Chem.* 32:919-924 (1997)8 Elsevier, Paris.

Andreani et al., "Synthesis of lactams with potential cardiotonic activity," *Eur. J. Med. Chem.* 28:825-829 (1993).

Andreani et al., "In Vivo Cardiotonic Activity of Pyridylmethylene-2-indolinones," *Arzneimittel-Forschung Drug Research* 48:727-729 (1998) 8.

Arteaga et al., "Blockade of the Type I Somatomedin Receptor Inhibits Growth of Human Breast Cancer Cells in Athymic Mice," *J. Clin. Invest.* 84:1418-1423 (1989) copyright The American Society for Clinical Investigation, Inc.

Arvidsson et al., "Tyr-716 in the Platelet-Derived Growth Factor β-Receptor Kinase Insert is Involved in GRB2 Binding and Ras Activation," *Molecular and Cellular Biology* 14:6715-6726, 1994.

Autrey and Tahk, "The Synthesis and Sterochemistry of Some Isatylideneacetic Acid Derivatives," *Tetrahedron* 23:901-917 (1967) 8Pergamon Press.

Bahner and Brotherton, "6-Dimethylaminochrysene and Other Analogs of 4-(4-Dimethylamino)stilbene," *J. Med. Chem.* 12:722-723 (1969).

Bahner et al., "Benzylideneindenes with Oxygen Attached to the Indene Ring," *J. Med. Chem.* 12:721-722 (1969).

Bamfield et al., "Diels-Alder Reactions of Oxindolylideneacetone," *J. Chem. Soc. (C)* 1028-1030 (1966) 8.

Barbier, et al., "Synthesis of Isobrassilexin, A Biologically Active Isomer of Brassilexin, a Cruciferae Phytoalexin," *Synthetic Communications* 23(22):3109-3117 (1993) 8 Marcel Dekker, Inc.

Baserga, "Oncogenes and the Strategy of Growth Factors," *Cell* 79:927-930 (1994) 8 Cell Press.

Baserga, "The Insulin-like Growth Factor I Receptor: A Key to Tumor Growth?" *Cancer Research* 55:249-252 (1995).

Beilstein Reg. No. 233511 (1997).

Beilstein Reg. No. 235647 (1997).

Beilstein Reg. No. 236050, Beilstein Reference No. 4-21-00-06355.

Beilstein Reg. No. 252929 (1998).

Benzies, et al., "2-Formyl-3-Methoxymethylindole, 3-Ethoxymethyl-2-Formylindoline and 2-Formyl-3-Methylindole," *Synthetic Communications*: 16(4), 1799-1807 (1986) 8 Mercel Dekker, Inc.

Blake and Jaques, "Anisotropic Effects in α-Substituted Methoxystilbenes," *J. Chem. Soc. Perkin II*: 1660-1663 (1973) 8 Pergamon, Oxford.

Bolen et al., "The Src family of tyrosine protein kinases in hemopoietic signal transduction," *FASEB J.* 6:3403-3409 (1992).

Bolen, "Nonreceptor tyrosine protein kinases," *Oncogene* 8:2025-2031 (1993) copyright MacMillan Press Ltd.

Bonner et al., "Structure and Biological Activity of Human Homologs of the *raf/mil* Oncogene," *Molecular and Cellular Biology* 5:1400-1407 (1985) 8 The American Society for Microbiology.

Borsche et al., "Über vielkernige kondensierte Systeme mit heterocyclischen Ringen. XIII.," *Liebigs Ann. Chem.* 550:160-174 (1941).

Buzzetti et al., "Cinnamamide Analogs as Inhibitors of Protein Tyrosine Kinases," *Il Farmaco* 48:615-636 (1993).

Cance et al., "Novel Protein Kinases Expressed in Human Breast Cancer," *Int. J. Cancer* 54:571-577 (1993) 8 Wiley-Liss, Inc.

Canoira Rodriguez, "Synthesis of Oxindole Derivatives from N-Alkenyl-o-Chloroanilides with Zero-Valent Nickel Complex," *J. Heterocyclic Chem.* 22:1511-1518 (1985).

Carpenedo et al., "Identification and Measurement of Oxindole (2-Indolinone) in the Mammalian Brain and Other Rat Organs," *Analytical Biochemistry* 244:74-79 (1997) 8 Academic Press, Inc.

Chao, "Growth Factor Signaling: Where Is the Specificity?" *Cell* 68:995-997 (1992) copyright Cell Press.

Chatten et al., "Substituted Oxindoles. Part VI. Polarographic Reduction of Substituted *trans*-3-Benzylideneindol-2(3*H*)-ones," *J. Chem. Soc. Perkin II*: 469-473 (1973).

Chatterjee, et al., "Acylation of Indoles by Duff Reaction and Vilsmeier-Haack Formylation and Conformation of N-Formylindoles," *J. Org. Chem.*, 38:4002-4004 8The American Chemical Society, 1973.

Chen et al., "Effects of 3,3-Dipyridylmethyl-1-Phenyl-2-Indolinone on γ-Aminobutyric Acid Elicited Chloride Current of Snail Central Neuron," *Chinese Journal of Physiology* 40:149-156 (1997).

Claesson-Welsh, "Signal Transduction by the PDGF Receptors," *Progress in Growth Factor Research* 5:37-54 (1994) 8 Elsevier Science Ltd.

Coda et al., "(Z)- and (E)-Arylidene-1,3-dihydroindol-2-ones: Configuration, Conformation and Infrared Carbonyl Stretching Frequencies," *J. Chem. Soc. Perkin Trans. II*: 615-619 (1984).

Coda et al., "3-(4-methylbenzilidene)-1,3-dihydroindol-2-one," *Journal of the Chemical Society, Perkin Transactions* 2 4:615-620 (1984) Database Crossfire, Beilstein Reference No. 6-21.

Coppola et al., "A Functional Insulin-Like Growth Factor I Receptor Is Required for the Mitogenic and Transforming Activities of the Epidermal Growth Factor Receptor," *Molecular and Cellular Biology* 14:4588-4595 (1994) 8 The American Society for Microbiology.

Daisley and Walker, "Thin-layer chromatographic separation of some substituted 3-benzylidine-indol-2(3H)-ones," *J. Chromatography* 100:240-242 (1974) 8 Elsevier Scientific Publishing Company.

Damiani et al., "Inhibition of Copper-Mediated Low Density Lipoprotein Peroxidation by Quinoline and Indolinone Nitroxide Radicals," *Biochemical Pharmacology* 48:1155-1161 (1994) copyright Elsevier Science Ltd.

Dati et al., "Inhibition of c-erbB-2 oncogene expression by estrogens in human breast cancer cells," *Oncogene* 5:1001-1006 (1990).

Davis et al., "Synthesis and Microbiological Properties of 3-Amino-1-Hydroxy-2-Indolinone and Related Compounds," *Journal of Medicinal Chemistry* 16:1043-1045 (1973) 8American Chemical Society.

De Vries et al., "The fms-Like Tyrosine Kinase, a Receptor for Vascular Endothelial Growth Factor," *Science* 255:989-991 (1992).

Decker and Lohmann-Matthes, "A quick and simple method for the quantitation of lactate dehydrogenase release in measurements of cellular cytotoxicity and tumor necrosis factor (TNF) activity," *J. Immunol. Methods* 15:61-69 (1988) copyright Elsevier.

Decodts et al., "Suicide inhibitors of proteases. Lack of activity of halomethyl derivatives of some aromatic lactams," *Eur. J. Med. Chem* 18: 107-111 (1983).

Desimoni et al., "Catalysis with Inorganic Cations. V$^1$ Intramolecular Hetero Diels-Alder versus Ene Reactions: Effect of Magnesium perchlorate on Chemoselectivity,"*Tetrahedron* 52(36) 12009-12018 (1196) 8 Pergamon, 1996.

Dickson et al., "13. Tyrosine kinase receptor—nuclear protooncogene interactions in breast cancer," *Cancer Treatment Res.* 61:249-273 (1992) 8 Kluwer Academic Publishers.

Elliott and Rivers, "Reduction of Some Oxindolylidene Derivatives to 3-Substituted Oxindoles by Sodium Borohydride," *J. Med. Chem.* 29:2438-2440 (1964).

Elliott et al., "1-methyl-2-(3-oxindolidenmethyl)-pyridinium," *Journal of Organic Chemistry* 29:2438-2440 (1964) Database Crossfire, Beilstein Reference No. 5-24.

Fanfl et al., "Distinct Phosphotyrosines on a Growth Factor Receptor Bind to Specific Molecules That Mediate Different Signaling Pathways," *Cell* 69:413-423 (1992) 8 Cell Press.

Fendly et al., Characterization of Murine Monoclonal Antibodies Reactive to Either the Human Epidermal Growth Factor Receptor or HER2/neu Gene Product, *Cancer Research* 50:1550-1558, 1990.

Ferrara and Henzel, "Pituitary Follicular Cells Secrete a Novel Heparin-Binding Growth Factor Specific for Vascular Endothelial Cells," *Biochemical and Biophysical Research*, 1989.

Fingl and Woodbury, "Chapter 1—General Principles," in *The Pharmacological Basis of Therapeutics* 5th edition, Goodman and Gilman editors, MacMillan Publishing Co., Inc., New York, pp. 1-46 (1975) 8 MacMillan Publishing Co. Inc.

Fischer et al., Beilsteins Handbuch Der Organischen Chemie, Band 2, vol. 22, p. 231, (1953).

Fischer, H., "The Pyrroles, Paper 4: Pyrrole Aldehyde (II) and Pyrrole Nitrile," Zerweck, W. Chemische Berichte, (1923), pp. 519-527, vol. 55.

Floege et al., "Factors involved in the regulation of mesangial cell proliferation in vitro and in vivo," *Kidney International* 43:S47-S54 (1993) 8 International Society of Nephrology.

Floege et al., "Heparin suppresses mesangial cell proliferation and matrix expansion in experimental mesangioproliferative glomerulonephritis," *Kidney International* 43:369-380 (1993) 8 International Society of Nephrology.

Folkman and Shing, "Angiogenesis," *J. Biol. Chem.* 267:10931-10934 (1992) 8 The American Society for Biochemistry and Molecular Biology.

Folkman, "Ch. 24. Angiogenesis," *Congress of Thrombosis and Haemostasis* (Verstraete et al., eds.) Leuven-University Press, Leuven pp. 583-596 (1987).

Folkman, "Tumor Angiogenesis: Therapeutic Implications," *New England J. Medicine* 285:1182-1186 (1971).

Folkman, "What is the Evidence that Tumors are Angiogenesis Dependent?" *Journal of the National Cancer Institute* 82:4-6 (1990).

Folkman, "Angiogenesis in Psoriasis: Therapeutic Implications," *J. Invest. Dermatol.* 59:40-43 (1973) copyright The Williams & Wilkins Co.

Gazit et al., "Tyrphostins. 2. Heterocyclic and α-Substituted Benzylidenemalononitrile Tyrphostins as Potent Inhibitors of EGF Receptor and ErbB2/neu Tyrosine Kinases," *J. Med. Chem.* 34:1896-1907 (1991) copyright Am. Clem. Soc.

Gennaro (editor), *Remington's Pharmaceutical Sciences* (1990) (Table of Contents Only).

Goldring and Goldring, "Cytokines and Cell Growth Control," *Critical Reviews in Eukaryotic Gene Expression* 1:301-326 (1991).

Gottardis et al., "Estradiol-Stimulated Growth of MCF-7 Tumors Implanted in Athymic Mice: A Model to Study the Tumoristatic Action of Tamoxifen," *J. Steroid Biochem.* 30:311-314 (1988) 8 Pergamon Press.

Graziani et al., "Hepatocyte Growth Factor/Scatter Factor Stimulates the Ras-Guanine Nucleotide Exchanger," *The Journal of Biological Chemistry* 268:9165-9168 (1993) 8American Society for Biochemistry and Molecular Biology.

Hayler et al., Development of Large-Scale Syntheses of Ropinirole in the Pursuit if a Manufacturing Process, *Organic Process Research & Development* 2(1) 3-9 (1998) 8The American Chemical Society and Royal Society of Chemistry.

Hewgill and Stewart, "Phenanthrene-4,5-quinones: a Synthesis of Morphenol," *J. Chem. Soc. Perkin Trans. I*:1305-1311 (1988).

Hirao et al., "Rhodium-Catalyzed Carbonylation of 2-Alkynylaniline: Syntheses of 1,3-Dihydroindol-2-ones," *Tetrahedron Letters* 36(35), 1995, 8Pergamon.

Hodges et al., "Chemical and biological properties of some oxindolidyl-3-methines," *Canadian J. Chemistry* 46:2189-2194 (1968).

Honegger et al., "Point Mutation at the ATP Binding Site of EGF Receptor Abolishes Protein-Tyrosine Kinase Activity and Alters Cellular Routing," *Cell* 51:199-209 (1987) 8 Cell Press.

Houch et al., "Dual Regulation of Vascular Endothelial Growth Factor Bioavailability by Genetic and Proteolytic Mechanisms," *J. Biol. Chem.* 267:26031-26037 (1992)8 American Society for Biochemistry and Molecular Biology, Inc.

Howard et al., "Synthesis and aldose reductase inhibitory activity of substituted 2(1*H*)-benzimidazolone- and oxindole-1-acetic acids," *Eur. J. Med. Chem.* 27:779-789 (1992) 8 Elsevier, Paris.

Howard, Harry R., "Lactam Derivatives," U.S. Appl. No. 60/015,134, filed 1996.

Hu et al., "Interaction of Phosphatidylinositol 3-Kinase-Associated p85 with Epidermal Growth Factor and Platelet-Derived Growth Factor Receptors," *Molecular and Cellular Biology* 12:981-990, 1992.

Ijaz et al., "The Conversion of o,β-Dinitrostyrenes into Indoles and the Preparation of Oxindole Quinones," *J. Chem. Res. (S)*: 116 (1990).

Jellinek et al., "Inhibition of Receptor Binding by High-Affinity RNA Ligands to Vascular Endothelial Growth Factor," *Biochemistry* 33:10450-10456 (1994) 8 American Chemical Society.

Kashishian and Cooper, "Phosphorylation Sites at the C-terminus of the Platelet-Derived Growth Factor Receptor Bind Phospholipase Cγ1," *Molecular Biology of the Cell* 4:49-57 (1993) 8 The American Society for Cell Biology.

Kashishian et al., "Phosphorylation sites in the PDGF receptor with different specificites for binding GAP and PI3 kinase in vivo," *The EMBO Journal* 11:1373-1382 (1992).

Kato et al., "Simultaneous Determination of Amfenac Sodium and its Metabolite (7-Benzoyl-2-Oxindole) in Human Plasma by High-Performance Liquid Chromatography," *Journal of Chromatography* 616:67-71 (1993) 8Elsevier Science.

Katritzky et al., "Color and Constitution. Part 8[1]. Some Novel Dyestuffs Containing Indoxyl Residues," *J. Heterocyclic Chem.* 25:1287-1292 (1988).

Kazlauskas et al., "The 64-kDa protein that associates with the platelet-derived growth factor receptor β subunit via Tyr-1009 is the SH2-containing phosphotyrosine phosphatase Syp," *Proc. Natl. Acad. Sci. USA* 90:6939-6942 (1993).

Kendall and Thomas, "Inhibition of vascular endothelial cell growth factor activity by an endogenously encoded soluble receptor," *Proc. Natl. Acad. Sci. USA* 90:10705-10709 (1993).

Khalil and Abdel-Rahman, "Synthesis of New Mero- and Asymmetrical Pyrazolo-Monomethine Cyanine Dyes," *J. Indian Chem. Soc.* 54:904-907 (1977) 8The Indian Chemical Society.

Kikumoto et al., "The Reactions of Oxindoles and Isatin with Nitrobenzyl Chlorides," *Tetrahedron* 22: 3337-3343 (1966) 8Pergamon Press Ltd.

Kim et al., "Inhibition of vascular endothelial growth factor-induced angiogenesis suppresses tumour growth in vivo," *Nature* 362:841-844 (1993).

Kinsella et al., "Protein Kinase C Regulates Endothelial Cell Tube Formation on Basement Membrane Matrix, Matrigel," *Exp. Cell Research* 199:56-62 (1992) 8 Academic Press, Inc.

Klagsbrun and Soker, "VEGF/VPF: the angiogenesis factor found?" *Current Biology* 3:699-702 (1993) 8Current Biology.

Kobayashi et al., "Anti-tumor Activity of Indole Derivatives," *Yakugaku Zasshi* 97:1033-1039 (1977).

Koch et al., "SH2 and SH3 Domains: Elements That Control Interactions of Cytoplasmic Signaling Proteins," *Science* 252:668-674 (1991).

Kohler and Milstein, "Continuous cultures of fused cells secreting antibody of predefined specificity," *Nature* 256:495-497 (1975).

Komada and Kitamura, "The cell dissociation and motility triggered by scatter factor/hepatocyte growth factor are mediated through the cytoplasmic domain of the c-Met receptor," *Oncogene* 8:2381-2390 (1993).

Korc et al., "Overexpression of the Epidermal Growth Factor Receptor in Human Pancreatic Cancer Is Associated with Concomitant Increases in the Levels of Epidermal Growth Factor and Transforming Growth Factor Alpha," *J. Clin. Invest.* 90:1352-1360 (1992) copyright The American Society for Clinical Investigtion, Inc.

Korzeniewski and Callewaert, "An Enzyme-Release Assay for Natural Cytotoxicity," *J. Immunol. Methods* 64:313-320 (1983) 8 Elsevier Science Publishers.

Kovac and Stetinova, "Furan derivatives. LXXX. Synthesis and properties of substituted furfurylidenoxindoles," *Chem. rvesu* 30:484-492 (1976).

Krueger and Saito, "A human transmembrane protein-tyrosine-phosphatase, PTPb, is expressed in brain and has an N-terminal receptor domain homologous to carbonic anhydrases," *Proc. Natl. Acad. Sci. USA* 89:7417-7421 (1992).

Kumabe et al., "Amplification of α-platelet-derived growth factor receptor gene lacking an exon coding for a portion of the extracellular region in a primary brain tumor of glial origin," *Oncogene* 7:627-633 (1992).

Lal et al., "Novel Diuretic Agents: Syntheses of Substituted Isatylidenes & 3-Alkyl or 3-Arylalkyl-2-oxindoles," *Indian Journal of Chemistry* 13: 898-903 (1975).

Larock and Babu, "Synthesis of Nitrogen Heterocycles via Palladium-catalyzed Intramolecular Cyclization," *Tetrahedron Letters* 28:5291-5294 (1987) copyright Pergamon Journals Ltd.

Lee and Donoghue, "Intracellular Retention of Membrane-Anchored v-sis Protein Abrogates Autocrine Signal T transduction," *J. Cell. Biol.* 118:1057-1070 (1992) 8The Rockefeller University Press.

Levitzki and Gazit, "Tyrosine Kinase Inhibition: An Approach to Drug Development," *Science* 267:1782-1788 (1995).

Maass et al., "Viral Resistance to the Thiazolo-Iso-Indolinones, a New Class of Nonnucleoside Inhibitors of Human Immunodeficiency Virus Type 1 Reverse Transcriptase," *Antimicrobial Agents and Chemotherapy* 37:2612-2617 (1993) 8American Society for Microbiology.

Macaulay et al., "Autocrine Function for Insulin-like Growth Factor I in Human Small Cell Lung Cancer Cell Lines and Fresh Tumor Cells," *Cancer Research* 50:2511-2517 (1990).

Mariani et al., "Inhibition of angiogenesis by FCE 26806, a potent tyrosine kinase inhibitor," *Experimental Therapeutics—Proceedings of the American Association for Cancer Research* 35:381 at abstract No. 2268 (Mar. 1994).

Martin-Leon et al., "On the Cyclization to the Elusive Amino-4H-pyran Ring Some New Facts," *Liebigs Ann. Chem.* 101-104 (1990) copyright VCH Veilaxs of Sellschaft mbH 8VCH.

Mel'Nikova TV et al., "Indole chemistry. XXXVIII. Cleavage of a carbon-carbon bond during the reaction of 2-amiinoindoles with difunctional compounds," *Chemical Abstracts* 80 (1974) Abstract No. 003413.

Millauer et al., "High Affintiy VEGF Binding and Developmental Expression Suggest Flk-1 as a Major Regulator of Vasculogenesis and Angiogenesis," *Cell* 72:835-846 (1993) 8 Cell Press.

Mohammadi et al., "Structures of the Tyrosine Kinase Domain of Fibroblast Growth Factor Receptor in Complex with Inhibitors," *Science* 276:955-960 (1997) 8 American Association for the Advancement of Science.

Moreto et al., "Study of the Laxative Properties of the Disodium Salt of the Sulfuric Diester of 3,3 Bis-(4-Hydroxyphenyl)-7-Methyl-2-Indolinone (DAN-603) in the Rat," *European Journal of Pharmacology* 36:221-226 (1976) 8North-Holland Publishing Company.

Moreto et al., "3,3-Bis-(4-Hydroxyphenyl)-7-Methyl-2-Indolinone (BHMI), the Active Metabolite of the Laxative Sulisatin," *Arzneimittel-Forschung Drug Research* 29:1561-1564 (1979).

Morrison et al., "Signal Transduction From Membrane to Cytoplasm: Growth Factors and Membrane-Bound Oncogene Products Increase Raf-1 Phosphorylation and Associated Protein Kinase Activity," *Proc. Natl. Acad. Sci. USA* 85:8855-8859 (1988).

Mosmann, "Rapid Colorimetric Assay for Cellular Growth and Survival: Application to Proliferation and Cytotoxicity Assays," *J. Immunol. Methods* 65:55-63 (1983) copyright Elsevier Publishers B.V.

Neber and Röcker, "On the action of benzaldehydes on the free o-aminophenylacetic acid (II)," *Chem. Ber.* 56:1710-1716 (1923) (German and English Translation).

Nishimura et al., "Two Signaling Molecules Share a Phosphotyrosine-Containing Binding Site in the Platelet-Derived Growth Factor Receptor," *Molecular and Cellular Biology* 13:6889-6896, 1993.

Nodiff et al., "Antimalarial Phenanthrene Amino Alcohols. 1. Fluorine-Containing 3- and 6-Substituted 9-Phenanthrenemethanols," *J. Med. Chem.* 14:921-925 (1971).

Nodiff et al., "Antimalarial Phenanthrene Amino Alcohols. 3. Halogen-containing 9-phenanthrenemethanols," *Chemical Abstracts*, vol. 83, abstract No. 188214 (1975).

Osborne et al., "Effect of Estrogens and Antiestrogens on Growth of Human Breast Cancer Cells in Athymic Nude Mice," *Cancer Research* 45:584-590 (1985).

O'Sullivan and Rothery, "The Preparation and Possible Clinical Significance of 4'-Dialkylaminoisoindogenides," *Clinica Chimica Acta* 62:181-182 (1975) 8Elsevier Scientific Publishing Company.

Ozzello and Sordat, "Behavior of Tumors Produced by Transplantation of Human Mammary Cell Lines in Athymic Nude Mice," *Eur. J. Cancer* 16:553-559 (1980).

Pavlenko et al., "Introduction of aminomethyl groups into heterocyclic CH-acid molecules," *Dopov. Akad. Nauk Ukr Rsrs. Ser. B: Geol., Khim. Biol. Nauki* 7:64-66 (1980) We should add thqat we are Sub. Abstract.

Perkin et al., "Harmine and Harmaline. Part II. The Synthesis of isoHarman," *J. Chem. Soc.* 103:1973-1985 (1913).

Plate et al., "Vascular endothelial growth factor is potential tumor angiogenesis factor in human *gliomas in vivo*," *Nature* 359:845-848 (1992).

Plowman et al., "Receptor Tyrosine Kinases as Targets for Drug Intervention," *DN&P* 7:334-339 (1994).

Quallich et al., Á General Oxindole Synthesis, *J. Synthetic Organic Chemistry*: 51-51 (1993).

Quinn et al., "Fetal liver kinase 1 is a receptor for vascular endothelial growth factor and is selectively expressed in vascular endothelium," *Proc. Natl. Acad. Sci. USA* 90:7533-7537 (1993).

Rozakis-Adcock et al., "Association of the Shc and Grb2/Sem5 SH2-containing proteins is implicated in activation of the Ras pathway by tyrosine kinases," *Nature* 360:689-692 (1992).

Ruveda and Gonzalez, "Geometric isomerism in benzylideneoxindoles," *Spectrochimica Acta* 26A:1275-1277 (1970).

Rygaard and Povlsen, "Heterotransplantation of a Human Malignant Tumour to 'Nude' Mice," *Acta Path. Microbiol. Scand.* 77:758-760 (1969).

Sainsbury et al., "Electrochemical Oxidation of Aromatic Ethers. Part 5.[1] Further Studies of the Coupling Reactions of Alkoxylated Aralkyl- and Aryl-amides," *J.C.S. Perkin I* 108-114.

Saito and Streuli, "Molecular Characterization of Protein Tyrosine Phosphatases," *Cell Growth & Differentation* 2:59-65 (1991) 8Molecular Biolody Journal of the American Association for Cancer Research.

Sandberg-Nordqvist et al., "Characterization of Insulin-Like Growth Factor 1 in Human Primary Brain Tumors," *Cancer Research* 53:2475-2478 (1993).

Schindler et al., "Über Dibenz[b,f]-azocin-Derivate," *Helvetica Chimica Acta* 49:985-989 (1966).

Schlessinger and Ullrich, "Growth Factor Signalling by Receptor Tyrosine Kinases," *Neuron* 9:383-391 (1992) 8 Cell Press.

Schuchter et al., "Successful Treatment of Murine Melanoma with Bryostatin 1," *Cancer Research* 51:682-687 (1991).

Seibert et al., "Clonal Variation of MCF-7 Breast Cancer Cells in Vitro and in Athymic Nude Mice," *Cancer Research* 43:2223-2234 (1983).

Shafie and Grantham, "Role of Hormones in the Growth and Regression of Human Breast Cancer Cells (MCF-7) Transplanted Into Athymic Nude Mice," *J. Natl. Cancer Institute* 67:51-56, 1981.

Shibuya et al., "Nucleotide sequence and expression of a novel human receptor-type tyrosine kinase gene (flt) closely realted to the fms family," *Oncogene* 5:519-524 (1990).

Shiraishi et al., "Specific inhibitors of Tyrosine-Specific Protein Kinase, Synthetic 4-Hydroxycinnamamide Derivatives," *Biochemical and Biophysical Research Communications* 147:322-328 (1987)8 Academic Press.

Shiraishi et al., "Specific Inhibitors of Tyrosine-specific Protein Kinases: Properties of 4-Hydroxycinnamamide Derivatives in Vitro," *Cancer Research* 49:2374-2378 (1989).

Shweiki et al., "Vascular endothelial growth factor induced by hypoxia may mediate hypoxia-initiated angiogenesis," *Nature* 359:843-845 (1992).

Singh et al., "Indolinone Derivatives as Potential Antimicrobial Agents," *Zentralbl. Mikrobiol.* 144:105-109 (1989) copyright Veb Gustav Fischer Veriag Jena.

Singh et al., "Synthesis and Anticonvulsant Activity of New 1-Substituted 1'-Methyl-3-Chloro-2-Oxospiro (Azetidin-3', 4-Indol-2' Ones)," *Bollettino Chimico Farmaceutico* 133:76-79 (1994).

Skehan et al., "New Colorimetric Cytotoxicity Assay for Anticancer-Drug Screening," *J. Natl. Cancer Inst.* 82:1107-1112 (1990).

Slamon et al., "Studies of the HER-2/neu Proto-oncogene in Human Breast and Ovarian Cancer," *Science* 244:707-712 (1989).

Soldi et al., "Platelet-Activating Factor (PAF) Induces the Early Tyrosine Phosphorylation of Focal Adhesion Kinase (p125$^{FAK}$) in Human Endothelial Cells," *Oncogene* 13:515-525 (1996).

Songyang et al., "SH2 Domains Recognize Specific Phosphopeptide Sequences," *Cell* 72:767-778 (1993) 8 Cell Press.

Songyang et al., "Specific Motifs Recognized by the SH2 Domains of Csk, 3BP2, fps/fes, GRB-2, HCP, SHC, Syk and Vav," *Molecular and Cellular Biology* 14:2777-2785 (1994) 8 American Society for Microbiology.

Spada, et al., "Small molecule inhibitors of tyrosine kinase activity," *Expert Opinion on Therapeutic Patents* 5:805-817 (1995) 8Ashley Publications.

Stetinova et al., "Stereochemistry and Photoisomerisation of Furfurylideneoxindoles," *Collection Czechoslov. Chem. Commun.* 42:2201-2206 (1977).

Stolle, Beilstein Reg. No. 273650, *J. Prakt. Chem.*, vol. 2, p. 128 (1930).

Stolle, Beilstein Reg. No. 305045, J. Prakt. Chem., vol. 2, p. 128 (1930).

Sumpter and Miller, "Chapter IV—Oxindole," in *Heterocyclic Compounds With Indole and Carbazole Systems*, 8 Interscience Publishers, Inc., New York, pp. 134-153 (1954).

Sun et al, "Synthesis and Biological Evaluations of 3-Substituted Indolin-2-ones: A Novel Class of Tyrosine Kinase Inhibitors That Exhibit Selectivity toward Particular Receptor Tyrosine Kinases,", 1999.

Sun et al., "Design, Synthesis, and Evaluations of Substituted 3-[(3- or 4-Carboxyethylpyrrol-2-yl) methylidenyl]indolin-2-ones as Inhibitors of VEGF, FGF, and PDGF Receptor Tyrosine Kinases," *Journal of Medicinal Chemistry* 42: 5120-5130 (1999) 8American Chemical Society.

Superti-Furga et al., "A functional screen in yeast for regulators and antagonizers of heterologous protein tyrosine kinases," *Nature Biotech.* 14:600-605 (1996).

Superti-Furga et al., "Csk inhibition of c-Src activity requires both the SH2 and SH3 domains of Src," *EMBO J.* 12:2625-2634 (1993) 8 Oxford University Press.

Tacconi and Marinone, "Preparazione e caratteristiche di alcuni 3-ossindolidenderivati," *Ricerca Scientifica* 38:1239-1244 (1968).

Tacconi et al., "(Z)- and (E)-3-Alkylidene-1,3-dihydroindol-2-ones: Influence of Configuration on the Transmission of the Inductive Effect of the Carbonyl Group," *J.C.S. Perkin II* 150-154 (1976).

Takano et al., "Inhibition of angiogenesis by a novel diaminoanthraquinone that inhibits Protein Kinase C," *Mol. Bio. Cell* 4:358A at abstract No. 2076 (1993).

Terrett et al., "Combinatorial Synthesis—The Design of Compound Libraries and their Application to Drug Discovery," *Tetrahedron* 51(30):8135-8173 (1995) copyright Pergamon! all even pages missing!

Thio et al., "The Interconversion of 2-(2-Aminophenyl)-3-piperolidinone and 3-(2-piperidylmethyl)-2-indolinone: A Reversible N=N' Transacylation," *Notes* (1971) 479-482.

Thompson et al., "Facile Dimerisation of 3-Benzylideneindoline-2-thiones," *J. Chem. Soc. Perkin Trans. (I)* 1835-1837 (1993).

Torp et al., "Expression of the Epidermal Growth Factor Receptor Gene in Human Brain Metastases," *APMIS* 100:713-719 (1992).

Traxler, "Protein tyrosine kinase inhibitors in cancer treatment," *Expert Opinion on Therapeutic Patents* 7(6):571-588 (1997) 8 Ashley Publications Ltd.

Treibs, von Alfred et al., "Über isoindigoide Farbstoffe der Pyrrol-Reihe," *Liebigs Ann. Chem.* 702:112-130 (1967) (With English Translation).

Tsai et al., "The Effect of 3,3-Di-Pyridyl Methyl-1-Phenyl-2-Indolinone on the Nerve Terminal Currents of Mouse Skeletal Muscles," *Neuorpharmacology* 31:943-947 (1992) 8Pergamon Press.

Tuzi et al., "Expression of growth factor receptors in human brain tumours," *Br. J. Cancer* 63:227-233 (1991).

Twamley-Stein et al., "The Src family tyrosine kinases are required for platelet-derived growth factor-mediated signal transduction in NIH 3T3 cells," *Proc. Natl. Acad. Sci. USA* 90:7696-7700 (1993).

Ullrich and Schlessinger, "Signal Transduction by Receptors with Tyrosine Kinase Activity," *Cell* 61:203-212 (1990) copyright Cell Press.

Vaisman et al., "Characterization of the Receptors for Vascular Endothelial Growth Factor," *J. Biol. Chem.* 265:19461-19466 (1990) 8 The American Society for Biochemistry and Molecular Biology.

Varma and Gupta, "Nucleophilic Reactions of 2-Methyl-3-(4'-carbomethoxyphenyl)-4-quinazolinones with 2-Indolinones," *J. Indian Chem. Soc.* 66:804-805 (1989) 8 The Indian Chemical Society.

Voller et al., "Ch. 45—Enzyme-Linked Immunosorbent Assay," in *Manual of Clinical Immunology*, $2^{nd}$ edition, Rose and Friedman editors, American Society of Microbiology, Washington, D.C., pp. 359-371 (1980); @ American Society for Microbiology.

Wahl et al., "3-benzilidene-5-methyl-1,3-dihydroindol-2-one," *Ann. Chim.* 350 (1926), Database Crossfire, Beilstein Reference No. 2-21-00-00290.

Wahl et al., "Chimie Organique—Sur les iso-indogenides," *C.R. Hebd. Seances Acad. Sci.* 149:132-134 (1909).

Wahl, Beilstein Reg. No. 191439, *Bull. Soc. Chim. Fr.*, p. 1038 (1909).

Wahl, Beilstein Reg. No. 231732, *Bull. Soc. Chim. Fr.*, pp. 1035-1038 (1909).

Walker et al., "Synthesis of New 3-(Pyridylmethylene)-, 3-(Pyridylmethyl)-, 3-(Piperidylmethyl)-, and 3-(-62 -Alkylaminoethyl)-2-indolinones. The Reduction of Isoindogenides, Nitro Compounds, and Pyridines in a Series of 2-Indolinones," *J. Med. Chem.* 8:626-637 (1965).

Walker, "Synthesis of a α-(p-Aminophenyl)- and α-(p-Chlorophenyl)-β-aryl-propionitriles by Catalytic Reduction of Stilbenenitriles," *J. Med. Chem.* 8:583-588 (1965).

Warri et al., "Estrogen Suppression of erbB2 Expression is Associated with Increased Growth Rate of ZR-75-I Human Breast Cancer Cells In Vitro and in Nude Mice," *Int. J. Cancer* 49:616-623 (1991) 8 Wiley-Leiss, Inc.

Weidner et al., "Tumor Angiogenesis and Metastasis—Correlation in Invasive Breast Carcinoma," *New England J. Medicine* 324:1-7 (1991) 8 Massachusetts Medical Society.

Winkelmann et al., "Chemotherapeutically Active Nitro Compounds: 4. 5-Nitroimidazoles (Part I)," *Arzneim.-Forsch./Drug Res.* 27:2251-2263 (1977).

Wright et al., "Cyclic Hydroxamic Acids Derived from Indole," *J. Am. Chem. Soc.* 78:221-224 (1956).

Wright et al., "Inhibition of Angiogenesis in Vitro and In Ovo With an Inhibitor of Cellular Protein Kinases, MDL 27032," *J. Cellular Physiology* 152:448-457 (1992).

Young and Babbitt, "2-(2-Methyl-3-indolyl)-1,4-benzoquinone, a Reversible Redox Substrate at the Carbon-Paste Electrode in Acidic Aqueous-Ethanolic Media," *J. Org. Chem.* 47:1571-1572 (1982) copyright Am. Chem. Soc.

Zaman et al., "Tyrosine Kinase Activity of Purified Recombinant Cytoplasmic Domain of Platelet-Derived Growth Factor β-Receptor (β-PDGFR) and Discovery of a Novel Inhibitor of Receptor Tyrosine Kinases," *Biochemical Pharmacology* 57:57-64 (1999) 8Elsevier Science Inc.

Zhang et al., "Microtubule Effects of Welwistatin, a Cyanobacterial Indolinone that Circumvents Multiple Drug Resistance," *Molecular Pharmacology* 49:228-234 (1996) 8The American Society for Pharmacology and Experimental Pharmaceutics.

Zhungietu et al., "Reaction of Indoles and 2-Ketoindolines With Some Aldehydes," *Chemical Abstracts*, vol. 78, abstract No. 111201 (1990).

* cited by examiner

PYRROLE SUBSTITUTED 2-INDOLINONE PROTEIN KINASE INHIBITORS

CROSS-REFERENCE INFORMATION

This application is a division of U.S. application Ser. No. 11/028,477, filed Jan. 4, 2005, which is a continuation of U.S. application Ser. No. 10/412,690, filed Apr. 14, 2003, abandoned, which is a division of U.S. application Ser. No. 09/783,264, filed Feb. 15, 2001, now U.S. Pat. No. 6,573,293, which claims priority under 35 U.S.C. 119(e) to U.S. Provisional Applications Ser. Nos. 60/182,710, filed Feb. 15, 2000, 60/216,422 filed Jul. 6, 2000 and 60/243,532, filed Oct. 27, 2000, the disclosures of which are incorporated by reference herein in their entirety.

BACKGROUND OF THE INVENTION

1. Field of Invention

The present invention relates to certain 3-pyrrole substituted 2-indolinone compounds which modulate the activity of protein kinases ("PKs"). The compounds of this invention are therefore useful in treating disorders related to abnormal PK activity. Pharmaceutical compositions comprising these compounds, methods of treating diseases utilizing pharmaceutical compositions comprising these compounds and methods of preparing them are also disclosed.

2. State of the Art

The following is offered as background information only and is not admitted to be prior art to the present invention.

PKs are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer).

The PKs can be conveniently broken down into two classes, the protein tyrosine kinases (PTKs) and the serine-threonine kinases (STKs).

One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, *Neuron*, 9:303-391 (1992) which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated α subunits and two β subunits which cross the cell membrane and which contain the tyrosine kinase domain.

A third RTK subfamily is referred to as the platelet derived growth factor receptor ("PDGFR") group, which includes PDGFRα, PDGFRβ, CSFIR, c-kit and c-fms. These receptors consist of glycosylated extracellular domains composed of variable numbers of immunoglobin-like loops and an intracellular domain wherein the tyrosine kinase domain is interrupted by unrelated amino acid sequences.

Another group which, because of its similarity to the PDGFR subfamily, is sometimes subsumed into the later group is the fetus liver kinase ("flk") receptor subfamily. This group is believed to be made up of kinase insert domain-receptor fetal liver kinase-1 (KDR/FLK-1, VEGF-R2), flk-1R, flk-4 and fms-like tyrosine kinase 1 (flt-1).

A further member of the tyrosine kinase growth factor receptor family is the fibroblast growth factor ("FGF") receptor subgroup. This group consists of four receptors, FGFR1-4, and seven ligands, FGF1-7. While not yet well defined, it appears that the receptors consist of a glycosylated extracellular domain containing a variable number of immunoglobin-like loops and an intracellular domain in which the tyrosine kinase sequence is interrupted by regions of unrelated amino acid sequences.

Still another member of the tyrosine kinase growth factor receptor family is the vascular endothelial growth factor ("VEGF") receptor subgroup. VEGF is a dimeric glycoprotein similar to PDGF but has different biological functions and target cell specificity in vivo. In particular, VEGF is presently thought to play an essential role is vasculogenesis and angiogenesis.

A more complete listing of the known RTK subfamilies is described in Plowman et al., *DN&P*, 7(6):334-339 (1994) which is incorporated by reference, including any drawings, as if fully set forth herein.

In addition to the RTKs, there also exists a family of entirely intracellular PTKs called "non-receptor tyrosine kinases" or "cellular tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fps, Fak, Jak and Ack) have been identified. The Src subfamily appear so far to be the largest group of CTKs and includes Src, Yes, Fyn, Lyn, Lck, Blk, Hck, Fgr and Yrk. For a more detailed discussion of CTKs, see Bolen, *Oncogene*, 8:2025-2031 (1993), which is incorporated by reference, including any drawings, as if fully set forth herein.

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes.

RTKs, CTKs and STKs have all been implicated in a host of pathogenic conditions including, significantly, cancer.

Other pathogenic conditions which have been associated with PTKs include, without limitation, psoriasis, hepatic cirrhosis, diabetes, angiogenesis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. Some of this effort has involved biomimetic approaches using large molecules patterned on those involved in the actual cellular processes (e.g., mutant ligands (U.S. Pat. No. 4,966,849); soluble receptors and antibodies (App. No. WO 94/10202, Kendall and Thomas, *Proc. Nat'l Acad. Sci.,* 90:10705-09 (1994), Kim, et al., *Nature,* 362:841-844 (1993)); RNA ligands (Jelinek, et al., *Biochemistry,* 33:10450-56); Takano, et al., *Mol. Bio. Cell* 4:358A (1993); Kinsella, et al., *Exp. Cell Res.* 199:56-62 (1992); Wright, et al., *J. Cellular Phys.,* 152:448-57) and tyrosine kinase inhibitors (WO 94/03427; WO 92/21660; WO 91/15495; WO 94/14808; U.S. Pat. No. 5,330,992; Mariani, et al., *Proc. Am. Assoc. Cancer Res.,* 35:2268 (1994)).

In addition to the above, attempts have been made to identify small molecules which act as PK inhibitors. For example, bis-monocylic, bicyclic and heterocyclic aryl compounds (PCT WO 92/20642), vinyleneazaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP App. No. 0 566 266 A1), selenaindoles and selenides (PCT WO 94/03427), tricyclic polyhydroxylic compounds (PCT WO 92/21660) and benzylphosphonic acid compounds (PCT WO 91/15495) have all been described as PTK inhibitors useful in the treatment of cancer.

SUMMARY OF THE INVENTION

The present invention is directed to certain 3-pyrrole substituted 2-indolinone compounds which exhibit PK modulating ability and are therefore useful in treating disorders related to abnormal PK activity.

Accordingly, in one aspect, the present invention relates to 3-pyrrole substituted 2-indolinones of Formula (I):

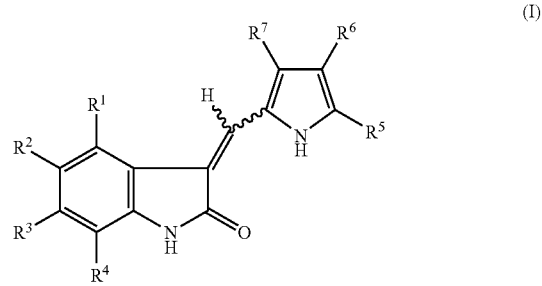

(I)

wherein:
$R^1$ is selected from the group consisting of hydrogen, halo, alkyl, cyclkoalkyl, aryl, heteroaryl, heteroalicyclic, hydroxy, alkoxy, —(CO)$R^{15}$, —N$R^{13}R^{14}$, —(CH$_2$)$_r R^{16}$ and —C(O)N$R^8R^9$;

$R^2$ is selected from the group consisting of hydrogen, halo, alkyl, trihalomethyl, hydroxy, alkoxy, cyano, —N$R^{13}R^{14}$, N$R^{13}$C(O)$R^{14}$, —C(O)$R^{15}$, aryl, heteroaryl, —S(O)$_2$N$R^{13}R^{14}$ and —SO$_2R^{20}$ (wherein $R^{20}$ is alkyl, aryl, aralkyl, heteroaryl and heteroaralkyl);

$R^3$ is selected from the group consisting of hydrogen, halogen, alkyl, trihalomethyl, hydroxy, alkoxy, —(CO)$R^{15}$, —N$R^{13}R^{14}$, aryl, heteroaryl, —N$R^{13}$S(O)$_2R^{14}$, —S(O)$_2$N$R^{13}R^{14}$, —N$R^{13}$C(O)$R^{14}$, —N$R^{13}$C(O)O$R^{14}$ and —SO$_2R^{20}$ (wherein $R^{20}$ is alkyl, aryl, aralkyl, heteroaryl and heteroaralkyl);

$R^4$ is selected from the group consisting of hydrogen, halogen, alkyl, hydroxy, alkoxy and —N$R^{13}R^{14}$;

$R^5$ is selected from the group consisting of hydrogen, alkyl and —C(O)$R^{10}$;

$R^6$ is selected from the group consisting of hydrogen, alkyl and —C(O)$R^{10}$;

$R^7$ is selected from the group consisting of hydrogen, alkyl, aryl, heteroaryl, —C(O)$R^{17}$ and —C(O)$R^{10}$; or $R^6$ and $R^7$ may combine to form a group selected from the group consisting of —(CH$_2$)$_4$—, —(CH$_2$)$_5$— and —(CH$_2$)$_6$—; with the proviso that at least one of $R^5$, $R^6$ or $R^7$ must be $R^8$ and $R^9$ are independently selected from the group consisting of hydrogen, alkyl and aryl;

$R^{10}$ is selected from the group consisting of hydroxy, alkoxy, aryloxy, —N($R^{11}$)(CH$_2$)$_n R^{12}$, and —N$R^{13}R^{14}$;

$R^{11}$ is selected from the group consisting of hydrogen and alkyl;

$R^{12}$ is selected from the group consisting of —N$R^{13}R^{14}$, hydroxy, —C(O)$R^{15}$, aryl, heteroaryl, —N$^+$(O$^-$)$R^{13}R^{14}$, —N(O)$R^{13}$, and —NHC(O)$R^a$ (wherein $R^a$ is unsubstituted alkyl, haloalkyl, or aralkyl);

$R^{13}$ and $R^{14}$ are independently selected from the group consisting of hydrogen, alkyl, cyanoalkyl, cycloalkyl, aryl and heteroaryl; or $R^{13}$ and $R^{14}$ may combine to form a heterocyclo group;

$R^{15}$ is selected from the group consisting of hydrogen, hydroxy, alkoxy and aryloxy;

$R^{16}$ is selected from the group consisting of hydroxy, —C(O)$R^{15}$, —N$R^{13}R^{14}$ and —C(O)N$R^{13}R^{14}$;

$R^{17}$ is selected from the group consisting of alkyl, cycloalkyl, aryl and heteroaryl;

$R^{20}$ is alkyl, aryl, aralkyl or heteroaryl; and n and r are independently 1, 2, 3, or 4;

or a pharmaceutically acceptable salt thereof.

Preferably, $R^1$ is selected from the group consisting of hydrogen, halo, alkyl, cyclkoalkyl, aryl, heteroaryl, heteroalicyclic, hydroxy, alkoxy, —C(O)$R^{15}$, —N$R^{13}R^{14}$, —(CH$_2$)$_r$ $R^{16}$ and —C(O)N$R^8R^9$;

$R^2$ is selected from the group consisting of hydrogen, halo, alkyl, trihalomethyl, hydroxy, alkoxy, —N$R^{13}R^{14}$, N$R^{13}$C (O)$R^{14}$, —C(O)$R^{15}$, aryl, heteroaryl, and —S(O)$_2$N$R^{13}R^{14}$;

$R^3$ is selected from the group consisting of hydrogen, halogen, alkyl, trihalomethyl, hydroxy, alkoxy, —(CO)$R^{15}$, —N$R^{13}R^{14}$, aryl, heteroaryl, —N$R^{13}$S(O)$_2R^{14}$, —S(O)$_2$ N$R^{13}R^{14}$, —N$R^{13}$C(O)$R^{14}$, and —N$R^{13}$C(O)O$R^{14}$;

$R^4$ is selected from the group consisting of hydrogen, halogen, alkyl, hydroxy, alkoxy and —N$R^{13}R^{14}$;

$R^5$ is selected from the group consisting of hydrogen, alkyl and —C(O)$R^{10}$;

$R^6$ is selected from the group consisting of hydrogen, alkyl and —C(O)$R^{10}$;

$R^7$ is selected from the group consisting of hydrogen, alkyl, aryl, heteroaryl, —C(O)$R^{17}$ and —C(O)$R^{10}$;

$R^6$ and $R^7$ may combine to form a group selected from the group consisting of —(CH$_2$)$_4$—, —(CH$_2$)$_5$— and —(CH$_2$)$_6$—; with the proviso that at least one of $R^5$, $R^6$ or $R^7$ must be —C(O)$R^{10}$;

$R^8$ and $R^9$ are independently selected from the group consisting of hydrogen, alkyl and aryl;

$R^{10}$ is selected from the group consisting of hydroxy, alkoxy, aryloxy, —N($R^{11}$)(CH$_2$)$_n R^{12}$ and —N$R^{13}R^{14}$;

$R^{11}$ is selected from the group consisting of hydrogen and alkyl;

$R^{12}$ is selected from the group consisting of —N$R^{13}R^{14}$, hydroxy, —C(O)$R^{15}$, aryl and heteroaryl;

$R^{13}$ and $R^{14}$ are independently selected from the group consisting of hydrogen, alkyl, cycloalkyl, aryl and heteroaryl;

$R^{13}$ and $R^{14}$ may combine to form a group selected from the group consisting of —(CH$_2$)$_4$—, —(CH$_2$)$_5$—, —(CH$_2$)$_2$O (CH$_2$)$_2$—, and —(CH$_2$)$_2$N(CH$_3$)(CH$_2$)$_2$—;

$R^{15}$ is selected from the group consisting of hydrogen, hydroxy, alkoxy and aryloxy;

$R^{16}$ is selected from the group consisting of hydroxy, —C(O)$R^{15}$—, —N$R^{13}R^{14}$ and —C(O)N$R^{13}R^{14}$;

$R^{17}$ is selected from the group consisting of alkyl, cycloalkyl, aryl and heteroaryl; and n and r are independently 1, 2, 3, or 4;

or a pharmaceutically acceptable salt thereof.

In a second aspect this invention is directed to a pharmaceutical composition comprising one or more compound(s) of Formula (I) or a pharmaceutically acceptable salt thereof and a pharmaceutically acceptable excipient.

In a third aspect, this invention is directed to a method of treating diseases mediated by abnormal protein kinase activity, in particular, receptor tyrosine kinases (RTKs), non-receptor protein tyrosine kinases (CTKs) and serine/threonine protein kinases (STKs), in an organism, in particular humans, which method comprises administering to said organism a pharmaceutical composition comprising a compound of Formula (I). Such diseases include by way of example and not limitation, cancer, diabetes, hepatic cirrhosis, cardiovasacular disease such as atherosclerosis, angiogenesis, immunological disease such as autoimmune disease and renal disease.

In a fourth aspect, this invention is directed to a method of modulating of the catalytic activity of PKs, in particular, receptor tyrosine kinases (RTKs), non-receptor protein tyrosine kinases (CTKs) and serine/threonine protein kinases (STKs), using a compound of this invention which may be carried out in vitro or in vivo. In particular, the receptor protein kinase whose catalytic activity is modulated by a compound of this invention is selected from the group consisting of EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R and FGFR-4R. The cellular tyrosine kinase whose catalytic activity is modulated by a compound of this invention is selected from the group consisting of Src, Frk, Btk, Csk, Abl, ZAP70, Fes/Fps, Fak, Jak, Ack, Yes, Fyn, Lyn, Lck, Blk, Hck, Fgr and Yrk. The serine-threonine protein kinase whose catalytic activity is modulated by a compound of this invention is selected from the group consisting of CDK2 and Raf.

In a fifth aspect, this invention is directed to the use of a compound of Formula (I) in the preparation of a medicament which is useful in the treatment of a disease mediated by abnormal PK activity.

In a sixth aspect, this invention is directed to an intermediate of Formula (II):

wherein:

$R^5$ is selected from the group consisting of hydrogen, alkyl and —C(O)$R^{10}$;

$R^6$ is selected from the group consisting of hydrogen, alkyl and —C(O)$R^{10}$;

$R^7$ is selected from the group consisting of hydrogen, alkyl, aryl, heteroaryl, —C(O)$R^{17}$ and —C(O)$R^{10}$;

$R^6$ and $R^7$ may combine to form a group selected from the group consisting of —(CH$_2$)$_4$—, —(CH$_2$)$_5$— and —(CH$_2$)$_6$—; with the proviso that at least one of $R^5$, $R^6$ or $R^7$ must be —C(O)$R^{10}$;

$R^{10}$ is selected from the group consisting of hydroxy, alkoxy, aryloxy, —N($R^{11}$)(CH$_2$)$_n R^{12}$ and —N$R^{13}R^{14}$;

$R^{11}$ is selected from the group consisting of hydrogen and alkyl;

$R^{12}$ is selected from the group consisting of —N$R^{13}R^{14}$, hydroxy, —C(O)$R^{15}$, aryl and heteroaryl;

$R^{13}$ and $R^{14}$ are independently selected from the group consisting of hydrogen, alkyl, cyanoalkyl, cycloalkyl, aryl and heteroaryl; or $R^{13}$ and $R^{14}$ may combine to form a heterocyclo group;

$R^{15}$ is selected from the group consisting of hydrogen, hydroxy, alkoxy and aryloxy;

$R^{17}$ is selected from the group consisting of alkyl, cycloalkyl, aryl and heteroaryl; and n is 1, 2, 3, or 4.

Preferaby, $R^5$ or $R^6$, in the compound of formula II, is —C(O)$R^{10}$;

$R^6$ is selected from the group consisting of hydrogen, and alkyl, more preferably hydrogen or methyl;

$R^5$ is selected from the group consisting of hydrogen, and alkyl, more preferably hydrogen or methyl when $R^6$ is —COR$^{10}$;

$R^6$ is selected from the group consisting of hydrogen, and alkyl, more preferably hydrogen or methyl when $R^5$ is —COR$^{10}$;

$R^7$ is selected from the group consisting of hydrogen, alkyl, and aryl, more preferably hydrogen, methyl or phenyl;

$R^{10}$ is selected from the group consisting of hydroxy, alkoxy, —N($R^{11}$)(CH$_2$)$_n R^{12}$ and —NR$^{13}$R$^{14}$;

$R^{11}$ is selected from the group consisting of hydrogen and alkyl, more preferably hydrogen or methyl;

$R^{12}$ is selected from the group consisting of —NR$^{13}$R$^{14}$;

$R^{13}$ and $R^{14}$ are independently selected from the group consisting of hydrogen, or alkyl; or $R^{13}$ and $R^{14}$ may combine to form a heterocyclo group; and n is 1, 2 or 3.

Within the above preferred groups, more preferred groups of intermediate compounds are those wherein $R^5$, $R^6$, $R^{11}$, $R^{12}$, $R^{13}$ or $R^{14}$ are independently groups described in the section titled "preferred embodiments" herein below.

In a seventh aspect, this invention is directed to methods of preparing compounds of Formula (I).

Lastly, this invention is also directed to identifying a chemical compound that modulates the catalytic activity of a protein kinase by contacting cells expressing said protein kinase with a compound or a salt of the present invention and then monitoring said cells for an effect.

DETAILED DESCRIPTION OF THE INVENTION

Definitions

Unless otherwise stated the following terms used in the specification and claims have the meanings discussed below:

"Alkyl" refers to a saturated aliphatic hydrocarbon radical including straight chain and branched chain groups of 1 to 20 carbon atoms (whenever a numerical range; e.g. "1-20", is stated herein, it means that the group, in this case the alkyl group, may contain 1 carbon atom, 2 carbon atoms, 3 carbon atoms, etc. up to and including 20 carbon atoms). Alkyl groups containing from 1 to 4 carbon atoms are refered to as lower alkyl groups. When said lower alkyl groups lack substituents, they are referred to as unsubstituted lower alkyl groups. More preferably, an alkyl group is a medium size alkyl having 1 to 10 carbon atoms e.g., methyl, ethyl, propyl, 2-propyl, n-butyl, iso-butyl, tert-butyl, pentyl, and the like. Most preferably, it is a lower alkyl having 1 to 4 carbon atoms e.g., methyl, ethyl, propyl, 2-propyl, n-butyl, iso-butyl, or tert-butyl, and the like. The alkyl group may be substituted or unsubstituted. When substituted, the substituent group(s) is preferably one or more, more preferably one to three, even more preferably one or two substituent(s) independently selected from the group consisting of halo, hydroxy, unsubstituted lower alkoxy, aryl optionally substituted with one or more groups, preferably one, two or three groups which are independently of each other halo, hydroxy, unsubstituted lower alkyl or unsubstituted lower alkoxy groups, aryloxy optionally substituted with one or more groups, preferably one, two or three groups which are independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more groups, preferably one, two or three groups which are independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and the nitrogen atoms in the group being optionally substituted with one or more groups, preferably one, two or three groups which are independently of each other halo, hydroxy, unsubstituted lower alkyl or unsubstituted lower alkoxy groups, 5- or 6-member heteroalicyclic group having from 1 to 3 heteroatoms selected from the group consisting of nitrogen, oxygen and sulfur, the carbon and nitrogen (if present) atoms in the group being optionally substituted with one or more groups, preferably one, two or three groups which are independently of each other halo, hydroxy, unsubstituted lower alkyl or unsubstituted lower alkoxy groups, mercapto, (unsubstituted lower alkyl)thio, arylthio optionally substituted with one or more groups, preferably one, two or three groups which are independently of each other halo, hydroxy, unsubstituted lower alkyl or unsubstituted lower alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, $R^{18}$S(O)—, $R^{18}$S(O)$_2$—, —C(O)OR$^{18}$, $R^{18}$C(O)O—, and —NR$^{18}$R$^{19}$, wherein $R^{18}$ and $R^{19}$ are independently selected from the group consisting of hydrogen, unsubstituted lower alkyl, trihalomethyl, unsubstituted (C$_3$-C$_6$)cycloalkyl, unsubstituted lower alkenyl, unsubstituted lower alkynyl and aryl optionally substituted with one or more, groups, preferably one, two or three groups which are independently of each other halo, hydroxy, unsubstituted lower alkyl or unsubstituted lower alkoxy groups.

Preferably, the alkyl group is substituted with one or two substituents independently selected from the group consisting of hydroxy, 5- or 6-member heteroalicyclic group having from 1 to 3 heteroatoms selected from the group consisting of nitrogen, oxygen and sulfur, the carbon and nitrogen (if present) atoms in the group being optionally substituted with one or more groups, preferably one, two or three groups which are independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and the nitrogen atoms in the group being optionally substituted with one or more groups, preferably one, two or three groups which are independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more groups, preferably one, two or three groups which are independently of each other halo, hydroxy, unsubstituted lower alkyl or unsubstituted lower alkoxy groups, or —NR$^{18}$R$^{19}$, wherein $R^{18}$ and $R^{19}$ are independently selected from the group consisting of hydrogen, unsubstituted lower alkyl. Even more preferably the alkyl group is substituted with one or two substituents which are independently of each other hydroxy, dimethylamino, ethylamino, diethylamino, dipropylamino, pyrrolidino, piperidino, morpholino, piperazino, 4-lower alkylpiperazino, phenyl, imidazolyl, pyridinyl, pyridazinyl, pyrimidinyl, oxazolyl, triazinyl, and the like.

"Cycloalkyl" refers to a 3 to 8 member all-carbon monocyclic ring, an all-carbon 5-member/6-member or 6-member/6-member fused bicyclic ring or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system.

Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. When substituted, the substituent group(s) is preferably one or more, more preferably one or two substituents, independently selected from the group consisting of unsubstituted lower alkyl, trihaloalkyl, halo, hydroxy, unsubstituted lower alkoxy, aryl optionally substituted with one or more, preferably one or two groups independently of each other halo, hydroxy, unsubstituted lower alkyl or unsubstituted lower alkoxy groups, aryloxy optionally substituted with one or more, preferably one or two groups independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more, preferably one or two groups independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and nitrogen atoms of the group being optionally substituted with one or more, preferably one or two groups independently of each other halo, hydroxy, unsubstituted lower alkyl or unsubstituted lower alkoxy groups, 5- or 6-member heteroalicyclic group having from 1 to 3 heteroatoms selected from the group consisting of nitrogen, oxygen and sulfur, the carbon and nitogen (if present) atoms in the group being optionally substituted with one or more, preferably one or two groups independently of each other halo, hydroxy, unsubstituted lower alkyl or unsubstituted lower alkoxy groups, mercapto, (unsubstituted lower alkyl)thio, arylthio optionally substituted with one or more, preferably one or two groups independently of each other halo, hydroxy, unsubstituted lower alkyl or unsubstituted lower alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, $R^{18}S(O)$—, $R^{18}S(O)_2$—, —$C(O)OR^{18}$, $R^{18}C(O)O$—, and —$NR^{18}R^{19}$ are as defined above.

"Alkenyl" refers to a lower alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like.

"Alkynyl" refers to a lower alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like.

"Aryl" refers to an all-carbon monocyclic or fused-ring polycyclic (i.e., rings which share adjacent pairs of carbon atoms) groups of 1 to 12 carbon atoms having a completely conjugated pi-electron system. Examples, without limitation, of aryl groups are phenyl, naphthalenyl and anthracenyl. The aryl group may be substituted or unsubstituted. When substituted, the substituted group(s) is preferably one or more, more preferably one, two or three, even more preferably one or two, independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^{18}S(O)$—, $R^{18}S(O)_2$—, —$C(O)OR^{18}$, $R^{18}C(O)O$—, and —$NR^{18}R^{19}$, with $R^{18}$ and $R^{19}$ as defined above. Preferably, the aryl group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

"Heteroaryl" refers to a monocyclic or fused ring (i.e., rings which share an adjacent pair of atoms) group of 5 to 12 ring atoms containing one, two, or three ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, the substituted group(s) is preferably one or more, more preferably one, two, or three, even more preferably one or two, independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^{18}S(O)$—, $R^{18}O)_2$—, —$C(O)OR^{18}$, $R^{18}C(O)O$—, and —$NR^{18}R^{19}$, with $R^{18}$ and $R^{19}$ as defined above. Preferably, the heteroaryl group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

"Heteroalicyclic" refers to a monocyclic or fused ring group having in the ring(s) of 5 to 9 ring atoms in which one or two ring atoms are heteroatoms selected from N, O, or $S(O)_n$ (where n is an integer from 0 to 2), the remaining ring atoms being C. The rings may also have one or more double bonds. However, the rings do not have a completely conjugated pi-electron system. Examples, without limitation, of unsubstituted heteroalicyclic groups are pyrrolidino, piperidino, piperazino, morpholino, thiomorpholino, homopiperazino, and the like. The heteroalicyclic ring may be substituted or unsubstituted. When substituted, the substituted group(s) is preferably one or more, more preferably one, two or three, even more preferably one or two, independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^{18}S(O)$—, $R^{18}S(O)_2$—, —$C(O)OR^{18}$, $R^{18}C(O)O$—, and —$NR^{18}R^{19}$, with $R^{18}$ and $R^{19}$ as defined above. Preferably, the heteroalicyclic group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

Preferably, the heteroalicyclic group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

"Heterocycle" means a saturated cyclic radical of 3 to 8 ring atoms in which one or two ring atoms are heteroatoms selected from N, O, or $S(O)_n$ (where n is an integer from 0 to 2), the remaining ring atoms being C, where one or two C atoms may optionally be replaced by a carbonyl group. The heterocyclyl ring may be optionally substituted independently with one, two, or three substituents selected from optionally substituted lower alkyl (substituted with 1 or 2 substituents independently selected from carboxy or ester), haloalkyl, cyanoalkyl, halo, nitro, cyano, hydroxy, alkoxy, amino, monoalkylamino, dialkylamino, aralkyl, heteroaralkyl, —COR (where R is alkyl) or ▓COOR where R is (hydrogen or alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof. Preferably, the heterocycle group is optionally substituted with one or two substituents independently selected from halo, unsubstituted lower alkyl, lower alkyl substituted with carboxy, ester hydroxy, mono or dialkylamino.

"Hydroxy" refers to an —OH group.

"Alkoxy" refers to both an —O-(unsubstituted alkyl) and an —O-(unsubstituted cycloalkyl) group. Representative examples include, but are not limited to, e.g., methoxy, ethoxy, propoxy, butoxy, cyclopropyloxy, cyclobutyloxy, cyclopentyloxy, cyclohexyloxy, and the like.

"Aryloxy" refers to both an —O-aryl and an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

"Mercapto" refers to an —SH group.

"Alkylthio" refers to both an —S-(unsubstituted alkyl) and an —S-(unsubstituted cycloalkyl) group. Representative examples include, but are not limited to, e.g., methylthio, ethylthio, propylthio, butylthio, cyclopropylthio, cyclobutylthio, cyclopentylthio, cyclohexylthio, and the like.

"Arylthio" refers to both an —S-aryl and an —S-heteroaryl group, as defined herein. Representative examples include, but are not limited to, phenylthio, pyridinylthio, furanylthio, thientylthio, pyrimidinylthio, and the like and derivatives thereof.

"Acyl" refers to a —C(O)—R" group, where R" is selected from the group consisting of hydrogen, unsubstituted lower alkyl, trihalomethyl, unsubstituted cycloalkyl, aryl optionally substituted with one or more, preferably one, two, or three substituents selected from the group consisting of unsubstituted lower alkyl, trihalomethyl, unsubstituted lower alkoxy, halo and —NR$^{18}$R$^{19}$ groups, heteroaryl (bonded through a ring carbon) optionally substituted with one or more, preferably one, two, or three substituents selected from the group consisting of unsubstituted lower alkyl, trihaloalkyl, unsubstituted lower alkoxy, halo and —NR$^{18}$R$^{19}$ groups and heteroalicyclic (bonded through a ring carbon) optionally substituted with one or more, preferably one, two, or three substituents selected from the group consisting of unsubstituted lower alkyl, trihaloalkyl, unsubstituted lower alkoxy, halo and —NR$^{18}$R$^{19}$ groups. Representative acy groups include, but are not limited to, acetyl, trifluoroacetyl, benzoyl, and the like "Aldehyde" refers to an acyl group in which R" is hydrogen.

"Thioacyl" refers to a —C(S)—R" group, with R" as defined herein.

"Ester" refers to a —C(O)O—R" group with R" as defined herein except that R" cannot be hydrogen.

"Acetyl" group refers to a —C(O)CH$_3$ group.

"Halo" group refers to fluorine, chlorine, bromine or iodine, preferably fluorine or chlorine.

"Trihalomethyl" group refers to a —CX$_3$ group wherein X is a halo group as defined herein.

"Trihalomethanesulfonyl" group refers to a X$_3$CS(=O)$_2$— groups with X as defined above.

"Cyano" refers to a —C≡N group.

"Methylenedioxy" refers to a —OCH$_2$O— group where the two oxygen atoms are bonded to adjacent carbon atoms.

"Ethylenedioxy" group refers to a —OCH$_2$CH$_2$O— where the two oxygen atoms are bonded to adjacent carbon atoms.

"S-sulfonamido" refers to a —S(O)$_2$NR$^{18}$R$^{19}$ group, with R$^{18}$ and R$^{19}$ as defined herein.

"N-sulfonamido" refers to a —NR$^{18}$S(O)$_2$R$^{19}$ group, with R$^{18}$ and R$^{19}$ as defined herein.

"O-carbamyl" group refers to a —OC(O)NR$^{18}$R$^{19}$ group with R$^{18}$ and R$^{19}$ as defined herein.

"N-carbamyl" refers to an R$^{18}$OC(O)NR$^{19}$— group, with R$^{18}$ and R$^{19}$ as defined herein.

"O-thiocarbamyl" refers to a —OC(S)NR$^{18}$R$^{19}$ group with R$^{18}$ and R$^{19}$ as defined herein.

"N-thiocarbamyl" refers to a R$^{18}$OC(S)NR$^{19}$— group, with R$^{18}$ and R$^{19}$ as defined herein.

"Amino" refers to an —NR$^{18}$R$^{19}$ group, wherein R$^{18}$ and R$^{19}$ are both hydrogen.

"C-amido" refers to a —C(O)NR$^{18}$R$^{19}$ group with R$^{18}$ and R$^{19}$ as defined herein.

"N-amido" refers to a R$^{18}$C(O)NR$^{19}$— group, with R$^{18}$ and R$^{19}$ as defined herein.

"Nitro" refers to a —NO$_2$ group.

"Haloalkyl" means an unsubstituted alkyl, preferably unsubstituted lower alkyl as defined above that is substituted with one or more same or different halo atoms, e.g., —CH$_2$Cl, —CF$_3$, —CH$_2$CF$_3$, —CH$_2$CCl$_3$, and the like.

"Aralkyl" means unsubstituted alkyl, preferably unsubstituted lower alkyl as defined above which is substituted with an aryl group as defined above, e.g., —CH$_2$phenyl, —(CH$_2$)$_2$phenyl, —(CH$_2$)$_3$phenyl, CH$_3$CH(CH$_3$)CH$_2$phenyl, and the like and derivatives thereof.

"Heteroaralkyl" group means unsubstituted alkyl, preferably unsubstituted lower alkyl as defined above which is substituted with a heteroaryl group, e.g., —CH$_2$pyridinyl, —(CH$_2$)$_2$pyrimidinyl, —(CH$_2$)$_3$imidazolyl, and the like, and derivatives thereof.

"Monoalkylamino" means a radical —NHR where R is an unsubstitued alkyl or unsubstituted cycloalkyl group as defined above, e.g., methylamino, (1-methylethyl)amino, cyclohexylamino, and the like.

"Dialkylamino" means a radical —NRR where each R is independently an unsubstitued alkyl or unsubstituted cycloalkyl group as defined above, e.g., dimethylamino, diethylamino, (1-methylethyl)-ethylamino, cyclohexylmethylamino, cyclopentylmethylamino, and the like.

"Cyanoalkyl" means unsubstituted alkyl, preferably unsubstituted lower alkyl as defined above, which is substituted with 1 or 2 cyano groups.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocyclo group is not substituted with the alkyl group.

The terms "2-indolinone", "indolin-2-one" and "2-oxindole" are used interchangeably herein to refer to a molecule having the chemical structure:

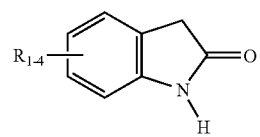

The term "pyrrole" refers to a molecule having the chemical structure:

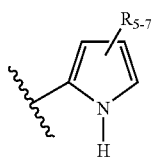

The term "pyrrole substituted 2-indolinone" and "3-pyrrolidenyl-2-indolinone" are used interchangeably herein to refer to a chemical compound having the general structure shown in Formula (I).

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the $R^6$ substituent in a compound of formula (I) is 2-hydroxyethyl, then the carbon to which the hydroxy group is attached is an asymmetric center and therefore the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The compounds of Formula (I) may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate RTK, CTK and/or STK activity and is not limited to any one tautomeric or structural isomeric form.

A "pharmaceutical composition" refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

The compound of Formula (I) may also act as a prod rug. A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the patent drug. An example, without limitation, of a prodrug would be a compound of the present invention which is administered as an ester (the "prodrug") to facilitate transmittal across a cell membrane where water solubility is detrimental to mobility but then is metabolically hydrolyzed to the carboxylic acid, the active entity, once inside the cell where water solubility is beneficial.

A further example of a prodrug might be a short polypeptide, for example, without limitation, a 2-10 amino acid polypeptide, bonded through a terminal amino group to a carboxy group of a compound of this invention wherein the polypeptide is hydrolyzed or metabolized in vivo to release the active molecule. The prodrugs of a compound of Formula (I) are within the scope of this invention.

Additionally, it is contemplated that a compound of Formula (I) would be metabolized by enzymes in the body of the organism such as human being to generate a metabolite that can modulate the activity of the protein kinases. Such metabolites are within the scope of the present invention.

As used herein, a "physiologically/pharmaceutically acceptable carrier" refers to a carrier or diluent that does not cause significant irritation to an organism and does not abrogate the biological activity and properties of the administered compound.

An "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts which retain the biological effectiveness and properties of the parent compound. Such salts include:

(i) acid addition salt which is obtained by reaction of the free base of the parent compound with inorganic acids such as hydrochloric acid, hydrobromic acid, nitric acid, phosphoric acid, sulfuric acid, and perhcloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid such as the L-malate salt of 5-(5-fluoro-2-oxo-1,2-dihydroindol-3-ylidenemethyl)-2,4-dimethyl-1H-pyrrole-3-carboxylic acid(2-diethylaminoethyl)amide; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"PK" refers to receptor protein tyrosine kinase (RTKs), non-receptor or "cellular" tyrosine kinase (CTKs) and serine-threonine kinases (STKs).

"Method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

"Modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

"Catalytic activity" refers to the rate of phosphorylation of tyrosine under the influence, direct or indirect, of RTKs and/or CTKs or the phosphorylation of serine and threonine under the influence, direct or indirect, of STKs.

"Contacting" refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium.

"In vivo" refers to procedures performed within a living organism such as, without limitation, a mouse, rat or rabbit.

"PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

"Organism" refers to any living entity comprised of at least one cell. A living organism can be as simple as, for example, a single eukariotic cell or as complex as a mammal, including a human being.

"Therapeutically effective amount" refers to that amount of the compound being administered which will relieve to some extent one or more of the symptoms of the disorder being treated. In reference to the treatment of cancer, a therapeutically effective amount refers to that amount which has the effect of:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and/or,
(4) relieving to some extent (or, preferably, eliminating) one or more symptoms associated with the cancer.

"Monitoring" means observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art.

The above-referenced effect is selected from a change or an absence of change in a cell phenotype, a change or absence of change in the catalytic activity of said protein kinase or a change or absence of change in the interaction of said protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

"Natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

Representative compounds of the present invention are shown in Table I below.

TABLE 1

| Example | Structure | Name |
| --- | --- | --- |
| 1 | 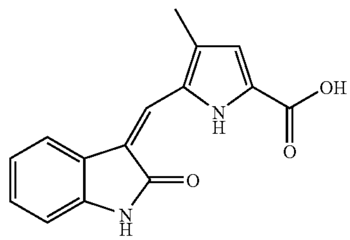 | 4-Methyl-5-(2-oxo-1,2-dihydroindol-3-ylidenemethyl)-1H-pyrrole-2-carboxylic acid |
| 2 | 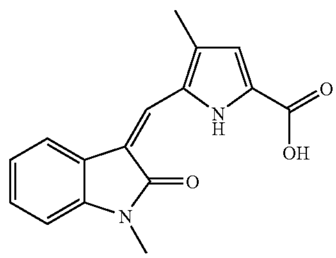 | 4-Methyl-5-(1-methyl-2-oxo-1,2-dihydroindol-3-ylidenemethyl)-1H-pyrrole-2-carboxylic acid |
| 3 | 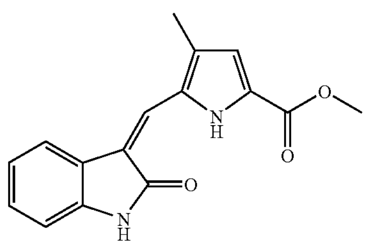 | 4-Methyl-5-(2-oxo-1,2-dihydroindol-3-ylidenemethyl)-1H-pyrrole-2-carboxylic acid methyl ester |
| 4 | 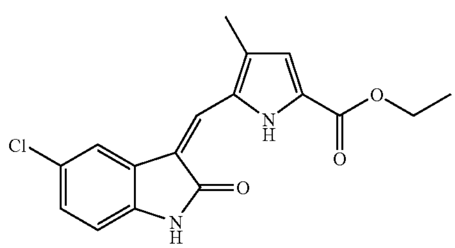 | 5-(5-Chloro-2-oxo-1,2-dihydroindol-3-ylidenemethyl)-4-methyl-1H-pyrrole-2-carboxylic acid ethyl ester |
| 5 | 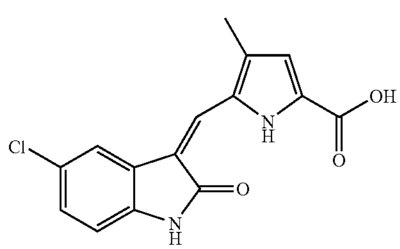 | 5-(5-Chloro-2-oxo-1,2-dihydroindol-3-ylidenemethyl)-4-methyl-1H-pyrrole-2-carboxylic acid |
| 6 | 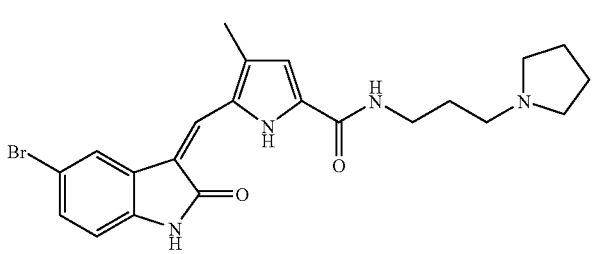 | 5-(5-Bromo-2-oxo-1,2-dihydroindol-3-ylidenemethyl)-4-methyl-1H-pyrrole-2-carboxylic acid (3-pyrrolidin-1-ylpropyl)amide |

TABLE 1-continued

| Example | Structure | Name |
|---|---|---|
| 7 | 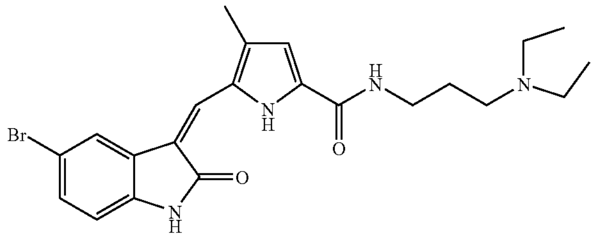 | 5-(5-Bromo-2-oxo-1,2-dihydroindol-3-ylidenemethyl)-4-methyl-1H-pyrrole-2-carboxylic acid (3-diethylaminopropyl)amide |
| 8 | 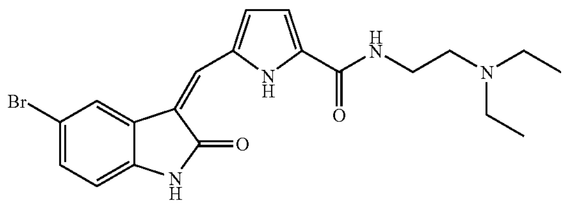 | 5-(5-Bromo-2-oxo-1,2-dihydroindol-3-ylidenemethyl)-1H-pyrrole-2-carboxylic acid (2-diethylaminoethyl)amide |
| 9 | 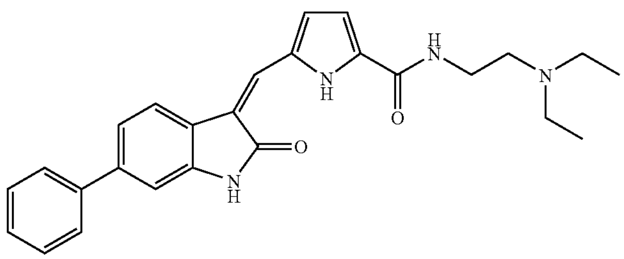 | 5-(2-Oxo-6-phenyl-1,2-dihydroindol-3-ylidenemethyl)-1H-pyrrole-2-carboxylic acid (2-diethylaminoethyl)amide |
| 10 | 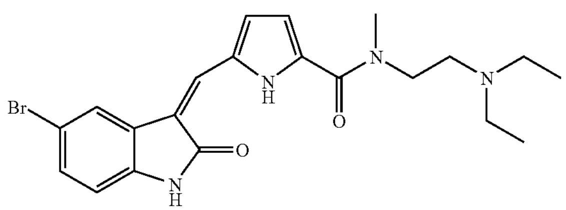 | 5-(5-Bromo-2-oxo-1,2-dihydrdindol-3-ylidenemethyl)-1H-pyrrole-2-carboxylic acid (2-diethylaminoethyl)methylamide |
| 11 | 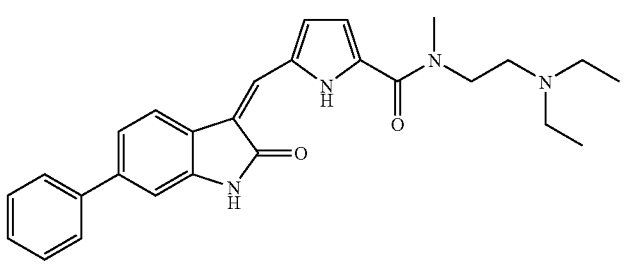 | 5-(2-Oxo-6-phenyl-1,2-dihydroindol-3-ylidenemethyl)-1H-pyrrole-2-carboxylic acid (3-diethylaminoethyl)methylamide |
| 12 | 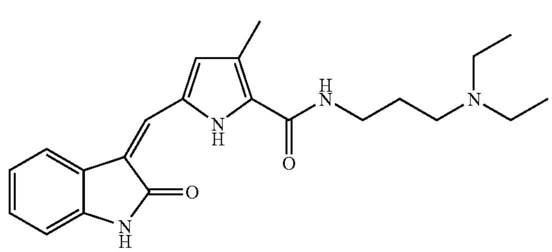 | 3-Methyl-5-(2-oxo-1,2-dihydroindol-3-ylidenemethyl)-1H-pyrrole-2-carboxylic acid (3-diethylaminopropyl)amide |

TABLE 1-continued

| Example | Structure | Name |
|---|---|---|
| 13 | 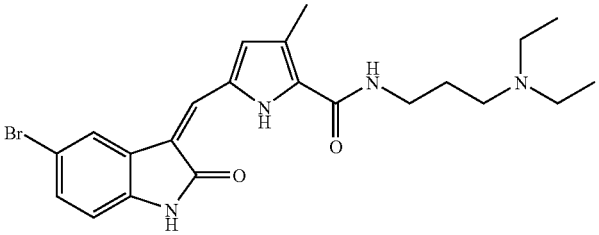 | 5-(5-Bromo-2-oxo-1,2-dihydroindol-3-ylidenemethyl)-3-methyl-1H-pyrrole-2-carboxylic acid (3-diethylaminopropyl)amide |
| 14 | 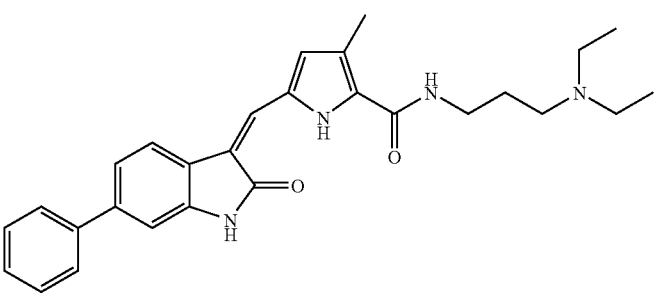 | 3-Methyl-5-(2-oxo-6-phenyl-1,2-dihydroindol-3-ylidenemethyl)-1H-pyrrole-2-carboxylic acid (3-diethylaminopropyl)amide |
| 15 | 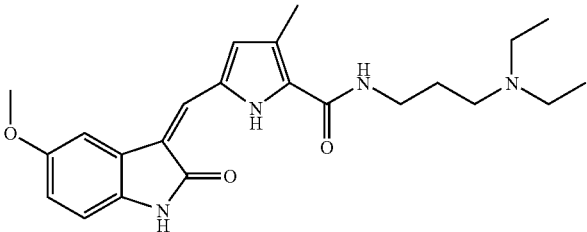 | 5-(5-Methoxy-2-oxo-1,2-dihydroindol-3-ylidenemethyl)-3-methyl-1H-pyrrole-2-carboxylic acid (3-diethylaminopropyl)amide |
| 16 | 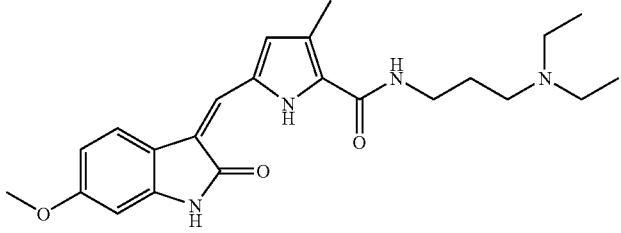 | 5-(6-Methoxy-2-oxo-1,2-dihydroindol-3-ylidenemethyl)-3-methyl-1H-pyrrole-2-carboxylic acid (3-diethylaminopropyl)amide |
| 17 | 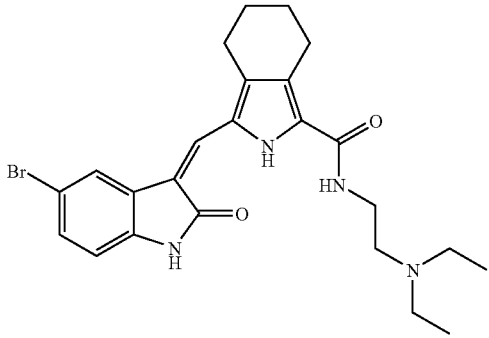 | 3-(5-Bromo-2-oxo-1,2-dihydroindol-3-ylidenemethyl)-4,5,6,7-tetrahydro-2H-isoindole-1-carboxylic acid (2-diethylaminoethyl)amide |

TABLE 1-continued

| Example | Structure | Name |
|---|---|---|
| 18 | 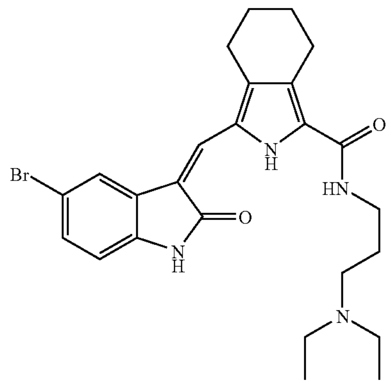 | 3-(5-Bromo-2-oxo-1,2-dihydroindol-3-ylidenemethyl)-4,5,6,7-tetrahydro-2H-isoindole-1-carboxylic acid (3-diethylaminopropyl)amide |
| 19 | 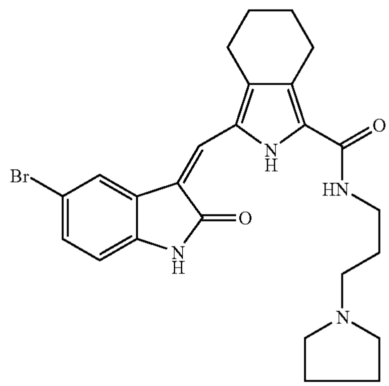 | 3-(5-Bromo-2-oxo-1,2-dihydroindol-3-ylidenemethyl)-4,5,6,7-tetrahydro-2H-isoindole-1-carboxylic acid (3-pyrrolidin-1-ylpropyl)amide |
| 20 | 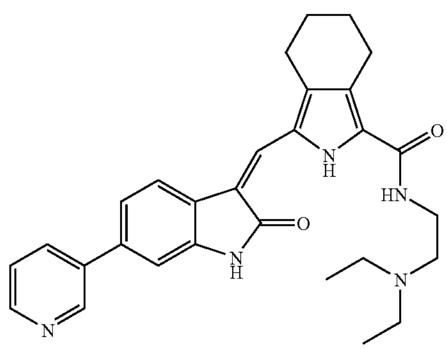 | 3-(2-Oxo-6-pyridin-3-yl-1,2-dihydroindol-3-ylidenemethyl)-4,5,6,7-tetrahydro-2H-isoindole-1-carboxylic acid (2-diethylaminoethyl)amide |
| 21 | 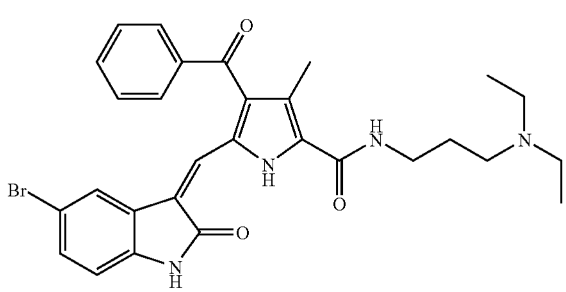 | 4-Benzoyl-5-(5-bromo-2-oxo-1,2-dihydroindol-3-ylidenemethyl)-3-methyl-1H-pyrrole-2-carboxylic acid (3-diethylaminopropyl)amide |

TABLE 1-continued

| Example | Structure | Name |
|---|---|---|
| 22 | 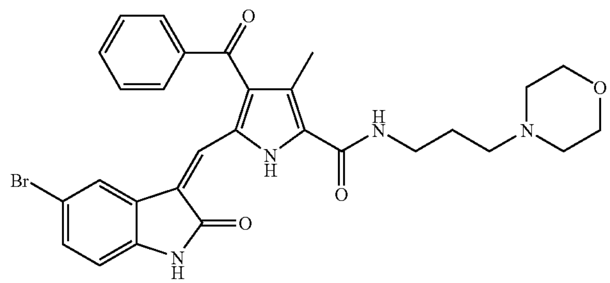 | 4-Benzoyl-5-(5-bromo-2-oxo-1,2-dihydroindol-3-ylidenemethyl)-3-methyl-1H-pyrrole-2-carboxylic acid (3-morpholin-4-ylpropyl)amide |
| 23 | 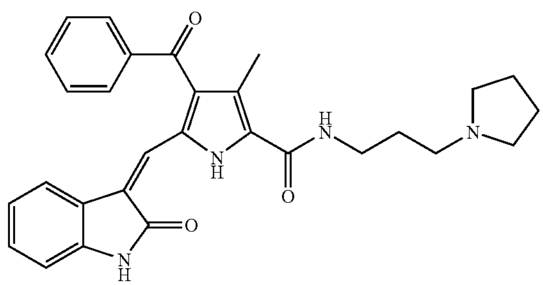 | 4-Benzoyl-3-methyl-5-(2-oxo-1,2-dihydroindol-3-ylidenemethyl)-1H-pyrrole-2-carboxylic acid (3-pyrrolidin-1-ylpropyl)amide |
| 24 | 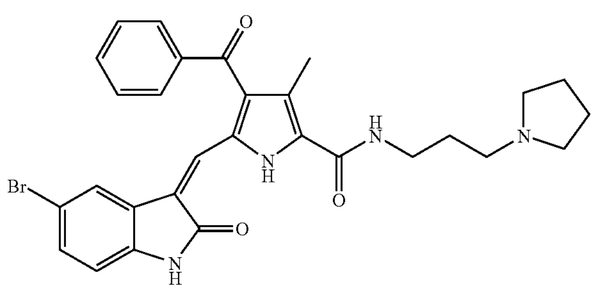 | 4-Benzoyl-5-(5-bromo-2-oxo-1,2-dihydroindol-3-ylidenemethyl)-3-methyl-1H-pyrrole-2-carboxylic acid (3-pyrrolidin-1-ylpropyl)amide |
| 25 | 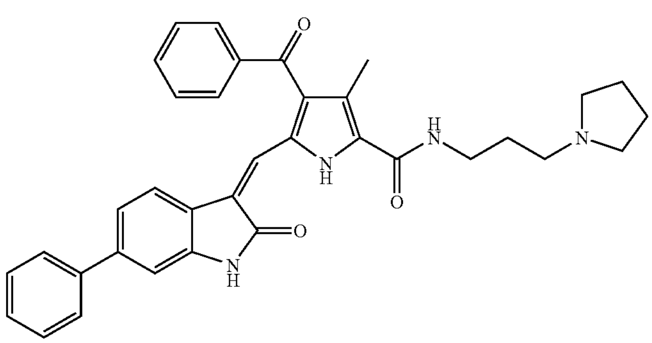 | 4-Benzoyl-3-methyl-5-(2-oxo-6-phenyl-1,2-dihydroindol-3-ylidenemethyl)-1H-pyrrole-2-carboxylic acid (3-pyrrolidin-1-ylpropyl)amide |
| 26 | 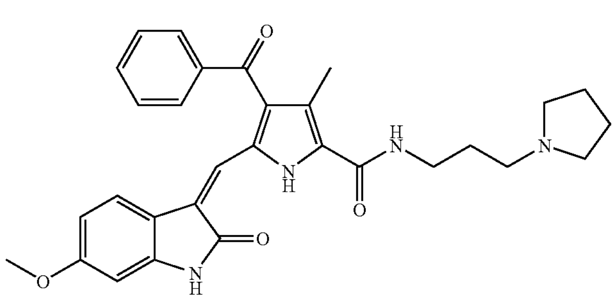 | 4-Benzoyl-5-(6-methoxy-2-oxo-1,2-dihydroindol-3-ylidenemethyl)-3-methyl-1H-pyrrole-2-carboxylic acid (3-pyrrolidin-1-ylpropyl)amide |

TABLE 1-continued

| Example | Structure | Name |
|---|---|---|
| 27 | 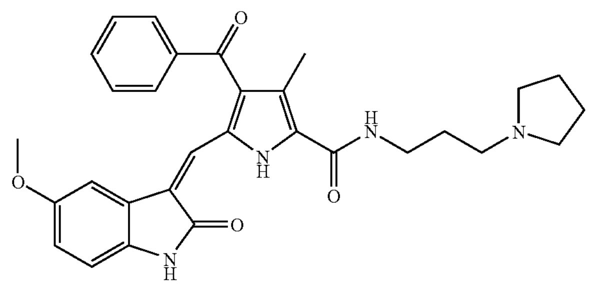 | 4-Benzoyl-5-(5-methoxy-2-oxo-1,2-dihydroindol-3-ylidenemethyl)-3-methyl-1H-pyrrole-2-carboxylic acid (3-pyrrolidin-1-ylpropyl)amide |
| 28 | 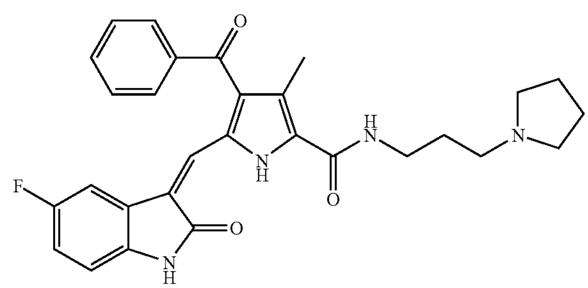 | 4-Benzoyl-5-(5-flouro-2-oxo-1,2-dihydroindol-3-ylidenemethyl)-3-methyl-1H-pyrrole-2-carboxylic acid (3-pyrrolidin-1-ylpropyl)amide |
| 29 | 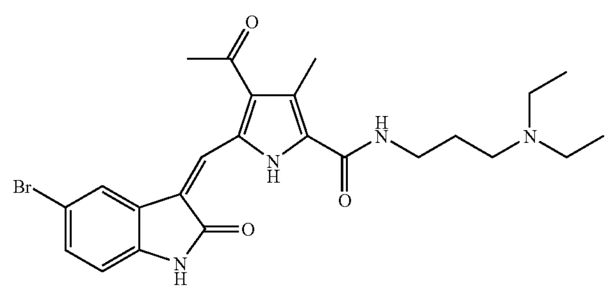 | 4-Acetyl-5-(5-bromo-2-oxo-1,2-dihydroindol-3-ylidenemethyl)-3-methyl-1H-pyrrole-2-carboxylic acid (3-diethylaminopropyl)amide |
| 30 | 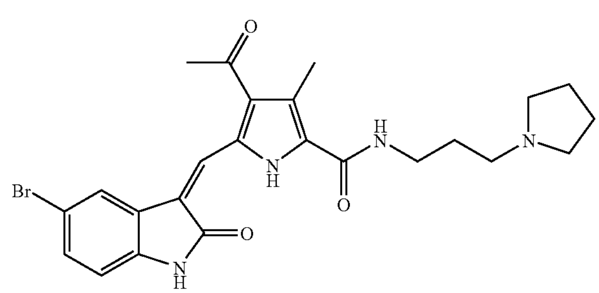 | 4-Acetyl-5-(5-bromo-2-oxo-1,2-dihydroindol-3-ylidenemethyl)-3-methyl-1H-pyrrole-2-carboxylic acid (3-pyrrolidin-1-ylpropyl)amide |
| 31 | 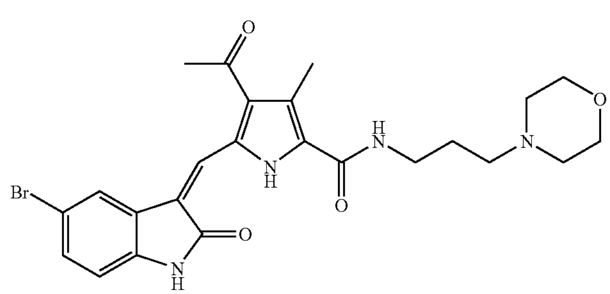 | 4-Acetyl-5-(5-bromo-2-oxo-1,2-dihydroindol-3-ylidenemethyl)-3-methyl-1H-pyrrole-2-carboxylic acid (3-morpholin-4-ylpropyl)amide |

TABLE 1-continued

| Example | Structure | Name |
|---|---|---|
| 32 | 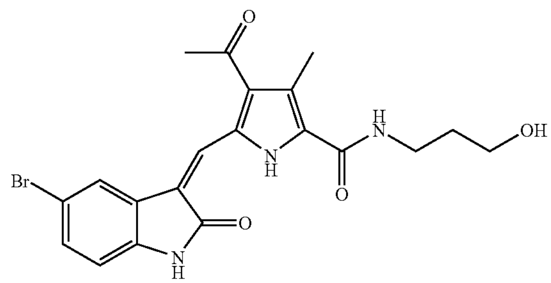 | 4-Acetyl-5-(5-bromo-2-oxo-1,2-dihydroindol-3-ylidenemethyl)-3-methyl-1H-pyrrole-2-carboxylic acid (3-hydroxy-propyl)amide |
| 33 | 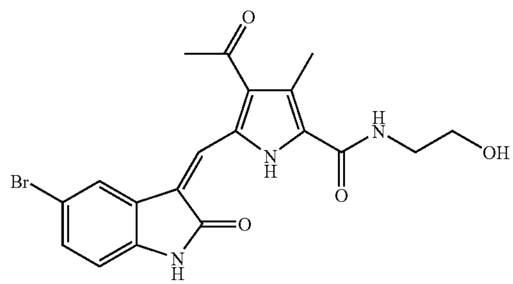 | 4-Acetyl-5-(5-bromo-2-oxo-1,2-dihydroindol-3-ylidenemethyl)-3-methyl-1H-pyrrole-2-carboxylic acid (2-hydroxy-ethyl)amide |
| 34 | 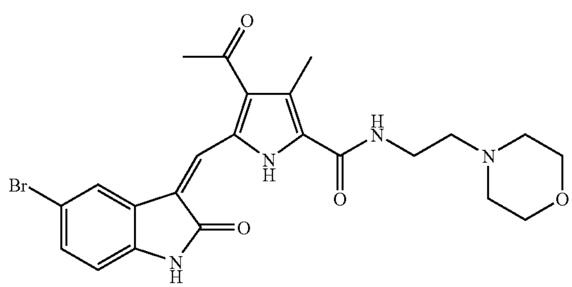 | 4-Acetyl-5-(5-bromo-2-oxo-1,2-dihydroindol-3-ylidenemethyl)-3-methyl-1H-pyrrole-2-carboxylic acid (2-morpholin-4-yl-ethyl)amide |
| 35 | 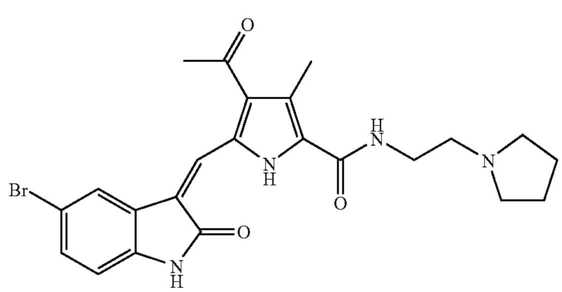 | 4-Acetyl-5-(5-bromo-2-oxo-1,2-dihydroindol-3-ylidenemethyl)-3-methyl-1H-pyrrole-2-carboxylic acid (2-pyrrolidin-1-yl-ethyl)amide |
| 36 | 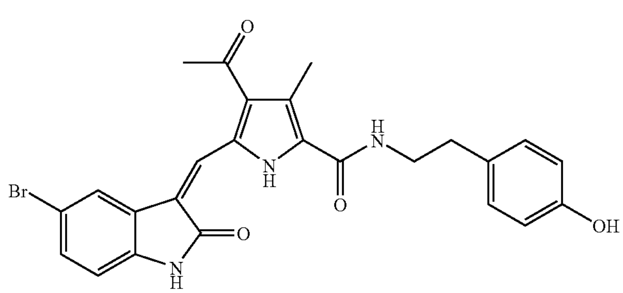 | 4-Acetyl-5-(5-bromo-2-oxo-1,2-dihydroindol-3-ylidenemethyl)-3-methyl-1H-pyrrole-2-carboxylic acid [2-(4-hydroxy-phenyl)-ethyl]amide |

TABLE 1-continued

| Example | Structure | Name |
|---|---|---|
| 37 | 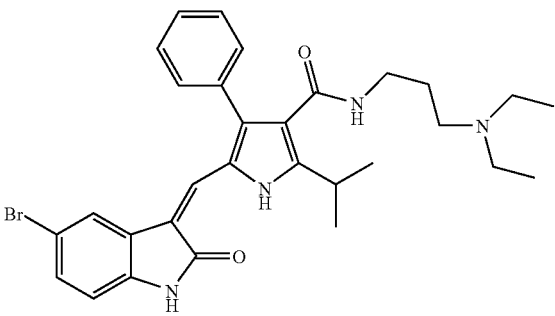 | 5-(5-Bromo-2-oxo-1,2-dihydroindol-3-ylidenemethyl)-2-isopropyl-4-phenyl-1H-pyrrole-3-carboxylic acid (3-diethylaminopropyl)amide |
| 38 | 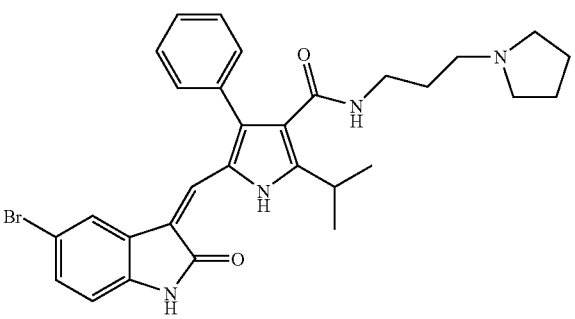 | 5-(5-Bromo-2-oxo-1,2-dihydroindol-3-ylidenemethyl)-2-isopropyl-4-phenyl-1H-pyrrole-3-carboxylic acid (3-pyrrolidin-1-ylpropyl)amide |
| 39 | 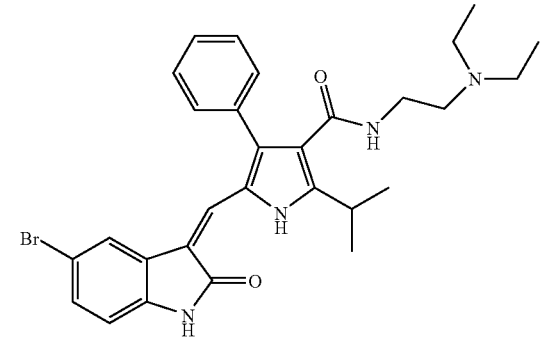 | 5-(5-Bromo-2-oxo-1,2-dihydroindol-3-ylidenemethyl)-2-isopropyl-4-phenyl-1H-pyrrole-3-carboxylic acid (2-diethylaminoethyl)amide |
| 40 | 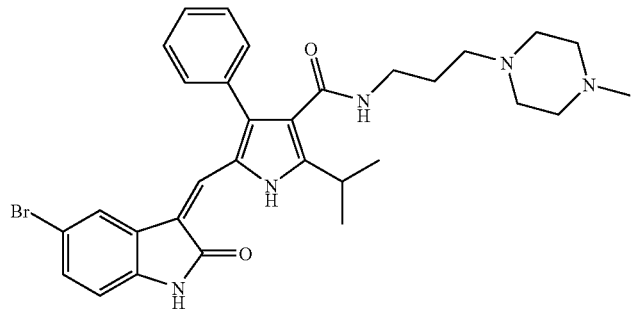 | 5-(5-Bromo-2-oxo-1,2-dihydroindol-3-ylidenemethyl)-2-isopropyl-4-phenyl-1H-pyrrole-3-carboxylic acid [3-(4-methyl-piperazin-1-yl)-propyl]amide |

TABLE 1-continued

| Example | Structure | Name |
|---|---|---|
| 41 | 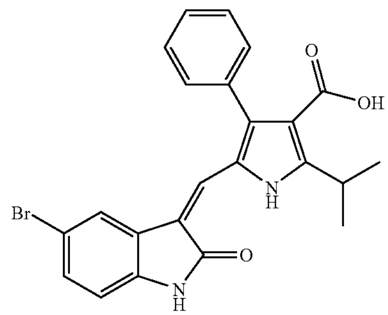 | 5-(5-Bromo-2-oxo-1,2-dihydroindol-3-ylidenemethyl)-2-isopropyl-4-phenyl-1H-pyrrole-3-carboxylic acid |
| 42 | 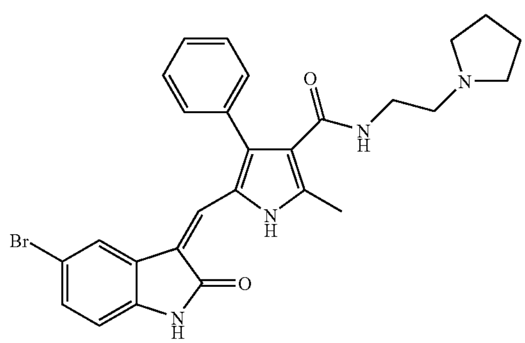 | 5-(5-Bromo-2-oxo-1,2-dihydroindol-3-ylidenemethyl)-2-methyl-4-phenyl-1H-pyrrole-3-carboxylic acid (2-pyrrolidin-1-yl-ethyl)amide |
| 43 | 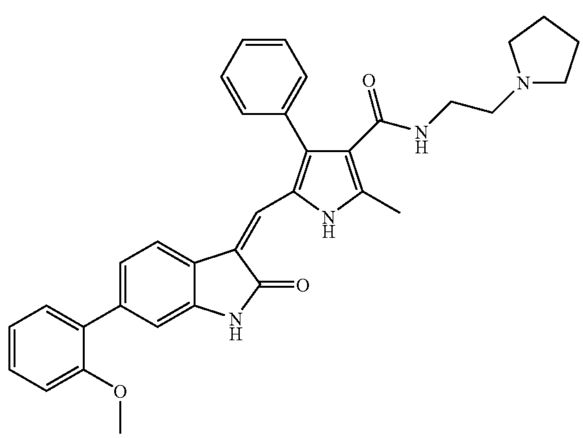 | 5-[6-(2-Methoxy-phenyl)-2-oxo-1,2-dihydroindol-3-ylidenemethyl]-2-methyl-4-phenyl-1H-pyrrole-3-carboxylic acid (2-pyrrolidin-1-yl-ethyl)amide |
| 44 | 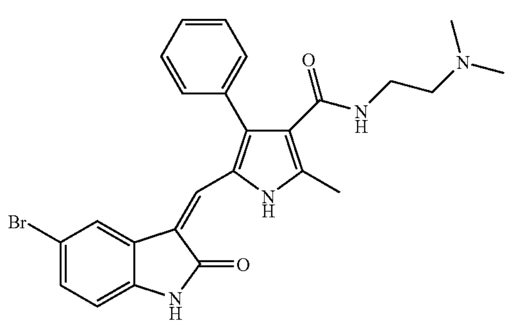 | 5-(5-Bromo-2-oxo-1,2-dihydroindol-3-ylidenemethyl)-2-methyl-4-phenyl-1H-pyrrole-3-carboxylic acid (2-diethylamino-ethyl)amide |

TABLE 1-continued

| Example | Structure | Name |
|---|---|---|
| 45 | 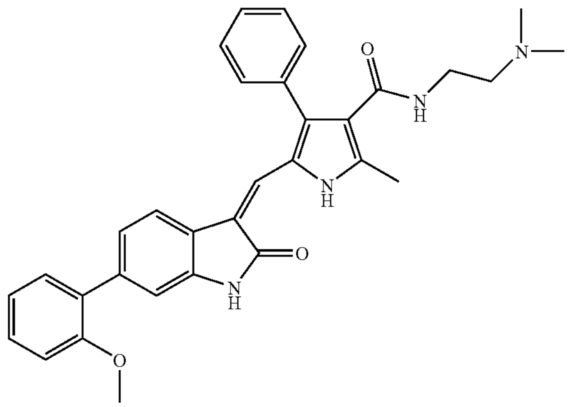 | 5-[6-(2-Methoxy-phenyl)-2-oxo-1,2-dihydroindol-3-ylidenemethyl]-2-methyl-4-phenyl-1H-pyrrole-3-carboxylic acid (2-dimethylamino-ethyl)amide |
| 46 | 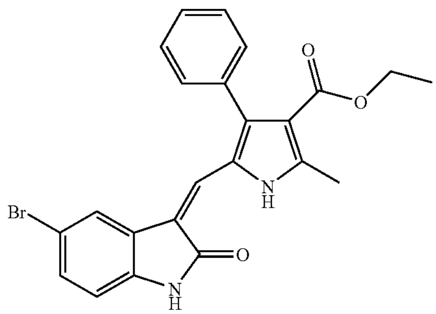 | 5-(5-Bromo-2-oxo-1,2-dihydroindol-3-ylidenemethyl)-2-methyl-4-phenyl-1H-pyrrole-3-carboxylic acid ethyl ester |
| 47 | 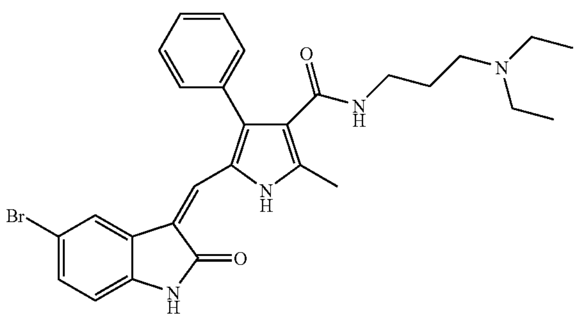 | 5-(5-Bromo-2-oxo-1,2-dihydroindol-3-ylidenemethyl)-2-methyl-4-phenyl-1H-pyrrole-3-carboxylic acid (3-diethylaminopropyl)amide |
| 48 | 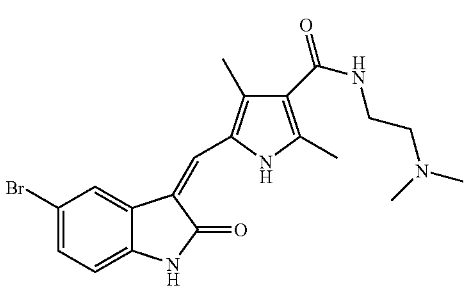 | 5-(5-Bromo-2-oxo-1,2-dihydroindol-3-ylidenemethyl)-2,4-dimethyl-1H-pyrrole-3-carboxylic acid (2-dimethylamino-ethyl)amide |

TABLE 1-continued

| Example | Structure | Name |
|---|---|---|
| 49 | 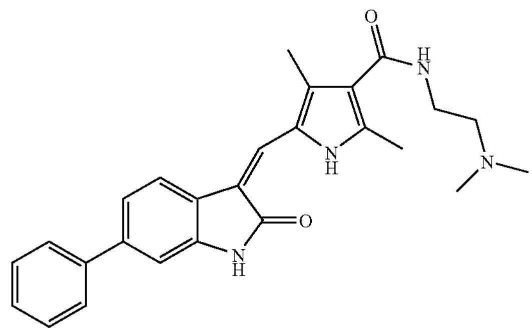 | 2,4-Dimethyl-5-(2-oxo-6-phenyl-1,2-dihydroindol-3-ylidenemethyl)-1H-pyrrole-3-carboxylic acid (2-dimethylamino-ethyl)amide |
| 50 | 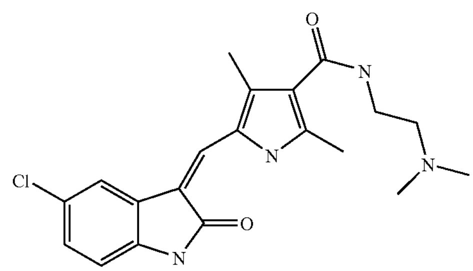 | 5-(5-Chloro-2-oxo-1,2-dihydroindol-3-ylidenemethyl)-2,4-dimethyl-1H-pyrrole-3-carboxylic acid (2-dimethylamino-ethyl)amide |
| 51 | 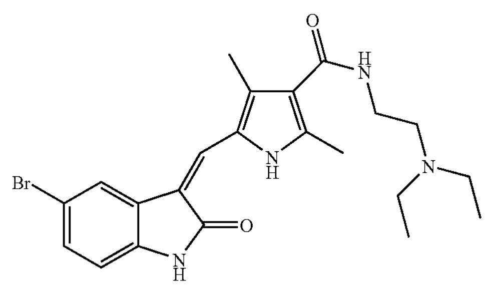 | 5-(5-Bromo-2-oxo-1,2-dihydroindol-3-ylidenemethyl)-2,4-dimethyl-1H-pyrrole-3-carboxylic acid (2-diethylaminoethyl)amide |
| 52 | 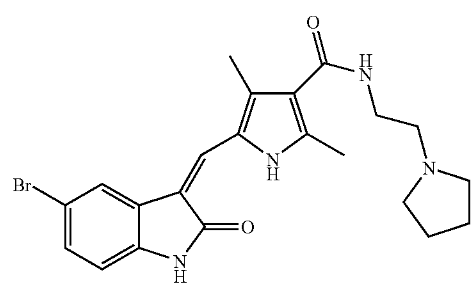 | 5-(5-Bromo-2-oxo-1,2-dihydroindol-3-ylidenemethyl)-2,4-dimethyl-1H-pyrrole-3-carboxylic acid (2-pyrrolidin-1-yl-ethyl)amide |
| 53 | 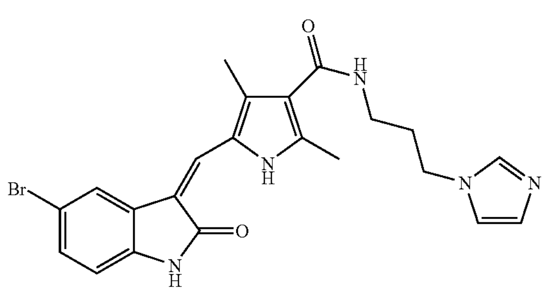 | 5-(5-Bromo-2-oxo-1,2-dihydroindol-3-ylidenemethyl)-2,4-dimethyl-1H-pyrrole-3-carboxylic acid (3-imidazol-1-ylpropyl)amide |

TABLE 1-continued

| Example | Structure | Name |
|---|---|---|
| 54 | 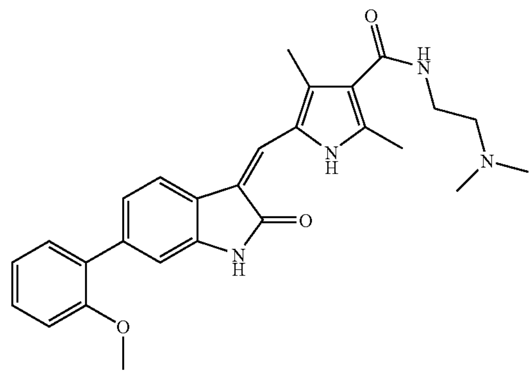 | 5-[6-(2-Methoxy-phenyl)-2-oxo-1,2-dihydroindol-3-ylidenemethyl]-2,4-dimethyl-1H-pyrrole-3-carboxylic acid (2-dimethylamino-ethyl)amide |
| 55 | 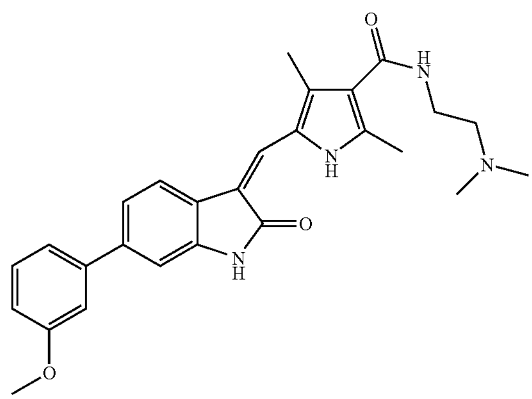 | 5-[6-(3-Methoxy-phenyl)-2-oxo-1,2-dihydroindol-3-ylidenemethyl]-2,4-dimethyl-1H-pyrrole-3-carboxylic acid (2-dimethylamino-ethyl)amide |
| 56 | 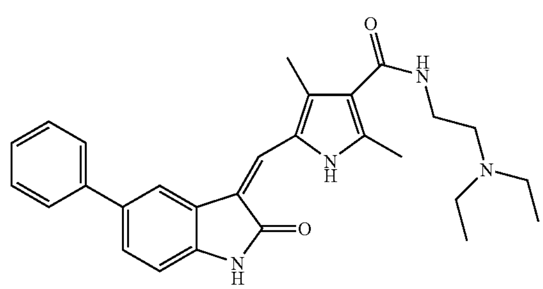 | 2,4-Dimethyl-5-(2-oxo-5-phenyl-1,2-dihydroindol-3-ylidenemethyl)-1H-pyrrole-3-carboxylic acid (2-diethylaminoethyl)amide |
| 57 | 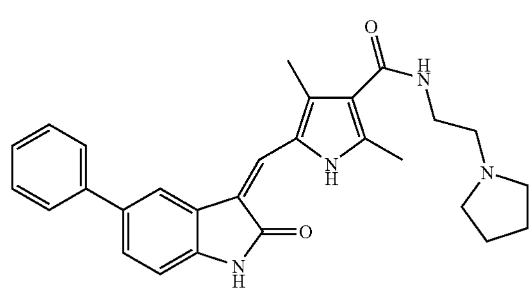 | 2,4-Dimethyl-5-(2-oxo-5-phenyl-1,2-dihydroindol-3-ylidenemethyl)-1H-pyrrole-3-carboxylic acid (2-pyrrolidin-1-yl-ethyl)amide |

TABLE 1-continued

| Example | Structure | Name |
|---|---|---|
| 58 | 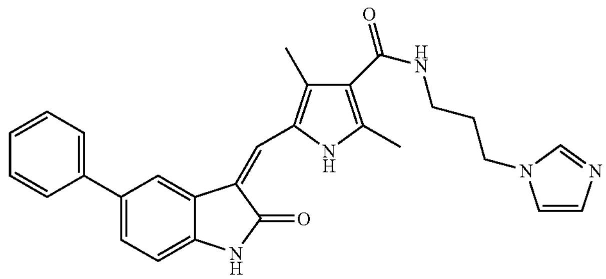 | 2,4-Dimethyl-5-(2-oxo-5-phenyl-1,2-dihydroindol-3-ylidenemethyl)-1H-pyrrole-3-carboxylic acid (3-imidazol-1-ylpropyl)amide |
| 59 | 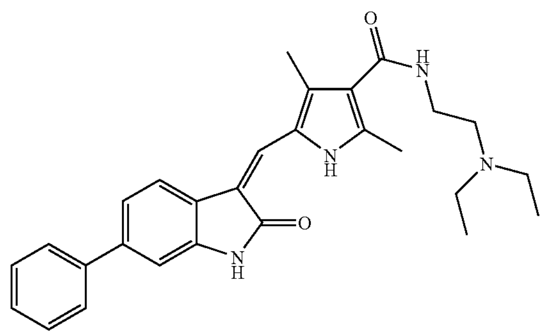 | 2,4-Dimethyl-5-(2-oxo-6-phenyl-1,2-dihydroindol-3-ylidenemethyl)-1H-pyrrole-3-carboxylic acid (2-diethylaminoethyl)amide |
| 60 | 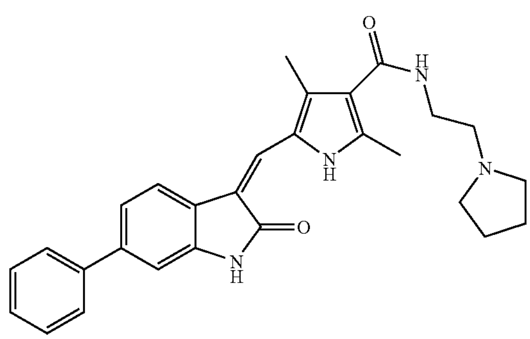 | 2,4-Dimethyl-5-(2-oxo-5-phenyl-1,2-dihydroindol-3-ylidenemethyl)-1H-pyrrole-3-carboxylic acid (2-pyrrolidin-1-yl-ethyl)amide |
| 61 | 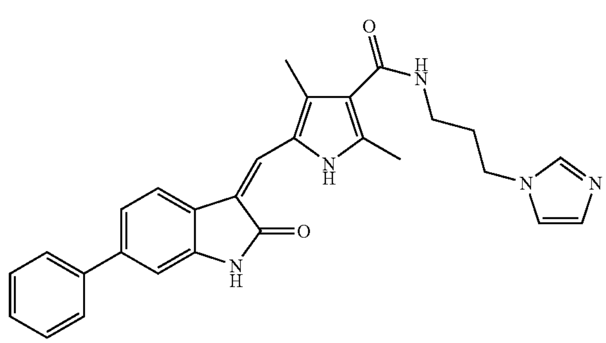 | 2,4-Dimethyl-5-(2-oxo-5-phenyl-1,2-dihydroindol-3-ylidenemethyl)-1H-pyrrole-3-carboxylic acid (3-imidazol-1-ylpropyl)amide |

TABLE 1-continued

| Example | Structure | Name |
|---|---|---|
| 62 | 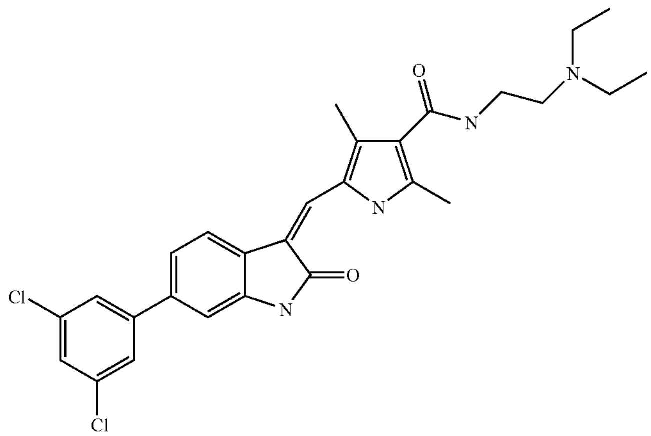 | 5-[6-(3,5-Dichloro-phenyl)-2-oxo-1,2-dihydroindol-3-ylidenemethyl]-2,4-dimethyl-1H-pyrrole-3-carboxylic acid (2-diethylaminoethyl)amide |
| 63 | 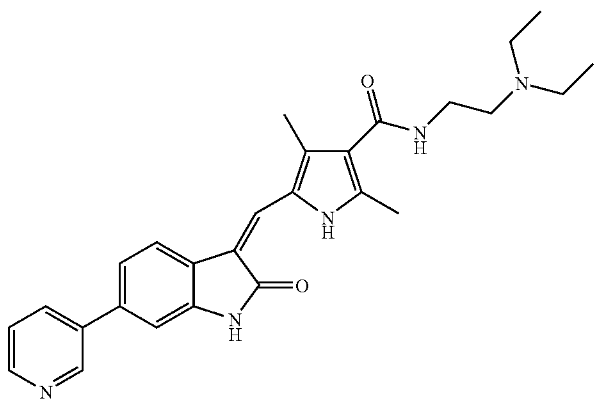 | 2,4-Dimethyl-5-(2-oxo-6-pyridin-3-yl-1,2-dihydroindol-3-ylidenemethyl)-1H-pyrrole-3-carboxylic acid (2-diethylaminoethyl)amide |
| 64 | 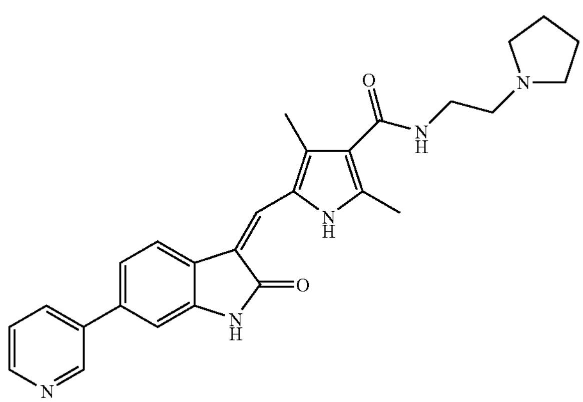 | 2,4-Dimethyl-5-(2-oxo-6-pyridin-3-yl-1,2-dihydroindol-3-ylidenemethyl)-1H-pyrrole-3-carboxylic acid (2-pyrrolidin-1-yl-ethyl)amide |
| 65 | 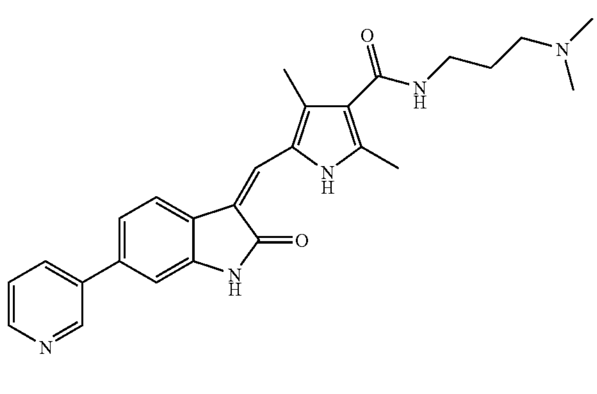 | 2,4-Dimethyl-5-(2-oxo-6-pyridin-3-yl-1,2-dihydroindol-3-ylidenemethyl)-1H-pyrrole-3-carboxylic acid (3-dimethylamino-propyl)amide |

TABLE 1-continued

| Example | Structure | Name |
|---|---|---|
| 66 | 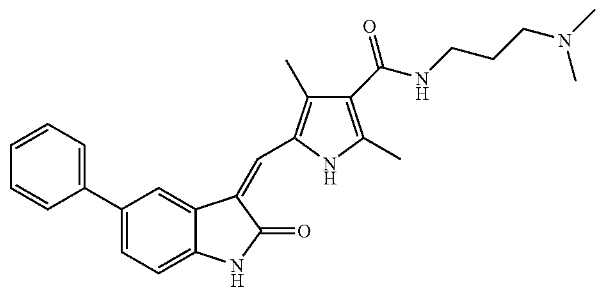 | 2,4-Dimethyl-5-(2-oxo-5-phenyl-1,2-dihydroindol-3-ylidenemethyl)-1H-pyrrole-3-carboxylic acid (3-dimethylamino-propyl)amide |
| 67 | 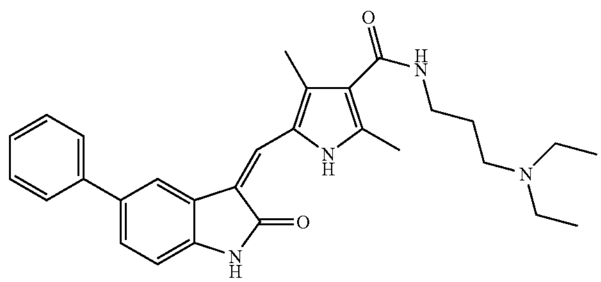 | 2,4-Dimethyl-5-(2-oxo-5-phenyl-1,2-dihydroindol-3-ylidenemethyl)-1H-pyrrole-3-carboxylic acid (3-diethylaminopropyl)amide |
| 68 | 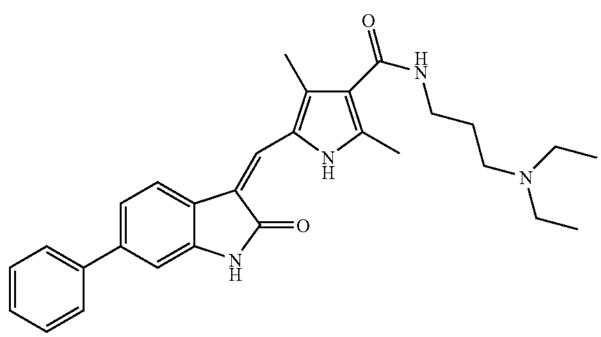 | 2,4-Dimethyl-5-(2-oxo-6-phenyl-1,2-dihydroindol-3-ylidenemethyl)-1H-pyrrole-3-carboxylic acid (3-diethylaminopropyl)amide |
| 69 | 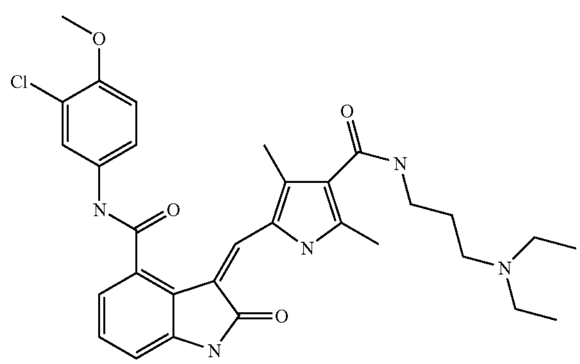 | 3-[4-(3-Diethylamino-propylcarbamoyl)-3,5-dimethyl-1H-pyrrol-2-ylmethylene]-2-oxo-2,3-dihydro-1H-indole-4-carboxylic acid (3-chloro-4-methoxy-phenyl)amide |
| 70 | 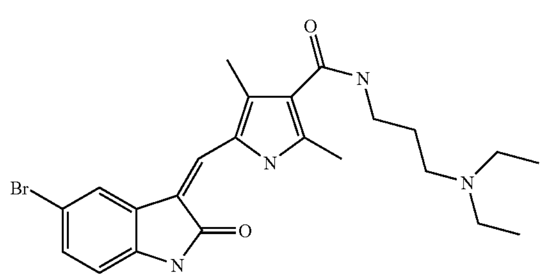 | 5-(5-Bromo-2-oxo-1,2-dihydroindol-3-ylidenemethyl)-2,4-dimethyl-1H-pyrrole-3-carboxylic acid (3-diethylaminopropyl)amide |

TABLE 1-continued

| Example | Structure | Name |
|---|---|---|
| 71 | 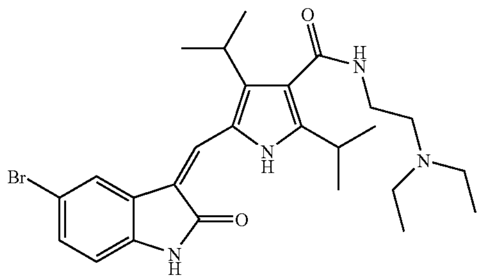 | 5-(5-Bromo-2-oxo-1,2-dihydroindol-3-ylidenemethyl)-2,4-diisoproyl-1H-pyrrole-3-carboxylic acid (3-diethylaminoethyl)amide |
| 72 | 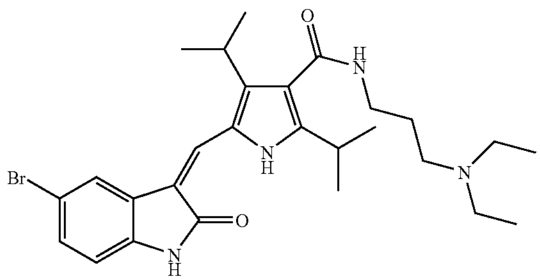 | 5-(5-Bromo-2-oxo-1,2-dihydroindol-3-ylidenemethyl)-2,4-diisoproyl-1H-pyrrole-3-carboxylic acid (3-diethylaminopropyl)amide |
| 73 | 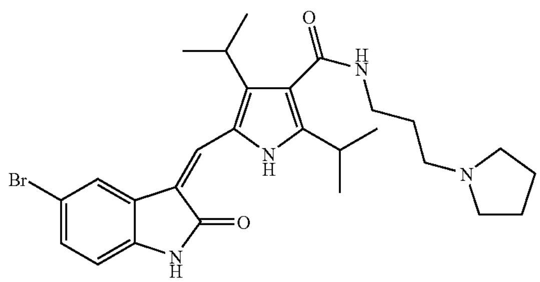 | 5-(5-Bromo-2-oxo-1,2-dihydroindol-3-ylidenemethyl)-2,4-diisoproyl-1H-pyrrole-3-carboxylic acid (3-pyrrolidin-1-ylpropyl)amide |
| 74 | 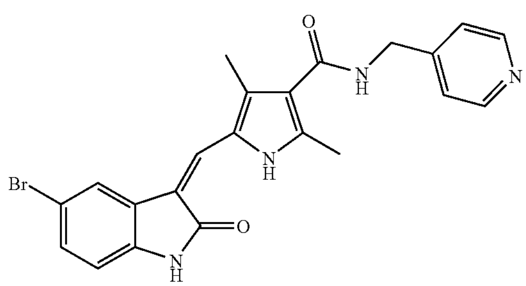 | 5-(5-Bromo-2-oxo-1,2-dihydroindol-3-ylidenemethyl)-2,4-dimethyl-1H-pyrrole-3-carboxylic acid (pyridin-4-ylmethyl)amide |
| 75 | 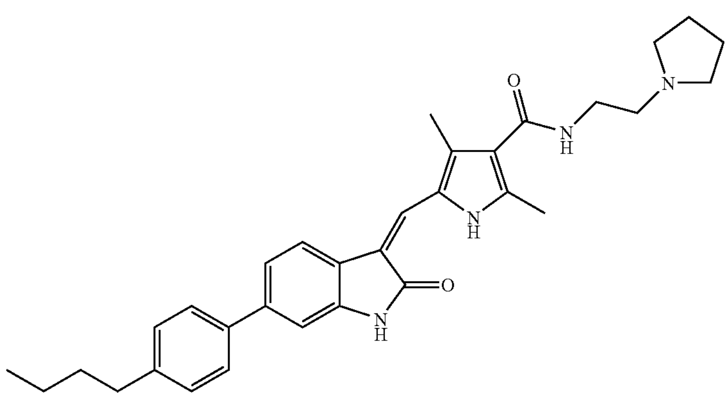 | 5-[6-(4-Butyl-phenyl)-2-oxo-1,2-dihydroindol-2-ylidenemethyl]-2,4-dimethyl-1H-pyrrole-3-carboxylic acid (2-pyrrolidin-1-yl-ethyl)amide |

TABLE 1-continued

| Example | Structure | Name |
|---|---|---|
| 76 | 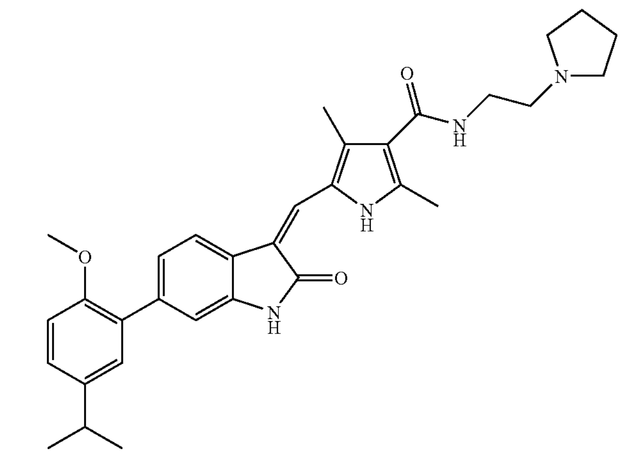 | 5-[6-(Isopropyl-2-methoxy-phenyl)-2-oxo-1,2-dihydroindol-3-ylidenemethyl]-2,4-dimethyl-1H-pyrrole-3-carboxylic acid (2-pyrrolidin-1-yl-ethyl)amide |
| 77 | 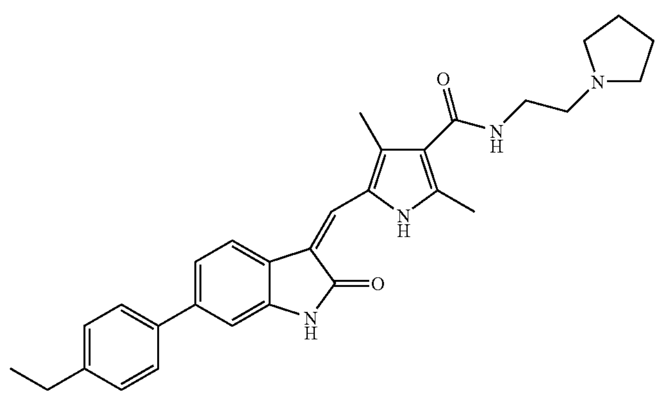 | 5-[6-(4-Ethyl-phenyl)-2-oxo-1,2-dihydroindol-3-ylidenemethyl]-2,4-dimethyl-1H-pyrrole-3-carboxylic acid (2-pyrrolidin-1-yl-ethyl)amide |
| 78 | 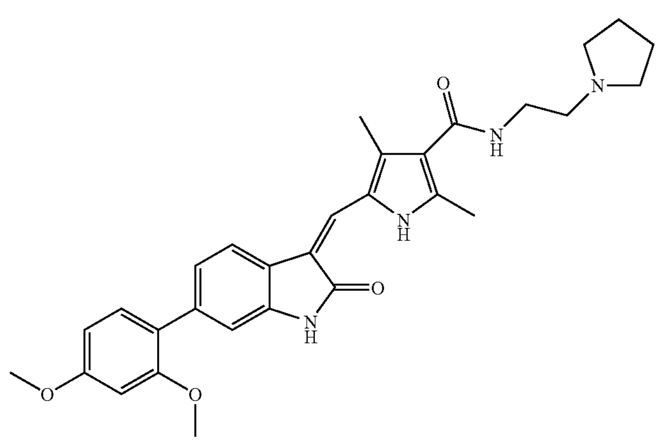 | 5-[6-(2,4-Dimethoxy-phenyl)-2-oxo-1,2-dihydroindol-3-ylidenemethyl]-2,4-dimethyl-1H-pyrrole-3-carboxylic acid (2-pyrrolidin-1-yl-ethyl)amide |

TABLE 1-continued

| Example | Structure | Name |
|---|---|---|
| 79 | 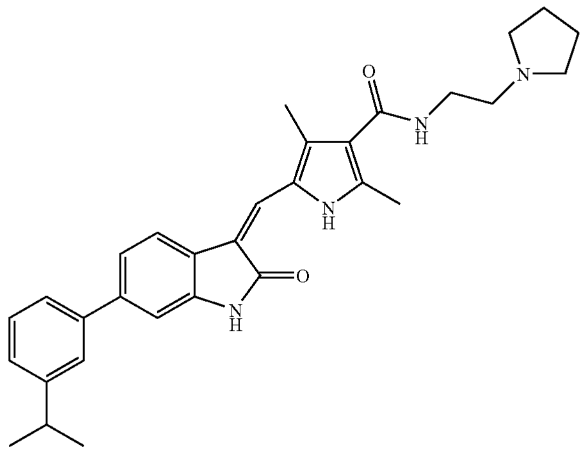 | 5-[6-(3-Isopropyl-phenyl)-2-oxo-1,2-dihydroindol-3-ylidenemethyl]-2,4-dimethyl-1H-pyrrole-3-carboxylic acid (2-pyrrolidin-1-yl-ethyl)amide |
| 80 | 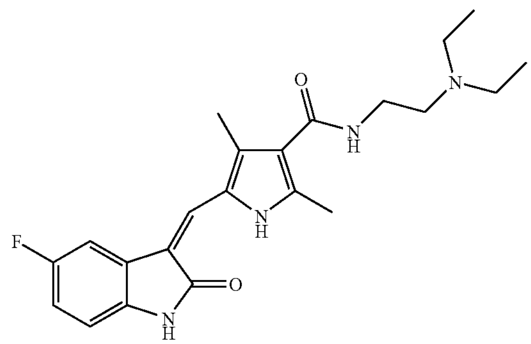 | 5-(5-Fluoro-2-oxo-1,2-dihydroindol-3-ylidenemethyl)-2,4-dimethyl-1H-pyrrole-3-carboxylic acid (2-diethylaminoethyl)amide |
| 81 | 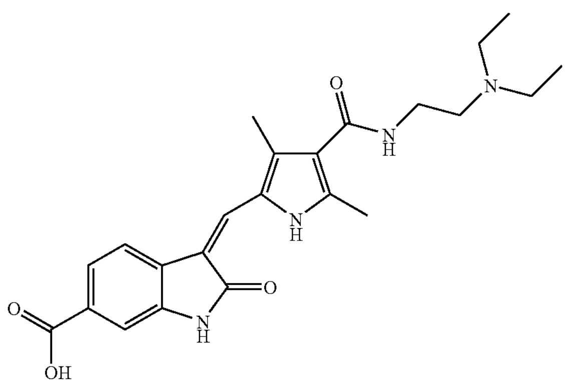 | 3-[4-(2-diethylaminoethylcarbamoyl)-3,5-dimethyl-1H-pyrrol-2-ylmethylene]-2-oxo-2,3-dihydro-1H-indole-6-carboxylic acid. |
| 82 | 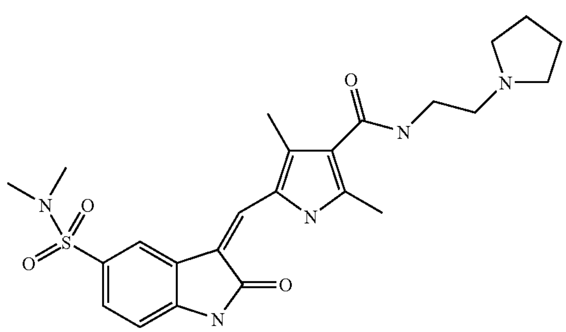 | 5-(5-Dimethylsulfamoyl-2-oxo-1,2-dihydroindol-3-ylidenemethyl)-2,4-dimethyl-1H-pyrrole-3-carboxylic acid (2-pyrrolidin-1-yl-ethyl)amide |

TABLE 1-continued

| Example | Structure | Name |
|---|---|---|
| 83 | 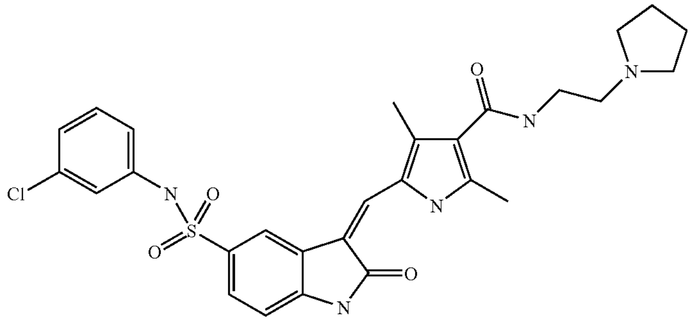 | 5-[5-(3-Chloro-phenylsulfamoyl)-2-oxo-1,2-dihydroindol-3-ylidenemethyl]-2,4-dimethyl-1H-pyrrole-3-carboxylic acid (2-pyrrolidin-1-yl-ethyl)amide |
| 84 | 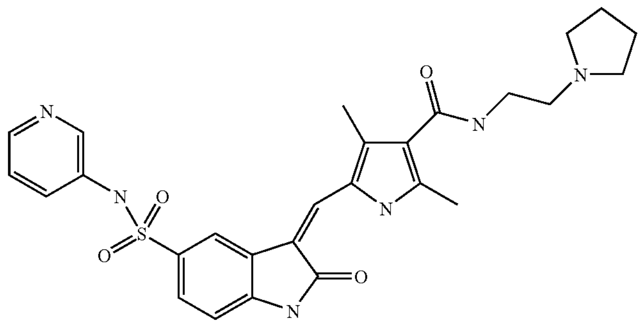 | 2,4-Dimethyl-5-[2-oxo-5-(pyridin-3-ylsulfamoyl)-1,2-dihydroindol-3-ylidenemethyl]-1H-pyrrole-3-carboxylic acid (2-pyrrolidin-1-yl-ethyl)amide |
| 85 | 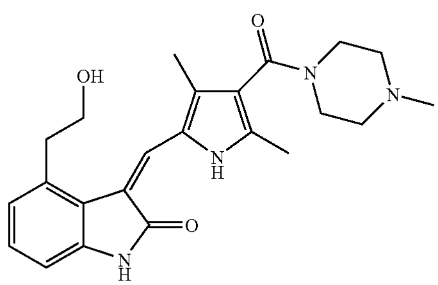 | 3-[3,5-Dimethyl-4-(4-methyl-piperazine-1-carbonyl)-1H-pyrrol-2-ylmethylene]-4-(2-hydroxy-ethyl)-1,3-dihydroindol-2-one |
| 86 | 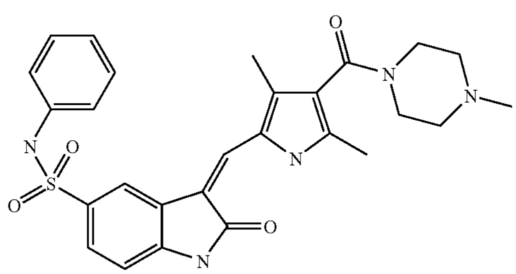 | 3-[3,5-Dimethyl-4-(4-methyl-piperazine-1-carbonyl)-1H-pyrrol-2-ylmethylene]-2-oxo-2,3-dihydro-1H-indole-5-sulfonic acid phenylamide |
| 87 | 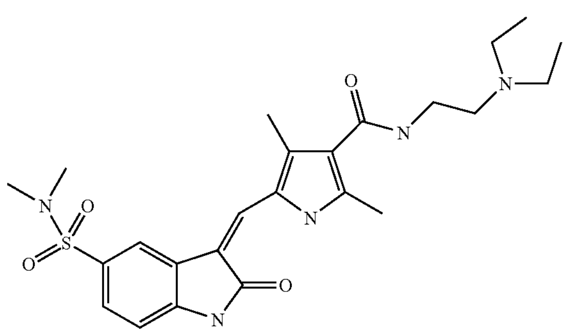 | 5-(5-Dimethylsulfamoyl-2-oxo-1,2-dihydroindol-3-ylidenemethyl)-2,4-dimethyl-1H-pyrrole-3-carboxylic acid (2-diethylaminoethyl)amide |

TABLE 1-continued

| Example | Structure | Name |
|---|---|---|
| 88 | 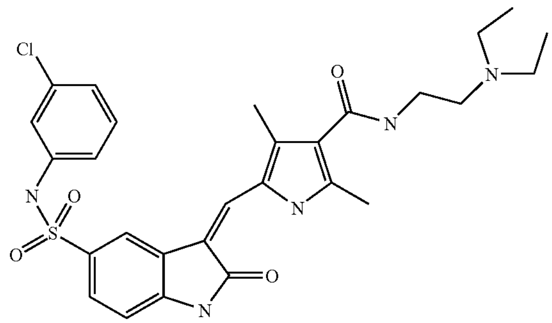 | 5-[5-(3-Chloro-phenylsulfamoyl)-2-oxo-1,2-dihydroindol-3-ylidenemethyl]-2,4-dimethyl-1H-pyrrole-3-carboxylic acid (2-diethylaminoethyl)amide |
| 89 | 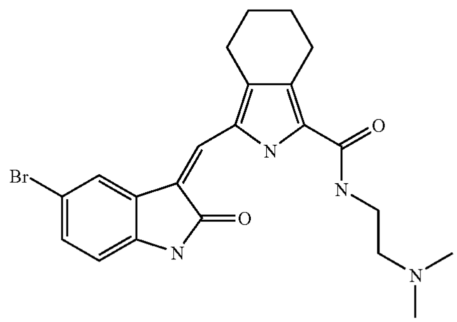 | 3-(5-Bromo-2-oxo-1,2-dihydro-indol-3-ylidenemethyl)-4,5,6,7-tetrahydro-2H-isoindole-1-carboxylic acid (2-dimethylamino-ethyl)-amide |
| 90 | 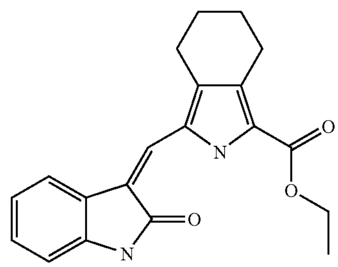 | 3-(2-Oxo-1,2-dihydro-indol-3-ylidenemethyl)-4,5,6,7-tetrahydro-2H-isoindole-1-carboxylic acid ethyl ester |
| 91 | 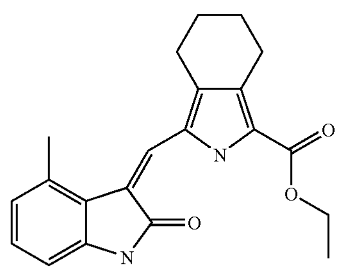 | 3-(4-Methyl-2-oxo-1,2-dihydro-indol-3-ylidenemethyl)-4,5,6,7-tetrahydro-2H-isoindole-1-carboxylic acid ethyl ester |
| 92 | 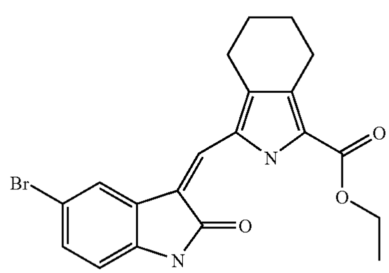 | 3-(5-Bromo-2-oxo-1,2-dihydro-indol-3-ylidenemethyl)-4,5,6,7-tetrahydro-2H-isoindole-1-carboxylic acid ethyl ester |

TABLE 1-continued

| Example | Structure | Name |
| --- | --- | --- |
| 93 | 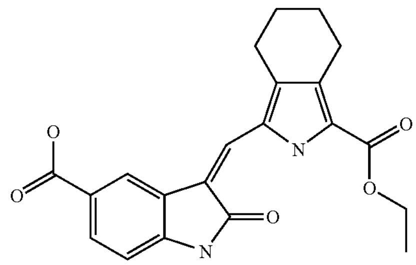 | 3-(3-Ethoxycarbonyl-4,5,6,7-tetrahydro-2H-isoindol-1-ylmethylene)-2-oxo-2,3-dihydro-1H-indole-5-carboxylic acid |
| 94 | 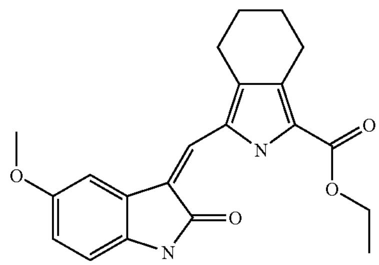 | 3-(5-Methoxy-2-oxo-1,2-dihydro-indol-3-ylidenemethyl)-4,5,6,7-tetrahydro-2H-isoindole-1-carboxylic acid ethyl ester |
| 95 | 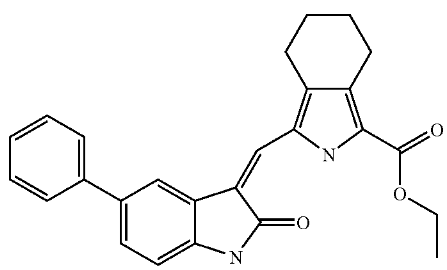 | 3-(2-Oxo-5-phenyl-1,2-dihydro-indol-3-ylidenemethyl)-4,5,6,7-tetrahydro-2H-isoindole-1-carboxylic acid ethyl ester |
| 96 | 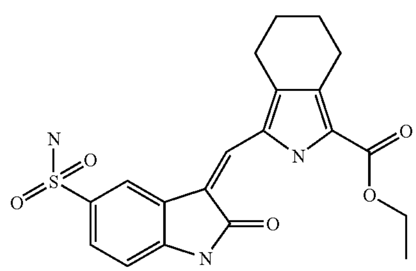 | 3-(2-Oxo-5-sulfamoyl-1,2-dihydro-indol-3-ylidenemethyl)-4,5,6,7-tetrahydro-2H-isoindole-1-carboxylic acid ethyl ester |
| 97 | 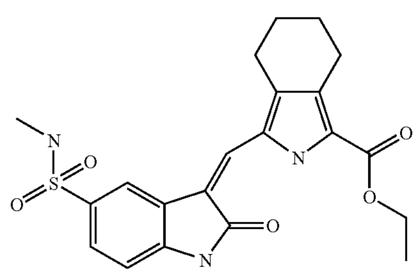 | 3-(5-Methylsulfamoyl-2-oxo-1,2-dihydro-indol-3-ylidenemethyl)-4,5,6,7-tetrahydro-2H-isoindole-1-carboxylic acid ethyl ester |

TABLE 1-continued

| Example | Structure | Name |
|---|---|---|
| 98 | 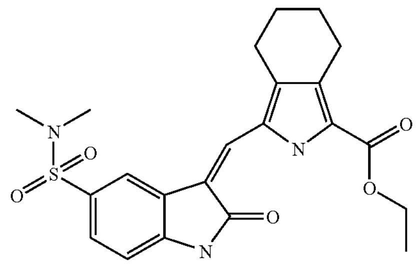 | 3-(5-Dimethylsulfamoyl-2-oxo-1,2-dihydro-indol-3-ylidenemethyl)-4,5,6,7-tetrahydro-2H-isoindole-1-carboxylic acid ethyl ester |
| 99 | 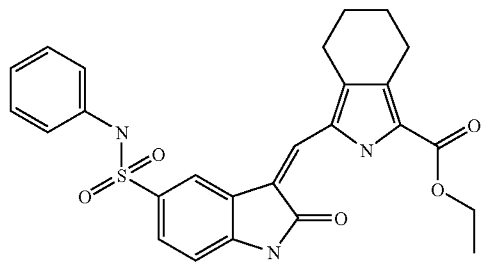 | 3-(2-Oxo-5-phenylsulfamoyl-1,2-dihydro-indol-3-ylidenemethyl)-4,5,6,7-tetrahydro-2H-isoindole-1-carboxylic acid ethyl ester |
| 100 | 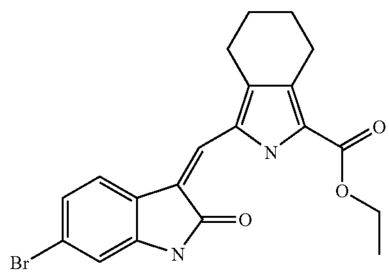 | 3-(6-Bromo-2-oxo-1,2-dihydro-indol-3-ylidenemethyl)-4,5,6,7-tetrahydro-2H-isoindole-1-carboxylic acid ethyl ester |
| 101 | 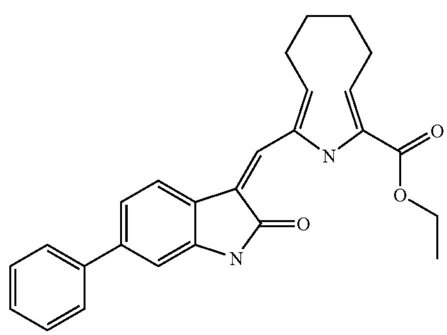 | 3-(2-Oxo-6-phenyl-1,2-dihydro-indol-3-ylidenemethyl)-4,5,6,7-tetrahydro-2H-isoindole-1-carboxylic acid ethyl ester |
| 102 | 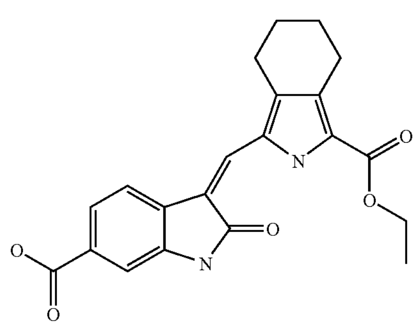 | 3-(3-Ethoxycarbonyl-4,5,6,7-tetrahydro-2H-isoindrol-1-ylmethylene)-2-oxo-2,3-dihydro-1H-indole-6-carboxylic acid |

TABLE 1-continued

| Example | Structure | Name |
|---|---|---|
| 103 | 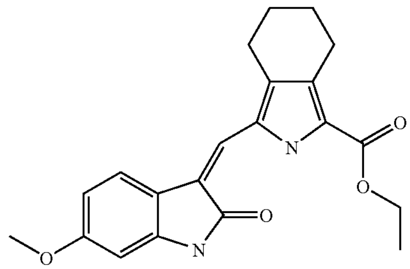 | 3-(6-Methoxy-2-oxo-1,2-dihydro-indol-3-ylidenemethyl)-4,5,6,7-tetrahydro-2H-isoindole-1-carboxylic acid ethyl ester |
| 104 | 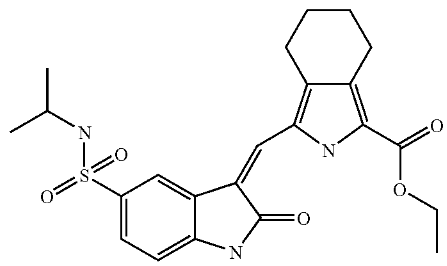 | 3-(5-Isopropylsulfamoyl-2-oxo-1,2-dihydro-indol-3-ylidenemethyl)-4,5,6,7-tetrahydro-2H-isoindole-1-carboxylic acid ethyl ester |
| 105 | 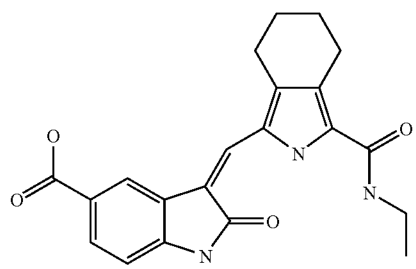 | 3-(3-Methylcarbamoyl-4,5,6,7-tetrahydro-2H-isoindol-1-ylmethylene)-2-oxo-2,3-dihydro-1H-indole-5-carboxylic acid |
| 106 | 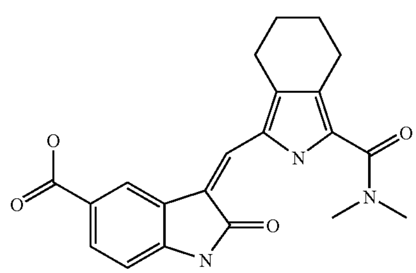 | 3-(3-Dimethylcarbamoyl-4,5,6,7-tetrahydro-2H-isoindol-1-ylmethylene)-2-oxo-2,3-dihydro-1H-indole-5-carboxylic acid |
| 107 | 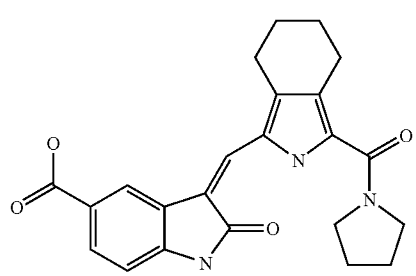 | 2-Oxo-3-[3-(pyrrolidine-1-carbonyl)-4,5,6,7-tetrahydro-2H-isoindol-1-ylmethylene]-2,3-dihydro-1H-indole-5-carboxylic acid |

TABLE 1-continued

| Example | Structure | Name |
|---|---|---|
| 108 | 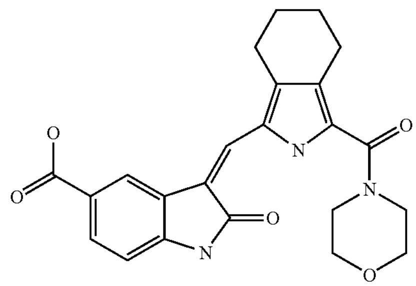 | 3-[3-(Morpholine-4-carbonyl)-4,5,6,7-tetrahydro-2H-isoindol-1-ylmethylene]-2-oxo-2,3-dihydro-1H-indole-5-carboxylic acid |
| 109 | 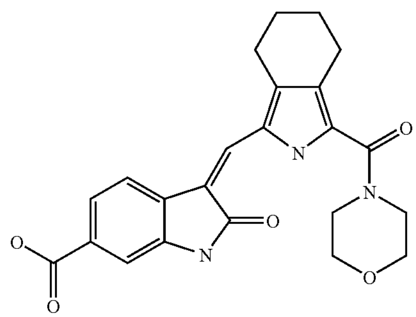 | 3-[3-(Morpholine-4-carbonyl)-4,5,6,7-tetrahydro-2H-isoindol-1-ylmethylene]-2-oxo-2,3-dihydro-1H-indole-6-carboxylic acid |
| 110 | 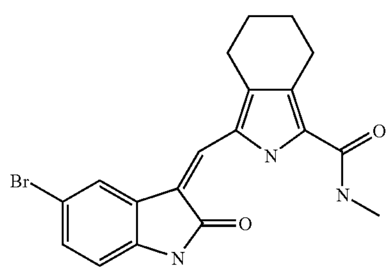 | 3-(5-Bromo-2-oxo-1,2-dihydro-indol-3-ylidenemethyl)-4,5,6,7-tetrahydro-2H-isoindole-1-carboxylic acid methylamide |
| 111 | 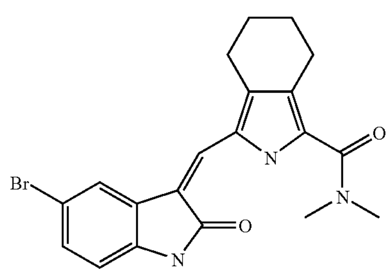 | 3-(5-Bromo-2-oxo-1,2-dihydro-indol-3-ylidenemethyl)-4,5,6,7-tetrahydro-2H-isoindole-1-carboxylic acid dimethylamide |
| 112 | 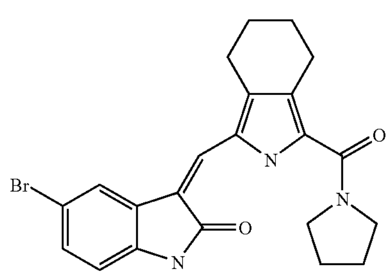 | 5-Bromo-3-[3-(pyrrolidine-1-carbonyl)-4,5,6,7-tetrahydro-2H-isoindol-1-ylmethylene]-1,3-dihydro-indol-2-one |

TABLE 1-continued

| Example | Structure | Name |
| --- | --- | --- |
| 113 | 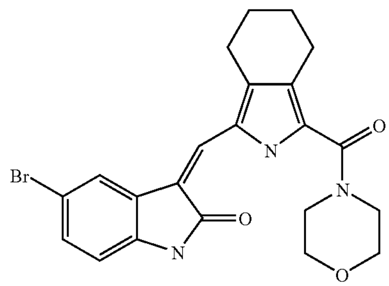 | 5-Bromo-3-[3-(morpholine-4-carbonyl)-4,5,6,7-tetrahydro-2H-isoindol-1-ylmethylene]-1,3-dihydro-indol-2-one |
| 114 | 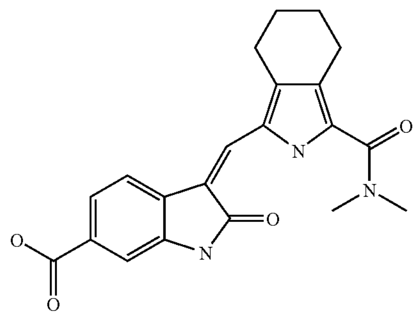 | 3-(3-Dimethylcarbamoyl-4,5,6,7-tetrahydro-2H-isoindol-1-ylmethylene)-2-oxo-2,3-dihydro-1H-indole-6-carboxylic acid |
| 115 | 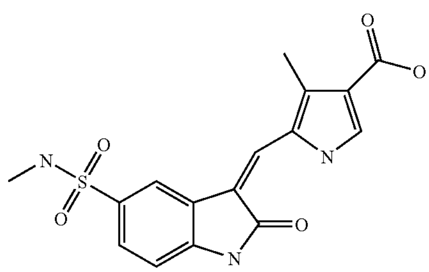 | 4-Methyl-5-(5-methylsulfamoyl-2-oxo-1,2-dihydro-indol-3-ylidenemethyl)-1H-pyrrole-3-carboxylic acid |
| 116 | 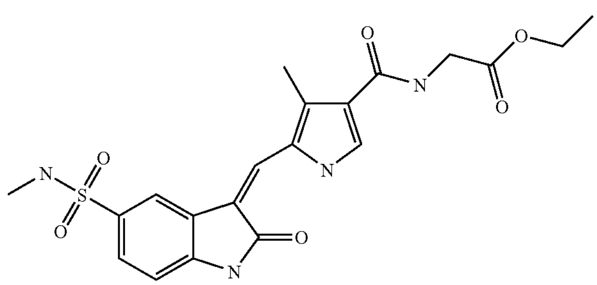 | {[4-Methyl-5-(4-methyl-5-methylsulfamoyl-2-oxo-1,2-dihydro-indol-3-ylidenemethyl)-1H-pyrrole-3-carbonyl]-amino}-acetic acid ethyl ester |
| 117 | 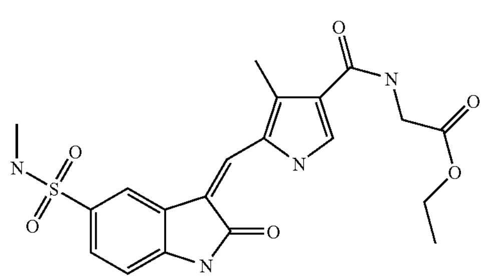 | {[4-Methyl-5-(5-methylsulfamoyl-2-oxo-1,2-dihydro-indol-3-ylidenemethyl)-1H-pyrrole-3-carbonyl]-amino}-acetic acid ethyl ester |

TABLE 1-continued

| Example | Structure | Name |
|---|---|---|
| 118 | 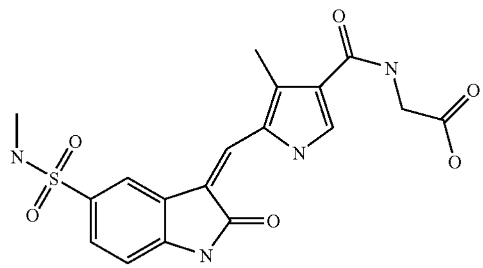 | {[4-Methyl-5-(5-methylsulfamoyl-2-oxo-1,2-dihydro-indol-3-ylidenemethyl)-1H-pyrrole-3-carbonyl]-amino}-acetic acid |
| 119 | 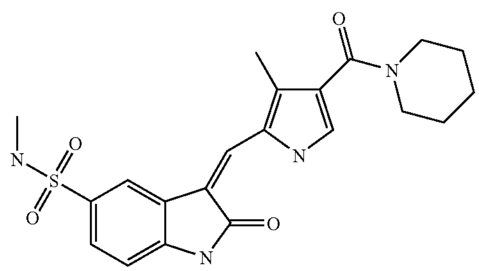 | 3-[3-Methyl-4-(piperidine-1-carbonyl)-1H-pyrrol-2-ylmethylene]-2-oxo-2,3-dihydro-1H-indole-5-sulfonic acid methylamide |
| 120 | 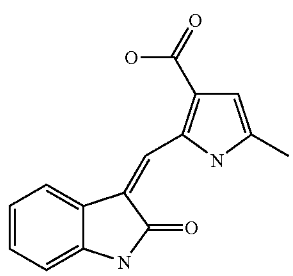 | 5-Methyl-2-(2-oxo-1,2-dihydro-indol-3-ylidenemethyl)-1H-pyrrole-3-carboxylic acid |
| 121 | 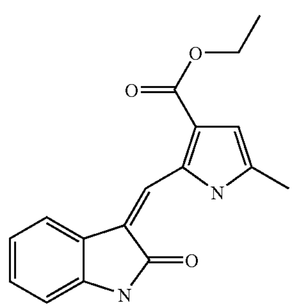 | 5-Methyl-2-(2-oxo-1,2-dihydro-indol-3-ylidenemethyl)-1H-pyrrole-3-carboxylic acid ethyl ester |
| 122 | 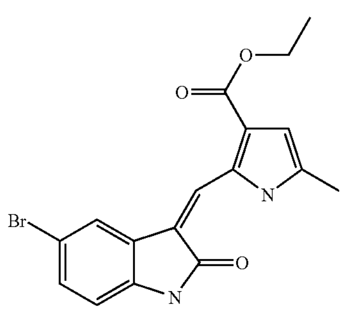 | 2-(5-Bromo-2-oxo-1,2-dihydro-indol-3-ylidenemethyl)-5-methyl-1H-pyrrole-3-carboxylic acid ethyl ester |

TABLE 1-continued

| Example | Structure | Name | |
|---|---|---|---|
| 123 | 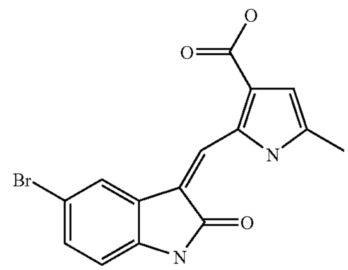 | 2-(5-Bromo-2-oxo-1,2-dihydro-indol-3-ylidenemethyl)-5-methyl-1H-pyrrole-3-carboxylic acid | |
| 124 | 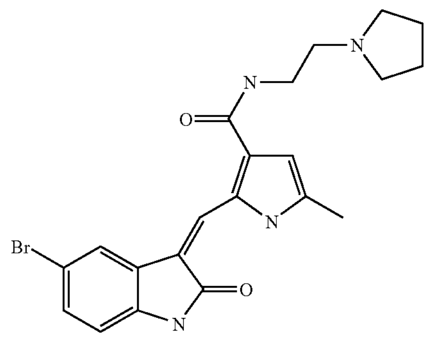 | 2-(5-Bromo-2-oxo-1,2-dihydro-indol-3-ylidenemethyl)-5-methyl-1H-pyrrole-3-carboxylic acid (2-pyrrolidin-1-yl-ethyl)-amide | |
| 125 | 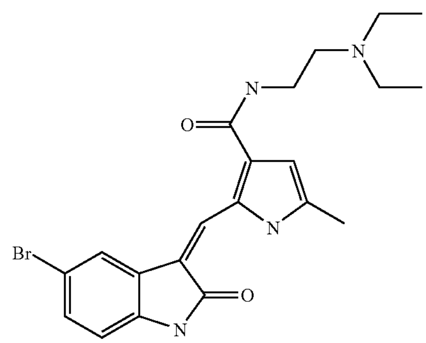 | 2-(5-Bromo-2-oxo-1,2-dihydro-indol-3-ylidenemethyl)-5-methyl-1H-pyrrole-3-carboxylic acid (2-diethylamino-ethyl)-amide | |
| 133 | 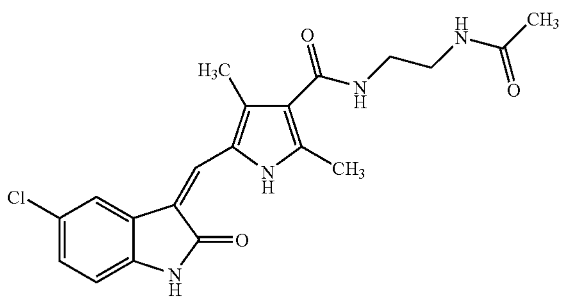 | 5-[5-Chloro-2-oxo-1,2-dihydro-indol-(3Z)-ylidenemethyl]-2,4-dimethyl-1H-pyrrole-3-carboxylic acid (2-acetylamino-ethyl)-amide | 399 [M − 1] |
| 134 | 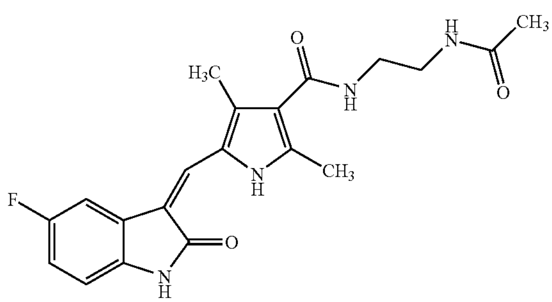 | 5-[5-Fluoro-2-oxo-1,2-dihydro-indol-(3Z)-ylidenemethyl]-2,4-dimethyl-1H-pyrrole-3-carboxylic acid (2-acetylamino-ethyl)-amide | 383 [M − 1] |

TABLE 1-continued

| Example | Structure | Name | |
|---|---|---|---|
| 135 | 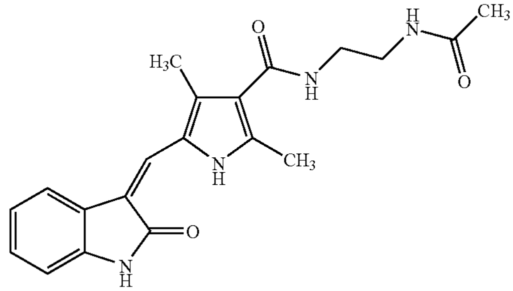 | 2,4-Dimethyl-5-[2-oxo-1,2-dihydro-indol-(3Z)-ylidenemethyl]-1H-pyrrole-3-carboxylic acid (2-acetylamino-ethyl)-amide | 365 [M − 1] |
| 136 | 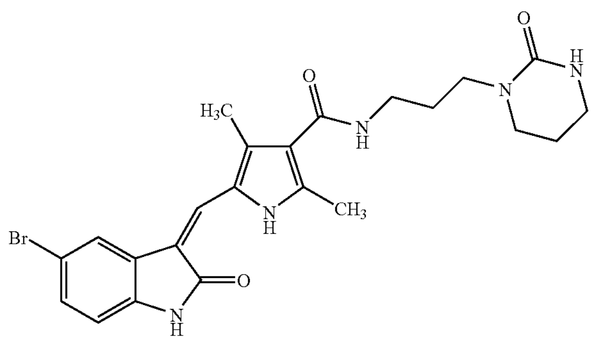 | 5-[5-Bromo-2-oxo-1,2-dihydro-indol-(3Z)-ylidenemethyl]-2,4-dimethyl-1H-pyrrole-3-carboxylic acid [3-(2-oxo-tetrahydro-pyrimidin-1-yl)-propyl]-amide | 500 [M + 1]<br>502 [M + 1] |
| 137 | 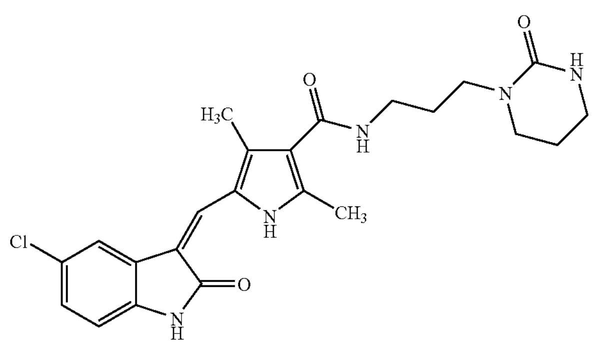 | 5-[5-Chloro-2-oxo-1,2-dihydro-indol-(3Z)-ylidenemethyl]-2,4-dimethyl-1H-pyrrole-3-carboxylic acid [3-(2-oxo-tetrahydro-pyrimidin-1-yl)-propyl]-amide | 454 [M − 1] |
| 138 | 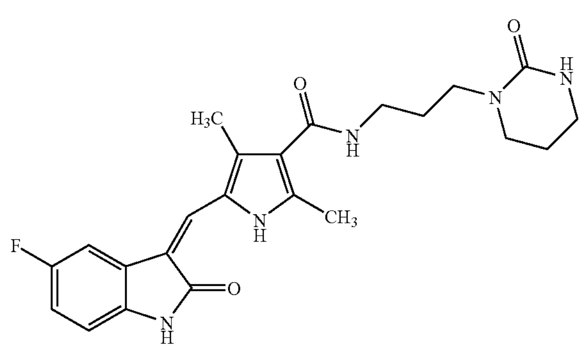 | 5-[5-Fluoro-2-oxo-1,2-dihydro-indol-(3Z)-ylidenemethyl]-2,4-dimethyl-1H-pyrrole-3-carboxylic acid [3-(2-oxo-tetrahydro-pyrimidin-1-yl)-propyl]-amide | 438 [M − 1] |

TABLE 1-continued

| Example | Structure | Name | |
|---|---|---|---|
| 139 | 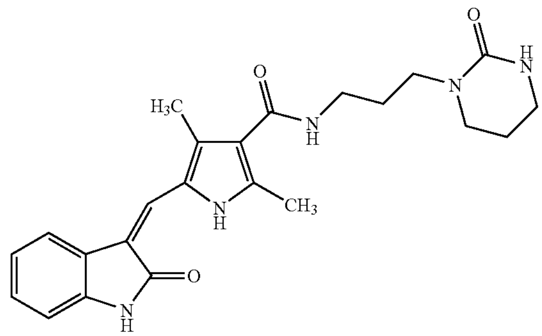 | 2,4-Dimethyl-5-[2-oxo-1,2-dihydro-indol-(3Z)-ylidenemethyl]-1H-pyrrole-3-carboxylic acid [3-(2-oxo-tetrahydro-pyrimidin-1-yl)-propyl]-amide | 422 [M + 1] |
| 140 | 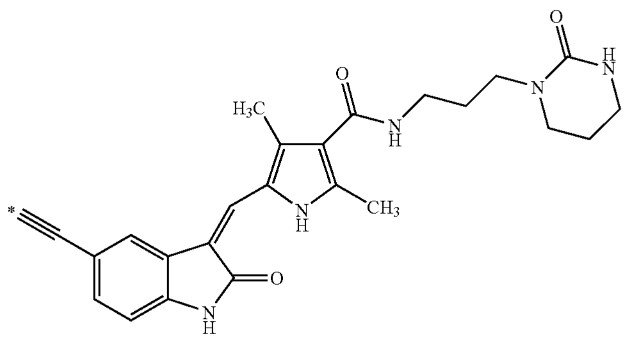 | 5-[5-Cyano-2-oxo-1,2-dihydro-indol-(3Z)-ylidenemethyl]-2,4-dimethyl-1H-pyrrole-3-carboxylic acid [3-(2-oxo-tetrahydro-pyrimidin-1-yl)-propyl]-amide | 447 [M + 1] |
| 141 | 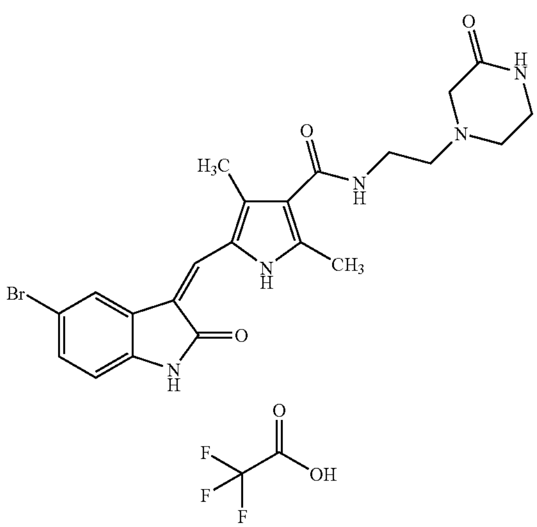 | Trifluoro-acetate5-[2-({5-[5-bromo-2-oxo-1,2-dihydro-indol-(3Z)-ylidenemethyl]-2,4-dimethyl-1H-pyrrole-3-carbonyl}-amino)-ethyl]-2-oxo-piperazin-1-ium; | 486 [M + 1] 488 [M + 1] |
| 126 | 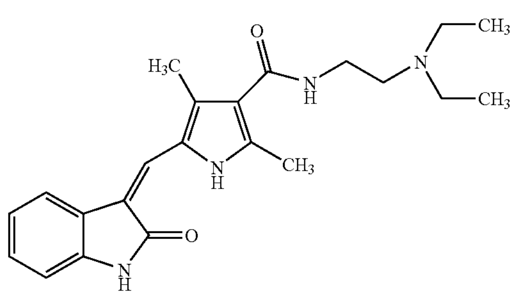 | 2,4-Dimethyl-5-[2-oxo-1,2-dihydro-indol-(3Z)-ylidenemethyl]-1H-pyrrole-3-carboxylic acid (2-diethylaminoethyl)-amide | 381 [M + 1] |

TABLE 1-continued

| Example | Structure | Name | |
|---|---|---|---|
| 127 | 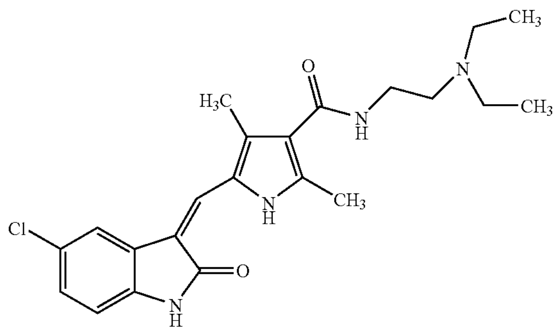 | 5-[5-Chloro-2-oxo-1,2-dihydro-indol-(3Z)-ylidenemethyl]-2,4-dimethyl-1H-pyrrole-3-carboxylic acid (2-diethylaminoethyl)-amide | 415 [M + 1] |
| 128 | 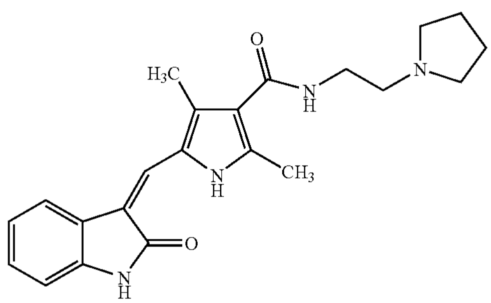 | 2,4-Dimethyl-5-[2-oxo-1,2-dihydro-indol-(3Z)-ylidenemethyl]-2,4-dimethyl-1H-pyrrole-3-carboxylic acid (2-pyrrolidin-1-ylethyl)-amide | 379 [M + 1] |
| 129 | 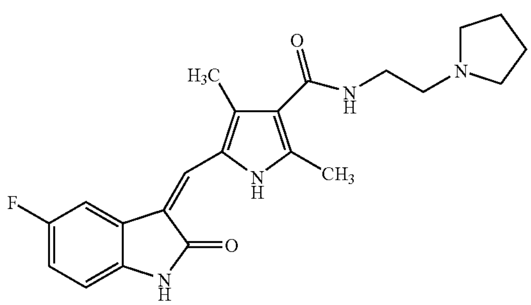 | 5-[5-Fluoro-2-oxo-1,2-dihydro-indol-(3Z)-ylidenemethyl]-2,4-dimethyl-1H-pyrrole-3-carboxylic acid (2-pyrrolidin-1-ylethyl)-amide | 397 [M + 1] |
| 130 | 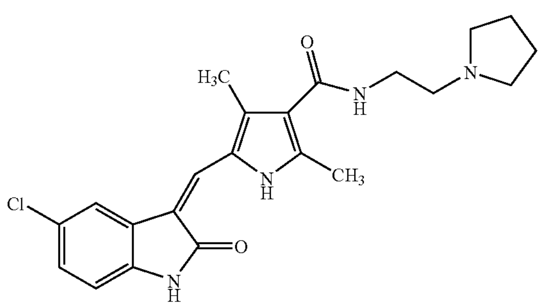 | 5-[5-Chloro-2-oxo-1,2-dihydro-indol-(3Z)-ylidenemethyl]-1H-pyrrole-3-carboxylic acid (2-pyrrolidin-1-ylethyl)-amide | 413 [M + 1] |
| 131 | 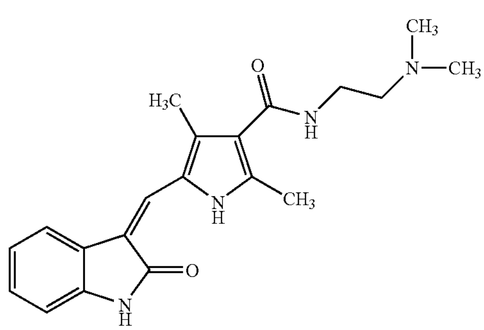 | 2,4-Dimethyl-5-[2-oxo-1,2-dihydro-indol-(3Z)-ylidenemethyl]-2,4-dimethyl-1H-pyrrole-3-carboxylic acid (2-dimethylaminoethyl)-amide | 353 [M + 1] |

TABLE 1-continued

| Example | Structure | Name | |
|---|---|---|---|
| 132 | 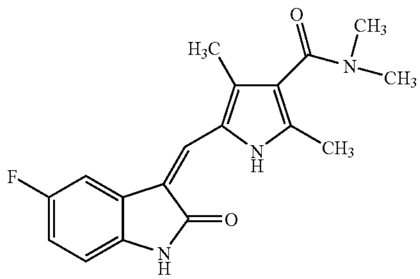 | 5-[5-Fluoro-2-oxo-1,2-dihydro-indol-(3Z)-ylidenemethyl]-2,4-dimethyl-1H-pyrrole-3-carboxylic acid (2-dimethylaminoethyl)-amide | 371 [M + 1] |
| 142 | 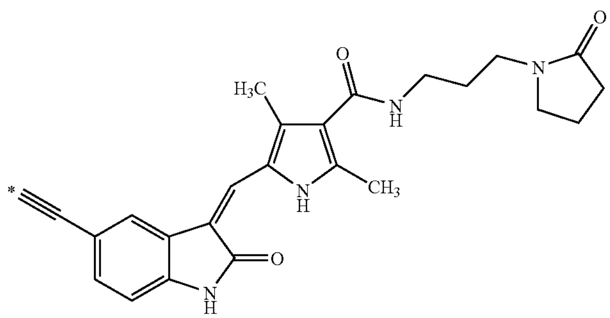 | 5-[5-Cyano-2-oxo-1,2-dihydro-indol-(3Z)-ylidenemethyl]-2,4-dimethyl-1H-pyrrole-3-carboxylic acid [3-(2-oxo-pyrrolidin-1-yl)-ethyl]-amide | 430 [M − 1] |
| 143 | 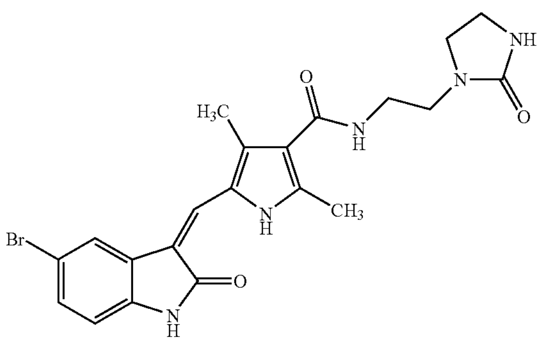 | 5-[5-Bromo-2-oxo-1,2-dihydro-indol-(3Z)-ylidenemethyl]-2,4-dimethyl-1H-pyrrole-3-carboxylic acid [2-(2-oxo-imidazolidin-1-yl)-ethyl]-amide | 470 [M − 1]<br>472 [M − 1] |
| 144 | 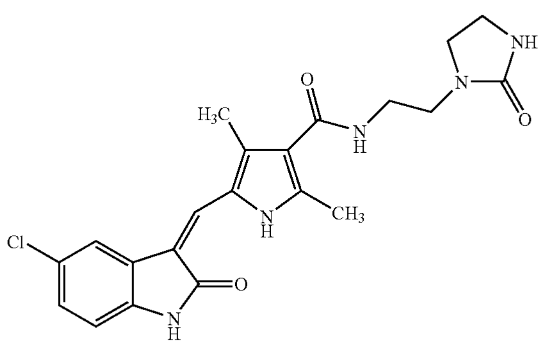 | 5-[5-Chloro-2-oxo-1,2-dihydro-indol-(3Z)-ylidenemethyl]-2,4-dimethyl-1H-pyrrole-3-carboxylic acid [2-(2-oxo-imidazolidin-1-yl)-ethyl]-amide | 428 [M + 1] |

TABLE 1-continued

| Example | Structure | Name | |
|---|---|---|---|
| 145 | 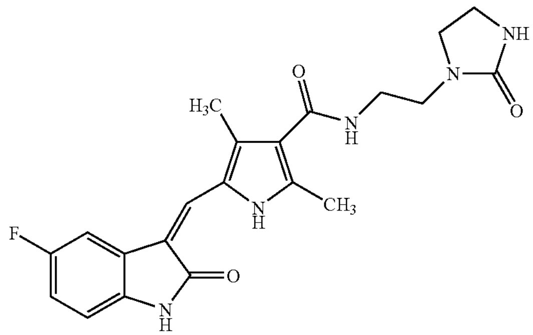 | 5-[5-Fluoro-2-oxo-1,2-dihydro-indol-(3Z)-ylidenemethyl]-2,4-dimethyl-1H-pyrrole-3-carboxylic acid [2-(2-oxo-imidazolidin-1-yl)-ethyl]-amide | 412 [M + 1] |
| 146 | 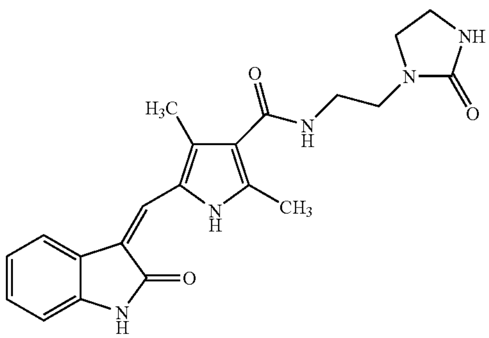 | 2,4-Dimethyl-5-[2-oxo-1,2-dihydro-indol-(3Z)-ylidenemethyl]-1H-pyrrole-3-carboxylic acid [3-(2-oxo-imidazolidin-1-yl)-ethyl]-amide | 392 [M − 1] |
| 147 | 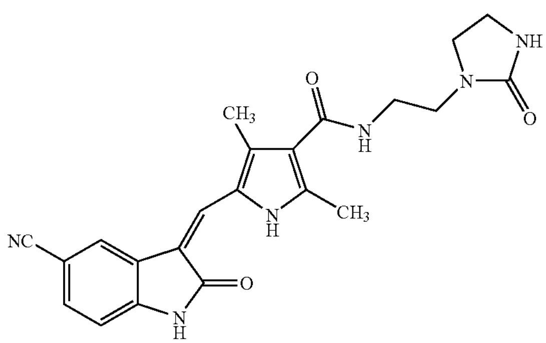 | 5-[5-Cyano-2-oxo-1,2-dihydro-indol-(3Z)-ylidenemethyl]-2,4-dimethyl-1H-pyrrole-3-carboxylic acid [2-(2-oxo-imidazolidin-1-yl)-ethyl]-amide | 419 [M + 1] |
| 148 | 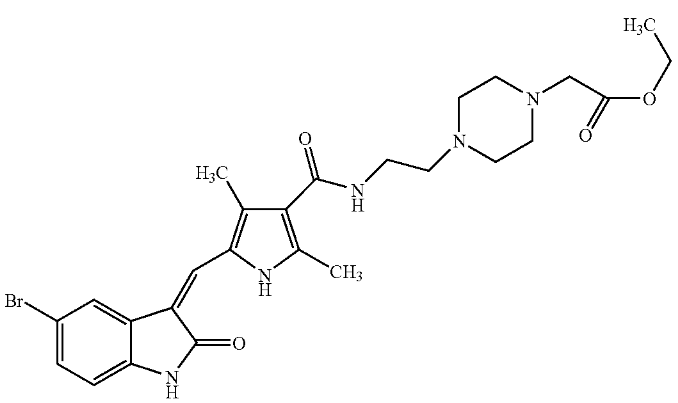 | {4-[2-({5-[5-Bromo-2-oxo-1,2-dihydro-indol-(3Z)-ylidenemethyl]-2,4-dimethyl-1H-pyrrole-3-carbonyl}amino)-ethyl]-piperazin-1-yl}-acetic acid ethyl ester | 558 [M + 1]<br>560 [M + 1] |

TABLE 1-continued

| Example | Structure | Name | |
|---|---|---|---|
| 149 | 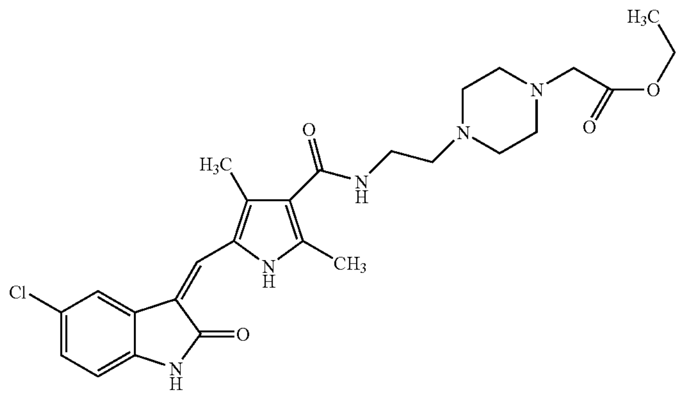 | {4-[2-({5-[5-Chloro-2-oxo-1,2-dihydro-indol-(3Z)-ylidenemethyl]-2,4-dimethyl-1H-pyrrole-3-carbonyl}-amino)-ethyl]-piperazin-1-yl}-acetic acid ethyl ester | 514 [M + 1] |
| 150 | 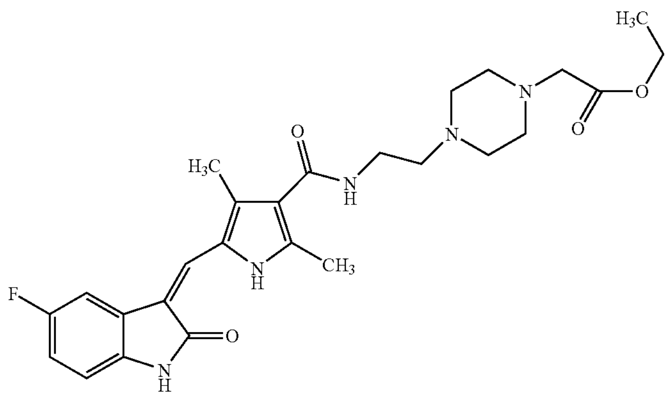 | {4-[2-({5-[5-Fluoro-2-oxo-1,2-dihydro-indol-(3Z)-ylidenemethyl]-2,4-dimethyl-1H-pyrrole-3-carbonyl}-amino)-ethyl]-piperazin-1-yl}-acetic acid ethyl ester | 498 [M + 1] |
| 153 | 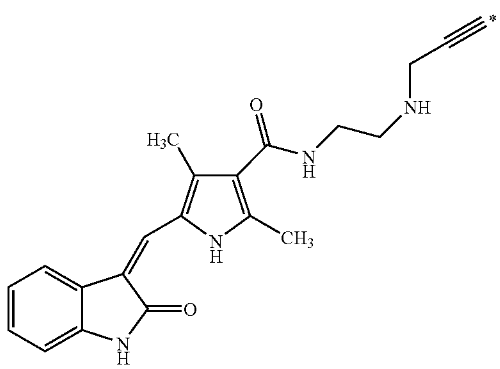 | 2,4-Dimethyl-5-[2-oxo-1,2-dihydro-indol-(3Z)-ylidenemethyl]-1H-pyrrole-3-carboxylic acid [2-(cyanomethyl-amino)-ethyl]-amide | 362 [M − 1] |
| 154 | 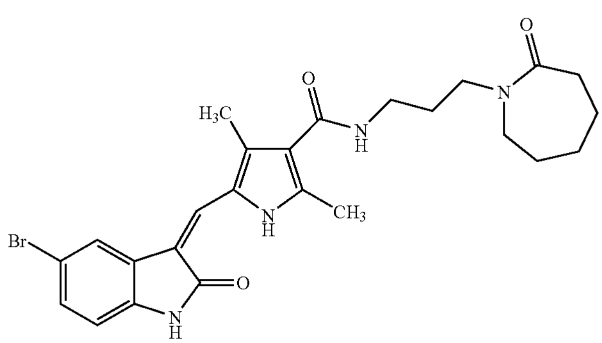 | 5-[5-Bromo-2-oxo-1,2-dihydro-indol-(3Z)-ylidenemethyl]-2,4-dimethyl-1H-pyrrole-3-carboxylic acid [3-(2-oxo-azepan-1-yl)-propyl]-amide | 511 [M − 1]<br>513 [M − 1] |

TABLE 1-continued

| Example | Structure | Name | |
|---|---|---|---|
| 155 | 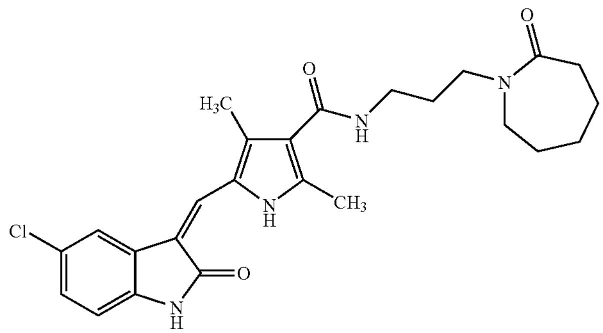 | 5-[5-Chloro-2-oxo-1,2-dihydro-indol-(3Z)-ylidenemethyl]-2,4-dimethyl-1H-pyrrole-3-carboxylic acid [3-(2-oxo-azepan-1-yl)-propyl]-amide | 469 [M + 1] |
| 156 | 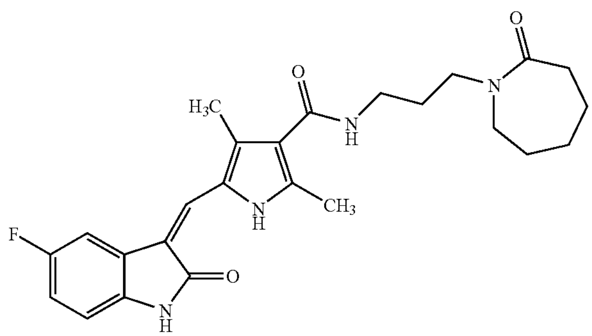 | 5-[5-Fluoro-2-oxo-1,2-dihydro-indol-(3Z)-ylidenemethyl]-2,4-dimethyl-1H-pyrrole-3-carboxylic acid [3-(2-oxo-azepan-1-yl)-propyl]-amide | 453 [M + 1] |
| 157 | 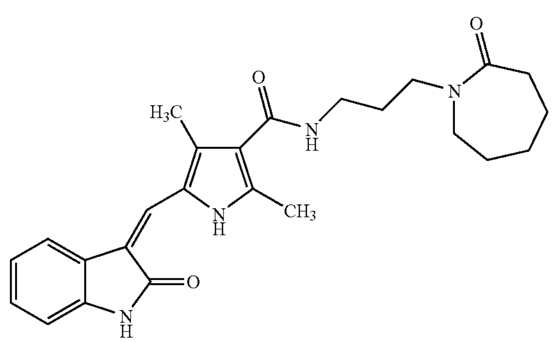 | 2,4-Dimethyl-5-[2-oxo-1,2-dihydro-indol-(3Z)-ylidenemethyl]-1H-pyrrole-3-carboxylic acid [3-(2-oxo-azepan-1-yl)-propyl]-amide | 435 [M + 1] |
| 158 | 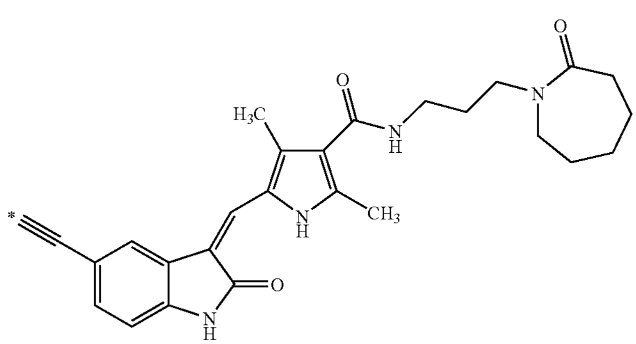 | 5-[5-Cyano-2-oxo-1,2-dihydro-indol-(3Z)-ylidenemethyl]-2,4-dimethyl-1H-pyrrole-3-carboxylic acid [3-(2-oxo-azepan-1-yl)-propyl]-amide | 460 [M + 1] |

TABLE 1-continued

| Example | Structure | Name | |
|---|---|---|---|
| 159 | 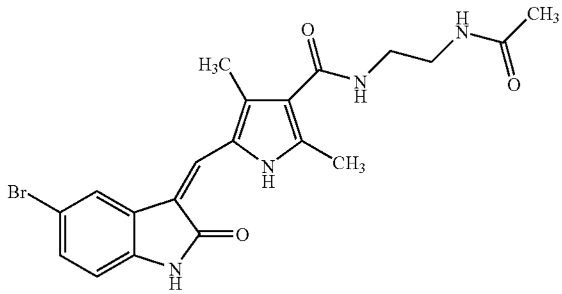 | 5-[5-Bromo-2-oxo-1,2-dihydro-indol-(3Z)-ylidenemethyl]-2,4-dimethyl-1H-pyrrole-3-carboxylic acid [3-(2-oxo-azepan-1-yl)-propyl]-amide | 443 [M − 1] 445 [M − 1] |
| 160 | 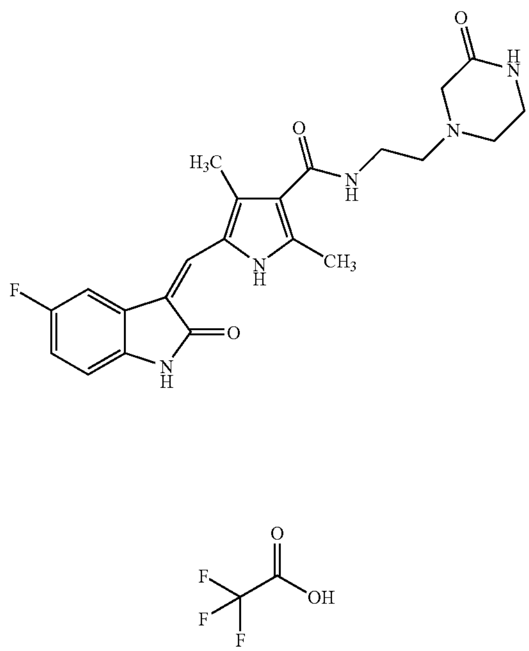 | Trifluoro-acetate4-[2-({5-[5-fluoro-2-oxo-1,2-dihydro-indol-(3Z)-ylidenemethyl]-2,4-dimethyl-1H-pyrrole-3-carbonyl}-amino)-ethyl]-2-oxo-piperazin-1-ium; | 426 [M + 1] |
| 161 | 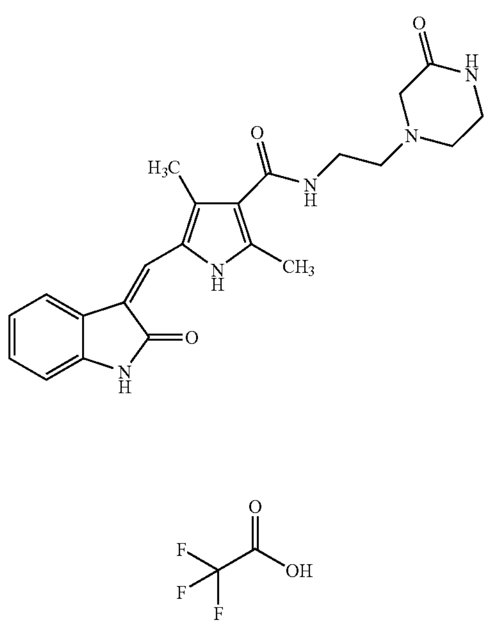 | Trifluoro-acetate4-[2-({2,4-dimethyl-5-[-2-oxo-1,2-dihydro-indol-(3Z)-ylidenemethyl]-1H-pyrrole-3-carbonyl}-amino)-ethyl]-2-oxo-piperazin-1-ium; | 408 [M + 1] |

TABLE 1-continued

| Example | Structure | Name | |
|---|---|---|---|
| 162 | 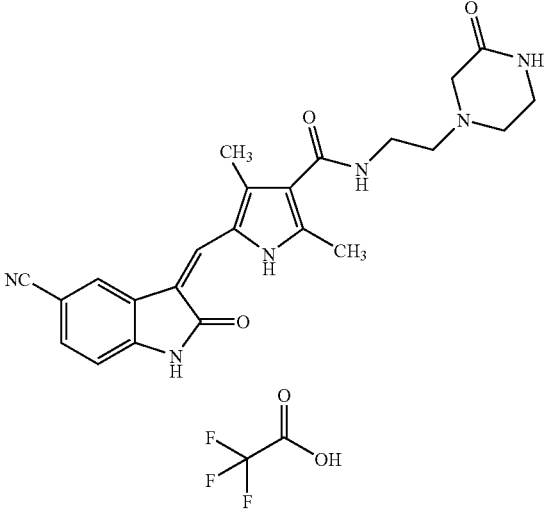 | Trifluoro-acetate4-[2-({5-[5-cyano-2-oxo-1,2-dihydro-indol-(3Z)-ylidenemethyl]-2,4-dimethyl-1H-pyrrole-3-carbonyl}-amino)-ethyl]-2-oxo-piperazin-1-ium; | 433 [M + 1] |
| 163 | 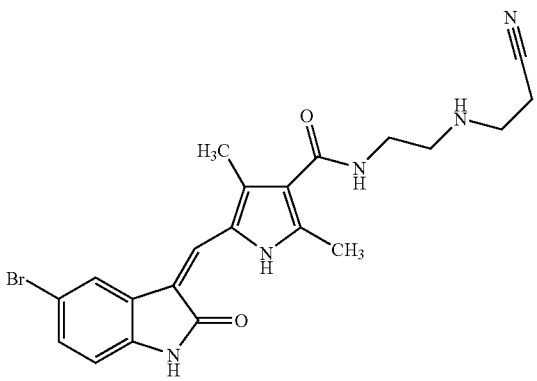 | 5-[5-Bromo-2-oxo-1,2-dihydro-indol-(3Z)-ylidenemethyl]-2,4-dimethyl-1H-pyrrole-3-carboxylic acid [2-(2-cyano-ethylamino)-ethyl]-amide | 454 [M − 1] 456 [M − 1] |
| 164 | 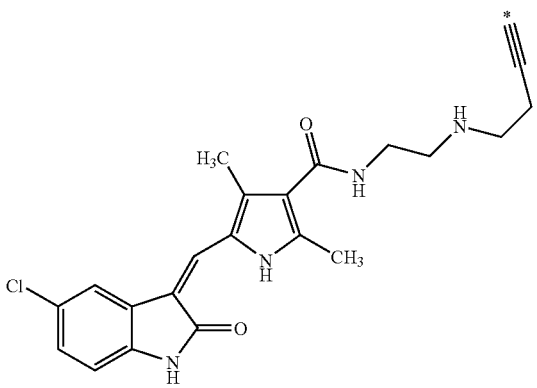 | 5-[5-Chloro-2-oxo-1,2-dihydro-indol-(3Z)-ylidenemethyl]-2,4-dimethyl-1H-pyrrole-3-carboxylic acid [2-(2-cyano-ethylamino)-ethyl]-amide | 410 [M − 1] |

TABLE 1-continued

| Example | Structure | Name | |
|---|---|---|---|
| 165 | 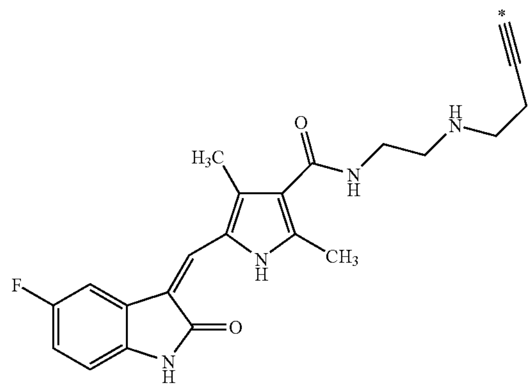 | 5-[5-Fluoro-2-oxo-1,2-dihydro-indol-(3Z)-ylidenemethyl]-2,4-dimethyl-1H-pyrrole-3-carboxylic acid [2-(2-cyano-ethylamino)-ethyl]-amide | 394 [M − 1] |
| 166 | 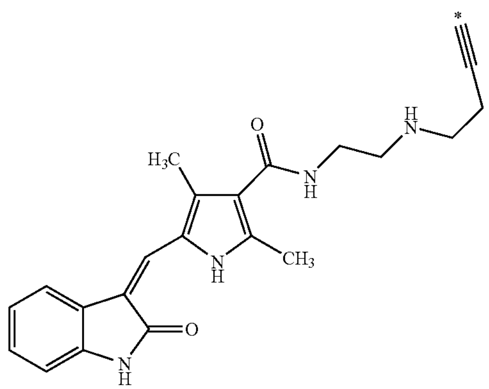 | 2,4-Dimethyl-5-[2-oxo-1,2-dihydro-indol-(3Z)-ylidenemethyl]-1H-pyrrole-3-carboxylic acid [2-(2-cyano-ethylamino)-ethyl]-amide | 376 [M − 1] |
| 167 | 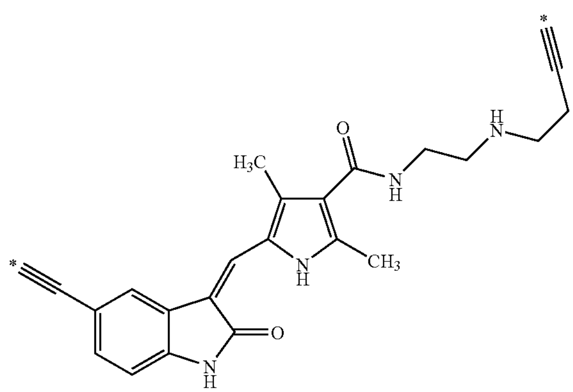 | 5-[5-Cyano-2-oxo-1,2-dihydro-indol-(3Z)-ylidenemethyl]-2,4-dimethyl-1H-pyrrole-3-carboxylic acid [2-(2-cyano-ethylamino)-ethyl]-amide | 401 [M − 1] |
| 168 | 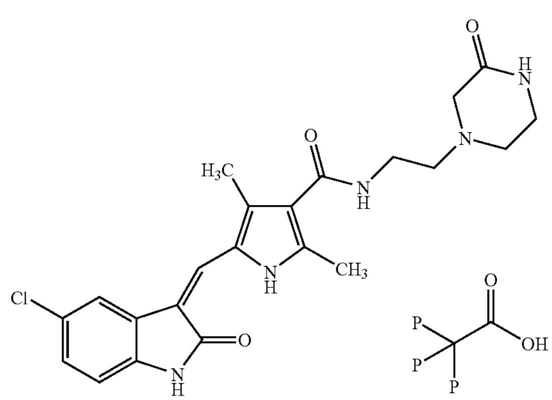 | Trifluoro-acetate4-[2-({5-[5-chloro-2-oxo-1,2-dihydro-indol-(3Z)-ylidenemethyl]-2,4-dimethyl-1H-pyrrole-3-carbonyl}-amino)-ethyl]-2-oxo-piperazin-1-ium; | 440 [M − 1] |

TABLE 1-continued

| Example | Structure | Name | |
|---|---|---|---|
| 168 | 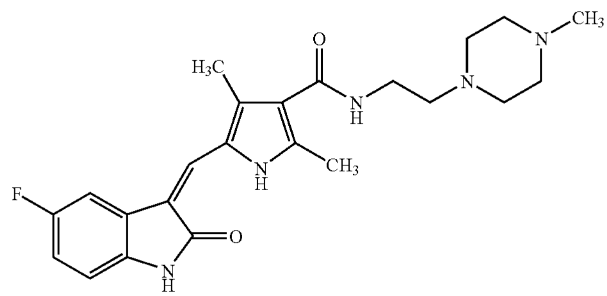 | 5-[5-Fluoro-2-oxo-1,2-dihydro-indol-(3Z)-ylidenemethyl]-2,4-dimethyl-1H-pyrrole-3-carboxylic acid [2-(4-methyl-piperazin-1-yl)-ethyl]-amide | 424 [M − 1] |
| 169 | 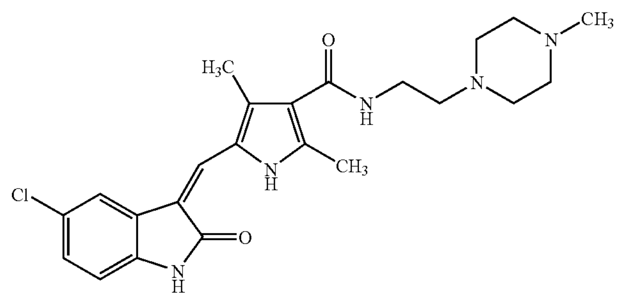 | 5-[5-Chloro-2-oxo-1,2-dihydro-indol-(3Z)-ylidenemethyl]-2,4-dimethyl-1H-pyrrole-3-carboxylic acid [2-(4-methyl-piperazin-1-yl)-ethyl]-amide | 440 [M − 1] |
| 170 | 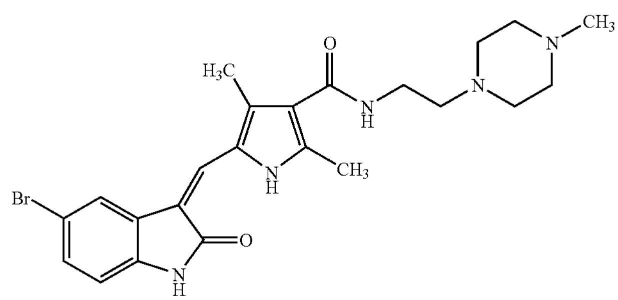 | 5-[5-Bromo-2-oxo-1,2-dihydro-indol-(3Z)-ylidenemethyl]-2,4-dimethyl-1H-pyrrole-3-carboxylic acid [2-(4-methyl-piperazin-1-yl)-ethyl]-amide | 484 [M − 1]<br>486 [M − 1] |
| 171 | 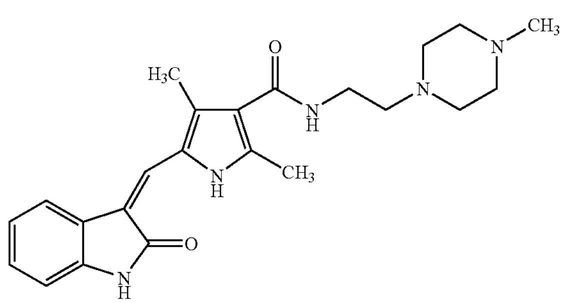 | 2,4-Dimethyl-5-[2-oxo-1,2-dihydro-indol-(3Z)-ylidenemethyl]-1H-pyrrole-3-carboxylic acid [2-(4-methyl-piperazin-1-yl)-ethyl]-amide | 406 [M − 1] |
| 172 | 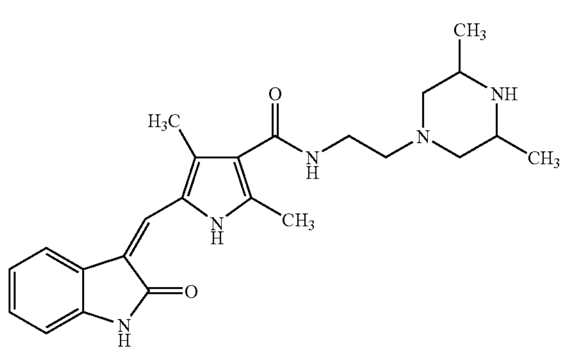 | 2,4-Dimethyl-5-[2-oxo-1,2-dihydro-indol-(3Z)-ylidenemethyl]-1H-pyrrole-3-carboxylic acid [2-(3,5-dimethyl-piperazin-1-yl)-ethyl]-amide | 422 [M + 1] |

TABLE 1-continued

| Example | Structure | Name | |
|---|---|---|---|
| 173 | 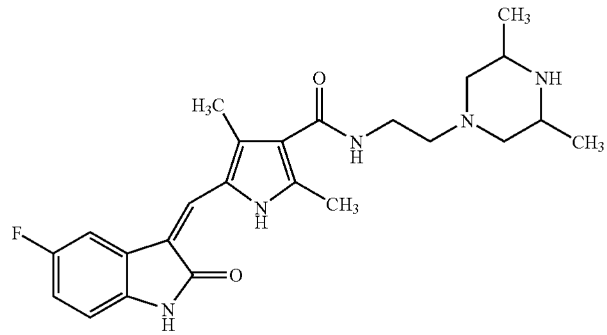 | 5-[5-Fluoro-2-oxo-1,2-dihydro-indol-(3Z)-ylidenemethyl]-2,4-dimethyl-1H-pyrrole-3-carboxylic acid [2-(3,5-dimethyl-piperazin-1-yl)-ethyl]-amide | 438 [M − 1] |
| 174 | 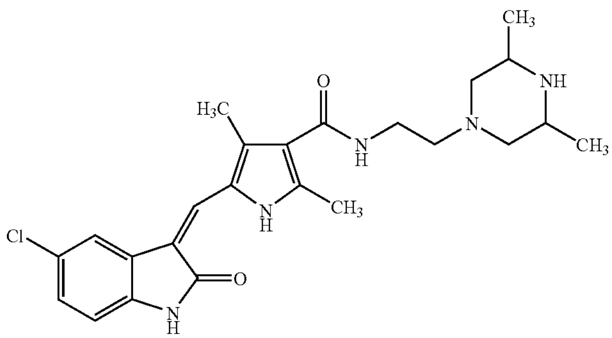 | 5-[5-Chloro-2-oxo-1,2-dihydro-indol-(3Z)-ylidenemethyl]-2,4-dimethyl-1H-pyrrole-3-carboxylic acid [2-(3,5-dimethyl-piperazin-1-yl)-ethyl]-amide | 456 [M − 1] |
| 175 | 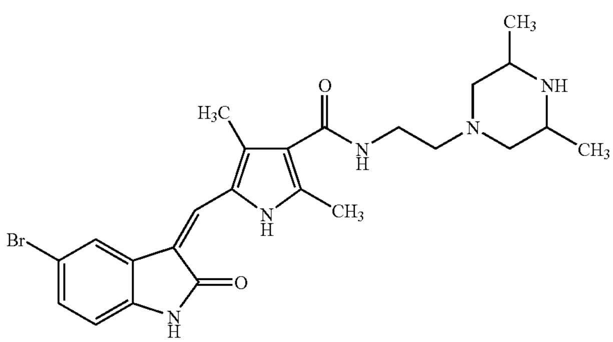 | 5-[5-Bromo-2-oxo-1,2-dihydro-indol-(3Z)-ylidenemethyl]-2,4-dimethyl-1H-pyrrole-3-carboxylic acid [2-(3,5-dimethyl-piperazin-1-yl)-ethyl]-amide | 498 [M − 1]<br>500 [M − 1] |
| 176 | 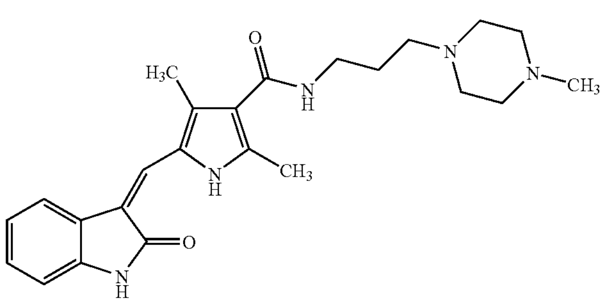 | 2,4-Dimethyl-5-[2-oxo-1,2-dihydro-indol-(3Z)-ylidenemethyl]-1H-pyrrole-3-carboxylic acid [3-(4-methyl-piperazin-1-yl)-propyl]-amide | 422 [M + 1] |

TABLE 1-continued

| Example | Structure | Name | |
|---|---|---|---|
| 177 | 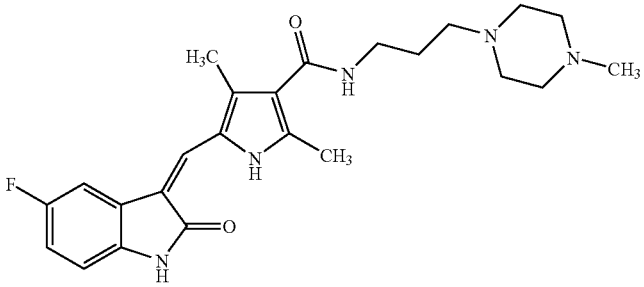 | 5-[5-Fluoro-2-oxo-1,2-dihydro-indol-(3Z)-ylidenemethyl]-2,4-dimethyl-1H-pyrrole-3-carboxylic acid [3-(4-methyl-piperazin-1-yl)-propyl]-amide | 438 [M − 1] |
| 178 | 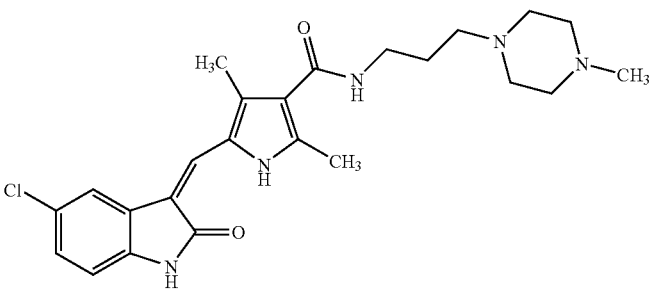 | 5-[5-Chloro-2-oxo-1,2-dihydro-indol-(3Z)-ylidenemethyl]-2,4-dimethyl-1H-pyrrole-3-carboxylic acid [3-(4-methyl-piperazin-1-yl)-propyl]-amide | 454 [M − 1] |
| 179 | 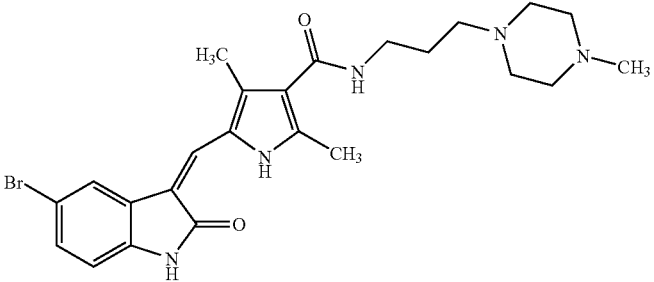 | 5-[5-Bromo-2-oxo-1,2-dihydro-indol-(3Z)-ylidenemethyl]-2,4-dimethyl-1H-pyrrole-3-carboxylic acid [3-(4-methyl-piperazin-1-yl)-propyl]-amide | 498 [M − 1]<br>500 [M − 1] |
| 180 | 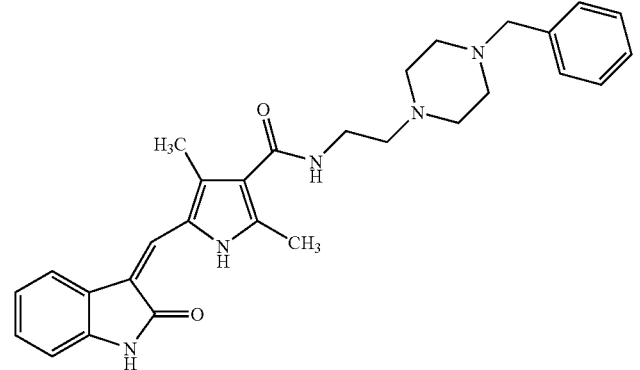 | 2,4-Dimethyl-5-[2-oxo-1,2-dihydro-indol-(3Z)-ylidenemethyl]-1H-pyrrole-3-carboxylic acid [2-(4-benzyl-piperazin-1-yl)-ethyl]-amide | 482 [M − 1] |

TABLE 1-continued

| Example | Structure | Name | |
|---|---|---|---|
| 181 | 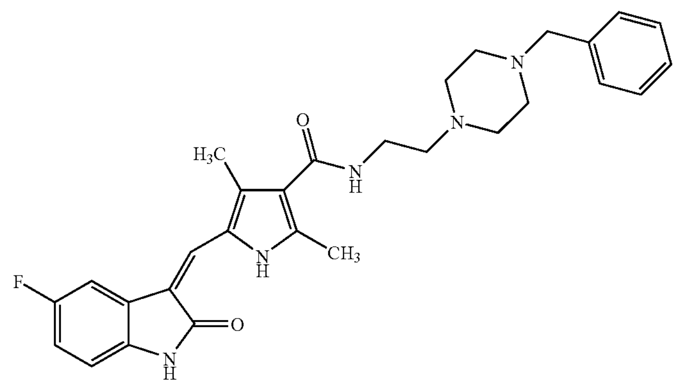 | 5-[5-Fluoro-2-oxo-1,2-dihydro-indol-(3Z)-ylidenemethyl]-2,4-dimethyl-1H-pyrrole-3-carboxylic acid [2-(4-benzyl-piperazin-1-yl)-ethyl]-amide | 500 [M − 1] |
| 182 | 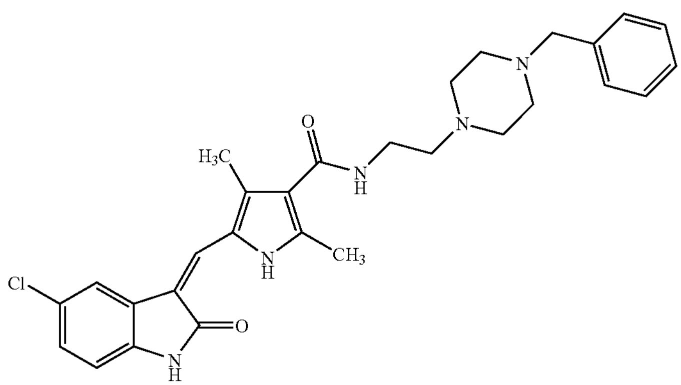 | 5-[5-Chloro-2-oxo-1,2-dihydro-indol-(3Z)-ylidenemethyl]-2,4-dimethyl-1H-pyrrole-3-carboxylic acid [2-(4-benzyl-piperazin-1-yl)-ethyl]-amide | 517 [M − 1] |
| 183 | 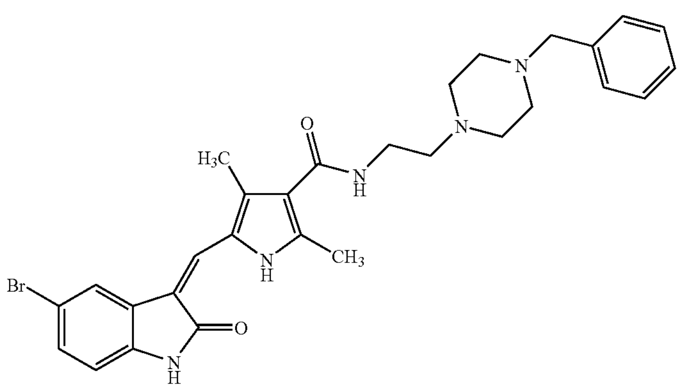 | 5-[5-Bromo-2-oxo-1,2-dihydro-indol-(3Z)-ylidenemethyl]-2,4-dimethyl-1H-pyrrole-3-carboxylic acid [2-(4-benzyl-piperazin-1-yl)-ethyl]-amide | 560 [M − 1]<br>562 [M − 1] |
| 184 | 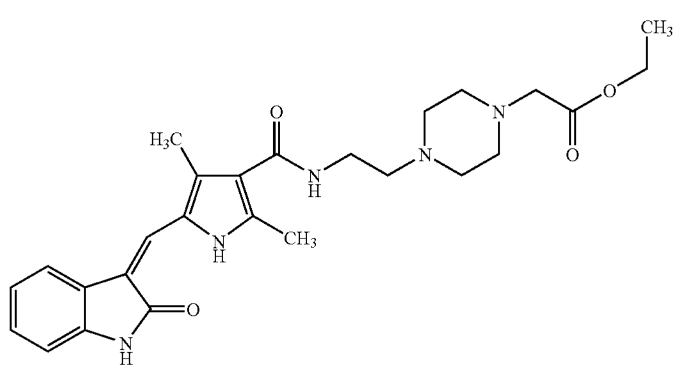 | 5-[5-Chloro-2-oxo-1,2-dihydro-indol-(3Z)-ylidenemethyl]-2,4-dimethyl-1H-pyrrole-3-carboxylic acid (3-pyrrolidin-1yl-2-one)-amide | 480 [M + 1] |

TABLE 1-continued

| Example | Structure | Name | |
|---|---|---|---|
| 185 | 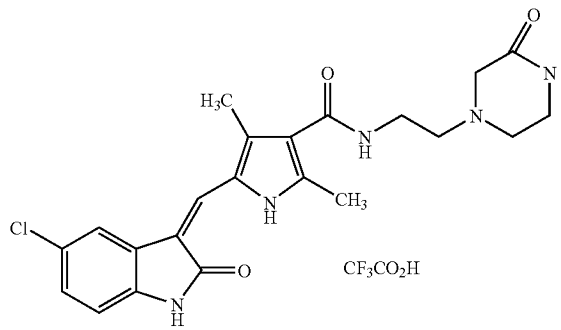 | Trifluoroacetate 4-[2-({5-[5-Chloro-2-oxo-1,2-dihydro-indol-(3Z)-ylidenemethyl]-2,4-dimethyl-1H-pyrrole-3-carbonyl}-amino)-ethyl]-2-oxo-piperazin-1-ium | 440 [M − 1] |
| 186 | 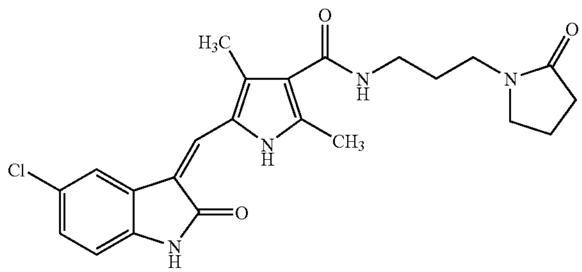 | 5-[5-Chloro-2-oxo-1,2-dihydro-indol-(3Z)-ylidenemethyl]-2,4-dimethyl-1H-pyrrole-3-carboxylic acid (3-pyrrolidin-1yl-2-one)-amide | |
| 187 | 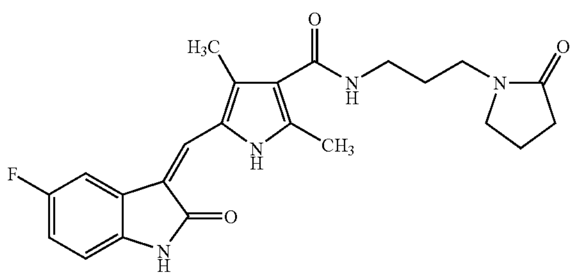 | 5-[5-Fluoro-2-oxo-1,2-dihydro-indol-(3Z)-ylidenemethyl]-2,4-dimethyl-1H-pyrrole-3-carboxylic acid (3-pyrrolidin-1yl-2-one)-amide | |
| 188 | 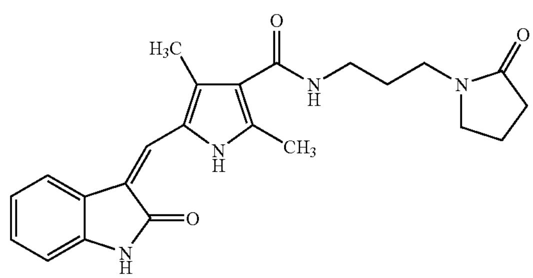 | 5-[2-oxo-1,2-dihydro-indol-(3Z)-ylidenemethyl]-2,4-dimethyl-1H-pyrrole-3-carboxylic acid (3-pyrrolidin-1yl-2-one)-amide | |
| 189 | 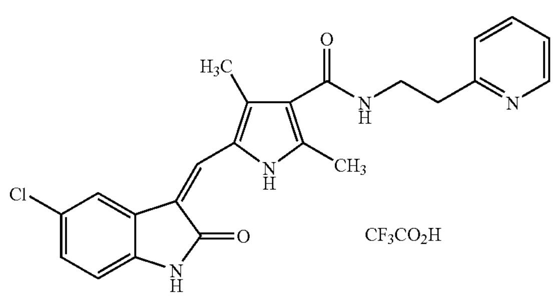 | 5-[5-Chloro-2-oxo-1,2-dihydro-indol-(3Z)-ylidenemethyl]-2,4-dimethyl-1H-pyrrole-3-carboxylic acid (2-pyridin-2-ylethyl)-amide | |

TABLE 1-continued

| Example | Structure | Name |
| --- | --- | --- |
| 190 | 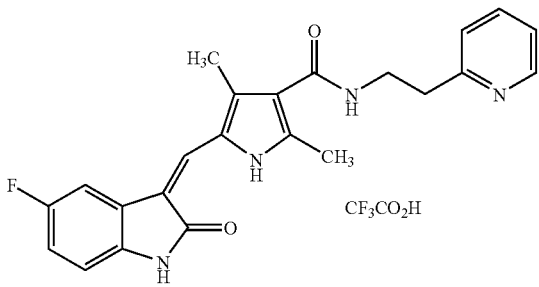 | 5-[5-Fluoro-2-oxo-1,2-dihydro-indol-(3Z)-ylidenemethyl]-2,4-dimethyl-1H-pyrrole-3-carboxylic acid (2-pyridin-2-ylethyl)-amide trifluroracetate salt |
| 191 | 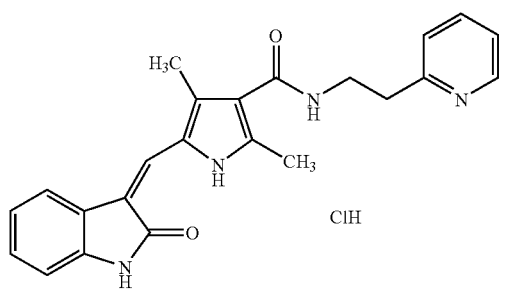 | 5-[2-oxo-1,2-dihydro-indol-(3Z)-ylidenemethyl]-2,4-dimethyl-1H-pyrrole-3-carboxylic acid (2-pyridin-2-ylethyl)-amide hydrochloride salt |
| 192 | 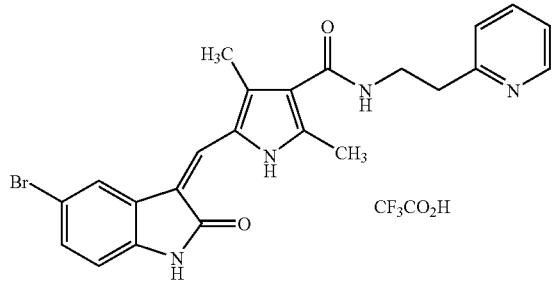 | 5-[5-Bromo-2-oxo-1,2-dihydro-indol-(3Z)-ylidenemethyl]-2,4-dimethyl-1H-pyrrole-3-carboxylic acid (2-pyridin-2-ylethyl)-amide trifluroracetate salt |
| 193 | 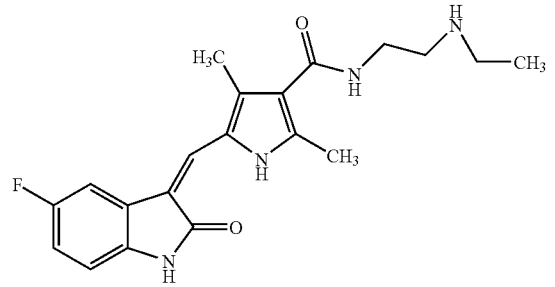 | 5-[5-Fluoro-2-oxo-1,2-dihydro-indol-(3Z)-ylidenemethyl]-2,4-dimethyl-1H-pyrrole-3-carboxylic acid (2-ethylaminoethyl)-amide |
| 194 | 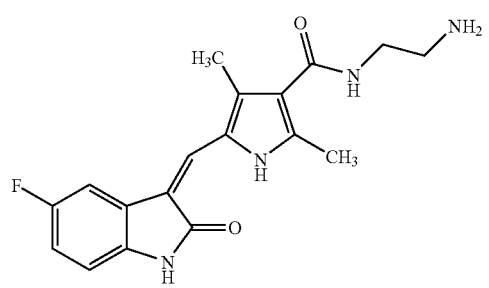 | 5-[5-Fluoro-2-oxo-1,2-dihydro-indol-(3Z)-ylidenemethyl]-2,4-dimethyl-1H-pyrrole-3-carboxylic acid (2-aminoethyl)-amide |

TABLE 1-continued

| Example | Structure | Name |
|---|---|---|
| 195 | 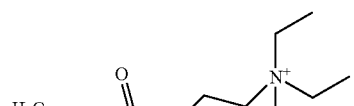 | 5-[5-Fluoro-2-oxo-1,2-dihydro-indol-(3Z)-ylidenemethyl]-2,4-dimethyl-2,4-dimethyl-1H-pyrrole-3-carboxylic acid (2-diethyl-N-oxoaminoethyl)-amide |
| 196 | 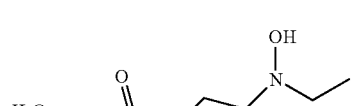 | 5-[5-Fluoro-2-oxo-1,2-dihydro-indol-(3Z)-ylidenemethyl]-2,4-dimethyl-1H-pyrrole-3-carboxylic acid (2-ethyl-N-hydroxy-aminoethyl)-amide |
| 197 | 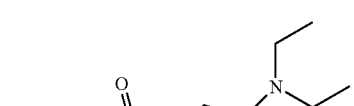 | 5-[5-Fluoro-2-oxo-1,2-dihydro-indol-(3Z)-ylidenemethyl]-2,4-dimethyl-1H-pyrrole-3-carboxylic acid (2-diethylamino-2-hydroxyethyl)-amide |
| 198 | 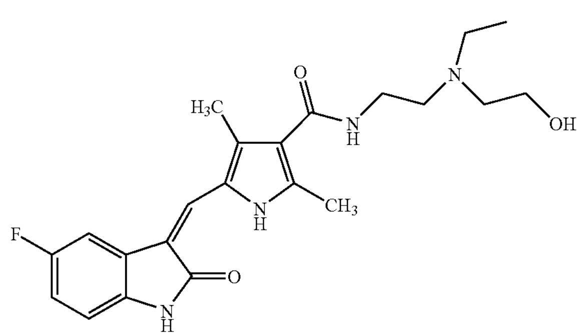 | 5-[5-Fluoro-2-oxo-1,2-dihydro-indol-(3Z)-ylidenemethyl]-2,4-dimethyl-1H-pyrrole-3-carboxylic acid [2-ethyl-2-(2-hydroxyethyl)aminoethyl]-amide |

TABLE 1-continued

| Example | Structure | Name |
|---|---|---|
| 199 | 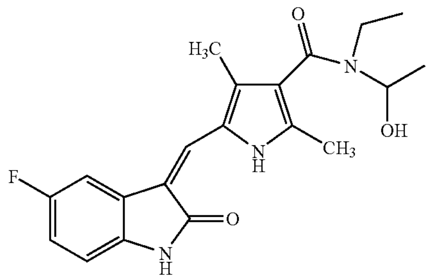 | 5-[5-Fluoro-2-oxo-1,2-dihydro-indol-(3Z)-ylidenemethyl]-2,4-dimethyl-1H-pyrrole-3-carboxylic acid [2-ethyl-2-(1-hydroxyethyl)aminoethyl]-amide |
| 200 | 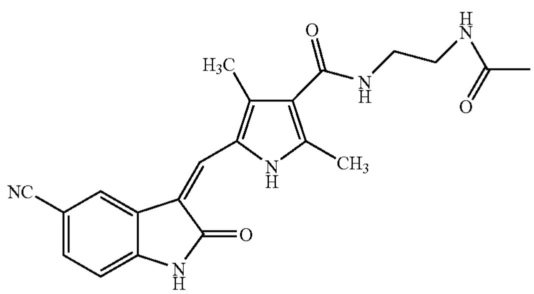 | 5-[5-Cyano-2-oxo-1,2-dihydro-indol-(3Z)-ylidenemethyl]-2,4-dimethyl-1H-pyrrole-3-carboxylic acid (2-N-acetylaminoethyl)-amide |
| 201 | 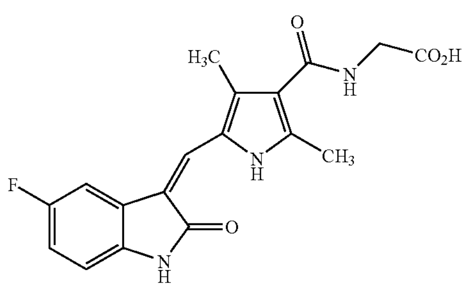 | 5-[5-Fluoro-2-oxo-1,2-dihydro-indol-(3Z)-ylidenemethyl]-2,4-dimethyl-1H-pyrrole-3-carboxylic acid (carboxymethyl)-amide |
| 202 | 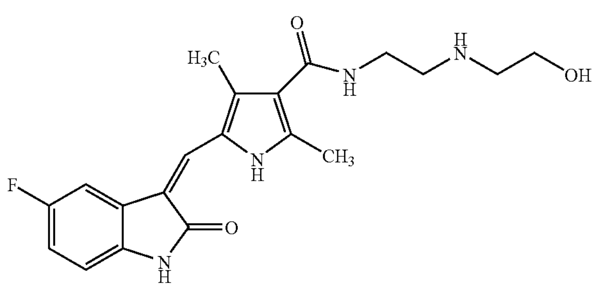 | 5-[5-Fluoro-2-oxo-1,2-dihydro-indol-(3Z)-ylidenemethyl]-1H-pyrrole-3-carboxylic acid [2-(2-hydroxethylamino)ethyl]-amide |
| 203 | 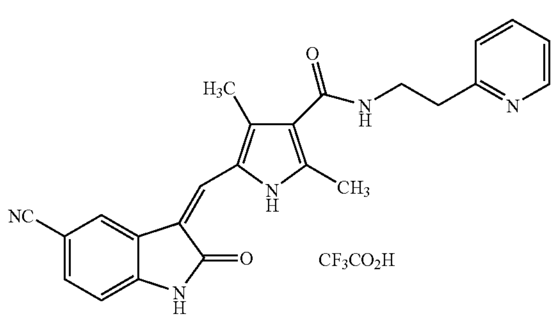 | 5-[5-Cyano-2-oxo-1,2-dihydro-indol-(3Z)-ylidenemethyl]-1H-pyrrole-3-carboxylic acid (2-pyridin-2-ylethyl)-amide trifluroacetate |

TABLE 1-continued

| Example | Structure | Name |
|---|---|---|
| 204 | 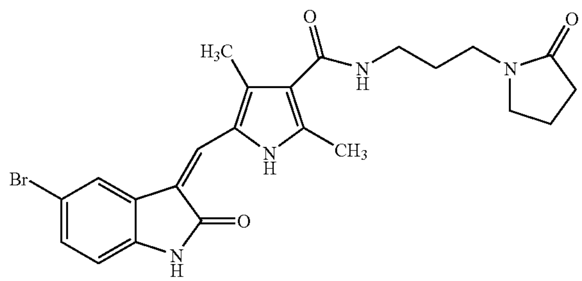 | 5-[5-Bromo-2-oxo-1,2-dihydro-indol-(3Z)-ylidenemethyl]-1H-pyrrole-3-carboxylic acid (2-pyrrolidin-1-yl-2-onepropyl)-amide trifluroacetate |

The compound numbers correspond to the Example numbers in the Examples section. That is, the synthesis of Compound 1 in Table 1 is described in Example 1. The compounds presented in Table 1 are exemplary only and are not tribe construed as limiting the scope of this invention in any manner.

PREFERRED EMBODIMENTS

While the broadest definition is set forth in the Summary of the Invention, certain compounds of Formula (I) set forth below are preferred.
(1) A preferred group of compounds of Formula, (I) is that wherein $R^1$, $R^3$, and $R^4$ are hydrogen.
(2) Another preferred group of compounds of Formula (I) is that wherein $R^1$, $R^2$, and $R^4$ are hydrogen.
(3) Another preferred group of compounds of Formula (I) is that wherein $R^1$, $R^2$, and $R^3$ are hydrogen.
(4) Another preferred group of compounds of Formula (I) is that wherein $R^2$, $R^3$, and $R^4$ are hydrogen.
(5) Another preferred group of compounds of Formula (I) is that wherein $R^1$, $R^2$, $R^3$ and $R^4$ are hydrogen.
(6) Yet another preferred group of compounds of Formula (I) is that wherein $R^5$, $R^6$ or $R^7$, preferably $R^5$ or $R^6$, more preferably $R^6$ is —$COR^{10}$ wherein $R^{10}$ is —$NR^{11}(CH_2)_n R^{12}$ wherein:
$R^{11}$ is hydrogen or lower unsubstituted alkyl, preferably hydrogen or methyl;
n is 2, 3 or 4, preferably 2 or 3; and
$R^{12}$ is —$NR^{13}R^{14}$ wherein $R^{13}$ and $R^{14}$ are independently alkyl, more preferably lower unsubstituted lower alkyl or $R^{13}$ and $R^{14}$ combine to form a group selected from —$(CH_2)_4$—, —$(CH_2)_5$—, —$(CH_2)_2$—O—$(CH_2)_2$— or —$(CH_2)_2N(CH_3)(CH_2)_2$—, preferably $R^{13}$ and $R^{14}$ are independently hydrogen, methyl, ethyl, or combine to form morpholin-4-yl, pyrrolidin-1-yl, piperazin-1-yl, or 4-methylpiperazin-1-yl.
More preferably, $R^5$ or $R^6$ in (6) above is N-(2-dimethylaminoethyl-)aminocarbonyl, N-(2-ethylaminoethyl)-N-methylaminocarbonyl, N-(3-dimethylaminopropyl)aminocarbonyl, N-(2-diethylaminoethyl)aminocarbonyl, N-(3-ethylaminopropyl)aminocarbonyl, N-(3-diethylaminopropyl)aminocarbonyl, 3-pyrrolidin-1-ylpropylaminocarbonyl, 3-morpholin-4-ylpropylaminocarbonyl, 2-pyrrolidin-1-ylethylaminocarbonyl, 2-morpholin-4-ylethylaminocarbonyl, 2-(4-methylppiperazin-1-yl)ethylaminocarbonyl, 2-(4-methylpiperazin-1-yl)propylaminocarbonyl, 2-(3,5-dimethylpiperazin-1-y) ethylaminocarbonyl or 2-(3,5-dimethylpiperazin-1-y) propylaminocarbonyl, even more preferably N-(2-diethylaminoethyl)aminocarbonyl or N-(2-ethylaminoethyl) aminocarbonyl.
(7) Yet another preferred group of compounds of Formula (I) is that wherein $R^5$, $R^6$ or $R^7$, preferably $R^5$ or $R^6$, more preferably $R^6$ is —$COR^{10}$ wherein $R^{10}$ is —$NR^{13}R^{14}$ wherein $R^{13}$ is hydrogen and $R^{14}$ is alkyl, preferably lower alkyl substituted with hydroxy, aryl, heteroaryl, heteroalicyclic, or carboxy, more preferably methyl, ethyl, propyl or butyl substituted with hydroxy, aryl, heteroalicyclic such as piperidine, piperazine, morpholine and the like, heteroaryl, or carboxy. Even more preferably within this group (7), $R^5$ or $R^6$ is 2-ethoxycarbonylmethyl-aminocarbonyl, carboxymethylaminocarbonyl, 3-hydroxypropylaminocarbonyl, 2-hydroxyethylaminocarbonyl, 3-triazin-1-ylpropylaminocarbonyl, triazin-1-ylethylaminocarbonyl, 4-hydroxyphenylethylaminocarbonyl, 3-imidazol-1-ylpropylaminocarbonyl, pyridin-4-ylmethylaminocarbonyl, 2-pyridin-2-ylethylaminocarbonyl or 2-imidazol-1-ylethylaminocarbonyl.
(8) Yet another preferred group of compounds of Formula (I) is that wherein $R^5$, $R^6$ or $R^7$, preferably $R^5$ or $R^6$, more preferably $R^6$ is —$COR^{10}$ wherein $R^{10}$ is —$NR^{11}(CH_2)_n R^{12}$ wherein:
$R^{11}$ is hydrogen or alkyl, preferably hydrogen or methyl;
n is 2, 3 or 4, preferably 2 or 3; and
$R^{12}$ is —$NR^{13}R^{14}$ wherein $R^{13}$ and $R^{14}$ together combine to form a heterocycle, preferably a 5, 6 or 7 membered heterocycle containing a carbonyl group and 1 or 2 nitrogen atoms. Preferably, $R^5$ or $R^6$ is 2-(3-ethoxycarbonylmethylpiperazin-1-yl)ethylaminocarbonyl, 2-(3-oxopiperazin-1-yl)ethylaminocarbonyl, 2-(imidazolidin-1-yl-2-one)ethylaminocarbonyl, 2-(tetrahydropyrimidin-1-yl-2-one)ethylaminocarbonyl, 2-(2-oxopyrrolidin-1-yl)ethylaminocarbonyl, 3-(4-methylpiperazin-1-yl)propylaminocarbonyl, 3-(3-ethoxycarbonylmethylpiperazin-1-yl)-propylaminocarbonyl, 3-(3-oxopiperazin-1-yl)propylaminocarbonyl, 3-(imidazolidin-1-yl-2-one)propylaminocarbonyl, 3-(tetrahydropyrimidin-1-yl-2-one)propylaminocarbonyl, 3-(2-oxopyrrolidin-1-yl)propylaminocarbonyl, 2-(2-oxohomopiperidin-1-yl)ethylaminocarbonyl or 3-(2-oxohomopiperidin-1-yl)propylaminocarbonyl.

(9) Yet another preferred group of compounds of Formula (I) is that wherein $R^5$, $R^6$ or $R^7$, preferably $R^5$ or $R^6$, more preferably $R^6$ is —$COR^{10}$ wherein:
(a) $R^{10}$ is —$NR^{11}(CH_2)_nR^{12}$ wherein:
$R^{11}$ is hydrogen or alkyl, preferably hydrogen or methyl;
n is 2, 3 or 4, preferably 2 or 3; and
$R^{12}$ is —$NR^{13}R^{14}$ wherein $R^{13}$ is hydrogen and $R^{14}$ is cyanoalkyl or —$NHCOR^a$ where $R^a$ is alkyl; or
(b) $R^{10}$ is —$NR^{13}R^{14}$ wherein $R^{13}$ and $R^{14}$ together combine to form a heterocycle not containing a carbonyl group within the ring. Preferably, $R^5$ or $R^6$ is 2-(2-cyanoethylamino)ethylaminocarbonyl, 2-(acetylamino) ethylaminocarbonyl, morpholinocarbonyl, piperidin-1-ylcarbonyl, 2-cyanomethylaminoethylaminocarbonyl or piperidin-1-ylcarbonyl.

(10) Another preferred group of compounds of Formula (I) is that wherein $R^5$ is —$COR^{10}$ wherein $R^{10}$ is —$NR^{13}R^{14}$ wherein $R^{13}$ is hydrogen and $R^{14}$ is lower alkyl substituted with hydroxy, lower alkyl substituted with hydroxyalkylamino, carboxy, or —$NR^{18}R^{19}$ wherein $R^{18}$ and $R^{19}$ are independently hydrogen or lower unsubstituted alkyl, more preferably $R^5$ is 2-[(diethylamino)-2-hydroxyethyl] aminocarbonyl, 2-(N-ethyl-N-2-hydroxyethylamino) ethylaminocarbonyl, carboxymethylamino-carbonyl, or 2-(2-hydroxyethylamino)ethylamino-carbonyl.

(11) Yet another preferred group of compounds of Formula (I) is that wherein $R^6$ is —$COR^{10}$ wherein $R^{10}$ is —$NR^{13}R^{14}$ wherein $R^{13}$ is hydrogen and $R^{14}$ is lower alkyl substituted with hydroxy, lower alkyl substituted with hydroxyalkylamino, carboxy, or —$NR^{18}R^{19}$ wherein $R^{18}$ and $R^{19}$ are independently hydrogen or lower unsubstituted alkyl; more preferably $R^6$ is [2-(diethylamino)-2-hydroxy]ethylaminocarbonyl, 2-(N-ethyl-N-2-hydroxyethyl-amino) ethylaminocarbonyl, carboxymethylaminocarbonyl, or 2-(2-hydroxyethylamino)ethylamino-carbonyl.

(12) Yet another preferred group of compounds of Formula (I) is that wherein $R^5$ is —$COR^{10}$ wherein $R^{10}$ is —$NR^{11}(CH_2)_nR^{12}$ wherein $R^{12}$ is —$N^+(O^-)NR^{13}R^{14}$ or —$N(OH)R^{13}$ wherein $R^{13}$ and $R^{14}$ are independently selected from the group consisting of hydrogen and unsubstituted lower alkyl, preferably $R^5$ is 2-(N-hydroxy-N-ethylamino)-ethylaminocarbonyl or 2-[$N^+(O^-)(C_2H_5)_2$]ethyl-aminocarbonyl

(13) Yet another preferred group of compounds of Formula (I) is that wherein $R^6$ is —$COR^{10}$ wherein $R^{10}$ is —$NR^{11}(CH_2)_nR^{12}$ wherein $R^{12}$ is —$N^+(O^-)NR^{13}R^{14}$ or —$N(OH)R^{13}$ wherein $R^{13}$ and $R^{14}$ are independently selected from the group consisting of hydrogen and unsubstituted lower alkyl, preferably $R^6$ is 2-(N-hydroxy-N-ethylamino)ethylaminocarbonyl or 2-[$N^+(O^-)(C_2H_5)_2$]ethylaminocarbonyl.

(14) In the above preferred groups (6)-(13) when $R^5$ is —$COR^{10}$, then a more preferred group of compounds is that wherein:
$R^6$ is selected from the group consisting of hydrogen and alkyl, preferably hydrogen, methyl, ethyl, isopropyl, tert-butyl, isobutyl, or n-butyl, more preferably hydrogen or methyl; and
$R^7$ is selected from the group consisting of hydrogen, alkyl, aryl, heteroaryl, and —$C(O)R^{17}$ wherein $R^{17}$ is hydroxy, alkyl or aryl, more preferably hydrogen, methyl, ethyl, isopropyl, n-, iso or tert-butyl, phenyl, benzoyl, acetyl or carboxy, even more preferably methyl, hydrogen or phenyl.

(15) In the above preferred groups (6)-(13) when $R^5$ is —$COR^{10}$, then another more preferred group of compounds is that wherein $R^6$ and $R^7$ combine to form —$(CH_2)_4$—.

(16) In the above preferred groups (6)-(13) when $R^6$ is —$COR^{10}$, then a more preferred group of compounds is that wherein:
$R^5$ is selected from the group consisting of hydrogen and alkyl, preferably hydrogen, methyl, ethyl, isopropyl, tert-butyl, isobutyl, or n-butyl, more preferably hydrogen or methyl; and
$R^7$ is selected from the group consisting of hydrogen, alkyl, aryl, heteroaryl, and —$C(O)R^{17}$, wherein $R^{17}$ is hydroxy, alkyl or aryl, more preferably hydrogen, methyl, ethyl, isopropyl, n-, iso or tert-butyl, phenyl, benzoyl, acetyl or carboxy, even more preferably methyl, hydrogen or phenyl.

(17) Within the above preferred and more preferred groups (6)-(16), an even more preferred group of compounds is that wherein:
$R^1$ is hydrogen, alkyl, —$C(O)NR^8R^9$, unsubstituted cycloalkyl or aryl, preferably hydrogen, phenyl, 3,4-dimethoxyphenylaminocarbonyl, 4-methoxy-3-chlorophenylaminocarbonyl, even more preferably hydrogen or methyl, most preferably hydrogen;
$R^2$ is cyano, hydrogen, halo, lower alkoxy, aryl or —$S(O)_2NR^{13}R^{14}$ wherein $R^{13}$ is hydrogen and $R^{14}$ is hydrogen, aryl or alkyl, preferably $R^2$ is hydrogen, chloro, bromo, fluoro, methoxy, ethoxy, phenyl, dimethylaminosulfonyl, 3-chlorophenyl-aminosulfonyl, carboxy, methoxy, aminosulfonyl, methylaminosulfonyl, phenylaminosulfonyl, pyridin-3-yl-aminosulfonyl, dimethylaminosulfonyl, isopropylamino-sulfonyl, more preferably hydrogen, fluoro, or bromo;
$R^3$ is selected from the group consisting of hydrogen, lower alkoxy, —$C(O)R^{15}$, —$NR^{13}C(O)R^{14}$, aryl preferably aryl optionally substituted with one or two substitutents selected from the group consisting of lower alkyl, halo, or lower alkoxy, and heteroaryl, preferably heteroaryl optionally substituted with one or two substitutents selected from the group consisting of lower alkyl, halo, or lower alkoxy, preferably hydrogen, methoxy, carboxy, phenyl, pyridin-3-yl, 3,4-dichlorophenyl, 2-methoxy-5-isopropylphenyl, 4-n-butylphenyl, 3-isopropylphenyl, more preferably hydrogen or phenyl; and
$R^4$ is hydrogen.

(18) Another more preferred group of compounds of Formula (I) is that wherein:
$R^1$ is hydrogen, alkyl, —$C(O)NR^8R^9$, unsubstituted cycloalkyl or aryl, preferably hydrogen, 3,4-dimethoxyphenyl-aminocarbonyl, 4-methoxy-3-chlorophenylaminocarbonyl, even more preferably hydrogen or methyl, particularly hydrogen;
$R^2$ is cyano, hydrogen, halo, lower alkoxy, aryl or —$S(O)_2NR^{13}R^{14}$ wherein $R^{13}$ is hydrogen and $R^{14}$ is hydrogen, aryl or alkyl, preferably $R^2$ is hydrogen, chloro, bromo, fluoro, methoxy, ethoxy, phenyl, dimethylaminosulfonyl, 3-chlorophenyl-aminosulfonyl, carboxy, methoxy, aminosulfonyl, methylaminosulfonyl, phenylaminosulfonyl, pyridin-3-yl-aminosulfonyl, dimethylaminosulfonyl, isopropylamino-sulfonyl, more preferably hydrogen, fluoro, or bromo;
$R^3$ is selected from the group consisting of hydrogen, lower alkoxy, —$C(O)R^{15}$, —$NR^{13}C(O)R^{14}$, aryl preferably aryl optionally substituted with one or two substitutents selected from the group consisting of lower alkyl, halo, or lower alkoxy, and heteroaryl, preferably heteroaryl optionally substituted with one or two substitutents selected from the group consisting of lower alkyl, halo, or lower alkoxy, preferably hydrogen, methoxy, carboxy, phenyl, pyridin-3-yl, 3,4-dichlorophenyl, 2-methoxy-5-isopropylphenyl, 4-n-butylphenyl, 3-isopropylphenyl, more preferably hydrogen or phenyl; and $R^4$ is hydrogen.

Within the above preferred group (18) a more preferred group of compounds is wherein:

$R^5$ is —$COR^{10}$ where $R^{10}$ is as defined in the Summary of the Invention, preferably —$NR^{11}(CH_2)_nR^{12}$ or —$NR^{13}R^{14}$ as defined in the Summary of the Invention.

$R^6$ is selected from the group consisting of hydrogen and alkyl, preferably hydrogen, methyl, ethyl, isopropyl, tert-butyl, isobutyl, or n-butyl, more preferably hydrogen or methyl; and $R^7$ is selected from the group consisting of hydrogen, alkyl, aryl, heteroaryl, and —$C(O)R^{17}$ wherein $R^{17}$ is hydroxy, alkyl or aryl, more preferably hydrogen, methyl, ethyl, isopropyl, n-, iso or tert-butyl, phenyl, benzoyl, acetyl or carboxy, even more preferably methyl, hydrogen or phenyl.

In the above preferred group (18) another more preferred group of compounds is that wherein:

$R^6$ is —$COR^{10}$ where $R^{10}$ is as defined in the Summary of the Invention, preferably —$NR^{11}(CH_2)_nR^{12}$ or —$NR^{13}R^{14}$ as defined in the Summary of the Invention.

$R^5$ is selected from the group consisting of hydrogen and alkyl, preferably hydrogen, methyl, ethyl, isopropyl, tert-butyl, isobutyl, or n-butyl, more preferably hydrogen or methyl; and $R^7$ is selected from the group consisting of hydrogen, alkyl, aryl, heteroaryl, and —$C(O)R^{17}$ wherein $R^{17}$ is hydroxy, alkyl or aryl, more preferably hydrogen, methyl, ethyl, isopropyl, n-, iso or tert-butyl, phenyl, benzoyl, acetyl or carboxy, even more preferably methyl, hydrogen or phenyl.

(19) Another more preferred group of compounds of Formula (I) is that wherein:

$R^1$ and $R^4$ are hydrogen;

$R^2$ is selected from the group consisting of hydrogen, halo, lower alkoxy, —$C(O)R^{15}$ and —$S(O)_2NR^{13}R^{14}$;

$R^3$ is selected from the group consisting of hydrogen, lower alkoxy, —$C(O)R^{15}$, —$S(O)_2NR^{13}R^{14}$, aryl and heteroaryl;

$R^5$ is —$C(O)R^{10}$;

$R^6$ is selected from the group consisting of hydrogen and lower alkyl; and $R^7$ is selected from the group consisting of hydrogen, lower alkyl and —$C(O)R^{17}$.

It is another presently preferred embodiment of this invention that, in a compound having a structure as described in (15):

$R^{10}$ is selected from the group consisting of hydroxy, lower alkoxy and —$NR^{11}(CH_2)_nR^{12}$, wherein n is 2 or 3;

$R^{11}$ is selected from the group consisting of hydrogen, and lower alkyl; and, $R^{12}$ is selected from the group consisting of aryl and —$NR^{13}R^{14}$.

It is a further presently preferred embodiment of this invention that, in a compound having a structure as described in the previous two paragraphs, $R^{13}$ and $R^{14}$ are independently selected from the group consisting of hydrogen, lower alkyl, and, combined, —$(CH_2)_4$—, —$(CH_2)_5$—, —$CH_2)_2O(CH_2)_2$— or —$(CH_2)_2N(CH_3)(CH_2)_2$—.

(20) Another presently preferred embodiment of this invention is a compound in which:

$R^1$ is selected from the group consisting of hydrogen, lower alkyl, —$(CH_2)_rR^{16}$ and —$C(O)NR^8R^9$;

$R^2$ is selected from the group consisting of hydrogen, halogen, aryl and —$S(O)_2NR^{13}R^{14}$;

$R^3$ is selected from the group consisting of hydrogen, lower alkyl, lower alkoxy, aryl, heteroaryl and —$C(O)R^{15}$;

$R^4$ is hydrogen;

$R^5$ is selected from the group consisting of hydrogen and lower alkyl;

$R^6$ is —$C(O)R^{10}$;

$R^7$ is selected from the group consisting of hydrogen, lower alkyl and aryl;

$R^{16}$ is selected from the group consisting of hydroxy and —$C(O)R^{15}$; and, r is 2 or 3.

A presently preferred embodiment of this invention is a compound having as structure described in the paragraph just above in which $R^3$ is aryl optionally substituted with one or more groups selected from the group consisting of lower alkyl, lower alkoxy and halo.

(21) Likewise, it is a presently preferred embodiment of this invention that, in a compound in which:

$R^1$ is selected from the group consisting of hydrogen, lower alkyl, —$(CH_2)_rR^{16}$ and —$C(O)NR^8R^9$;

$R^2$ is selected from the group consisting of hydrogen, halogen, aryl and —$S(O)_2NR^{13}R^{14}$;

$R^3$ is selected from the group consisting of hydrogen, lower alkyl, lower alkoxy, aryl, heteroaryl and —$C(O)R^{15}$;

$R^4$ is hydrogen;

$R^5$ is selected from the group consisting of hydrogen and lower alkyl;

$R^6$ is —$C(O)R^{10}$;

$R^7$ is selected from the group consisting of hydorgen, lower alkyl and aryl;

$R^{16}$ is selected from the group consisting of hydroxy and —$C(O)R^{15}$; and, r is 2 or 3, $R^{10}$ is selected from the group consisting of hydroxy, lower alkoxy, —$NR^{13}R^{14}$ and —$NR^{11}(CH_2)_nR^2$, wherein n is 1, 2 or 3, $R^{11}$ is hydrogen and $R^{12}$ is selected from the group consisting of hydroxy, lower alkoxy, —$C(O)R^{15}$, heteroaryl and —$NR^{13}R^{14}$.

(22) A further presently preferred embodiment of this invention is a compound having a structure as described in the paragraph immediately above in which $R^{13}$ and $R^{14}$ are independently selected from the group consisting of hydrogen, lower alkyl, heteroaryl and, combined, —$(CH_2)_4$—, —$(CH_2)_5$—, —$(CH_2)_2O(CH_2)_2$—, or —$(CH_2)_2N(CH_3)(CH_2)_2$—.

(23) Another presently preferred embodiment of this invention is a compound in which:

$R^1$ is —$C(O)NR^8R^9$, wherein $R^8$ is hydrogen and $R^9$ is aryl optionally substituted with one or more groups selected from the group consisting of halo, hydroxy and lower alkoxy;

$R^2$ is selected from the group consisting of hydrogen, halogen, aryl and —$S(O)_2NR^{13}R^{14}$;

$R^3$ is selected from the group consisting of hydrogen, lower alkyl, lower alkoxy, aryl, heteroaryl and —$C(O)R^{15}$;

$R^4$ is hydrogen;

$R^5$ is selected from the group consisting of hydrogen and lower alkyl;

$R^6$ is —$C(O)R^{10}$;

$R^7$ is selected from the group consisting of hydrogen, lower alkyl and aryl;

$R^{16}$ is selected from the group consisting of hydroxy and —C(O)$R^5$; and, r is 2 or 3,

(24) A still further presently preferred embodiment of this invention is a compound in which:

$R^1$ is selected from the group consisting of hydrogen and lower alkyl;

$R^2$ is selected from the group consisting of hydrogen, halo, lower alkoxy, aryl, —C(O)$R^{15}$ and —S(O)$_2$N$R^{13}R^{14}$;

$R^3$ is selected from the group consisting of hydrogen, halo, aryl, heteroaryl and —C(O)$R^5$;

$R^4$ is hydrogen;

$R^5$ is —C(O)$R^{10}$; and, $R^6$ and $R^7$ combine to form a —(CH$_2$)$_4$— group.

In a compound having a structure as described in the paragraph immediately above, it is a presently preferred embodiment that $R^{10}$ is selected from the group consisting of hydroxy, alkoxy, —N$R^{13}R^{14}$ and —NH(CH$_2$)$_n$N$R^{13}R^{14}$ wherein n is 2 or 3.

It is a presently preferred embodiment of this invention that, in a compound having a structure as described in the two paragraphs immediately above, $R^{13}$ and $R^{14}$ are independently selected from the group consisting of hydrogen, lower alkyl, and, combined, —(CH$_2$)$_4$—, —(CH$_2$)$_5$—, —(CH$_2$) 20 (CH$_2$)$_2$— or —(CH$_2$)$_2$N(CH$_3$)(CH$_2$)$_2$—.

Utility

The PKs whose catalytic activity is modulated by the compounds of this invention include protein tyrosine kinases of which there are two types, receptor tyrosine kinases (RTKs) and cellular tyrosine kinases (CTKs), and serine-threonine kinases (STKs). RTK mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects on the extracellular microenvironment, etc.). See, Schlessinger and Ullrich, 1992, *Neuron* 9:303-391.

It has been shown that tyrosine phosphorylation sites on growth factor receptors function as high-affinity binding sites for SH2 (src homology) domains of signaling molecules. Fantl et al., 1992, *Cell* 69:413-423, Songyang et al., 1994, *Mol. Cell. Biol.* 14:2777-2785), Songyang et al., 1993, *Cell* 72:767-778, and Koch et al., 1991, *Science* 252:668-678. Several intracellular substrate proteins that associate with RTKs have been identified. They may be divided into two principal groups: (1) substrates that have a catalytic domain, and (2) substrates which lack such domain but which serve as adapters and associate with catalytically active molecules. Songyang et al., 1993, *Cell* 72:767-778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, *Cell* 72:767-778. These observations suggest that the function of each RTK is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

STKs, being primarily cytosolic, affect the internal biochemistry of the cell, often as a down-line response to a PTK event. STKs have been implicated in the signaling process which initiates DNA synthesis and subsequent mitosis leading to cell proliferation.

Thus, PK signal transduction results in, among other responses, cell proliferation, differentiation, growth and metabolism. Abnormal cell proliferation may result in a wide array of disorders and diseases, including the development of neoplasia such as carcinoma, sarcoma, glioblastoma and hemangioma, disorders such as leukemia, psoriasis, arteriosclerosis, arthritis and diabetic retinopathy and other disorders related to uncontrolled angiogenesis and/or vasculogenesis.

A precise understanding of the mechanism by which the compounds of this invention inhibit PKs is not required in order to practice the present invention. However, while not hereby being bound to any particular mechanism or theory, it is believed that the compounds interact with the amino acids in the catalytic region of PKs. PKs typically possess a bi-lobate structure wherein ATP appears to bind in the cleft between the two lobes in a region where the amino acids are conserved among PKs. Inhibitors of PKs are believed to bind by non-covalent interactions such as hydrogen bonding, van der Waals forces and ionic interactions in the same general region where the aforesaid ATP binds to the PKs. More specifically, it is thought that the 2-indolinone component of the compounds of this invention binds in the general space normally occupied by the adenine ring of ATP. Specificity of a particular molecule for a particular PK may then arise as the result of additional interactions between the various substituents on the 2-indolinone core and the amino acid domains specific to particular PKs. Thus, different indolinone substituents may contribute to preferential binding to particular PKs. The ability to select compounds active at different ATP (or other nucleotide) binding sites makes the compounds of this invention useful for targeting any protein with such a site. The compounds disclosed herein thus have utility in in vitro assays for such proteins as well as exhibiting in vivo therapeutic effects through interaction with such proteins.

Additionally, the compounds of the present invention provide a therapeutic approach to the treatment of many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia are also contemplated by this invention. Indications may include, but are not limited to brain cancers, bladder cancers, ovarian cancers, gastric cancers, pancreas cancers, colon cancers, blood cancers, lung cancers and bone cancers.

Further examples, without limitation, of the types of disorders related to inappropriate PK activity that the compounds described herein may be useful in preventing, treating and studying, are cell proliferative disorders, fibrotic disorders and metabolic disorders.

Cell proliferative disorders, which, may be prevented, treated or further studied by the present invention include cancer, blood vessel proliferative disorders and mesangial cell proliferative disorders.

Blood vessel proliferative disorders refer to disorders related to abnormal vasculogenesis (blood vessel formation) and angiogenesis (spreading of blood vessels). While vasculogenesis and angiogenesis play important roles in a variety of normal physiological processes such as embryonic development, corpus luteum formation, wound healing and organ regeneration, they also play a pivotal role in cancer development where they result in the formation of new capillaries needed to keep a tumor alive. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness.

Two structurally related RTKs have been identified to bind VEGF with high affinity: the fms-like tyrosine 1 (flt-1) receptor (Shibuya et al., 1990, Oncogene, 5:519-524; De Vries et al., 1992, Science, 255:989-991) and the KDR/FLK-1 receptor, also known as VEGF-R2. Vascular endothelial growth factor (VEGF) has been reported to be an endothelial cell specific mitogen with in vitro endothelial cell growth promoting activity. Ferrara & Henzel, 1989, Biochem. Biophys. Res. Comm., 161:851-858; Vaisman et al., 1990, J. Biol. Chem., 265:19461-19566. Information set forth in U.S. application Ser. Nos. 08/193,829, 08/038,596 and 07/975,750, strongly suggest that VEGF is not only responsible for endothelial cell proliferation, but also is the prime regulator of normal and pathological angiogenesis. See generally, Klagsburn & Soker, 1993, Current Biology, 3(10)699-702; Houck, et al., 1992, J. Biol. Chem., 267:26031-26037.

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, 1992, J. Biological Chem., 267(16):10931-34. Uncontrolled vasculogenesis and/or angiogenesis has been associated with diseases such as diabetes as well as with malignant solid tumors that rely on vascularization for growth. Klagsburn & Soker, 1993, Current Biology, 3(10):699-702; Folkham, 1991, J. Natl. Cancer Inst., 82:4-6; Weidner, et al., 1991, New Engl. J. Med., 324: 1-5.

The surmised role of VEGF in endothelial cell proliferation and migration during angiogenesis and vasculogenesis indicates an important role for the KDR/FLK-1 receptor in these processes. Diseases such as diabetes mellitus (Folkman, 198, in XIth Congress of Thrombosis and Haemostasis (Verstraeta, et al., eds.), pp. 583-596, Leuven University Press, Leuven) and arthritis, as well as malignant tumor growth may result from uncontrolled angiogenesis. See e.g., Folkman, 1971, N. Engl. J. Med., 285:1182-1186. The receptors to which VEGF specifically binds are an important and powerful therapeutic target for the regulation and modulation of vasculogenesis and/or angiogenesis and a variety of severe diseases which involve abnormal cellular growth caused by such processes. Plowman, et al., 1994, DN&P, 7(6):334-339. More particularly, the KDR/FLK-1 receptor's highly specific role in neovascularization make it a choice target for therapeutic approaches to the treatment of cancer and other diseases which involve the uncontrolled formation of blood vessels.

Thus, the present invention provides compounds capable of regulating and/or modulating tyrosine kinase signal transduction including KDR/FLK-1 receptor signal transduction in order to inhibit or promote angiogenesis and/or vasculogenesis, that is, compounds that inhibit, prevent, or interfere with the signal transduced by KDR/FLK-1 when activated by ligands such as VEGF. Although it is believed that the compounds of the present invention act on a receptor or other component along the tyrosine kinase signal transduction pathway, they may also act directly on the tumor cells that result from uncontrolled angiogenesis.

Although the nomenclature of the human and murine counterparts of the generic "flk-I" receptor differ, they are, in many respects, interchangeable. The murine receptor, Flk-1, and its human counterpart, KDR, share a sequence homology of 93.4% within the intracellular domain. Likewise, murine FLK-I binds human VEGF with the same affinity as mouse VEGF, and accordingly, is activated by the ligand derived from either species. Millauer et al., 1993, Cell, 72:835-846; Quinn et al., 1993, Proc. Natl. Acad. Sci. USA, 90:7533-7537. FLK-1 also associates with and subsequently tyrosine phosphorylates human RTK substrates (e.g., PLC-γ or p85) when co-expressed in 293 cells (human embryonal kidney fibroblasts).

Models which rely upon the FLK-1 receptor therefore are directly applicable to understanding the KDR receptor. For example, use of the murine FLK-1 receptor in methods which identify compounds that regulate the murine signal transduction pathway are directly applicable to the identification of compounds which may be used to regulate the human signal transduction pathway, that is, which regulate activity related to the KDR receptor. Thus, chemical compounds identified as inhibitors of KDR/FLK-1 in vitro, can be confirmed in suitable in vivo models. Both in vivo mouse and rat animal models have been demonstrated to be of excellent value for the examination of the clinical potential of agents acting on the KDR/FLK-1 induced signal transduction pathway.

Thus, the present invention provides compounds that regulate, modulate and/or inhibit vasculogenesis and/or angiogenesis by affecting the enzymatic activity of the KDR/FLK-1 receptor and interfering with the signal transduced by KDR/FLK-1. Thus the present invention provides a therapeutic approach to the treatment of many kinds of solid tumors including, but not limited to, glioblastoma, melanoma and Kaposi's sarcoma, and ovarian, lung, mammary, prostate, pancreatic, colon and epidermoid carcinoma. In addition, data suggests the administration of compounds which inhibit the KDR/Flk-1 mediated signal transduction pathway may also be used in the treatment of hemangioma, restenois and diabetic retinopathy.

Furthermore, this invention relates to the inhibition of vasculogenesis and angiogenesis by other receptor-mediated pathways, including the pathway comprising the flt-1 receptor.

Receptor tyrosine kinase mediated signal transduction is initiated by extracellular interaction with a specific growth factor (ligand), followed by receptor dimerization, transient stimulation of the intrinsic protein tyrosine kinase activity and autophosphorylation. Binding sites are thereby created for intracellular signal transduction molecules which leads to the formation of complexes with a spectrum of cytoplasmic signalling molecules that facilitate the appropriate cellular response, e.g., cell division and metabolic effects to the extracellular microenvironment. See, Schlessinger and Ullrich, 1992, Neuron, 9:1-20.

The close homology of the intracellular regions of KDR/FLK-1 with that of the PDGF-β receptor (50.3% homology) and/or the related flt-1 receptor indicates the induction of overlapping signal transduction pathways. For example, for the PDGF-β receptor, members of the src family (Twamley et al., 1993, Proc. Natl. Acad. Sci. USA, 90:7696-7700), phosphatidylinositol-3'-kinase (Hu et al., 1992, Mol. Cell. Biol., 12:981-990), phospholipase cγ (Kashishian & Cooper, 1993, Mol. Cell. Biol., 4:49-51), ras-GTPase-activating protein, (Kashishian et al., 1992, EMBO J., 11:1373-1382), PTP-ID/syp (Kazlauskas et al., 1993, Proc. Natl. Acad. Sci. USA, 10

90:6939-6943), Grb2 (Arvidsson et al., 1994, *Mol. Cell. Biol.*, 14:6715-6726), and the adapter molecules Shc and Nck (Nishimura et al., 1993, *Mol. Cell. Biol.*, 13:6889-6896), have been shown to bind to regions involving different autophosphorylation sites. See generally, Claesson-Welsh, 1994, *Prog. Growth Factor Res.*, 5:37-54. Thus, it is likely that signal transduction pathways activated by KDR/FLK-1 include the ras pathway (Rozakis et al., 1992, *Nature*, 360:689-692), the PI-3'-kinase, the src-mediated and the plcγ-mediated pathways. Each of these pathways may play a critical role in the angiogenic and/or vasculogenic effect of KDR/FLK-1 in endothelial cells. Consequently, a still further aspect of this invention relates to the use of the organic compounds described herein to modulate angiogenesis and vasculogenesis as such processes are controlled by these pathways.

Conversely, disorders related to the shrinkage, contraction or closing of blood vessels, such as restenosis, are also implicated and may be treated or prevented by the methods of this invention.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. An increased extracellular matrix resulting in a hepatic scar can also be caused by a viral infection such as hepatitis. Lipocytes appear to play a major role in hepatic cirrhosis. Other fibrotic disorders implicated include atherosclerosis.

Mesangial cell proliferative disorders refer to disorders brought about by abnormal proliferation of mesangial cells. Mesangial proliferative disorders include various human renal diseases such as glomerulonephritis, diabetic nephropathy and malignant nephrosclerosis as well as such disorders as thrombotic microangiopathy syndromes, transplant rejection, and glomerulopathies. The RTK PDGFR has been implicated in the maintenance of mesangial cell proliferation. Floege et al., 1993, *Kidney International* 43:47S-54S.

Many cancers are cell proliferative disorders and, as noted previously, PKs have been associated with cell proliferative disorders. Thus, it is not surprising that PKs such as, for example, members of the RTK family have been associated with the development of cancer. Some of these receptors, like EGFR (Tuzi et al., 1991, *Br. J. Cancer* 63:227-233, Torp et al., 1992, *APMIS* 100:713-719) HER2/neu (Slamon et al., 1989, *Science* 244:707-712) and PDGF-R (Kumabe et al., 1992, *Oncogene*, 7:627-633) are over-expressed in many tumors and/or persistently activated by autocrine loops. In fact, in the most common and severe cancers these receptor over-expressions (Akbasak and Suner-Akbasak et al., 1992, *J. Neurol. Sci.*, 111:119-133, Dickson et al., 1992, *Cancer Treatment Res.* 61:249-273, Korc et al., 1992, *J. Clin. Invest.* 90:1352-1360) and autocrine loops (Lee and Donoghue, 1992, *J. Cell. Biol.*, 118:1057-1070, Korc et al., supra, Akbasak and Suner-Akbasak et al., supra) have been demonstrated. For example, EGFR has been associated with squamous cell carcinoma, astrocytoma, glioblastoma, head and neck cancer, lung cancer and bladder cancer. HER2 has been associated with breast, ovarian, gastric, lung, pancreas and bladder cancer. PDGFR has been associated with glioblastoma and melanoma as well as lung, ovarian and prostate cancer. The RTK c-met has also been associated with malignant tumor formation. For example, c-met has been associated with, among other cancers, colorectal, thyroid, pancreatic, gastric and hepatocellular carcinomas and lymphomas. Additionally c-met has been linked to leukemia. Over-expression of the c-met gene has also been detected in patients with Hodgkins disease and Burkitts disease.

IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., 1989, *J. Clin. Invest.* 84:1418-1423) and small lung tumor cells (Macauley et al., 1990, *Cancer Res.*, 50:2511-2517). In addition, IGF-I, while integrally involved in the normal growth and differentiation of the nervous system, also appears to be an autocrine stimulator of human gliomas. Sandberg-Nordqvist et al., 1993, *Cancer Res.* 53:2475-2478. The importance of IGF-IR and its ligands in cell proliferation is further supported by the fact that many cell types in culture (fibroblasts, epithelial cells, smooth muscle cells, T-lymphocytes, myeloid cells, chondrocytes and osteoblasts (the stem cells of the bone marrow)) are stimulated to grow by IGF-I. Goldring and Goldring, 1991, *Eukaryotic Gene Expression*, 1:301-326. Baserga and Coppola suggest that IGF-IR plays a central role in the mechanism of transformation and, as such, could be a preferred target for therapeutic interventions for a broad spectrum of human malignancies. Baserga, 1995, *Cancer Res.*, 55:249-252, Baserga, 1994, *Cell* 79:927-930, Coppola et al., 1994, *Mol. Cell. Biol.*, 14:4588-4595.

STKs have been implicated in many types of cancer including, notably, breast cancer (Cance, et al., *Int. J. Cancer*, 54:571-77 (1993)).

The association between abnormal PK activity and disease is not restricted to cancer. For example, RTKs have been associated with diseases such as psoriasis, diabetes mellitus, endometriosis, angiogenesis, atheromatous plaque development, Alzheimer's disease, restenosis, von Hippel-Lindau disease, epidermal hyperproliferation, neurodegenerative diseases, age-related macular degeneration and hemangiomas. For example, EGFR has been indicated in corneal and dermal wound healing. Defects in Insulin-R and IGF-1R are indicated in type-II diabetes mellitus. A more complete correlation between specific RTKs and their therapeutic indications is set forth in Plowman et al., 1994, *DN&P* 7:334-339.

As noted previously, not only RTKs but CTKs including, but not limited to, src, abl, fps, yes, fyn, lyn, lck, blk, hck, fgr and yrk (reviewed by Bolen et al., 1992, *FASEB J.*, 6:3403-3409) are involved in the proliferative and metabolic signal transduction pathway and thus could be expected, and have been shown, to be involved in many PTK-mediated disorders to which the present invention is directed. For example, mutated src (v-src) has been shown to be an oncoprotein ($pp60^{v-src}$) in chicken. Moreover, its cellular homolog, the proto-oncogene $pp60^{c-src}$ transmits oncogenic signals of many receptors. Over-expression of EGFR or HER2/neu in tumors leads to the constitutive activation of $pp60^{c-src}$, which is characteristic of malignant cells but absent in normal cells. On the other hand, mice deficient in the expression of c-src exhibit an osteopetrotic phenotype, indicating a key participation of c-src in osteoclast function and a possible involvement in related disorders.

Similarly, Zap70 has been implicated in T-cell signaling which may relate to autoimmune disorders.

STKs have been associated with inflamation, autoimmune disease, immunoresponses, and hyperproliferation disorders such as restenosis, fibrosis, psoriasis, osteoarthritis and rheumatoid arthritis.

PKs have also been implicated in embryo implantation. Thus, the compounds of this invention may provide an effective method of preventing such embryo implantation and thereby be useful as birth control agents. Additional disorders which may be treated or prevented using the compounds of this invention are immunological disorders such as autoimmune disease, AIDS and cardiovasular disorders such as atherosclerosis.

Finally, both RTKs and CTKs are currently suspected as being involved in hyperimmune disorders.

Examples of the effect of a number of exemplary compounds of this invention on several PTKs are shown in Table 2 below.

The compounds and data presented are not to be construed as limiting the scope of this invention in any manner whatsoever.

Administration and Pharmaceutical Composition

A compound of the present invention or a phearmaceutically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

As used herein, "administer" or "administration" refers to the delivery of a compound of Formula (I) or a pharmaceutically acceptable salt thereof or of a pharmaceutical composition containing a compound of Formula (I) or a pharmaceutically acceptable salt thereof of this invention to an organism for the purpose of prevention or treatment of a PK-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

Pharmaceutical compositions which may also be used include hard gelatin capsules. As a non-limiting example, the active compound capsule oral drug product formulation may be as 50 and 200 mg dose strengths (formulation codes J-011248-AA-00 and J-011248-AA-01, respectively). The two dose strengths are made from the same granules by filling into different size hard gelatin capsules, size 3 for the 50 mg capsule and size 0 for the 200 mg capsule. The composition of the formulation may be, for example, as indicated in Table 2.

TABLE 2

| Ingredient Name/Grade | Concentration in Granulation (% w/w) | Amount in 50 mg Capsule (mg) | Amount in 200 mg Capsule (mg) |
|---|---|---|---|
| Formulation Code | J-011248-AA | J-011248-AA-00 | J-011248-AA-01 |
| Active Compound NF | 65.0 | 50.0 | 200.0 |
| Mannitol NF | 23.5 | 18.1 | 72.4 |
| Croscarmellose sodium NF | 6.0 | 4.6 | 18.4 |
| Povidone K 30 NF | 5.0 | 3.8 | 15.2 |
| Magnesium stearate NF | 0.5 | 0.38 | 1.52 |
| Capsule, Swedish yellow NF |  | Size 3 | Size 0 |

The capsules may be packaged into brown glass or plastic bottles to protect the active compound from light. The containers containing the active compound capsule formulation must be stored at controlled room temperature (15-30° C.).

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the fomulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharamcologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addtion, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide ($Ca(OH)_2$), etc.).

Pharmaceutical compositions suitable for use in the present invention include compositions wherein the active ingredients are contained in an amount sufficient to achieve the intended purpose, e.g., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

At present, the therapeutically effective amounts of compounds of Formula (I) may range from approximately 25 mg/m$^2$ to 1500 mg/m$^2$ per day; preferably about 3 mg/m$^2$/day. Even more preferably 50 mg/qm qd till 400 mg/qd.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

It is also an aspect of this invention that a compound described herein, or its salt or prodrug, might be combined with other chemotherapeutic agents for the treatment of the diseases and disorders discussed above. For instance, a compound, salt or prodrug of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma); estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

A compound, salt or prodrug of this invention can also be used in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

It is contemplated that a compound, salt or prodrug of this invention can also be used in combination with natural product based chemotherapeutic agents such as, without limitation, the vinca alkaloids, e.g., vinblastin (used in the treatment of breast and testicular cancer), vincristine and vindesine; the epipodophyloroxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound, salt or prodrug of this invention could also be used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors such as anastrozole.

Finally, it is also contemplated that the combination of a compound of this invention will be effective in combination with mitoxantrone or paclitaxel for the treatment of solid tumor cancers or leukemias such as, without limitation, acute myelogenous (non-lymphocytic) leukemia.

General Synthetic Procedure

The following general methodology may be employed to prepare the compounds of this invention:

The appropriately substituted 2-oxindole (1 equiv.), the appropriately substituted aldehyde (1.2 equiv.) and a base (0.1 equiv.) are mixed in a solvent (1-2 ml/mmol 2-oxindole) and the mixture is then heated for from about 2 to about 12 hours. After cooling, the precipitate that forms is filtered, washed with cold ethanol or ether and vacuum dried to give the solid product. If no precipitate forms, the reaction mixture is concentrated and the residue is triturated with dichloromethane/ether, the resulting solid is collected by filtration and then dried. The product may optionally be further purified by chromatography.

The base may be an organic or an inorganic base. If an organic base is used, preferably it is a nitrogen base. Examples of organic nitrogen bases include, but are not limited to, diisopropylamine, trimethylamine, triethylamine, aniline, pyridine, 1,8-diazabicyclo[5.4.1]undec-7-ene, pyrrolidine and piperidine.

Examples of inorganic bases are, without limitation, ammonia, alkali metal or alkaline earth hydroxides, phosphates, carbonates, bicarbonates, bisulfates and amides. The alkali metals include, lithium, sodium and potassium while the alkaline earths include calcium, magnesium and barium.

In a presently preferred embodiment of this invention, when the solvent is a protic solvent, such as water or alcohol, the base is an alkali metal or an alkaline earth inorganic base, preferably, a alkali metal or an alkaline earth hydroxide.

It will be clear to those skilled in the art, based both on known general principles of organic synthesis and on the disclosures herein which base would be most appropriate for the reaction contemplated.

The solvent in which the reaction is carried out may be a protic or an aprotic solvent, preferably it is a protic solvent. A "protic solvent" is a solvent which has hydrogen atom(s) covalently bonded to oxygen or nitrogen atoms which renders the hydrogen atoms appreciably acidic and thus capable of being "shared" with a solute through hydrogen bonding. Examples of protic solvents include, without limitation, water and alcohols.

An "aprotic solvent" may be polar or non-polar but, in either case, does not contain acidic hydrogens and therefore is not capable of hydrogen bonding with solutes. Examples, without limitation, of non-polar aprotic solvents, are pentane, hexane, benzene, toluene, methylene chloride and carbon tetrachloride. Examples of polar aprotic solvents are chloroform, tetrahydrofuran, dimethylsulfoxide and dimethylformamide.

In a presently preferred embodiment of this invention, the solvent is a protic solvent, preferably water or an alcohol such as ethanol.

The reaction is carried out at temperatures greater than room temperature. The temperature is generally from about 30° C. to about 150° C., preferably about 80° C. to about 100° C., most preferable about 75° C. to about 85° C., which is about the boiling point of ethanol. By "about" is meant that the temperature range is preferably within 10 degrees Celcius of the indicated temperature, more preferably within 5 degrees Celcius of the indicated temperature and, most preferably, within 2 degrees Celcius of the indicated temperature. Thus, for example, by "about 75° C." is meant 75° C.±10° C., preferably 75° C.±5° C. and most preferably, 75° C.±2° C.

2-Oxindoles and aldehydes, may be readily synthesized using techniques well known in the chemical arts. It will be appreciated by those skilled in the art that other synthetic pathways for forming the compounds of the invention are available and that the following is offered by way of example and not limitation.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

Method A: Formylation of Pyrroles $POCl_3$ (1.1 equiv.) is added dropwise to dimethylformamide (3 equiv.) at −10° C. followed by addition of the appropriate pyrrole dissolved in dimethylformamide. After stirring for two hours, the reaction mixture is diluted with $H_2O$ and basified to pH 11 with 10 N KOH. The precipitate which forms is collected by filtration, washed with $H_2O$ and dried in a vacuum oven to give the desired aldehyde.

Method B: Saponification of Pyrrolecarboxylic Acid Esters

A mixture of a pyrrolecarboxylic acid ester and KOH (2-4 equiv.) in EtOH is refluxed until reaction completion is indicated by thin layer chromatography (TLC). The cooled reaction mixtrue is acidified to pH 3 with 1 N HCl. The precipitate which forms is collected by filtration, washed with $H_2O$ and dried in a vacuum oven to give the desired pyrrolecarboxylic acid.

Method C: Oxidation

To a stirred solution of a pyrrolecarboxylic acid dissolved in dimethylformamide (0.3M) is added 1-ethyl-3-(3-dimethylamino-propyl)carbodiimide (1.2 equiv.), 1-hydroxybenzotriazole (1.2 equiv.), and triethylamine (2 equiv.). The appropriate amine is added (1 equiv.) and the reaction stirred until completion is indicated by TLC. Ethyl acetate is then added to the reaction mixture and the solution washed with saturated $NaHCO_3$ and brine (with extra salt), dried over anhydrous $MgSO_4$ and concentrated to afford the desired amide.

Method D: Condensation of Aldehydes and Oxindoles Containing Carboxylic Acid Substituents A mixture of the oxindole (1 equivalent), 1 equivalent of the aldehyde and 1-3 equivalents of piperidine (or pyrrolidine) in ethanol (0.4 M) is stirred at 90-100° C. until reaction completion is indicated by TLC. The mixture is then concentrated and the residue acidified with 2N HCl. The precipitate that forms is washed with $H_2O$ and EtOH and then dried in a vacuum oven to give the product.

Method E: Condensation of Aldehydes and Oxindoles not Containing Carboxylic Acid Substituents A mixture of the oxindole (1 equivalent), 1 equivalent of the aldehyde and 1-3 equivalents of piperidine (or pyrrolidine) in ethanol (0.4 M) is stirred at 90-100° C. until reaction completion is indicated by TLC. The mixture is cooled to room temperature and the solid which forms is collected by vacuum filtration, washed with ethanol and dried to give the product. If a precipitate does not form upon cooling of the reaction mixture, the mixture is concentrated and purified by column chromatography.

C. Examples of Oxindole Syntheses

The following examples of the synthesis of representative oxindoles is not to be construed as limiting the scope of this invention in any manner whatsoever. Alternate routes to the oxindoles shown as well as other oxindoles to be used to make the compounds of this invention will become apparent to those skilled in the art based on the following disclosures. Such syntheses and oxindoles are within the scope and spirit of this invention.

5-Amino-2-oxindole

5-Nitro-2-oxindole (6.3 g) was hydrogenated in methanol over 10% palladium on carbon to give 3.0 g (60% yield) of the title compound as a white solid.

5-Bromo-2-oxindole

2-Oxindole (1.3 g) in 20 mL acetonitrile was cooled to −10° C. and 2.0 g N-bromosuccinimide was slowly added with stirring. The reaction was stirred for 1 hour at −10° C. and 2 hours at 0° C. The precipitate was collected, washed with water and dried to give 1.9 g (90% yield) of the title compound.

4-Methyl-2-oxindole

Diethyl oxalate (30 mL) in 20 mL of dry ether was added with stirring to 19 g of potassium ethoxide suspended in 50 mL of dry ether. The mixture was cooled in an ice bath and 20 mL of 3-nitro-o-xylene in 20 mL of dry ether was slowly added. The thick dark red mixture was heated to reflux for 0.5 hr, concentrated to a dark red solid, and treated with 10% sodium hydroxide until almost all of the solid dissolved. The dark red mixture was treated with 30% hydrogen peroxide until the red color changed to yellow. The mixture was treated alternately with 10% sodium hydroxide and 30% hydrogen peroxide until the dark red color was no longer present. The solid was filtered off and the filtrate acidified with 6N hydrochloric acid. The resulting precipitate was collected by vacuum filtration, washed with water, and dried under vacuum to give 9.8 g (45% yield) of 2-methyl-6-nitrophenylacetic acid as an off-white solid. The solid was hydrogenated in methanol over 10% palladium on carbon to give 9.04 g of the title compound as a white solid.

7-Bromo-5-chloro-2-oxindole

5-Chloro-2-oxindole (16.8 g) and 19.6 g of N-bromosuccinimide were suspended in 140 mL of acetonitrile and refluxed for 3 hours. Thin layer chromatography (silica, ethyl acetate) at 2 hours of reflux showed 5-chloro-2-oxindole or N-bromosuccinimide (Rf 0.8), product (Rf 0.85) and a second product (Rf 0.9) whose proportions did not change after another hour of reflux. The mixture was cooled to 10° C., the precipitate was collected by vacuum filtration, washed with 25 mL of ethanol and sucked dry for 20 minutes in the funnel to give 14.1 g of wet product (56% yield). The solid was suspended in 200 mL of denatured ethanol and slurry-washed by stirring and refluxing for 10 minutes. The mixture was cooled in an ice bath to 10° C. The solid product was collected by vacuum filtration, washed with 25 mL of ethanol and dried under vacuum at 40° C. to give 12.7 g (51% yield) of 7-bromo-5-chloro-2-oxindole.

5-Fluoro-2-oxindole

5-Fluoroisatin (8.2 g) was dissolved in 50 mL of hydrazine hydrate and refluxed for 1.0 hr. The reaction mixtures were then poured in ice water. The precipitate was then filtered, washed with water and dried in a vacuum oven to afford the title compound.

5-Nitro-2-oxindole

2-Oxindole (6.5 g) was dissolved in 25 mL concentrated sulfuric acid and the mixture maintained at −10 to −15° C. while 2.1 mL of fuming nitric acid was added dropwise. After the addition of the nitric acid the reaction mixture was stirred at 0° C. for 0.5 hr and poured into ice-water. The precipitate was collected by filtration, washed with water and crystallized from 50% acetic acid. The crystalline product was then filtered, washed with water and dried under vacuum to give 6.3 g (70%) of 5-nitro-2-oxindole.

5-Aminosulfonyl-2-oxindole

To a 100 mL flask charged with 27 mL of chlorosulfonic acid was added slowly 13.3 g of 2-oxindole. The reaction temperature was maintained below 30° C. during the addition. After the addition, the reaction mixture was stirred at room temperature for 1.5 hr, heated to 68° C. for 1 hr, cooled, and poured into water. The precipitate was washed with water and dried in a vacuum oven to give 11.0 g of 5-chlorosulfonyl-2-oxindole (50% yield) which was used without further purification.

5-Chlorosulfonyl-2-oxindole (2.1 g) was added to 10 mL of ammonium hydroxide in 10 mL of ethanol and stirred at room temperature overnight. The mixture was concentrated and the solid collected by vacuum filtration to give 0.4 g (20% yield) of the title compound as an off-white solid.

5-Isopropylaminosulfonyl-2-oxindole

To a 100 mL flask charged with 27 mL chlorosulfonic acid was slowly added 13.3 g 2-oxindole. The reaction temperature was maintained below 30° C. during the addition. The reaction mixture was stirred at room temperature for 1.5 hour, heated to 68° C. for 1 hour, cooled, and poured into water. The precipitate which formed was filtered, washed with water and dried in a vacuum oven to give 11.0 g (50%) of 5-chlorosulfonyl-2-oxindole which was used without further purification.

A suspension of 3 g 5-chlorosulfonyl-2-oxindole, 1.15 g isopropylamine and 1.2 mL of pyridine in 50 mL of dichloromethane was stirred at room temperature for 4 hours during which time a white solid formed. The solid was collected by vacuum filtration, slurry-washed with hot ethanol, cooled, collected by vacuum filtration and dried under vacuum at 40° C. overnight to give 1.5 g (45%) of 5-isopropylaminosulfonyl-2-oxindole.

$^1$HNMR (360 MHz, DMSO-d6) δ 10.69 (s, br, 1H, NH), 7.63 (dd, J=2 and 8 Hz, 1H), 7.59 (d, J=2 Hz, 1H), 7.32 (d, J=7 Hz, 1H, NH—$SO_2$—), 6.93 (d, J=8 Hz, 1H), 3.57 (s, 2H), 3.14-3.23 (m, 1H, CH—$(CH_3)_2$), 0.94 (d, J=7 Hz, 6H, 2×$CH_3$).

5-Phanylaminosulfonyl-2-oxindole

A suspension of 5-chlorosulfonyl-2-oxindole (1.62 g, 7 mmol), aniline (0.782 mL, 8.4 mmol) and pyridine (1 mL) in dichloromethane (20 ml) was stirred at room temperature for 4 hours. The reaction mixture was diluted with ethyl acetate (300 mL) and acidified with 1N hydrochloric acid (16 mL). The organic layer was washed with sodium bicarbonate and brine, dried and concentrated. The residue was washed with ethanol (3 mL) and then chromatographed on silica gel eluting with methanol/dichloromethane 1:9 to give of 5-phenylaminosulfonyl-2-oxindole.

$^1$HNMR (360 MHz, DMSO-d6) δ 10.71 (s, br, 1H, NH), 10.10 (s, br, 1H, NH), 7.57-7.61 (m, 2H), 7.17-7.22 (m, 2H), 7.06-7.09 (m, 2H), 6.97-7.0 (m, 1H), 6.88 (d, J=8.4 Hz, 1H), 3.52 (s, 2H).

2-Oxo-2,3-dihydro-1H-indole-5-sulfonic acid pyridin-3-ylamide

A solution of 5-chlorosufonyl-2-oxindole (3 g) and 3-aminopyridine (1.46 g) in pyridine (15 mL) was stirred at room temperature overnight at which time a brown solid was present. The solid was filtered, washed with ethanol and dried under vacuum to yield 1.4 g (38%) of 2-oxo-2,3-dihydro-1H-indole-5-sulfonic acid pyridin-3-ylamide.

$^1$HNMR (360 MHz, DMSO-d6) δ 10.74 (s, 1H, NH), 10.39 (s, 1H, SO$_2$NH), 8.27-8.28 (d, 1H), 8.21-8.23 (m, 1H), 7.59-7.62 (m, 2H), 7.44-7.68 (m, 1H), 7.24-7.28 (m, 1H), 6.69-6.71 (d, 1H), 3.54 (s, 2H). MS m/z (APCI+) 290.2.

5-Phenylonindole

5-Bromo-2-oxindole (5 g, 23.5 mmol) was dissolved in 110 mL toluene and 110 mL ethanol with stirring and a little heat. Tetrakis(triphenylphosphine)palladium(0) (1.9 g, 1.6 mmol) was added followed by 40 mL (80 mmol) 2M aqueous sodium carbonate. To this mixture was added benzene boronic acid (3.7 g, 30.6 mmol) and the mixture was heated in a 100° C. oil bath for 12 hours. The reaction was cooled, diluted with ethyl acetate (500 mL), washed with saturated sodium bicarbonate (200 mL), water (200 mL), 1N HCl (200 mL) and brine (200 mL). The organic layer was dried over magnesium sulfate and concentrated to afford a brown solid. Trituration with dichloromethane afforded 3.8 g (77%) of 5-phenyl-2-oxindole as a tan solid.

$^1$H NMR (360 MHz, DMSO-d6) δ 10.4 (br s, 1H, NH), 7.57 (dd, J=1.8 and 7.2 Hz, 1H), 7.5 to 7.35 (m, 5H), 7.29 (m, 1H), 6.89 (d, J=8.2 Hz, 1H), 3.51 (s, 2H, CH$_2$CO). MS m/z 209 [M$^+$].

In similar fashion, the following oxindoles can be prepared:

6-(3,5-Dichlorophenyl)-1,3-dihydroindol-2-one $^1$HNMR (360 MHz, DMSO-d6) δ 10.46 (br, 1H, NH), 7.64 (d, J=1.8 Hz, 2H), 7.57 (m, 1H), 7.27 (m, 2H), 7.05 (d, J=1.1 Hz, 1H), 3.5 (s, 2H). MS-EI m/z 277/279 [M]$^+$.

6-(4-Butylphenyl)-1,3-dihydroindol-2-one $^1$H NMR (360 MHz, DMSO-d6) δ 10.39 (s, 1H, NH), 7.49 (d, J=8.0 Hz, 2H), 7.25 (d, J=8 Hz, 3H), 7.17 (dd, J=1.5 and 7.8 Hz, 1H), 6.99 (d, J=1.5 Hz, 1H), 3.48 (s, 2H, CH$_2$CO), 2.60 (t, J=7.5 Hz, 2 Hz, CH$_2$CH$_3$), 1.57 (m, 2H, CH$_2$), 1.32 (m, 2H, CH$_2$), 0.9 (t, J=7.5 Hz, 3H, CH$_3$).

6-(5-Isopropyl-2-methoxyphenyl)-1,3-dihydroindol-2-one $^1$H NMR (360 MHz, DMSO-d6) δ 10.29 (br s, 1H, NH), 7.16-7.21 (m, 2H), −7.08 (d, J=2.4 Hz, 1H), 6.97-7.01 (m, 2H), 6.89 (d, J=0.8 Hz, 1H), 3.71 (s, 3H, OCH$_3$), 3.47 (s, 2H, CH$_2$CO), 2.86 (m, 1H, CH(CH$_3$)$_2$), 1.19 (d, J=6.8 Hz, 6H, CH(CH$_3$)$_2$). MS-EI m/z 281 [M]$^+$.

6-(4-Ethylphenyl)-1,3-dihydroindol-2-one $^1$H NMR (360 MHz, DMSO-d6) δ 10.39 (br s, 1H, NH), 7.50 (d, J=8.2 Hz, 2H), 7.28 (d, J=8.2 Hz, 2H), 7.25 (d, J=7.5 Hz, 1H), 7.17 (dd, J=1.6 & 7.5 Hz, 1H), 6.99 (d, J=1.6 Hz, 1H), 3.48 (s, 2H, CH$_2$CO), 2.63 (q, J=7.6 Hz, 2H, CH$_2$CH$_3$), 1.20 (t, J=7.6 Hz, 3H, CH$_2$CH$_3$). MS-EI m/z 237 [M]$^+$.

6-(3-Isopropylphenyl)-1,3-dihydroindol-2-one $^1$H NMR (360 MHz, DMSO-d6) δ 10.37 (br s, 1H, NH), 7.43 (m, 1H), 7.35-7.39 (m, 1H), 7.17-7.27 (m, 3H), 7.01 (d, J=1.8 Hz, 1H), 3.49 (s, 2H, CH$_2$CO), 2.95 (m, 1H, CH(CH$_3$)$_2$), 1.24 (d, J=6.8 Hz, 6H, CH(CH$_3$)$_2$). MS-EI m/z 251 [M]$^+$.

6-(2,4-Dimethoxyphenyl)-1,3-dihydroindol-2-one $^1$H NMR (360 MHz, DMSO-d6) δ 10.28 (br s, 1H, NH), 7.17 (m, 2H), 6.93 (dd, J=1.6 & 7.6 Hz, 1H), 6.86 (d, J=1.6 Hz, 1H), 6.63 (d, J=2.4 Hz, 1H), 6.58 (dd, J=2.4 & 8.5 Hz, 1H), 3.79 (s, 3H, OCH$_3$), 3.74 (s, 3H, OCH$_3$), 3.45 (s, 2H, CH$_2$CO). MS-EI m/z 269 [M]$^+$.

6-Pyridin-3-yl-1,3-dihydroindol-2-one $^1$H NMR (360 MHz, DMSO-d6) δ 10.51 (s, 1H, NH), 8.81 (d, J=2.5 Hz, 1H), 8.55 (dd, J=1.8 and 5.7 Hz, 1H), 8 (m, 1H), 7.45 (dd, J=5.7 and 9.3 Hz, 1H), 7.3 (m, 2H), 7.05 (s, 1H), 3.51 (s, 2H, CH$_2$CO). MS m/z 210 [M]$^+$.

2-Oxo-2,3-dihydro-1H-indole-4-carboxylic acid (3-chloro-4-ethoxyphenyl)-amide To a solution of 4-carboxy-2-oxindole (200 mg, 1.13 mmol) and 3-chloro-4-methoxyphenylamine (178 mg, 1.13 mmol) in dimethylformamide (15 mL) at room temperature was added benzotriazol-1-yloxytris(dimethylamino)phosphonium hexafluorophosphate (BOP reagent, 997 mg, 2.26 mmol) followed by 4-dimethylaminopyridine (206 mg, 1.69 mmol). The mixture was stirred at room temperature for 72 hours. The reaction was then diluted with ethyl acetate (300 mL), washed with saturated sodium bicarbonate (100 mL), water, 2N hydrochloric acid (100 mL)) water (3×200 mL) and brine. It was then dried over magnesium sulfate and concentrated. The residue was triturated with ethyl acetate to give 2-oxo-2,3-dihydro-1H-indole-4-carboxylic acid (3-chloro-4-methoxyphenyl)-amide as a pink solid.

$^1$HNMR (360 MHz, DMSO-d6) δ 10.50 (s, br, 1H, NH), 10.12 (s, br, 1H, NH), 7.9 (s, J=2.5 Hz, 1H), 7.62 (dd, J=2.5 & 9 Hz, 1H), 7.38 (d, J=7.6 Hz, 1H), 7.32 (t, J=7.6 Hz, 1H), 7.13 (d, J=9 Hz, 1H), 6.98 (d, J=7.6 Hz, 1H), 3.83 (s, 3H, OCH$_3$), 3.69 (s, 2H, CH$_2$). MS-EI m/z 316 [M]$^+$.

4-Carboxy-2-oxindole

A solution of trimethylsilyldiazomethane in hexane (2 M) was added dropwise to a solution of 2.01 g 2-chloro-3-carboxynitrobenzene in 20 mL methanol at room temperature until no further gas evolution occurred. Acetic acid was then added to quench excess trimethylsilyldiazomethane. The reaction mixture was evaporated under vacuum and the residue was dried in an oven overnight. The 2-chloro-3-methoxycarbonylnitrobenzene obtained was pure enough for the following reaction.

Dimethyl malonate (6.0 mL) was added to an ice-cold suspension of 2.1 g sodium hydride in 15 mL DMSO. The reaction mixture was stirred at 100° C. for 1 hour and then cooled to room temperature. 2-Chloro-3-methoxycarbonylnitrobenzene (2.15 g) was added in one portion and the mixture was heated to 100° C. for 1.5 hours. The reaction mixture was then cooled to room temperature, poured into ice water, acidified to pH 5 and extracted with ethyl acetate. The organic layer was washed with brine, dried over anhydrous sodium sulfate and concentrated to give 3.0 g of the dimethyl 2-methoxycarbonyl-6-nitrophenyl-malonate.

Dimethyl 2-methoxycarbonyl-6-nitrophenylmalonate (3.0 g) was refluxed in 50 mL of 6 N hydrochloric acid overnight. The mixture was concentrated to dryness, 20 mL ethanol and 1.1 g of tin(II) chloride were added and the mixture was refluxed for 2 hours. The mixture was filtered through Celite, concentrated and chromatographed on silica gel using ethyl acetate:hexane:acetic acid as eluent to give 0.65 g (37%) of 4-carboxy-2-oxindole as a white solid.

$^1$HNMR (360 MHz, DMSO-d6) δ 12.96 (s, br, 1H, COOH), 10.74 (s, br, 1H, NH), 7.53 (d, J=8 Hz, 1H), 7.39 (t, J=8 Hz, 1H), 7.12 (d, J=8 Hz, 1H), 3.67 (s, 2H).

D. Synthesis of pyrrole substituted 2-indolinones

Example 1

4-Methyl-5-(2-oxo-1,2-dihydroindol-3-ylidenemethyl)-1H-pyrrole-2-carboxylic acid 4-Methyl-2-pyrrolecarboxylic acid ethyl ester (commercially available) was formylated using method A to give (73%) of 5-formyl-4-methyl-2-pyrrolecarboxylic acid ethyl ester. It was then hydrolysed using method B to give 5-formyl-4-methyl-1H-pyrrole-2-carboxylic acid (58%).

Oxindole (133 mg, 1 mmol) was condensed with 5-formyl-4-methyl-1H-pyrrole-2-carboxylic acid (153 mg) using method D to give 268 mg (100%) of the title compound as an orange-red solid.

$^1$HNMR (360 MHz, DMSO-d6) δ 13.84 (s, br, 1H, NH), 12.84 (s, br, 1H, COOH), 10.98 (s, br, 1H, NH), 7.82 (d, J=7.5 Hz, 1H), 7.67 (s, 1H, H-vinyl), 7.18 (t, J=7.5 Hz, 1H), 7.01 (t, J=7.5 Hz, 1H), 6.88 (d, J=7.5 Hz, 1H), 6.71 (d, J=2.2 Hz, 1H), 2.32 (s, 3H, CH$_3$). MS (negative mode) 266.8 [M−1]$^+$.

Example 2

4-Methyl-5-(1-methyl-2-oxo-1,2-dihydroindol-3-ylidenemethyl)-1H-pyrrole-2-carboxylic acid 1-Methyl-1,3-dihydroindol-2-one (147 mg, 1 mmol) was condensed with 5-formyl-4-methyl-1H-pyrrole-2-carboxylic acid (153 mg) using method D to give 250 mg (86%) of the title compound.

$^1$HNMR (360 MHz, DMSO-d6) δ 13.82 (s, br, 1H, NH), 12.88 (s, br, 1H, 7.83 (d, J=7.5 Hz, 1H), 7.65 (s, 1H, H-vinyl), 7.26 (t, J=7.5 Hz, 1H), 7.02-7.09 (m, 2H), 6.70 (d, J=2.2 Hz, 1H), 2.32 (s, 3H, CH$_3$). MS m/z 283.0 [M+1]$^+$.

Example 3

4-Methyl-5-(2-oxo-1,2-dihydroindol-3-ylidenemethyl)-1H-pyrrole-2-carboxylic acid methyl ester Oxindole (105 mg, 0.79 mmol) was condensed with 5-formyl-4-methyl-1H-pyrrole-2-carboxylic acid methyl ester (110 mg, 0.67 mmol) using method E to give 153.2 mg (81%) of the title compound.

$^1$HNMR (360 MHz, DMSO-d6) δ 13.98 (s, br, 1H, NH), 10.97 (s, br, 1H, NH), 7.82 (d, J=7.6 Hz, 1H), 7.67 (s, 1H, H-vinyl), 7.2 (dt, J=1.2 & 7.7 Hz, 1H), 7.01 (dt, J=1.2, 7.7 Hz, 1H), 6.90 (d, J=7.6. Hz, 1H), 6.77 (d, J=2 Hz, 1H). MS (ES) m/z 283 [M$^+$+1].

Example 4

5-(5-Chloro-2-oxo-1,2-dihydroindol-3-ylidenemethyl)-4-methyl-1H-pyrrole-2-carboxylic acid ethyl ester 5-Chloro-1,3-dihydroindol-2-one (2.22 g, 13.2 mmol) was condensed with 5-formyl-4-methyl-1H-pyrrole-2-carboxylic acid ethyl ester (2.43 g) using method E to give 4.1 g (94%) of the title compound as an orange solid.

$^1$HNMR (360 MHz, DMSO-d6) δ 13.95 (s, br, 1H, NH), 7.98 (d, J=2.2 Hz, 1H, H-4), 7.78 (s, 1H, H-vinyl), 7.18 (dd, J=2.2 & 8.3 Hz, 1H, H-6), 6.87 (d, J=8.3 Hz, 1H, H-7), 7.34 (d, J=1.8 Hz, 1H, H-3'), 4.27 (q, J=7.2 Hz, 2H, OCH$_2$CH$_3$), 2.33 (s, 3H, CH$_3$), 1.29 (t, J=7.2 Hz, 3H, OCH$_2$CH$_3$). MS-EI m/z 330 [M$^+$].

Example 5

5-(5-Chloro-2-oxo-1,2-dihydroindol-3-ylidenemethyl)-4-methyl-1H-pyrrole-2-carboxylic acid A mixture of S-(5-chloro-2-oxo-1,2-dihydroindol-3-ylidenemethyl)-4-methyl-1H-pyrrole-2-carboxylic acid ethyl ester (1.3 g, 4 mmol) and potassium hydroxide in methanol (25 mL) and ethanol (25 mL) was heated to reflux for overnight. Insoluble materials were removed by filtration and the mixture was neutralized with 6N hydrochloric acid to give 0.876 g (70%) of the title compound.

$^1$HNMR (360 MHz, DMSO-d6) δ 13.80 (s, br, 1H, NH), 12.90 (s, br, 1H, COOH), 11.06 (s, br, 1H, NH), 8.02 (d, J=1.8 Hz, 1H, H-4), 7.81 (s, 1H, H-vinyl), 7.20 (dd, J=1.8 & 8.3 Hz, 1H, H-6), 6.89 (d, J=8.3 Hz, 1H, H-7), 6.72 (d, J=1.8 Hz, 1H, H-3'), 2.35 (s, 3H, CH$_3$). MS-EI m/z 302 [M$^+$].

Example 6

5-(5-Bromo-2-oxo-1,2-dihydroindol-3-ylidenemethyl)-4-methyl-1H-pyrrole-2-carboxylic acid (3-pyrrolidin-1-yl-propyl)amide 5-Bromo-1,3-dihydroindol-2-one (0.16 g, 0.76 mmol) was condensed with 5-formyl-4-methyl-1H-pyrrole-2-carboxylic acid (3-pyrrolidin-1-ylpropyl)amide (0.2 g, prepared by method C) to give 60 mg (17%) of the title compound as an orange solid.

$^1$HNMR (300 MHz, DMSO-d6) δ 13.61 (s, br, 1H, NH), 11.02 (s, br, 1H, NH), 8.42 (t, J=5.8 Hz, 1H, CONHCH$_2$), 8.12 (d, J=1.8 Hz, 1H, H-4), 7.78 (s, 1H, H-vinyl), 7.30 (dd, J=1.8 & 8.4 Hz, 1H, H-6), 6.82 (d, J=8.4 Hz, 1H, H-7), 6.77 (d, J=2.4 Hz, 1H, H-3'), 3.22-3.31 (m, 2H, CH$_2$), 2.38-2.43 (m, 6H, 3×CH$_2$), 2.35 (s, 3H, CH$_3$), 1.62-1.71 (m, 6H, 3×CH$_2$). MS-EI m/z 456 and 458 [M$^+$−1 and M$^+$+2].

Example 7

5-(5-Bromo-2-oxo-1,2-dihydroindol-3-ylidenemethyl)-4-methyl-1H-pyrrole-2-carboxylic acid (3-diethylamino-propyl)amide 5-Bromo-1,3-dihydroindol-2-one (0.16 g, 0.75 mmol) was condensed with 5-formyl-4-methyl-1H-pyrrole-2-carboxylic acid (3-diethylaminopropyl)amide (0.2 g, prepared by method C) to give 30 mg (8%) of the title compound as an orange solid.

$^1$HNMR (300 MHz, DMSO-d6) δ 13.61 (s, br, 1H, NH), 11.02 (s, br, 1H, NH), 8.40 (m, 1H, CONHCH$_2$), 8.12 (d,

J=1.5 Hz, 1H, H-4), 7.78 (s, 1H, H-vinyl), 7.30 (dd, J=1.5 & 8.2 Hz, 1H, H-6), 6.82 (d, J=8.2 Hz, 1H, H-7), 6.78 (d, J=2.4 Hz, 1H, H-3'), 3.23 (m, 2H, CH$_2$), 2.38-2.45 (m, 6H, CH$_2$ & N(CH$_2$CH$_3$)$_2$), 2.35 (s, 3H, CH$_3$), 1.61 (m, 2H, CH$_2$), 0.93 (t, J=7.1 Hz, 6H, N(CH$_2$CH$_3$)$_2$). MS-EI m/z 458 and 460 [M$^+$−1 and M$^+$+2].

Example 8

5-(5-Bromo-2-oxo-1,2-dihydroindol-3-ylidenemethyl)-1H-pyrrole-2-carboxylic acid (2-diethylaminoethyl)amide 5-Bromo-1,3-dihydroindol-2-one (212 mg, 1 mmol) was condensed with 5-formyl-1H-pyrrole-2-carboxylic acid (2-diethylaminoethyl)amide (prepared from ethyl pyrrole-2-carboxylate by method A, B and then C) to give 162 mg (38%) of the title compound.

$^1$H NMR (300 MHz, DMSO-d6) δ 13.53 (s, br, 1H, NH), 11.06 (s, br, 1H, NH), 8.37 (t, 1H, CONHCH$_2$), 7.89 (m, 2H), 7.32 (dd, J=2.0 Hz, 1H), 6.96 (s, 1H), 6.80-6.84 (m, 2H), 3.3 (m, 2H, CH$_2$), 2.45-2.55 (m, 6H, N(CH$_2$CH$_3$)$_2$ & CH$_2$), 0.95 (t, J=7.2 Hz, 6H, N(CH$_2$CH$_3$)$_2$). MS-EI m/z 430 and 432 [M$^+$−1 and M$^+$+1].

Example 9

5-(2-Oxo-6-phenyl-1,2-dihydroindol-3-ylidenemethyl)-1H-pyrrole-2-carboxylic acid (2-diethylaminoethyl)amide 6-Phenyl-1,3-dihydroindol-2-one (209 mg, 1 mmol) was condensed with 5-formyl-1H-pyrrole-2-carboxylic acid (2-diethylaminoethyl)amide to give 182 mg (42%) of the title compound.

$^1$H NMR (300 MHz, DMSO-d6) δ 13.56 (s, br, 1H, NH), 11.06 (s, br, 1H, NH), 8.36 (t, 1H, CONHCH$_2$), 7.77 (s, 1H, H-vinyl), 7.73 (d, J=7.8 Hz, 1H), 7.64 (d, J=7.2 Hz, 2H), 7.46 (m, 2H), 7.32 (m, 2H), 7.11 (s, 1H), 6.96 (m, 1H), 6.80 (m, 1H), 3.31-3.32 (m, 2H, CH$_2$), 2.46-2.53 (m, 6H, N(CH$_2$CH$_3$)$_2$ & CH$_2$), 0.96 (t, J=6.9 Hz, 6H, N(CH$_2$CH$_3$)$_2$). MS-EI m/z 428 [M$^+$].

Example 10

5-(5-Bromo-2-oxo-1,2-dihydroindol-3-ylidenemethyl)-1H-pyrrole-2-carboxylic acid (2-diethylaminoethyl)-methyl-amide 5-Bromo-1,3-dihydroindol-2-one (212 mg, 1 mmol) was condensed with 5-formyl-1H-pyrrole-2-carboxylic acid (2-diethylaminoethyl)methylamide to give 246 mg (55%) of the title compound.

$^1$H NMR (360 MHz, DMSO-d6) δ 13.54 (s, br, 1H, NH), 11.06 (s, br, 1H, NH), 7.90 (m, 2H), 7.33 (dd, J=1.8 & 8.4 Hz, 1H), 6.82-6.85 (m, 3H), 3.55 (s, br, 2H, CH$_2$), 3.25 (s, br, 3H, NCH$_3$), 2.57 (t, J=6.5 Hz, 2H, CH$_2$), 2.45 (m, 4H, N(CH$_2$CH$_3$)$_2$), 0.91 (m, 6H, N(CH$_2$CH$_3$)$_2$). MS-EI m/z 444 and 446 [M$^+$−1 and M$^+$+1].

Example 11

5-(2-Oxo-6-phenyl-1,2-dihydroindol-3-ylidenemethyl)-1H-pyrrole-2-carboxylic acid (2-diethylaminoethyl)methylamide 6-Phenyl-1,3-dihydroindol-2-one (209 mg, 1 mmol) was condensed with 5-formyl-1H-pyrrole-2-carboxylic acid (2-diethylaminoethyl)methylamide to give 277 mg (63%) of the title compound.

$^1$H NMR (360 MHz, DMSO-d6) δ 13.58 (s, br, 1H, NH), 11.04 (s, br, 1H, NH), 7.78 (s, 1H, H-vinyl), 7.73 (d, J=7.8 Hz, 1H), 7.64 (d, J=7.5 Hz, 2H), 7.46 (m, 2H), 7.33-7.36 (m, 2H), 7.11 (s, 1H), 6.84 (m, 1H), 6.78 (m, 1H), 3.55 (s, br, 2H, CH$_2$), 3.25 (s, br, 3H, NCH$_3$), 2.58 (t, 2H, CH$_2$), 2.44 (m, 4H, N(CH$_2$CH$_3$)$_2$), 0.92 (m, 6H, N(CH$_2$CH$_3$)$_2$).

Example 12

3-Methyl-5-(2-oxo-1,2-dihydroindol-3-ylidenemethyl)-1H-pyrrole-2-carboxylic acid (3-diethylaminopropyl)amide Oxindole (66.5 mg, 0.5 mmol) was condensed with 5-formyl-3-methyl-1H-pyrrole-2-carboxylic acid (3-diethylaminopropyl)amide (prepared from 3-formyl-3-methyl-1H-pyrrole-2-carboxylic acid ethyl ester by method B then C) to give 39 mg (21%) of the title compound.

$^1$H NMR (300 MHz, DMSO-d6) δ 13.34 (s, br, 1H, NH), 10.88 (s, br, 1H, NH), 7.62-7.67 (m, 3H), 7.17 (m, 1H), 6.99 (m, 1H), 6.87 (d, J=7.6 Hz, 1H), 6.63 (d, J=1 Hz, 1H), 3.26-3.32 (m, 2H, CH$_2$), 2.41-2.48 (m, 6H, CH$_2$ & N(CH$_2$CH$_3$)$_2$), 2.29 (s, 3H, CH$_3$), 1.63 (m, 2H, CH$_2$), 0.93 (t, J=7.2 Hz, 6H, —N(CH$_2$CH$_3$)$_2$). MS-EI m/z 380 [M$^+$].

Example 13

5-(5-Bromo-2-oxo-1,2-dihydroindol-3-ylidenemethyl)-3-methyl-1H-pyrrole-2-carboxylic acid (3-diethylamino-propyl)amide 5-Bromo-1,3-dihydroindol-2-one (106 mg, 0.5 mmol) was condensed with 5-formyl-3-methyl-1H-pyrrole-2-carboxylic acid (3-diethylaminopropyl)amide to give 35 mg (15%) of the title compound.

$^1$H NMR (300 MHz, DMSO-d6) δ 13.35 (s, br, 1H, NH), 11.00 (s, br, 1H, NH), 7.89 (d, J=1.9 Hz, 1H, H-4), 7.80 (s, 1H, H-vinyl), 7.74 (t, J=5.3 Hz, 1H, CONHCH$_2$), 7.31 (dd, J=1.9 & 8.4 Hz, 1H, H-6), 6.83 (d, J=8.4 Hz, 1H, H-7), 6.63 (s, 1H, H-3'), 3.26 (m, 2H, CH$_2$), 2.41-2.48 (m, 6H, CH$_2$ & N(CH$_2$CH$_3$)$_2$), 2.29 (s, 3H, CH$_3$), 1.63 (m, 2H, CH$_2$), 0.93 (t, J=7.1 Hz, 6H, N(CH$_2$CH$_3$)$_2$). MS-EI m/z 458 and 460 [M$^+$−1 and M$^+$+1].

Example 14

3-Methyl-5-(2-oxo-6-phenyl-1,2-dihydroindol-3-ylidenemethyl)-1H-pyrrole-2-carboxylic acid (3-diethylaminopropyl)amide 6-Phenyl-1,3-dihydroindol-2-one (105 mg, 0.5 mmol) was condensed with 5-formyl-3-methyl-1H-pyrrole-2-carboxylic acid (3-diethylaminopropyl)amide to give 67.8 (30%) of the title compound.

$^1$H NMR (300 MHz, DMSO-d6) δ 13.37 (s, br, 1H, NH), 11.02 (s, br, 1H, NH), 7.23-7.73 (m, 11H), 3.29 (m, 2H, CH$_2$), 2.41-2.48 (m, 6H, CH$_2$ & N(CH$_2$CH$_3$)$_2$), 2.29 (s, 3H, CH$_3$), 1.64 (m, 2H, CH$_2$), 0.94 (t, J=7.0 Hz, 6H, N(CH$_2$CH$_3$)$_2$). MS-EI m/z 456 [M$^+$].

Example 15

5-(5-Methoxy-2-oxo-1,2-dihydroindol-3-ylidenemethyl)-3-methyl-1H-pyrrole-2-carboxylic acid (3-diethylamino-propyl)amide 5-Methoxy-1,3-dihydroindol-2-one (82.5 mg, 0.5 mmol) was condensed with 5-formyl-3-methyl-1H-pyrrole-2-carboxylic acid (3-diethylaminopropyl)amide to give 80 mg (39%) of the title compound.

$^1$H NMR (300 MHz, DMSO-d6) δ 13.45 (s, br, 1H, NH), 10.70 (s, br, 1H, NH), 7.68-7.70 (m, 2H), 7.32 (d, J=1.8 Hz, 1H), 6.72-6.79 (m, 2H), 6.60 (s, 1H), 3.73 (s, 3H, OCH$_3$), 3.28 (m, 2H, CH$_2$), 2.41-2.48 (m, 6H, CH$_2$ & N(CH$_2$CH$_3$)$_2$), 2.29 (s, 3H, CH$_3$), 1.63 (m, 2H, CH$_2$), 0.93 (t, J=7.0 Hz, 6H, N(CH$_2$CH$_3$)$_2$). MS m/z 410 [M$^+$].

Example 16

5-(6-Methoxy-2-oxo-1,2-dihydroindol-3-ylidenemethyl)-3-methyl-1H-pyrrole-2-carboxylic acid (3-diethylamino-propyl)amide 6-Methoxy-1,3-dihydroindol-2-one (82.5 mg, 0.5 mmol) was condensed with 5-formyl-3-methyl-1H-pyrrole-2-carboxylic acid (3-diethylaminopropyl)amide to give 63 mg (31%) of the title compound.

$^1$H NMR (300 MHz, DMSO-d6) δ 13.22 (s, br, 1H, NH), 10.86 (s, br, 1H, NH), 7.39-7.63 and 6.37-6.55 (m, 6H), 3.73 (s, 3H, OCH$_3$), 3.3 (m, 2H, CH$_2$), 2.45 (m, 6H, CH$_2$ & N(CH$_2$CH$_3$)$_2$), 2.28 (s, 3H, CH$_3$), 1.63 (m, 2H, CH$_2$), 0.93 (m, 6H, N(CH$_2$CH$_3$)$_2$). MS m/z 410 [M$^+$].

Example 17

3-(5-Bromo-2-oxo-1,2-dihydroindol-3-ylidenemethyl)-4,5,6,7-tetrahydro-2H-isoindole-1-carboxylic acid (2-diethylaminoethyl)amide 4,5,6,7-Tetrahydro-2H-isoindole-1-carboxylic acid ethyl ester (May, Donald A.; Lash, Timothy-D.; *J. Org. Chem.*, 1992, 57:18, 4820-4828) was formylated using method A then B to give 3-formyl-4,5,6,7-tetrahydro-2H-isoindole-1-carboxylic acid.

5-Bromo-1,3-dihydroindol-2-one (1.43 g, 6.8 mmol) was condensed with 3-formyl-4,5,6,7-tetrahydro-2H-isoindole-1-carboxylic acid (2-diethylaminoethyl)amide (1.97 g) to give 2.2 g (67%) of the title compound as a yellow-orange solid.

$^1$H NMR (360 MHz, DMSO-d6) δ 13.47 (s, 1H, NH), 11.0 (s, 1H, NH), 8.0 (d, 1H, NH), 7.70 (s, 1H, CH), 7.28 (dd, J=2.1 and 8.2 Hz, 1H, ArH), 7.16 (m, 1H, ArH), 6.8 (d, J=8.3 Hz, 1H, ArH), 3.3 (s, 2H, CONH), 2.5 (m, 6H, 3×NCH$_2$), 2.78 (br m, 2H, pyrrole CH$_2$), 2.72 (br m, 2H, pyrroleCH$_2$), 1.7 (br m, 4H, N(CH$_2$CH$_3$)$_2$), 1.74 (br s, 4H, CH$_2$CH$_2$CH$_2$CH$_2$), 0.96 (t, J=7.4 Hz, 6H, N(CH$_2$CH$_3$)$_2$). MS-EI m/z 484 and 486 [M$^+$−1 and M$^+$+1].

Example 18

3-(5-Bromo-2-oxo-1,2-dihydroindol-3-ylidenemethyl)-4,5,6,7-tetrahydro-2H-isoindole-1-carboxylic acid (3-diethylaminopropyl)amide 5-Bromo-1,3-dihydroindol-2-one (20 mg, 0.1 mmol) was condensed with 3-formyl-4,5,6,7-tetrahydro-2H-isoindole-1-carboxylic acid (3-diethylaminopropyl)amide (30 mg) to give 33 mg (46%) of the title compound as an orange solid.

$^1$H NMR (360 MHz, DMSO-d6) δ 10.9 (s, 1H, NH), 8.0 (m, 1H, NH), 7.68 (m, 1H, ArH), 7.4 (m, 1H, ArH), 7.29 (d, J=1.9 and 8.5 Hz, 1H, ArH), 6.8 (d, J=8 Hz, 1H, ArH), 2.7 (br m, 4H, 2×NCH$_2$), 2.4 (m, 8H, 4×NCH$_2$), 1.7 (br m, 4H, N(CH$_2$CH$_3$)$_2$), 1.6 (br m, 2H, CH$_2$CH$_2$CH$_2$), 0.93 (t, J=7.4 Hz, 6H, N(CH$_2$CH$_3$)$_2$). MS-EI m/z 499 and 501 [M$^+$ and M$^+$+2].

Example 19

3-(5-Bromo-2-oxo-1,2-dihydroindol-3-ylidenemethyl)-4,5,6,7-tetrahydro-2H-isoindole-1-carboxylic acid (3-pyrrolidin-1-ylpropyl)amide 5-Bromo-1,3-dihydroindol-2-one (80 mg, 0.4 mmol) was condensed with 3-formyl-4,5,6,7-tetrahydro-2H-isoindole-1-carboxylic acid (3-pyrrolidin-1-ylpropyl)amide (120 mg) to give 43 mg (22%) of the title compound as a tan-orange solid.

$^1$H NMR (360 MHz, DMSO-d6) δ 13.4 (s, 1H, NH), 10.9 (s, 1H, NH), 8.0 (m, 1H, NH), 7.69 (m, 1H, ArH), 7.49 (m, 1H, ArH), 7.28 (d, J=1.7 and 7.8 Hz, 1H, ArH), 6.8 (d, J=8 Hz, 1H, ArH), 3.3 (br m, 2H, 2×NCH$_2$), 2.8 (m, 4H, 2×pyrroleCH$_2$), 2.5 (br m, 4H, N(CH$_2$CH$_3$)$_2$), 1.6 (br m, 8H, 2×pyrroleCH$_2$CH$_2$, CH$_2$CH$_2$CH$_2$ and CONHCH$_2$). MS-EI m/z 497 and 499 [M$^+$ and M$^+$+2].

Example 20

3-(2-Oxo-6-pyridin-3-yl-1,2-dihydroindol-3-ylidenemethyl)-4,5,6,7-tetrahydro-2H-isoindole-1-carboxylic acid (2-diethylaminoethyl)amide 6-Pyridin-3-yl-1,3-dihydroindol-2-one (60 mg, 0.4 mmol) was condensed with 3-formyl-4,5,6,7-tetrahydro-2H-isoindole-1-carboxylic acid (2-diethylaminoethyl)amide (80 mg) to give 50 mg (38%) of the title compound as a reddish solid.

$^1$H NMR (360 MHz, DMSO-d6) δ 13.4 (s, 1H, NH), 11-(s, 1H, NH), 8.9 (d, 1H, NH), 8.7 (dd, 1H, ArH), 8.1 (dd, 1H, ArH), 7.9 (d, 1H, ArH), 7.6 (s, 1H, CH), 7.5 (dd, 1H, ArH), 7.3 (dd, 1H, ArH), 7.1 (m, 2H, ArH), 3.35 (m, 2H, CONHCH$_2$), 2.8 (m, 4H, 2× pyrroleCH$_2$), 2.5 (br m, 6H, N(CH$_2$CH$_3$)$_2$ and NCH$_2$), 1.75 (br s, 4H, 2× pyrroleCH$_2$CH$_2$), 0.9 (t, 6H, —N(CH$_2$CH$_3$)$_2$). MS-EI m/z 484 [M$^+$].

Example 21

4-Benzoyl-5-(5-bromo-2-oxo-1,2-dihydroindol-3-ylidenemethyl)-3-methyl-1H-pyrrole-2-carboxylic acid (3-diethylaminopropyl)amide To a mixture of benzoyl chloride (1 equiv.) and aluminum chloride (1 equiv.) in dichloroethane at 0° C. was added ethyl 3,5-dimethyl-2-pyrrolecarboxylate (1 equiv.). The mixture was stirred at 80° C. for 4 hr. The mixture was then extracted with ethyl acetate (EtOAc) and H$_2$O. The combined organic extracts were washed with saturated sodium bicarbonate and brine, dried and concentrated to give (51%) of 4-benzoyl-3,5-dimethyl-1H-pyrrole-2-carboxylic acid.

A mixture of 4-benzoyl-3,5-dimethyl-1H-pyrrole-2-carboxylic acid ethyl ester (4.13 g, 15.2 mmol) and ceric ammonium nitrate (33 g, 4 equiv.) in 50 mL of tetrahydrofuran (THF):acetic acid (HOAc):$H_2O$ 1:1:1 was refluxed overnight. The reaction mixture was then cooled, extracted with EtOAc and then basified to pH 9 with sodium carbonate. The organic layer was then washed with brine, dried ($MgSO_4$) and concentrated followed by column chromatography to give 3.25 g (75%) of 4-benzoyl-5-formyl-3-methyl-1H-pyrrole-2-carboxylic acid ethyl ester as a yellow solid.

5-Bromo-1,3-dihydro-indol-2-one was condensed with 4-benzoyl-5-formyl-3-methyl-1H-pyrrole-2-carboxylic acid using method D to give 4-benzoyl-5-(5-bromo-2-oxo-1,2-dihydro-indol-3-ylidenemethyl)-3-methyl-1H-pyrrole-2-carboxylic acid.

The above carboxylic acid was then coupled with N,N-diethyl-1,3-propanediamine using method C to give the title compound.

$^1$H NMR (360 MHz, DMSO-d6) δ 7.96 (m, 1H, CONHCH$_2$), 7.76 (d, J=7.0 Hz, 2H), 7.68 (t, 1H), 7.56 (m, 2H), 7.40 (s, 2H) 7.33 (dd, J=1.6 & 8.3 Hz, 1H, H-6), 6.84 (d, J=8.3 Hz, 1H, H-7), 3.33 (m, 2H, CH$_2$), 2.42-2.46 (m, 6H, 3×CH$_2$), 2.10 (s, 3H, CH$_3$), 1.65 (m, 2H, CH$_2$), 0.94 (t, J=7.0 Hz, 6H, N(CH$_2$CH$_3$)$_2$). MS Electron Impact m/z 564 [M$^+$+1].

Example 22

4-Benzoyl-5-(5-bromo-2-oxo-1,2-dihydroindol-3-ylidenemethyl)-3-methyl-1H-pyrrole-2-carboxylic acid (3-morpholin-4-ylpropyl)amide $^1$H NMR (360 MHz, DMSO-d6) δ 14.10 (s, 1H, NH), 11.14 (br s, 1H, NH), 7.92 (m, 1H, CONHCH$_2$), 7.75 (m, 2H), 7.69 (t, 1H), 7.56 (m, 2H), 7.42 (m, 2H), 7.33 (dd, J=1.9 & 8.3 Hz, 1H, H-6), 6.85 (d, J=8.3 Hz, 1H, H-7), 3.56 (m, 4H, 2×CH$_2$), 3.33 (m, 2H, CH$_2$), 2.35 (m, 6H, 3×CH$_2$), 2.10 (s, 3H, CH$_3$), 1.70 (m, 2H, CH$_2$).

Example 23

4-Benzoyl-3-methyl-5-(2-oxo-1,2-dihydroindol-3-ylidenemethyl)-1H-pyrrole-2-carboxylic acid (3-pyrrolidin-1-ylpropyl)amide $^1$H NMR (300 MHz, DMSO-d6) δ 14.18 (s, 1H, NH), 11.14 (br s, 1H, NH), 8.01 (m, 1H, CONHCH$_2$), 7.74 (m, 1H), 7.67 (m, 1H), 7.55 (m, 1H), 7.32 (s, 1H, H-vinyl), 7.17 (m, 1H), 6.92 (m, 1H), 3.36 (m, 2H, CH$_2$), 2.44 (m, 6H, 3×CH$_2$), 2.11 (s, 3H, CH$_3$), 1.65-1.75 (m, 6H, 3×CH$_2$). MS Electron Impact m/z 482 [M$^+$].

Example 24

4-Benzoyl-5-(5-bromo-2-oxo-1,2-dihydroindol-3-ylidenemethyl)-3'-methyl-1H-pyrrole-2-carboxylic acid (3-pyrrolidin-1-ylpropyl)amide $^1$H NMR (360 MHz, DMSO-d6) δ 14.01 (s, 1H, NH), 11.18 (br s, 1H, NH), 7.98 (m, 1H, CONHCH$_2$), 7.75 (m, 2H), 7.68 (m, 1H), 7.55 (m, 2H), 7.40 (m, 2H), 7.33 (dd, J=2.0 & 8.2 Hz, 1H, H-6), 6.84 (d, J=8.2 Hz, 1H, H-7), 3.34 (m, 2H, CH$_2$), 2.42-2.47 (m, 6H, 3×CH$_2$), 2.09 (s, 3H, CH$_3$), 1.70 (m, 2H, CH$_2$), 1.64 (m, 4H, 2×CH$_2$).

Example 25

4-Benzoyl-3-methyl-5-(2-oxo-6-phenyl-1,2-dihydroindol-3-ylidenemethyl)-1H-pyrrole-2-carboxylic acid (3-pyrrolidin-1-ylpropyl)amide $^1$H NMR (300 MHz, DMSO-d6) δ 14.15 (s, 1H, NH), 11.16 (br s, 1H, NH), 7.98 (m, 1H, CONHCH$_2$), 7.77 (d, J=7.7 Hz, 2H), 7.69 (m, 1H), 7.53-7.63 (m, 4H), 7.44 (m, 2H), 7.33-7.37 (m, 2H), 7.24 (s, 2H), 7.12 (s, 1H), 3.36 (m, 2H, CH$_2$), 2.43-2.48 (m, 6H, 3×CH$_2$), 2.12 (s, 3H, CH$_3$), 1.74 (m, 2H, CH$_2$), 1.69 (m, 4H, 2×CH$_2$). MS Electron Impact m/z 558 [M$^+$].

Example 26

4-Benzoyl-5-(6-methoxy-2-oxo-1,2-dihydroindol-3-ylidenemethyl)-3-methyl-1H-pyrrole-2-carboxylic acid (3-pyrrolidin-1-ylpropyl)amide $^1$H NMR (300 MHz, DMSO-d6) δ 13.99 (s, 1H, NH), 11.05 (br s, 1H, NH), 7.93 (m, 1H, CONHCH$_2$), 7.72 (m, 2H), 7.65 (m, 1H), 7.54 (m, 2H), 7.15 (s, 1H, H-vinyl), 7.04 (d, J=8.4 Hz, 1H, H-4), 6.51 (dd, J=2.3 & 8.4 Hz, 1H, H-5), 6.44 (d, J=2.3 Hz, 1H, H-7), 3.74 (s, 3H, OCH$_3$), 3.35 (m, 2H, CH$_2$), 2.42-2.46 (m, 6H, 3×CH$_2$), 2.10 (s, 3H, CH$_3$), 1.72 (m, 2H, CH$_2$), 1.65 (m, 4H, 2×CH$_2$). MS Electron Impact m/z 512 [M$^+$].

Example 27

4-Benzoyl-5-(5-methoxy-2-oxo-1,2-dihydroindol-3-ylidenemethyl)-3-methyl-1H-pyrrole-2-carboxylic acid (3-pyrrolidin-1-ylpropyl)amide $^1$H NMR (360 MHz, DMSO-d6) δ 14.24 (s, 1H, NH), 10.90 (br s, 1H, NH), 7.97 (m, 1H, CONHCH$_2$), 7.75 (d, J=7.2 Hz, 2H), 7.69 (m, 1H), 7.56 (m, 2H), 7.24 (s, 1H, H-vinyl), 6.79 (m, 2H), 6.66 (m, 1H), 3.67 (s, 3H, OCH$_3$), 3.34 (m, 2H, CH$_2$), 2.43-2.48 (m, 6H, 3×CH$_2$), 2.14 (s, 3H, CH$_3$), 1.71 (m, 2H, CH$_2$), 1.66 (m, 4H, 2×CH$_2$). MS Electron Impact m/z 512 [M$^+$].

Example 28

4-Benzoyl-5-(5-fluoro-2-oxo-1,2-dihydroindol-3-ylidenemethyl)-3-methyl-1H-pyrrole-2-carboxylic acid (3-pyrrolidin-1-ylpropyl)amide $^1$H NMR (300 MHz, DMSO-d6) δ 14.20 (s, 1H, NH), 11.14 (br s, 1H, NH), 8.03 (m, 1H, CONHCH$_2$), 7.75 (m, 2H), 7.68 (m, 1H), 7.55 (m, 2H), 7.38 (s, 1H, H-vinyl), 7.08 (m, 1H), 7.01 (m, 1H), 6.87 (m, 1H), 3.34 (m, 2H, CH$_2$), 2.42-2.48 (m, 6H, 3×CH$_2$), 2.09 (s, 3H, CH$_3$), 1.70 (m, 2H, CH$_2$), 1.65 (m, 4H, 2×CH$_2$). MS Electron Impact m/z 500 [M$^+$].

Example 29

4-Acetyl-5-(5-bromo-2-oxo-1,2-dihydroindol-3-ylidenemethyl)-3-methyl-1H-pyrrole-2-carboxylic acid (3-diethylaminopropyl)amide 5-Bromo-1,3-dihydro-indol-2-one was condensed with 4-acetyl-5-formyl-3-methyl-1H-pyrrole-2-carboxylic acid (3-diethylaminopropyl)amide (prepared from 4-acetyl-5-formyl-3-methyl-1H-pyrrole-2-carboxylic acid ethyl ester by method B then C) to give the title compound.

$^1$H NMR (300 MHz, DMSO-d6) δ 14.19 (s, 1H, NH), 11.19 (br s, 1H, NH), 8.15 (m, 1H, CONHCH$_2$), 8.11 (s, 1H, H-vinyl), 7.72 (d, J=1.8 Hz, 1H, H-4), 7.38 (dd, J=1.8 & 8.2 Hz, 1H, H-6), 6.87 (d, J=8.2 Hz, 1H, H-7), 3.27 (m, 2H, CH$_2$), 2.57 (s, 3H, CH$_3$CO), 2.46 (m, 9H, CH$_3$ & 3×CH$_2$), 1.64 (m, 2H, CH$_2$), 0.93 (t, J=7.1 Hz, 6H, N(CH$_2$CH$_3$)$_2$).

Example 30

4-Acetyl-5-(5-bromo-2-oxo-1,2-dihydroindol-3-ylidenemethyl)-3-methyl-1H-pyrrole-2-carboxylic acid (3-pyrrolidin-1-ylpropyl)amide $^1$H NMR (300 MHz, DMSO-d6) 8.14 (m, 1H, CONHCH$_2$), 8.10 (s, 1H, H-vinyl), 7.70 (d, 1H, H-4), 7.36 (dd, J=1.6 & 8.1 Hz, 1H, H-6), 6.85 (d, J=8.1 Hz, 1H, H-7), 3.32 (m, 2H, CH$_2$), 2.57 (s, 3H, CH$_3$CO), 2.44 (s, 3H, CH$_3$), 2.35-2.48 (m, 6H, 3×CH$_3$), 1.65-1.71 (m, 6H, 3×CH$_2$). MS m/z 499 & 501 [M$^+$] & [M$^+$+2].

Example 31

4-Acetyl-5-(5-bromo-2-oxo-1,2-dihydroindol-3-ylidenemethyl)-3-methyl-1H-pyrrole-2-carboxylic acid (3-morpholin-4-ylpropyl)amide $^1$H NMR (300 MHz, DMSO-d6) δ 14.20 (s, 1H, NH), 11.26 (br s, 1H, NH), 8.09 (m, 2H, H-vinyl & CONHCH$_2$), 7.73 (d, J=1.5 Hz, 1H, H-4), 7.38 (dd, J=1.5 & 8.3 Hz, 1H, H-6), 6.87 (d, J=8.3 Hz, 1H, H-7), 3.55 (m, 4H, 2×CH$_2$), 3.26 (m, 2H, CH$_2$), 2.57 (s, 3H, CH$_3$CO), 2.44 (s, 3H, CH$_3$), 2.35 (m, 6H, 3×CH$_3$), 1.68 (m, 2H, CH$_2$). MS-EI m/z 514 & 516 [M$^+$−1] & [M$^+$+1].

Example 32

4-Acetyl-5-(5-bromo-2-oxo-1,2-dihydroindol-3-ylidenemethyl)-3-methyl-1H-pyrrole-2-carboxylic acid (3-hydroxypropyl)amide $^1$H NMR (360 MHz, DMSO-d6) δ 14.17 (s, 1H, NH), 11.25 (br s, 1H, NH), 8.10, (s, 1H, H-vinyl), 8.03 (m, 1H, CONHCH$_2$), 7.71 (br s, 1H, H-4), 7.37 (br d, J=8.4 Hz, 1H, H-6), 6.87 (d, J=8.4 Hz, 1H, H-7), 4.51 (br s, 1H, OH), 3.51 (br s, 2H, CH$_2$), 3.36 (m, 2H, CH$_2$), 2.57 (s, 3H, CH$_3$CO), 2.43 (s, 3H, CH$_3$), 1.70 (m, 2H, CH$_2$). MS-EI m/z 445 & 447 [M$^+$−1] & [M$^+$+1].

Example 34

4-Acetyl-5-(5-bromo-2-oxo-1,2-dihydroindol-3-ylidenemethyl)-3-methyl-1H-pyrrole-2-carboxylic acid (2-morpholin-4-ylethyl)amide $^1$H NMR (360 MHz, DMSO-d6) δ 14.19 (s, 1H, NH), 11.14 (br s, 1H, NH), 8.10 (s, 1H, H-vinyl), 7.84 (m, 1H, CONHCH$_2$), 7.71 (d, J=1.8 Hz, 1H, H-4), 7.38 (dd, J=1.8 & 8.2 Hz, 1H, H-6), 6.87 (d, J=8.2 Hz, 1H, H-7), 3.58 (m, 4H, 2×CH$_2$), 3.40 (m, 2H, CH$_2$), 2.57 (s, 3H, CH$_3$CO), 2.49 (m, 4H, 2×CH$_2$), 2.45 (m, CH$_3$ & CH$_2$). MS-EI m/z 500 & 502 [M$^+$−1] & [M$^+$+1].

Example 35

4-Acetyl-5-(5-bromo-2-oxo-1,2-dihydroindol-3-ylidenemethyl)-3-methyl-1H-pyrrole-2-carboxylic acid (2-pyrrolidin-1-ylethyl)amide $^1$H NMR (360 MHz, DMSO-d6) δ 14.17 (s, 1H, NH), 11.23 (s, 1H, NH), 8.11 (s, 1H, H-vinyl), 7.91 (m, 1H, CONHCH$_2$), 7.73 (d, J=1.9 Hz, 1H, H-4), 7.39 (dd, J=1.9 & 8.3 Hz, 1H, H-6), 6.88 (d, J=8.3 Hz, 1H, H-7), 3.40 (m, 2H, CH$_2$), 2.62 (m, 2H, CH$_2$), 2.57 (s, 3H, CH$_3$CO), 2.49 (m, 4H, 2×CH$_2$), 2.44 (s, 3H, CH$_3$), 1.69 (m, 4H, 2×CH$_2$).

Example 36

4-Acetyl-5-(5-bromo-2-oxo-1,2-dihydroindol-3-ylidenemethyl)-3-methyl-1H-pyrrole-2-carboxylic acid [2-(4-hydroxyphenyl)ethyl]amide $^1$H NMR (300 MHz, DMSO-d6) δ 14.21 (s, 1H, NH), 11.18 (s, 1H,OH), 9.09 (s, 1H, NH), 8.06-8.10 (m, 2H), 7.73 (s, 1H), 7.38 (d, J=7.8 Hz, 1H), 7.04 (d, J=7.1 Hz, 2H), 6.88 (d, J=7.8 Hz, 1H), 6.67 (d, J=7.1 Hz, 2H), 3.42 (m, 2H, CH$_2$), 2.72 (m, 2H, CH$_2$), 2.56 (s, 3H, CH$_3$CO), 2.37 (s, 3H, CH$_3$). MS-EI m/z 507 & 509 [M$^+$−1] & [M$^+$+1].

Example 37

5-(5-Bromo-2-oxo-1,2-dihydroindol-3-ylidenemethyl)-2-isopropyl-4-phenyl-1H-pyrrole-3-carboxylic acid (3-diethylaminopropyl)amide A mixture of 2-aminoacetophenone hydrochloride (1 equiv.), ethyl isobutyrylacetate (1.2 equiv.) and sodium acetate (2.4 equiv.) in H$_2$O was stirred at 100° C. for 18 hours and then cooled to room temperature. The aqueous layer was decanted off and the oil was dissolved in ethyl acetate. It was then washed with water and brine and then dried to give (93%) of 2-isopropyl-4-phenyl-1H-pyrrole-3-carboxylic acid ethyl ester as a red brown oil.

$^1$HNMR (300 MHz, DMSO-d6) δ 11.21 (s, br, 1H, NH), 7.14-7.27 (m, 5H), 6.70 (d, J=2.7 Hz, 1H), 4.02 (q, J=7.1 Hz, 2H, OCH$_2$CH$_3$), 3.65 (m, 1H, CH(CH$_3$)$_2$), 1.22 (d, J=7.5 Hz, 6H, CH(CH$_3$)$_2$), 1.04 (t, J=7.1 Hz, 3H, OCH$_2$CH$_3$). MS-EI m/z 257 [M$^+$].

The above pyrrole was formylated using method A to give (41%) 5-formyl-2-isopropyl-4-phenyl-1H-pyrrole-3-carboxylic acid ethyl ester as a reddish solid.

$^1$HNMR (300 MHz, DMSO-d6) δ 12.35 (s, br, 1H, NH), 9.14 (s, 1H, CHO), 7.36 (s, 5H), 3.96 (q, J=7.1 Hz, 2H, OCH$_2$CH$_3$), 3.74 (m, 1H, CH(CH$_3$)$_2$), 1.29 (d, J=6.9 Hz, 6H, CH(CH$_3$)$_2$), 0.90 (t, J=7.1 Hz, 3H, OCH$_2$CH$_3$). MS-EI m/z 285 [M$^+$].

The pyrrolecarboxylic acid ester was hydrolysed using method B to give (57%) of 5-formyl-2-isopropyl-4-phenyl-1H-pyrrole-3-carboxylic acid as a beige solid.

$^1$HNMR (300 MHz, DMSO-d6) δ 12.28 (s, br, 1H, COOH), 12.02 (s, br, 1H, NH), 9.10 (s, 1H, CHO), 7.35 (s, 5H), 3.81 (m, 1H, CH(CH$_3$)$_2$), 1.28 (d, J=6.9 Hz, 6H, CH(CH$_3$)$_2$). MS-EI m/z 257 [M$^+$].

5-Bromo-1,3-dihydroindol-2-one (120 mg, 0.31 mmol) was condensed with 5-formyl-2-isopropyl-4-phenyl-1H-pyrrole-3-carboxylic acid (3-diethylaminopropyl)amide (prepared by method C) to give 120 mg (71%) of the title compound.

$^1$HNMR (300 MHz, DMSO-d6) δ 14.23 (s, br, 1H, NH), 11.08 (s, br, 1H, NH), 7.38-7.55 (m, 7H, Ar—H & CON-

HCH$_2$), 7.30 (s, 1H, H-vinyl), 7.26 (dd, J=1.86 & 7.8 Hz, 1H), 6.85 (d, J=8.7 Hz, 1H), 3.36 (m, 1H, CH(CH$_3$)$_2$), 3.07 (m, 2H, CH$_2$), 2.34 (q, J=7.1 Hz, 4H, N(CH$_2$CH$_3$)$_2$), 2.22 (t, J=6.9 Hz, 2H, CH$_2$), 1.40 (m, 2H, CH$_2$), 1.31 (d, J=6.9 Hz, 6H, CH(CH$_3$)$_2$), 0.86 (t, J=7.1 Hz, 6H, N(CH$_2$CH$_3$)$_2$). MS m/z 565.1 [M$^+$+1].

Example 38

5-(5-Bromo-2-oxo-1,2-dihydroindol-3-ylidenemethyl)-2-isopropyl-4-phenyl-1H-pyrrole-3-carboxylic acid (3-pyrrolidin-1-ylpropyl)amide 5-(5-bromo-2-oxo-1,2-dihydroindol-3-ylidenemethyl)-2-isopropyl-4-phenyl-1H-pyrrole-3-carboxylic acid (127 mg, 0.28 mmol) was condensed with 3-pyrrolidin-1-yl-propylamine (43 mg, 0.336 mmol) to give 140 mg (66%) of the title compound.

$^1$HNMR (300 MHz, DMSO-d6) δ 14.40 (s, br, 1H, NH), 7.38-7.47 (m, 7H), 7.23-7.27 (m, +2H), 6.84 (d, J=8.1 Hz, 1H), 3.36 (m, 1H, CH(CH$_3$)$_2$), 3.08 (m, 2H, CH$_2$), 2.30 (m, 4H, 2×CH$_2$), 2.20 (t, J=7.0 Hz, 2H, CH$_2$), 1.62 (m, 4H, 2×CH$_2$), 1.42 (t, J=7.0 Hz, 2H, CH$_2$), 1.31 (d, J=7.2 Hz, 6H, CH(CH$_3$)$_2$). MS-EI m/z 560 and 562 [M$^+$−1 and M$^+$+1].

Example 39

5-(5-Bromo-2-oxo-1,2-dihydroindol-3-ylidenemethyl)-2-isopropyl-4-phenyl-1H-pyrrole-3-carboxylic acid (2-diethylaminoethyl)amide 5-Bromo-1,3-dihydroindol-2-one (57 ,g. 0.27 mmol) was condensed with 5-formyl-2-isopropyl-4-phenyl-1H-pyrrole-3-carboxylic acid (2-diethylaminoethyl)amide (120 mg) to give 78 mg (53%) of the title compound as a yellow solid.

$^1$HNMR (300 MHz, DMSO-d6) δ 14.23 (s, br, 1H, NH), 11.09 (s, br, 1H, NH), 7.38-7.51 (m, 6H), 7.25-7.28 (m, 2H), 7.19 (t, 1H, CONHCH$_2$), 6.85 (d, J=7.8 Hz, 1H), 3.43 (m, 1H, CH(CH$_3$)$_2$), 3.11 (m, 2H, CH$_2$), 2.28-2.39 (m, 6H, N(CH$_2$CH$_3$)$_2$ & CH$_2$, 1.31 (d, J=6.9 Hz, CH(CH$_3$)$_2$), 0.85 (t, J=7.0 Hz, 6H, N(CH$_2$CH$_3$)$_2$. MS-EI m/z 548 and 550 [M$^+$−1 and M$^+$+1].

Example 40

5-(5-Bromo-2-oxo-1,2-dihydroindol-3-ylidenemethyl)-2-isopropyl-4-phenyl-1H-pyrrole-3-carboxylic acid [3-(4-methylpiperazin-1-yl)propyl]amide 5-Bromo-1,3-dihydroindol-2-one (53 mg, 0.25 mmol) was condensed with 5-formyl-2-isopropyl-4-phenyl-1H-pyrrole-3-carboxylic acid [3-(4-methylpiperazin-1-yl)propyl]amide (300 mg) to give 65 mg of the title compound.

$^1$HNMR (300 MHz, DMSO-d6) δ 14.22 (s, br, 1H, NH), 11.08 (s, br, 1H, NH), 7.23-7.50 (m, 9H), 6.85 (d, J=8.7 Hz, 1H), 3.37 (m, 1H, CH(CH$_3$)$_2$), 3.05 (m, 2H, CH$_2$), 2.24 (m, 8H, 4×CH$_2$), 2.11 (m, 5H, CH$_2$ & CH$_3$), 1.42 (m, 2H, CH$_2$), 1.31 (d, J=7.2 Hz, 6H, CH(CH$_3$)$_2$). MS-EI m/z 589 and 591 [M$^+$−1 and M$^+$+1].

Example 41

5-(5-Bromo-2-oxo-1,2-dihydroindol-3-ylidenemethyl)-2-isopropyl-4-phenyl-1H-pyrrole-3-carboxylic acid 5-Bromo-1,3-dihydroindol-2-one (170 mg, 0.8 mmol) was condensed with 5-formyl-2-isopropyl-4-phenyl-1H-pyrrole-3-carboxylic acid (205 mg) using method D to give 210 mg (58%) of the title compound as a yellow solid.

$^1$HNMR (300 MHz, DMSO-d6) δ 14.31 (s, br, 1H, NH), 11.16 (s, br, 1H, NH), 7.26-7.44 (m, 7H), 7.11 (s, 1H, H-vinyl), 6.85 (d, J=7.8 Hz, 1H), 3.78 (m, 1H, CH(CH$_3$)$_2$), 1.34 (d, J=6.9 Hz, 6H, CH(CH$_3$)$_2$). MS-EI m/z 452 [M$^+$+1.

Example 42

5-(5-Bromo-2-oxo-1,2-dihydroindol-3-ylidenemethyl)-2-methyl-4-phenyl-1H-pyrrole-3-carboxylic acid (2-pyrrolidin-1-ylethyl)amide 5-Bromo-1,3-dihydroindol-2-one (44 mg, 0.21 mmol) was condensed with 5-formyl-2-methyl-4-phenyl-1H-pyrrole-3-carboxylic acid (2-pyrrolidin-1-ylethyl)amide (70 mg, prepared in the same manner as the isopropyl analog, above) to give 0.03 g (27%) of the title compound as a yellow solid.

$^1$HNMR (300 MHz, DMSO-d6) δ 13.87 (s, br, 1H, NH), 11.11 (s, br, 1H, NH), 7.36-7.51 (m, 6H), 7.26 (dd, J=1.8. & 8.1 Hz, 1H), 7.2 (s, 1H, H-vinyl), 7.09 (m, 1H, CONHCH$_2$), 6.83 (d, J=8.1 Hz, 1H), 3.17 (m, 2H, NCH$_2$), 2.48 (m, CH$_3$), 2.29-2.35 (m, 6H, 3×NCH$_2$), 1.5.9 (m, 4H, 2×CH$_2$). MS-EI m/z 518 and 520 [M$^+$−1 and M$^+$+1.

Example 43

5-[6-(2-Methoxyphenyl)-2-oxo-1,2-dihydroindol-3-ylidenemethyl]-2-methyl-4-phenyl-1H-pyrrole-3-carboxylic acid (2-pyrrolidin-1-ylethyl)amide 6-(2-Methoxyphenyl)-1,3-dihydroindol-2-one (50 mg, 0.21 mmol) was condensed with 5-formyl-2-methyl-4-phenyl-1H-pyrrole-3-carboxylic acid (2-pyrrolidin-1-ylethyl)amide (70 mg) to give 0.04 g (35%) of the title compound as a yellow-orange solid.

$^1$HNMR (300 MHz, DMSO-d6) δ 13.82 (s, br, 1H, NH), 11.02 (s, br, 1H, NH), 7.48 (m, 2H), 7.43 (m, 1H), 7.38 (m, 2H), 7.32 (m, 1H), 7.24 (m, 2H), 7.16 (s, 1H, H-vinyl), 7.08 (m, 2H), 7.03 (m, 1H), 7.0 (m, 2H), 3.74 (s, 3H, OCH$_3$), 3.19 (m, 2H, NCH$_2$), 2.49 (m, CH$_3$), 2.32-2.38 (m, 6H, 3×NCH$_2$), 1.59 (m, 4H, 2×CH$_2$). MS-EI m/z 546 [M$^+$].

Example 44

5-(5-Bromo-2-oxo-1,2-dihydroindol-3-ylidenemethyl)-2-methyl-4-phenyl-1H-pyrrole-3-carboxylic acid (2-dimethylaminoethyl)amide 5-Bromo-1,3-dihydroindol-2-one (46 mg, 0.22 mmol) was condensed with 5-formyl-2-methyl-4-phenyl-1H-pyrrole-3-carboxylic acid (2-dimethylaminoethyl)amide (65 mg) to give 60 mg (55%) of the title compound as a yellow solid.

$^1$HNMR (360 MHz, DMSO-d6) δ 13.86 (s, br, 1H, NH), 11.09 (s, br, 1H, NH), 7.47-7.49 (m, 2H), 7.38-7.41 (m, 4H), 7.26 (dd, J=2.2 & 8.3 Hz, 1H), 7.21 (s, 1H, H-vinyl), 7.04 (m, 1H, CONHCH$_2$), 6.77 (d, J=8.3 Hz, 1H), 3.15 (m, 2H, NCH$_2$), 2.48 (m, CH$_3$), 2.16 (t, J=6.8 Hz, 2H, 3×NCH$_2$), 2.02 (s, 6H, 2×NCH$_3$). MS m/z 493 and 494.8 [M$^+$ and M$^+$+2].

Example 45

5-[6-(2-Methoxyphenyl)-2-oxo-1,2-dihydroindol-3-ylidenemethyl]-2-methyl-4-phenyl-1H-pyrrole-3-carboxylic acid (2-dimethylaminoethyl)amide

6-(2-Methoxyphenyl)-1,3-dihydroindol-2-one (53 mg, 0.22 mmol) was condensed with 5-formyl-2-methyl-4-phenyl-1H-pyrrole-3-carboxylic acid (2-dimethylaminoethyl)amide (65 mg) to give 0.05 g (44%) of the title compound as an orange gum.

$^1$HNMR (300 MHz, DMSO-d6) δ 13.82 (s, br, 1H, NH), 11.02 (s, br, 1H, NH), 7.37-7.52 (m, 5H), 7.32 (m, 1H), 7.22-7.27 (m, 2H), 7.16 (s, 1H), 7.08 (m, 2H), 7.03 (m, 1H), 7.0 (m, 2H), 3.74 (s, 3H, OCH$_3$), 3.15 (m, 2H, NCH$_2$), 2.49 (m, CH$_3$), 2.16 (t, J=6.5 Hz, 2H, NCH$_2$), 2.02 (s, 6H, 2×NCH$_3$). MS m/z 521 [M$^+$+1].

Example 46

5-(5-Bromo-2-oxo-1,2-dihydroindol-3-ylidenemethyl)-2-methyl-4-phenyl-1H-pyrrole-3-carboxylic acid ethyl ester

5-Bromo-1,3-dihydroindol-2-one (60 mg, 0.29 mmol) was condensed with 5-formyl-2-methyl-4-phenyl-1H-pyrrole-3-carboxylic acid ethyl ester (75 mg) to give 78 mg (60%) of the title compound as an orange solid.

$^1$HNMR (360 MHz, DMSO-d6) δ 14.01 (s, br, 1H, NH), 11.13 (s, br, 1H, NH), 7.42-7.46 (m, 3H), 7.27-7.34 (m, 4H), 7.12 (s, 1H), 6.84 (dd, J=2.2 & 8.3 Hz, 1H), 3.99-4.03 (m, 2H, OCH$_2$CH$_3$), 2.61 (s, 3H, CH$_3$), 0.98-1.03 (m, 3H, OCH$_2$CH$_3$). MS-EI m/z 450 and 452 [M$^+$−1 and M$^+$+1].

Example 47

5-(5-Bromo-2-oxo-1,2-dihydroindol-3-ylidenemethyl)-2-methyl-4-phenyl-1H-pyrrole-3-carboxylic acid (3-diethylaminopropyl)amide

5-bromo-1,3-dihydroindol-2-one (0.47 g, 2.2 mmol) was condensed with 5-formyl-2-methyl-4-phenyl-1H-pyrrole-3-carboxylic acid (3-diethylaminopropyl)amide (0.75 g) to give 0.11 g (42%) of the title compound as an orange solid.

$^1$HNMR (300 MHz, DMSO-d6) δ 13.86 (s, br, 1H, NH), 7.42-7.46 (m, 3H), 7.37-7.50 (m, 7H), 7.24-7.28 (m, 2H), 6.83 (d, J=8.1 Hz, 1H), 3.09 (m, 2H, NCH$_2$), 2.45 (s, 3H, CH$_3$), 2.38 (q, J=7.1 Hz, 4H, 2×NCH$_2$CH$_3$), 2.26 (t, J=6.9 Hz, 2H, NCH$_2$), 1.42 (m, 2H, NCH$_2$), 0.87 (t, J=7.1 Hz, 6H, 2×NCH$_2$CH$_3$). MS-EI m/z 535.0 and 537 [M$^+$ and M$^+$+2].

Example 48

5-(5-Bromo-2-oxo-1,2-dihydroindol-3-ylidenemethyl)-2,4-dimethyl-1H-pyrrole-3-carboxylic acid (2-dimethylaminoethyl)amide

A mixture of tert-butyl 3-oxobutyrate and sodium nitrite (1 equiv.) in acetic acid was stirred at room temperature to give tert-butyl-2-hydroximino-3-oxobutyrate.

Ethyl-3-oxobutyrate (1 equiv.), zinc dust (3.8 equiv.) and the crude tert-butyl-2-hydroximino-3-oxobutyrate in acetic acid was stirred at 60° C. for 1 hr. The reaction mixture was poured into H$_2$O and the filtrate was collected to give (65%) 2-tert-butyloxycarbonyl-3,5-dimethyl-4-ethoxycarbonylpyrrole.

A mixture of 2-tert-butyloxycarbonyl-3,5-dimethyl-4-ethoxycarbonylpyrrole and triethyl orthoformate (1.5 equiv.) in trifluoroacetic acid was stirred at 15° C. for 1 hour. The reaction was concentrated and the residue was purified to give (64%) 2,4-dimethyl-3-ethoxycarbonyl-5-formylpyrrole as yellow needles.

2,4-Dimethyl-3-ethoxycarbonyl-5-formylpyrrole was hydrolyzed using method B to give (90%) 5-formyl-2,4-dimethyl-1H-pyrrole-3-carboxylic acid.

$^1$H NMR (360 MHz, DMSO-d6) δ 12 (br s, 2H, NH and CO$_2$H), 9.58 (s, 1H, CHO), 2.44 (s, 3H, CH$_3$), 2.40 (s, 3H, CH$_3$). MS m/z 267 [M$^+$].

5-Bromo-1,3-dihydroindol-2-one (0.17 g, 0.8 mmol) was condensed with 5-formyl-2,4-dimethyl-1H-pyrrole-3-carboxylic acid (2-dimethylaminoethyl)amide (0.2 g, prepared by method C) using method B to give 0.3 g (83%) of the title compound as a yellow solid.

$^1$HNMR (360 MHz, DMSO-d6) δ 13.60 (s, br, 1H, NH), 10.94 (s, br, 1H, NH), 8.07 (d, J=1.8 Hz, 1H, H-4), 7.75 (s, 1H, H-vinyl), 7.44 (t, J=5.2 Hz, 1H, CONHCH$_2$), 7.24 (dd, J=1.8 & 8.4 Hz, 1H, H-6), 6.82 (d, J=8.4 Hz, 1H, H-7), 3.26-3.33 (m, 2H, NCH$_2$), 2.42 (s, 3H, CH$_3$), 2.41 (s, 3H, CH$_3$), 2.38 (t, J=6.7 Hz, 2H, NCH$_2$), 2.18 (s, 6H, N(CH$_3$)$_2$). MS-EI m/z 430 and 432 [M$^+$−1 and M$^+$+1].

Example 49

2,4-Dimethyl-5-(2-oxo-6-phenyl-1,2-dihydroindol-3-ylidenemethyl)-1H-pyrrole-3-carboxylic acid (2-dimethylaminoethyl)amide

6-Phenyl-1,3-dihydroindol-2-one (0.17 g, 0.8 mmol) was condensed with 5-formyl-2,4-dimethyl-1H-pyrrole-3-carboxylic acid (2-dimethylaminoethyl)amide (0.2 g) to give 0.13 g (36%) of the title compound as a yellow-orange solid.

$^1$HNMR (360 MHz, DMSO-d6) δ 13.59 (s, br, 1H, NH), 10.93 (, br, 1H, NH), 7.85 (d, J=7.92 Hz, 1H, H-4), 7.63-7.65 (m, 3H), 7.40-7.47 (m, 3H,), 7.32-7.36 (m, 1H, Ar—H), 7.30 (dd, J=1.6 & 7.9 Hz, 1H, H-5), 7.11 (d, J=1.6 Hz, 1H, H-7), 3.28-3.34 (m, 2H, NCH$_2$), 2.43 (s, 3H, CH$_3$), 2.41 (s, 3H, CH$_3$), 2.38 (t, J=6.8 Hz, 2H, NCH$_2$), 2.18 (s; 6H, N(CH$_3$)$_2$). MS-EI m/z 428 [M$^+$].

Example 50

5-(5-Chloro-2-oxo-1,2-dihydroindol-3-ylidenemethyl)-2,4-dimethyl-1H-pyrrole-3-carboxylic acid (2-dimethylaminoethyl)amide

5-Chloro-1,3-dihydroindol-2-one (0.1 g, 0.6 mmol) was condensed with 5-formyl-2,4-dimethyl-1H-pyrrole-3-carboxylic acid (2-dimethylaminoethyl)amide (0.15 g) to give 0.22 g (90%) of the title compound as a yellow solid.

$^1$HNMR (300 MHz, DMSO-d6) δ 13.61 (s, br, 1H, NH), 10.98 (, br, 1H, NH), 7.96 (d, J=2.0 Hz, 1H, H-4), 7.75 (s, 1H, H-vinyl), 7.50 (t, J=5.5 Hz, 1H, CONHCH$_2$), 7.12 (dd, J=2.0 & 8.3 Hz, 1H, H-6), 6.86 (d, J=8.3 Hz, 1H, H-7), 3.26-3.31 (m, 2H, NCH$_2$), 2.42 (s, 3H, CH$_3$), 2.40 (s, 3H, CH$_3$), 2.36 (t, J=6.6 Hz, 2H, NCH$_2$), 2.17 (s, 6H, N(CH$_3$)$_2$). MS-EI m/z 386 [M$^+$].

Example 51

5-(5-Bromo-2-oxo-1,2-dihydroindol-3-ylidenemethyl)-2,4-dimethyl-1H-pyrrole-3-carboxylic acid (2-diethylaminoethyl)amide 5-Bromo-1,3-dihydroindol-2-one (0.17 g, 0.8 mmol) was condensed with 5-formyl-2,4-dimethyl-1H-pyrrole-3-carboxylic acid (2-diethylaminoethyl)amide (0.2 g) to give 0.09 g (26%) of the title compound as a yellow solid.

$^1$HNMR (360 MHz, DMSO-d6) δ 13.61 (s, br, 1H, NH), 10.98 (, br, 1H, NH), 8.09 (d, J=1.7 Hz, 1H, H-4), 7.76 (s, 1H, H-vinyl), 7.42 (t, J=5.5 Hz, 1H, CONHCH$_2$), 7.24 (dd, J=1.7 & 8.0 Hz, 1H, H-6), 6.82 (d, J=8.0 Hz, 1H, H-7), 3.23-3.32 (m, 2H, NCH$_2$), 2.46-2.55 (m, 6H, 3×NCH$_2$), 2.43 (s, 3H, CH$_3$), 2.42 (s, 3H, CH$_3$), 0.96 (t, J=7.2 Hz, 6H, 2×NCH$_2$CH$_3$). MS-EI m/z 458 and 460 [M$^+$−1 and M$^+$+1].

Example 52

5-(5-Bromo-2-oxo-1,2-dihydroindol-3-ylidenemethyl)-2,4-dimethyl-1H-pyrrole-3-carboxylic acid (2-pyrrolidin-1-ylethyl)amide 5-Bromo-1,3-dihydroindol-2-one (0.09 g, 0.4 mmol) was condensed with 5-formyl-2,4-dimethyl-1H-pyrrole-3-carboxylic acid (2-pyrrolidin-1-ylethyl)amide (0.1 g) to give 0.14 g (81%) of the title compound as a yellow-orange solid.

$^1$HNMR (300 MHz, DMSO-d6) δ 13.61 (s, br, 1H, NH), 10.98 (, br, 1H, NH), 8.09 (d, J=1.9 Hz, 1H, H-4), 7.76 (s, 1H, H-vinyl), 7.53 (t, J=5.5 Hz, 1H, CONHCH$_2$), 7.24 (dd, J=1.9 & 8.5 Hz, 1H, H-6), 6.81 (d, J=8.5 Hz, 1H, H-7), 3.29-3.35 (m, 2H, NCH$_2$), 2.54 (t, J=6.9 Hz, 2H, NCH$_2$), 2.47 (m, under DMSO), 2.42 (s, 3H, CH$_3$), 2.40 (s, 3H, CH$_3$), 1.66-1.69 (m, 4H, 2×CH$_2$). MS-EI m/z 456 and 458 [M$^+$−1 and M$^+$+1].

Example 53

5-(5-Bromo-2-oxo-1,2-dihydroindol-3-ylidenemethyl)-2,4-dimethyl-1H-pyrrole-3-carboxylic acid (3-imidazol-1-ylpropyl)amide 5-Bromo-1,3-dihydroindol-2-one (0.09 g, 0.4 mmol) was condensed with 5-formyl-2,4-dimethyl-1H-pyrrole-3-carboxylic acid (3-imidazol-1-ylpropyl)amide (0.1 g) to give 0.1 g (59%) of the title compound as an orange solid.

$^1$HNMR (300 MHz, DMSO-d6) δ 13.63 (s, br, 1H, NH), 10.99 (, br, 1H, NH), 8.09 (d, J=2.2 Hz, 1H, H-4), 7.77 (s, 1H, H-vinyl), 7.71 (t, J=5.7 Hz, 1H, CONHCH$_2$), 7.65 (s, 1H, Ar—H), 7.25 (dd, J=2.2 & 8.4 Hz, 1H, H-6), 7.20 (s, 1H, Ar—H), 6.89 (s, 1H, Ar—H), 6.81 (d, J=8.4 Hz, 1H, H-7), 4.02 (t, J=6.7 Hz, 2H, NCH$_2$), 3.18 (q, J=6.7 Hz, 2H, NCH$_2$), 2.43 (s, 3H, CH$_3$), 2.41 (s, 3H, CH$_3$), 1.93 (m, 2H, CH$_2$). MS-EI m/z 467 and 469 [M$^+$−1 and M$^+$+1].

Example 54

5-[6-(2-Methoxyphenyl)-2-oxo-1,2-dihydroindol-3-ylidenemethyl]-2,4-dimethyl-1H-pyrrole-3-carboxylic acid (2-dimethylaminoethyl)amide 6-(2-Methoxyphenyl)-1,3-dihydroindol-2-one (30 mg, 0.13 mmol) was condensed with 5-formyl-2,4-dimethyl-1H-pyrrole-3-carboxylic acid (2-dimethylaminoethyl)amide (30 mg) to give 0.06 g (100%) of the title compound as a yellow-orange gum.

$^1$HNMR (300 MHz, DMSO-d6) δ 13.60 (s, br, 1H, NH), 10.89 (s, br, 1H, NH), 7.79 (d, J=8.4 Hz, 1H), 7.63 (s, 1H, H-vinyl), 7.46 (t, J=5.5 Hz, 1H, CONHCH$_2$), 7.28-7.35 (m, 2H), 6.99-7.11 (m, 4H), 3.76 (s, 3H, OCH$_3$), 3.27-3.31 (m, 2H, NCH$_2$), 2.43 (s, 3H, CH$_3$), 2.39 (s, 3H, CH$_3$), 2.37 (m, 2H, NCH$_2$), 2.18 (s, 6H, N(CH$_3$)$_2$). MS-EI m/z 458 [M$^+$].

Example 55

5-[6-(3-Methoxyphenyl)-2-oxo-1,2-dihydroindol-3-ylidenemethyl]-2,4-dimethyl-1H-pyrrole-3-carboxylic acid (2-dimethylaminoethyl)amide 6-(3-Methoxyphenyl)-1,3-dihydroindol-2-one (30 mg, 0.13 mmol) was condensed with 5-formyl-2,4-dimethyl-1H-pyrrole-3-carboxylic acid (2-dimethylaminoethyl)amide (30 mg) to give 8 mg (14%) of the title compound as a yellow-orange solid.

$^1$HNMR (360 MHz, DMSO-d6) δ 13.59 (s, br, 1H, NH), 10.92 (s, br, 1H, NH), 7.84 (d, J=7.6 Hz, 1H), 7.65 (s, 1H, H-vinyl), 7.42 (m, 1H, CONHCH$_2$), 7.36 (d, J=7.8 Hz, 1H), 7.29 (dd, J=1.6 & 7.6 Hz, 1H), 7.20 (d, J=7.8 Hz, 1H), 7.14 (d, J=2.8 Hz, 1H), 7.11 (d, J=1.6 Hz, 1H), 6.91 (dd, J=2.8 & 7.8 Hz, 1H), 3.82 (s, 3H, OCH$_3$), 3.21-3.33 (m, 2H, NCH$_2$), 2.43 (s, 3H, CH$_3$), 2.40 (s, 3H, CH$_3$), 2.36-2.40 (m, 2H, NCH$_2$), 2.18 (s, 6H, N(CH$_3$)$_2$). MS-EI m/z 458 [M$^+$].

Example 56

2,4-Dimethyl-5-(2-oxo-5-phenyl-1,2-dihydroindol-3-ylidenemethyl)-1H-pyrrole-3-carboxylic acid (2-diethylaminoethyl)amide 5-Phenyl-1,3-dihydroindol-2-one (80 mg, 0.4 mmol) was condensed with 5-formyl-2,4-dimethyl-1H-pyrrole-3-carboxylic acid (2-diethylaminoethyl)amide (0.1 g) using method B to give 79 mg (46%) of the title compound.

$^1$HNMR (300 MHz, DMSO-d6) δ 13.66 (s, br, 1H, NH), 10.95 (, br, 1H, NH), 8.15 (d, J=1.2 Hz, 1H), 7.81 (s, 1H, H-vinyl), 7.71 (d, J=7.5 Hz, 1H), 7.40-7.47 (m, 4H), 7.31 (m, 1H), 6.95 (d, J=8.1 Hz, 1H), 3.2-3.31 (m, 2H, NCH$_2$), 2.46-2.55 (m, 6H, 3×NCH$_2$), 2.44 (s, 6H, 2×CH$_3$), 0.96 (t, J=7.4 Hz, 6H, 2×NCH$_2$CH$_3$). MS-EI m/z 456 [M$^+$].

Example 57

2,4-Dimethyl-5-(2-oxo-5-phenyl-1,2-dihydroindol-3-ylidenemethyl)-1H-pyrrole-3-carboxylic acid (2-pyrrolidin-1-ylethyl)amide 5-Phenyl-1,3-dihydroindol-2-one (0.04 g, 0.2 mmol) was condensed with 5-formyl-2,4-dimethyl-1H-pyrrole-3-carboxylic acid (2-pyrrolidin-1-ylethyl)amide (0.04 g) to give the title compound as a yellow-orange solid.

$^1$HNMR (300 MHz, DMSO-d6) δ 13.65 (s, br, 1H, NH), 10.96 (, br, 1H, NH), 8.15 (d, J=1.0 Hz, 1H), 7.80 (s, 1H, H-vinyl), 7.71 (d, J=7.2 Hz, 2H), 7.49 (t, J=6.3 Hz, 1H, CONHCH$_2$), 7.41-7.46 (m, 3H), 7.31 (m, 1H), 6.95 (d, J=7.8 Hz, 1H), 4.08 (m, 4H, 2×NCH$_2$), 3.32 (m, 2H, NCH$_2$), 2.55 (t, J=7.1 Hz, 2H, NCH$_2$), 2.47 (m, under DMSO), 2.43 (s, 6H, 2×CH$_3$), 1.66 (m, 4H, 2×CH$_2$). MS-EI m/z 454 [M$^+$].

Example 58

2,4-Dimethyl-5-(2-oxo-5-phenyl-1,2-dihydroindol-3-ylidenemethyl)-1H-pyrrole-3-carboxylic acid (3-imidazol-1-ylpropyl)amide 5-Phenyl-1,3-dihydroindol-2-one (8 mg, 0.04 mmol) was condensed with 5-formyl-2,4-dimethyl-1H-pyrrole-3-carboxylic acid (3-imidazol-1-ylpropyl)amide (10 mg) to give 10 mg (59%) of the title compound as an orange solid.

$^1$HNMR (300 MHz, DMSO-d6) δ 13.67 (s, br, 1H, NH), 10.96 (, br, 1H, NH), 8.16 (d, J=1.2 Hz, 1H), 7.81 (s, 1H, H-vinyl), 7.65-7.72 (m, 4H), 7.44 (m, 3H), 7.31 (m, 1H, CONHCH$_2$), 7.21 (s, 1H, Ar—H), 4.02 (t, J=6.5 Hz, 2H, NCH$_2$), 3.19 (q, J=6.5 Hz, 2H, CONHCH$_2$), 2.44 (s, 6H, 2×CH$_3$), 1.93 (m, 2H, CH$_2$CH$_2$ CH$_2$). MS-EI m/z 465 [M$^+$].

Example 59

2,4-Dimethyl-5-(2-Oxo-6-phenyl-1,2-dihydroindol-3-ylidenemethyl)-1H-pyrrole-3-carboxylic acid (2-diethylaminoethyl)amide 6-Phenyl-1,3-dihydroindol-2-one (0.08 g, 0.4 mmol) was condensed with 5-formyl-2,4-dimethyl-1H-pyrrole-3-carboxylic acid (2-diethylaminoethyl)amide (0.1 g) to give 65 mg (38%) of the title compound as a yellow solid.

$^1$HNMR (300 MHz, DMSO-d6) δ 13.61 (s, br, 1H, NH), 10.99 (, br, 1H, NH), 7.86 (d, J=7.8 Hz, 1H), 7.62-7.66 (m, 3H), 7.40-7.47 (m, 3H), 7.28-7.36 (m, 2H), 7.10 (d, J=1.2 Hz, 1H), 3.26 (m, 2H, NCH$_2$), 2.46-2.55 (m, 6H, 3×NCH$_2$), 2.44 (s, 3H, CH$_3$), 2.41 (s, 3H, CH$_3$), 0.97 (t, J=7.2 Hz, 6H, 2×NCH$_2$CH$_3$). MS-EI m/z 456 [M$^+$].

Example 60

2,4-Dimethyl-5-(2-oxo-6-phenyl-1,2-dihydroindol-3-ylidenemethyl)-1H-pyrrole-3-carboxylic acid (2-pyrrolidin-1-ylethyl)amide 6-Phenyl-1,3-dihydroindol-2-one (30 mg, 0.15 mmol) was condensed with 5-formyl-2,4-dimethyl-1H-pyrrole-3-carboxylic acid (2-pyrrolidin-1-ylethyl)amide (40 mg) to give 5.9 mg (8.5%) of the title compound as a yellow-orange solid.

$^1$HNMR (300 MHz, DMSO-d6) δ 13.60 (s, br, 1H, NH), 10.99 (, br, 1H, NH), 7.86 (d, J=7.8 Hz, 1H), 7.63-7.66 (m, 3H), 7.51 (m, 1H, CONHCH$_2$), 7.45 (m, 2H), 7.28-7.36 (m, 2H), 7.10 (d, J=1.5 Hz, 1H), 3.31 (m, 6H, 3×NCH$_2$), 2.55 (t, J=6.6 Hz, 2H, NCH$_2$), 2.43 (s, 3H, CH$_3$), 2.40 (s, 3H, CH$_3$), 1.67 (m, 4H, 2×CH$_2$). MS-EI m/z 454 [M$^+$].

Example 61

2,4-Dimethyl-5-(2-oxo-6-phenyl-1,2-dihydroindol-3-ylidenemethyl)-1H-pyrrole-3-carboxylic acid (3-imidazol-1-ylpropyl)amide 6-Phenyl-1,3-dihydroindol-2-one (8 mg, 0.04 mmol) was condensed with 5-formyl-2,4-dimethyl-1H-pyrrole-3-carboxylic acid (3-imidazol-1-ylpropyl)amide (10 mg) to give 7.3 mg (43%) of the title compound as an orange solid.

$^1$HNMR (300 MHz, DMSO-d6) δ 13.62 (s, br, 1H, NH), 10.99 (, br, 1H, NH), 7.86 (d, J=8.2 Hz, 1H), 7.62-7.70 (m, 5H), 7.45 (m, 2H), 7.35 (m, 1H), 7.30 (dd, J=1.4 & 8.2 Hz, 1H), 7.21 (s, 1H), 7.10 (d, J=1.4 Hz, 1H), 6.89 (s, 1H), 4.02 (t, J=6.9 Hz, 2H, CH$_2$), 3.19 (m, 2H, NCH$_2$ CH$_2$), 2.43 (s, 3H, CH$_3$), 2.41 (s, 3H, CH$_3$), 1.93 (t, J=6.9 Hz, 2H, NCH$_2$). MS-EI m/z 465 [M$^+$].

Example 62

5-[6-(3,5-Dichlorophenyl)-2-oxo-1,2-dihydroindol-3-ylidenemethyl]-2,4-dimethyl-1H-pyrrole-3-carboxylic acid (2-diethylaminoethyl)amide 6-(3,5-Dichlorophenyl)-1,3-dihydroindol-2-one (64 mg, 0.23 mmol) was condensed with 5-formyl-2,4-dimethyl-1H-pyrrole-3-carboxylic acid (2-diethylaminoethyl)amide (60 mg) to give 53 mg (44%) of the title compound as a light brown solid.

$^1$HNMR (360 MHz, DMSO-d6) δ 13.62 (s, br, 1H, NH), 10.99 (s, 1H, NH), 7.89 (d, J=7.9 Hz, 1H, H-4), 7.69-7.71 (m, 3H), −7.55 (m, 1H, CONHCH$_2$), 7.37 (m, 2H), 7.14 (d, J=1.4 Hz, 1H, H-7), 3.27 (m, 2H, NCH$_2$), 2.48-2.58 (m, 6H, 3×NCH$_2$), 2.45 (s, 3H, CH$_3$), 2.42 (s, 3H, CH$_3$), 0.97 (t, J=6.8 Hz, 6H, 3×NCH$_2$CH$_3$). MS m/z 526.9 [M$^+$+1].

Example 63

2,4-Dimethyl-5-(2-oxo-6-pyridin-3-yl-1,2-dihydroindol-3-ylidenemethyl)-1H-pyrrole-3-carboxylic acid (2-diethylaminoethyl)amide 6-Pyridin-3-yl-1,3-dihydroindol-2-one (40 mg, 0.19 mmol) was condensed with 5-formyl-2,4-dimethyl-1H-pyrrole-3-carboxylic acid (2-diethylaminoethyl)amide (50 mg) give 29 mg (33%) of the title compound as a light orange solid.

$^1$HNMR (300 MHz, DMSO-d6) δ 13.62 (s, br, 1H, NH), 11.05 (s, br, 1H, NH), 8.86 (s, br, 1H), 8.53 (d, J=5.8 Hz, 1H), 8.04 (m, 1H), 7.91 (d, J=8.1 Hz, 1H), 7.70 (s, 1H, H-vinyl), 7.40-7.48 (m, 2H), 7.35 (d, J=7.5 Hz, 1H), 7.14 (s, 1H), 3.26 (m, 2H, NCH$_2$), 2.48-2.55 (m, 3×NCH$_2$), 2.42 (s, 3H, CH$_3$), 2.38 (s, 3H, CH$_3$), 0.96 (t, J=6.9 Hz, 6H, 2×NCH$_2$CH$_3$). MS-EI m/z 457 [M$^+$].

Example 64

2,4-Dimethyl-5-(2-oxo-6-pyridin-3-yl-1,2-dihydroindol-3-ylidenemethyl)-1H-pyrrole-3-carboxylic acid (2-pyrrolidin-1-ylethyl)amide 6-Pyridin-3-yl-1,3-dihydroindol-2-one (60 mg, 0.28 mmol) was condensed with 5-formyl-2,4-dimethyl-1H-pyrrole-3-carboxylic acid (2-pyrrolidin-1-ylethyl)amide (75 mg) to give 90 mg (71%) of the title compound as a light orange solid.

$^1$HNMR (300 MHz, DMSO-d6) δ 13.61 (s, br, 1H, NH), 11.05 (s, br, 1H, NH), 8.86 (d, J=1.5 Hz, 1H), 8.54 (dd, J=1.5 & 4.8 Hz, 1H), 8.05 (m, 1H), 7.91 (d, J=7.8 Hz, 1H), 7.70 (s, 1H, H-vinyl), 7.44-7.53 (m, 2H), 7.36 (dd, J=1.5 & 8.1 Hz, 1H), 7.15 (d, J=1.2 Hz, 1H), 3.33 (m, 2H, NCH$_2$), 2.47-2.57 (m, 6H, 3×NCH$_2$), 2.43 (s, 3H, CH$_3$), 2.41 (s, 3H, CH$_3$), 1.67 (m, 4H, 2×CH$_2$). MS-EI m/z 455 [M$^+$].

Example 65

2,4-Dimethyl-5-(2-oxo-6-pyridin-3-yl-1,2-dihydroindol-3-ylidenemethyl)-1H-pyrrole-3-carboxylic acid (3-dimethylaminopropyl)amide 6-Pyridin-3-yl-1,3-dihydroindol-2-one (42 mg, 0.2 mmol) was condensed with 5-formyl-2,4-dimethyl-1H-pyrrole-3-carboxylic acid (3-dimethylaminopropyl)amide (50 mg) to give 67 mg (75%) of the title compound as yellow-brown solid.

¹HNMR (360 MHz, DMSO-d6) δ 13.61 (s, br, 1H, NH), 11.00 (s, br, 1H, NH), 8.86 (s, br, 1H), 8.54 (s, br, 1H), 8.04 (m, 1H), 7.90 (d, J=8.0 Hz, 1H), 7.69 (s, 1H, H-vinyl), 7.63 (m, 1H), 7.45-7.48 (m, 1H), 7.35 (dd, J=1.7 & 8.0 Hz, 1H), 7.15 (d, J=1.7 Hz, 1H), 3.21-3.27 (m, 2H, NCH$_2$), 2.43 (s, 3H, CH$_3$), 2.41 (s, 3H, CH$_3$), 2.28 (m, 2H, NCH$_2$), 2.14 (s, 6H, 2×NCH$_3$), 1.64 (m, 2H, CH$_2$). MS-EI m/z 443 [M$^+$].

Example 66

2,4-Dimethyl-5-(2-oxo-5-phenyl-1,2-dihydroindol-3-ylidenemethyl)-1H-pyrrole-3-carboxylic acid (3-dimethylaminopropyl)amide 5-Phenyl-1,3-dihydroindol-2-one (67 mg, 0.32 mmol) was condensed with 5-formyl-2,4-dimethyl-1H-pyrrole-3-carboxylic acid (3-dimethylaminopropyl)amide (81 mg) to give 40 mg (28%) of the title compound as an orange solid.

¹HNMR (360 MHz, DMSO-d6) δ 13.66 (s, br, 1H, NH), 10.92 (s, br, 1H, NH), 8.14 (s, 1H), 7.79 (s, 1H), 7.71 (m, 2H), 7.62 (m, 1H), 7.44 (m, 3H), 7.32 (m, 1H), 6.95 (m, 1H), 3.33 (m, 2H, NCH$_2$), 2.43 (s, 6H, 2×CH$_3$), 2.27 (m, 2H, NCH$_2$), 2.13 (s, 6H, 2×NCH$_3$), 1.63 (m, 2H, CH$_2$). MS-EI m/z 442 [M$^+$].

Example 67

2,4-Dimethyl-5-(2-oxo-5-phenyl-1,2-dihydroindol-3-ylidenemethyl)-1H-pyrrole-3-carboxylic acid (3-diethylaminopropyl)amide 5-Phenyl-1,3-dihydroindol-2-one (1.5 g, 7.16 mmol) was condensed with 5-formyl-2,4-dimethyl-1H-pyrrole-3-carboxylic acid (3-diethylaminopropyl)amide (2 g) to give 1.3 g (40%) of the title compound as a yellow-orange solid.

¹HNMR (360 MHz, DMSO-d6) δ 13.64 (s, 1H, NH), 10.91 (s, 1H, NH), 8.14 (d, J=1.4 Hz, 1H, ArH), 7.8 (s, 1H, ArH), 7.7 (dd, J=1.2 and 8.5 Hz, 2H, ArH), 7.6 (t, J=5.3 Hz, 1H, CONHCH$_2$), 7.4 (m, 3H, ArH), 7.3 (t, J=7.4 Hz, 1H, ArH), 6.9 (d, J=8.0 Hz, 1H, ArH), 3.2 (m, 2H, CONHC$\underline{H}_2$), 2.5 (m, 12H, 3×NC$\underline{H}_2$ and 2×C$\underline{H}_3$), 1.61 (m, 2H, C$\underline{H}_2$CH$_2$CH$_2$), 0.93 (t, = 6.7 Hz, 6H, NCH$_2$C$\underline{H}_3$). MS-EI m/z 470 [M$^+$].

Example 68

2,4-Dimethyl-5-(2-oxo-6-phenyl-1,2-dihydroindol-3-ylidenemethyl)-1H-pyrrole-3-carboxylic acid (3-diethylaminopropyl)amide 6-Phenyl-1,3-dihydroindol-2-one (1.5 g, 7.16 mmol) was condensed with 5-formyl-2,4-dimethyl-1H-pyrrole-3-carboxylic acid (3-diethylaminopropyl)amide (2 g) to give 1.9 g (57%) of, the title compound as an orange solid.

¹HNMR (360 MHz, DMSO-d6) δ 13.58 (s, 1H, NH), 10.94 (s, 1H, NH), 7.8 (d, J=7.9 Hz, 1H, ArH), 7.6 (m, 4H, ArH), 7.4 (t, J=7.5 Hz, 2H, ArH), 7.3 (m, 2H), 7.1 (d, J=1.4 Hz, 1H, ArH), 3.2 (m, 2H, CONHCH$_2$), 2.5 (m, 12H, 3×NCH$_2$ and 2×CH$_3$), 1.61 (m, 2H, CH$_2$CH$_2$CH$_2$), 0.93 (t, J=6.7 Hz, 6H, NCH$_2$CH$_3$). MS-EI m/z 470 [M$^+$].

Example 69

3-[4-(3-Diethylaminopropylcarbamoyl)-3,5-dimethyl-1H-pyrrol-2-ylmethylene]-2-oxo-2,3-dihydro-1H-indole-4-carboxylic acid (3-chloro-4-methoxyphenyl)amide 2-Oxo-2,3-dihydro-1H-indole-4-carboxylic acid (3-chloro-4-methoxyphenyl)amide (1 g, 3.16 mmol) was condensed with 5-formyl-2,4-dimethyl-1H-pyrrole-3-carboxylic acid (3-diethylaminopropyl)amide (1 g, 3.58 mmol) to give 1.7 g (85%) of the title compound as a yellow-orange solid. MS-EI m/z 578.2 [M$^+$].

Example 70

5-(5-Bromo-2-oxo-1,2-dihydroindol-3-ylidenemethyl)-2,4-dimethyl-1H-pyrrole-3-carboxylic acid (3-diethylaminopropyl)amide 5-Bromo-1,3-dihydroindol-2-one (0.5 g, 2.36 mmol) was condensed with 5-formyl-2,4-dimethyl-1H-pyrrole-3-carboxylic acid (3-diethylaminopropyl)amide (0.51 g) to give 0.84 g of the title compound as a red-orange solid.

¹HNMR (360 MHz, DMSO-d6) δ 13.61 (s, 1H, NH), 10.99 (s, 1H, NH), 8.09 (d, J=1.8 Hz, 1H, ArH), 7.7 (m, 4H), 7.2 (dd, = 1.8 and 8.3 Hz, 2H, ArH), 6.8 (d, J=7.8 Hz, 1H, ArH), 3.3 (br s, 4H, 2×NCH$_2$), 3.2 (m, 2H, CONHCH$_2$), 2.6 (br s, 2H, NCH$_2$ and 2×CH$_3$), 2.4 (s, 6H, 2×CH$_3$), 1.66 (m, 2H, CH$_2$CH$_2$CH$_2$), 0.98 (t, J=7.1 Hz, 6H, NCH$_2$CH$_3$). MS-EI m/z 472 and 474 [M$^+$−1 and M$^+$+1].

Example 71

5-(5-Bromo-2-oxo-1,2-dihydroindol-3-ylidenemethyl)-2,4-diisopropyl-1H-pyrrole-3-carboxylic acid (2-diethylaminoethyl)amide 5-Bromo-1,3-dihydroindol-2-one (100 mg, 0.47 mmol) was condensed with 5-formyl-2,4-diisopropyl-1H-pyrrole-3-carboxylic-acid (2-diethylaminoethyl)amide (150 mg) to give 0.15 g (62%) of the title compound as a yellow-orange solid.

¹HNMR (300 MHz, DMSO-d6) δ 13.97 (s, 1H, NH), 10.95 (s, 1H, NH), 8.09 (d, J=1.3 Hz, 1H, ArH), 7.84 (m, 1H), 7.79 (s, 1H), 7.23 (dd, J=1.3 and 8.1 Hz, 1H, ArH), 6.8 (d, J=8.1 Hz, 1H, ArH), 3.5 (m, 1H, CH), 3.3 (m, 3H, CH and NHCH$_2$), 2.5 (br m, 6H, 3×NCH$_2$), 1.28 (d, J=6.9 Hz, 6H, 2×CH$_3$), 1.23 (d, J=6.6 Hz, 6H, 2×CH$_3$), 0.96 (m, 6H, 2×CH$_2$CH$_3$). MS-EI m/z 514 and 516 [M$^+$−1 and M$^+$+1].

Example 72

5-(5-Bromo-2-oxo-1,2-dihydroindol-3-ylidenemethyl)-2,4-diisopropyl-1H-pyrrole-3-carboxylic acid (3-diethylaminopropyl)amide 5-Bromo-1,3-dihydroindol-2-one (90 mg, 0.42 mmol) was condensed with 5-formyl-2,4-diisopropyl-1H-pyrrole-3-carboxylic acid (3-diethylaminopropyl)amide (140 mg) to give 54 mg (25%) of the title compound as red-brown solid.

¹HNMR (300 MHz, DMSO-d6) δ 13.98 (s, 1H, NH), 10.96 (s, 1H, NH), 8.09 (d, J=1.7 Hz, 2H), 7.78 (s, 1H, H-vinyl), 7.23 (dd, J=1.7 and 8.1 Hz, 1H, ArH), 6.82 (d, J=8.1 Hz, 1H, ArH), 3.5 (m, 1H, CH), 3.25 (m, 2H, NHCH$_2$), 3.15 (m, 1H, CH), 2.7 (br s, 6H, 3×NCH$_2$), 1.7 (br m, 2H, CH$_2$CH$_2$CH$_2$), 1.28 (d, J=6.9 Hz, 6H, 2×CH$_3$), 1.24 (d, J=5.9 Hz, 6H, 2×CH$_3$), 1.06 (m, 6H, 2×CH$_2$CH$_3$). MS-EI m/z 528 and 530 [M$^+$−1 and M$^+$+1].

Example 73

5-(5-Bromo-2-oxo-1,2-dihydroindol-3-ylidenemethyl)-2,4-diisopropyl-1H-pyrrole-3-carboxylic acid (3-pyrrolidin-1-ylpropyl)amide 5-Bromo-1,3-dihydroindol-2-one (130 mg, 0.6 mmol) was condensed with 5-formyl-2,4-diisopropyl-1H-pyrrole-3-carboxylic acid (3-pyrrolidin-1-ylpropyl)amide (150 mg, 0.45 mmol) to give 36 mg (15%) of the title compound as a tan-orange solid.

$^1$HNMR (300 MHz, DMSO-d6) δ 13.98 (s, 1H, NH), 10.97 (s, 1H, NH), 8.10 (d, J=1.6 Hz, 2H), 7.78 (s, 1H, H-vinyl), 7.23 (dd, J=1.6 and 7.6 Hz, 1H, ArH), 6.82 (d, J=7.6 Hz, 1H, ArH), 3.5 (m, 1H, CH), 3.25 (m, 2H, NHCH$_2$), 3.15 (m, 1H, CH), 2.7 (br s, 6H, 3×NCH$_2$), 1.7 (br m, 6H, 3×NCH$_2$CH$_2$), 1.28 (d, J=5.6 Hz, 6H, 2×CH$_3$), 1.24 (d, J=5.7 Hz, 6H, 2×CH$_3$). MS-EI m/z 526 and 528 [M$^+$−1 and M$^+$+1].

Example 74

5-(5-Bromo-2-oxo-1,2-dihydroindol-3-ylidenemethyl)-2,4-dimethyl-1H-pyrrole-3-carboxylic acid (pyridin-4-ylmethyl)amide 5-Bromo-1,3-dihydroindol-2-one (170 mg, 0.8 mmol) was condensed with 5-formyl-2,4-dimethyl-1H-pyrrole-3-carboxylic acid (pyridin-4-ylmethyl)amide (200 mg) to give 14 mg (4%) of the title compound as a yellow solid.

$^1$HNMR (300 MHz, DMSO-d6) δ 13.67 (s, 1H, NH), 11.01 (s, br, 1H, NH), 8.51 (dd, J=1.6 & 4.3 Hz, 2H), 8.23 (t, J=6.0 Hz, 1H, CONHCH$_2$); 8.11 (d, J=1.9 Hz, 1H), 7.78 (s, 1H, H-vinyl), 7.31 (d, J=6.0 Hz, 2H), 7.25 (dd, J=1.9 & 8.1 Hz, 1H), 6.82 (d, J=8.1 Hz, 1H), 4.45 (d, J=6.0 Hz, 2H, NCH$_2$), 2.46 (s, 6H, 2×CH$_3$). MS-EI m/z 450 and 452 [M$^+$−1 and M$^+$+1].

Example 75

5-(6-(4-Butylphenyl)-2-oxo-1,2-dihydroindol-3-ylidenemethyl]-2,4-dimethyl-1H-pyrrole-3-carboxylic acid (2-pyrrolidin-1-ylethyl)amide 5-[6-(4-Butylphenyl)]-1,3-dihydroindol-2-one (50 mg, 0.19 mmol) was condensed with 5-formyl-2,4-dimethyl-1H-pyrrole-3-carboxylic acid (2-pyrrolidin-1-ylethyl)amide (50 mg) to give 74 mg (76%) of the title compound as an orange solid.

$^1$HNMR (360 MHz, DMSO-d6) δ 13.58 (s, 1H, NH), 10.93 (s, br, 1H, NH), 7.82 (d, J=7.9 Hz, 1H), 7.63 (s, 1H, H-vinyl), 7.54 (d, J=7.9 Hz, 2H), 7.46 (m, 1H, CONH), 7.26 (m, 3H), 7.09 (s, 1H), 3.30 (m, 2H, CH$_2$), 2.52-2.63 (m, 4H, 2×CH$_2$), 2.49 (m, 4H, 2×CH$_2$), 2.43 (s, 3H, CH$_3$), 2.40 (s, 3H, CH$_3$), 1.68 (m, 4H, 2×CH$_2$), 1.58 (m, 2H, CH$_2$), 1.34 (m, 2H, CH$_2$), 0.91 (t, J=7.2 Hz, 3H, CH$_2$CH$_3$). MS-EI m/z 510 [M$^+$].

Example 76

5-[6-(5-Isopropyl-2-methoxyphenyl)-2-oxo-1,2-dihydroindol-3-ylidenemethyl]-2,4-dimethyl-1H-pyrrole-3-carboxylic acid (2-pyrrolidin-1-ylethyl)amide 6-(5-Isopropyl-2-methoxyphenyl)-1,3-dihydroindol-2-one (50 mg, 0.17 mmol) was condensed with 5-formyl-2,4-dimethyl-1H-pyrrole-3-carboxylic acid (2-pyrrolidin-1-ylethyl)amide (45 mg) to give 67 mg (75%) of the title compound as an orange solid.

$^1$HNMR (360 MHz, DMSO-d6) δ 13.60 (s, 1H, NH), 10.82 (s, br, 1H, NH), 7.77 (d, J=7.9 Hz, 1H), 7.61 (s, 1H, H-vinyl), 7.45 (m, 1H, CONH), 7.0-7.19 (m, 5H), 3.73 (s, 3H, OCH$_3$), 3.32 (m, 2H, CH$_2$), 2.87 (m, 1H, CH(CH$_3$)$_2$), 2.56 (m, 2H, CH$_2$), 2.48 (m, 4H, 2×CH$_2$), 2.43 (s, 3H, CH$_3$), 2.40 (s, 3H, CH$_3$), 1.68 (m, 4H, 2×CH$_2$), 1.21 (d, J=6.8 Hz, 6H, CH(CH$_3$)$_2$). MS m/z 527.2 [M$^+$+1].

Example 77

5-[6-(4-Ethylphenyl)-2-oxo-1,2-dihydroindol-3-ylidenemethyl]-2,4-dimethyl-1H-pyrrole-3-carboxylic acid (2-pyrrolidin-1-ylethyl)amide 6-(4-Ethylphenyl)-1,3-dihydroindol-2-one (45 mg, 0.19 mmol) was condensed 5-formyl-2,4-dimethyl-1H-pyrrole-3-carboxylic acid (2-pyrrolidin-1-ylethyl)amide (50 mg) to give 60 mg (65%) of the title compound as a yellow-orange solid.

$^1$HNMR (300 MHz, DMSO-d6) δ 13.59 (s, 1H, NH), 10.96 (s, br, 1H, NH), 7.83 (d, J=8.4 Hz, 1H), 7.64 (s, 1H, H-vinyl), 7.51-7.56 (m, 3H), 7.25-7.30 (m, 3H), 7.08 (d, J=1 Hz, 1H), 3.31 (m, 2H, CH$_2$), 2.63 (m, 2H, CH$_2$CH$_3$), 2.55 (m, 2H, CH$_2$), 2.49 (m, 4H, 2×CH$_2$), 2.42 (s, 3H, CH$_3$), 2.40 (s, 3H, CH$_3$), 1.67 (m, 4H, 2×CH$_2$), 1.20 (t, J=7.5 Hz, 3H, CH$_2$CH$_3$). MS-EI m/z 482 [M$^+$].

Example 78

5-[6-(2,4-Dimethoxyphenyl)-2-oxo-1,2-dihydroindol-3-ylidenemethyl]-2,4-dimethyl-1H-pyrrole-3-carboxylic acid (2-pyrrolidin-1-ylethyl)amide 6-(2,4-Dimethoxyphenyl)-1,3-dihydroindol-2-one (51 mg, 0.19 mmol) was condensed with 5-formyl-2,4-dimethyl-1H-pyrrole-3-carboxylic acid (2-pyrrolidin-1-ylethyl)amide (50 mg) to give 30 mg (31%) of the title compound as an orange solid.

$^1$HNMR (300 MHz, DMSO-d6) δ 13.59 (s, 1H, NH), 10.86 (s, br, 1H, NH), 7.75 (d, J=7.8 Hz, 1H), 7.60 (s, 1H, H-vinyl), 749 (m, 1H, CONH), 7.22 (d, J=8.4 Hz, 1H), 7.03 (m, 1H), 6.97 (s, 1H), 6.58-6.65 (m, 2H), 3.79 (s, 3H, OCH$_3$), 3.76 (s, 3H, OCH$_3$), 3.33 (m, 2H, CH$_2$), 2.55 (m, 2H, CH$_2$), 2.50 (m, 4H, 2×CH$_2$), 2.42 (s, 3H, CH$_3$), 2.39 (s, 3H, CH$_3$), 1.67 (m, 4H, 2×CH$_2$). MS-EI m/z 514 [M$^+$].

Example 79

5-[6-(3-Isopropylphenyl)-2-oxo-1,2-dihydroindol-3-ylidenemethyl]-2,4-dimethyl-1H-pyrrole-3-carboxylic acid (2-pyrrolidin-1-ylethyl)amide 6-(3-Isopropylphenyl)-1,3-dihydroindol-2-one (48 mg, 0.19 mmol) was condensed with 5-formyl-2,4-dimethyl-1H-pyrrole-3-carboxylic acid (2-pyrrolidin-1-ylethyl)amide (50 mg) to give 59 mg (63%) of the title compound as an orange solid.

¹HNMR (300 MHz, DMSO-d6) δ 13.63 (s, 1H, NH), 10.97 (s, br, 1H, NH), 7.87 (d, J=7.8 Hz, 1H), 7.68 ('s, 1H, H-vinyl), 7.24-7.55 (m, 6H), 7.13 (s, 1H), 3.34 (m, 2H, CH$_2$), 3.30 (m, 1H, CH(CH$_3$)$_2$), 2.60 (m; 2H, CH$_2$), 2.50 (m, 4H, 2×CH$_2$), 2.45 (s, 3H, CH$_3$), 2.43 (s, 3H, CH$_3$), 1.70 (m, 4H, 2×CH$_2$), 1.27 (d, J=6.9 Hz, 6H, CH(CH$_3$)$_2$). MS-EI m/z 496 [M$^+$].

Example 80

5-(5-Fluoro-2-oxo-1,2-dihydroindol-3-ylidenemethyl)-2,4-dimethyl-1H-pyrrole-3-carboxylic acid (2-diethylaminoethyl)amide 5-Fluoro-1,3-dihydroindol-2-one (0.54 g, 3.8 mmol) was condensed with 5-formyl-2,4-dimethyl-1H-pyrrole-3-carboxylic acid (2-diethylaminoethyl)amide to give 0.83 g (55%) of the title compound as a yellow green solid.

¹HNMR (360 MHz, DMSO-d6) δ 1.3.66 (s, 1H, NH), 10.83 (s, br, 1H, NH), 7.73 (dd, J=2.5 & 9.4 Hz, 1H), 7.69 (s, 1H, H-vinyl), 7.37 (t, 1H, CONHCH$_2$CH$_2$), 6.91 (m, 1H), 6.81-6.85 (m, 1H), 3.27 (m, 2H, CH$_2$), 2.51 (m, 6H, 3×CH$_2$), 2.43 (s, 3H, CH$_3$), 2.41 (s, 3H, CH$_3$), 0.96 (t, J=6.9 Hz, 6H, N(CH$_2$CH$_3$)$_2$). MS-EI m/z 398 [M$^+$].

Example 80 (Alternative Synthesis)

5-[5-Fluoro-2-oxo-1,2-dihydro-indol-(3Z)-ylidenemethyl]-2,4-dimethyl-1H-pyrrole-3-carboxylic acid (2-diethylamino-ethyl)amide Hydrazine hydrate (55%, 3000 mL) and 5-fluoroisatin (300 g) were heated to 100° C. An additional 5-fluoro-isatin (500 g) was added in portions (100 g) over 120 minutes with stirring. The mixture was heated to 110° C. and stirred for 4 hours. The mixture was cooled to room temperature and the solids collected by vacuum filtration to give crude (2-amino-5-fluoro-phenyl)-acetic acid hydrazide (748 g). The hydrazide was suspended in water (700 mL) and the pH of the mixture adjusted to <pH 3 with 12 N hydrochloric acid. The mixture was stirred for 12 hours at room temperature. The solids were collected by vacuum filtration and washed twice with water. The product was dried under vacuum to give 5-fluoro-1,3-dihydro-indol-2-one (600 g, 73% yield) as as a brown powder. ¹H-NMR (dimethylsulfoxide-d$_6$) δ 3.46 (s, 2H, CH$_2$), 6.75, 6.95, 7.05 (3×m, 3H, aromatic), 10.35 (s, 1H, NH). MS m/z 152 [M+1].

3,5-Dimethyl-1H-pyrrole-2,4-dicarboxylic acid 2-tert-butyl ester 4-ethyl ester (2600 g) and ethanol (7800 mL) were stirred vigorously while 10 N hydrochloric acid (3650 mL) was slowly added. The temperature increased from 25° C. to 35-C and gas evolution began. The mixture was warmed to 54° C. and stirred with further heating for one hour at which time the temperature was 67° C. The mixture was cooled to 5° C. and 32 L of ice and water were slowly added with stirring. The solid was collected by vacuum filtration and washed three times with water. The solid was air dried to constant weight to give of 2,4-dimethyl-1H-pyrrole-3-carboxylic acid ethyl ester (1418 g, 87% yield) as a pinkish solid. ¹H-NMR (dimethylsulfoxide-d$_6$) δ 2.10, 2.35 (2×s, 2×3H, 2×CH$_3$), 4.13 (q, 2H, CH$_2$), 6.37 (s, 1H, CH), 10.85 (s, 1H, NH). MS m/z 167 [M+1].

Dimethylformamide (322 g) and dichloromethane (3700 mL) were cooled in an ice bath to 4° C. and phosphorus oxychloride (684 g) was added with stirring. Solid 2,4-dimethyl-1H-pyrrole-3-carboxylic acid ethyl ester (670 g) was slowly added in aliquots over 15 minutes. The maximum temperature reached was 18° C. The mixture was heated to reflux for one hour, cooled to 10° C. in an ice bath and 1.6 L of ice water was rapidly added with vigorous stirring. The temperature increased to 15° C. 10 N Hydrochloric acid (1.6 L) was added with vigorous stirring. The temperature increased to 22° C. The mixture was allowed to stand for 30 minutes and the layers allowed to separate. The temperature reached a maximum of 40° C. The aqueous layer was adjusted to pH 12-13 with 10 N potassium hydroxide (3.8 L) at a rate that allowed the temperature to reach and remain at 55° C. during the addition. After the addition was complete the mixture was cooled to 10° C. and stirred for 1 hour. The solid was collected by vacuum filtration and washed four times with water to give 5-formyl-2,4-dimethyl-1H-pyrrole-3-carboxylic acid ethyl ester (778 g, 100% yield) as a yellow solid. ¹H-NMR (DMSO-d6) δ 1.25 (t, 3H, CH$_3$), 2.44, 2.48 (2×s, 2×3H, 2×CH$_3$), 4.16 (q, 2H, CH$_2$), 9.59 (s, 1H, CHO), 12.15 (br s, 1H, NH). MS m/z 195 [M+1].

5-Formyl-2,4-dimethyl-1H-pyrrole-3-carboxylic acid ethyl ester (806 g), potassium hydroxide (548 g), water (2400 mL) and methanol (300 mL) were refluxed for two hours with stirring and then cooled to 8° C. The mixture was extracted twice with dichloromethane. The aqueous layer was adjusted to pH 4 with 1000 mL of 10 N hydrochloric acid keeping the temperature under 15° C. Water was added to facilitate stirring. The solid was collected by vacuum filtration, washed three times with water and dried under vacuum at 50° C. to give 5-formyl-2,4-dimethyl-1H-pyrrole-3-carboxylic (645 g, 93.5% yield) acid as a yellow solid. NMR (DMSO-d6) δ 2.40, 2.43 (2×s, 2×3H, 2×CH$_3$), 9.57 (s, 1H, CHO), 12.07 (br s, 2H, NH+COOH). MS m/z 168 [M+1].

5-Formyl-2,4-dimethyl-1H-pyrrole-3-carboxylic acid (1204 g) and 6020 mL of dimethylformamide were stirred at room temperature while 1-(3-dimethyl-aminopropyl-3-ethylcarbodiimide hydrochloride (2071 g), hydroxybenzotriazole (1460 g), triethylamine (2016 mL) and diethylethylenediamine (1215 mL) were added. The mixture was stirred for 20 hours at room temperature. The mixture was diluted with 3000 mL of water, 2000 mL of brine and 3000 mL of saturated sodium bicarbonate solution and the pH adjusted to greater than 10 with 10 N sodium hydroxide. The mixture was extracted twice with 5000 mL each time of 10% methanol in dichloromethane and the extracts combined dried over anhydrous magnesium sulfate and rotary evaporated to dryness. The mixture was with diluted with 1950 mL of toluene and rotary evaporated again to dryness. The residue was triturated with 3:1 hexane:diethyl ether (4000 mL). The solids were collected by vacuum filtration, washed twice with 400 mL of ethyl acetate and dried under vacuum at 34° C. for 21 hours to give 5-formyl-2,4-dimethyl-1H-pyrrole-3-carboxylic acid (2-diethylamino-ethyl)amide (819 g, 43% yield) as a light brown solid. ¹H-NMR (dimethylsulfoxide-d$_6$) δ 0.96 (t, 6H, 2×CH$_3$), 2.31, 2.38 (2×s, 2×CH$_3$), 2.51 (m, 6H 3×CH$_2$), 3.28 (m, 2H, CH$_2$), 7.34 (m, 1H, amide NH), 9.56 (s, 1H, CHO), 11.86 (s, 1H, pyrrole NH). MS m/z 266 [M+1].

5-Formyl-2,4-dimethyl-1H-pyrrole-3-carboxylic acid (2-diethylaminoethyl)-amide (809 g), 5-fluoro-1,3-dihydroindol-2-one (438 g), ethanol (8000 mL) and pyrrolidine (13 mL) were heated at 78° C. for 3 hours. The mixture was cooled to room temperature and the solids collected by vacuum filtration and washed with ethanol. The solids were stirred with ethanol (5900 mL) at 72° C. for 30 minutes. The mixture was cooled to room temperature. The solids were collected by vacuum filtration, washed with ethanol and dried under vacuum at 54° C. for 130 hours to give 5-[5-fluoro-2-oxo-1,2-dihydro-indol-(3Z)-ylidenemethyl]-2,4-dimethyl-1H-pyrrole-3-carboxylic acid (2-diethylamino-ethyl)-amide (1013 g, 88% yield) as an orange solid. ¹H-NMR (dimethyl-

Example 81

3-[4-(2-Diethylaminoethylcarbamoyl)-3,5-dimethyl-1H-pyrrol-2-ylmethylene]-2-oxo-2,3-dihydro-1H-indole-6-carboxylic acid 2-Oxo-2,3-dihydro-1H-indole-6-carboxylic acid (80 mg, 0.45 mmol) was condensed with 5-formyl-2,4-dimethyl-1H-pyrrole-3-carboxylic acid (2-diethylaminoethyl)amide to give 210 mg (92%) of the title compound as a yellow orange solid.

$^1$HNMR (360 MHz, DMSO-d6) δ 13.6 (s, 1H, NH), 7.76 (d, J=8.0 Hz, 1H), 7.66 (s, 1H, H-vinyl), 7.57 (dd, J=1.5 & 8.0 Hz, 1H), 7.40-7.42 (m, 2H), 3.28 (m, 2H, CH$_2$), 2.88 (m, H-piperidine), 2.54 (m, 6H, 3×CH$_2$), 2.44 (s, 3H, CH$_3$), 2.40 (s, 3H, CH$_3$), 1.56 (m, H-piperidine), 0.97 (t, J=6.98 Hz, 6H, N(CH$_2$CH$_3$)$_2$). MS m/z 424 [M$^+$].

Example 82

5-(5-Dimethylsulfamoyl-2-oxo-1,2-dihydroindol-3-ylidenemethyl)-2,4-dimethyl-1H-pyrrole-3-carboxylic acid (2-pyrrolidin-1-ylethyl)amide 2-Oxo-2,3-dihydro-1H-indole-5-sulfonic acid dimethylamide (90 mg, 0.38 mmol) was condensed with 5-formyl-2,4-dimethyl-1H-pyrrole-3-carboxylic acid (2-pyrrolidin-1-ylethyl)amide (100 mg) to give 100 mg (54%) of the title compound as a yellow solid.

$^1$HNMR (360 MHz, DMSO-d6) δ 13.65 (s, 1H, NH), 11.30 (s, br, 1H, NH), 8.25 (d, 1H), 7.92 (s, 1H, H-vinyl), 7.48-7.53 (m, 2H), 7.07 (d, J=8.2 Hz, 1H), 3.33 (m, 2H, CH$_2$), 2.61 (s, 6H, N(CH$_3$)$_2$), 2.56 (t, 2H, —CH$_2$), 2.49 (m, 4H, 2×CH$_2$), 2.45 (s, 3H, CH$_3$), 2.44 (s, 3H, CH$_3$), 1.67 (m, 4H, 2×CH$_2$). MS-EI m/z 485 [M$^+$].

Example 83

5-[5-(3-Chlorophenylsulfamoyl)-2-oxo-1,2-dihydroindol-3-ylidenemethyl]-2,4-dimethyl-1H-pyrrole-3-carboxylic acid (2-pyrrolidin-1-ylethyl)amide 2-Oxo-2,3-dihydro-1H-indole-5-sulfonic acid (3-chlorophenyl)amide (120 mg, 0.38 mmol) was condensed with 5-formyl-2,4-dimethyl-1H-pyrrole-3-carboxylic acid (2-pyrrolidin-1-ylethyl)amide (100 mg) to give 150 mg (69%) of the title compound as a yellow orange solid.

$^1$HNMR (360 MHz, DMSO-d6) δ 13.55 (s, 1H, NH), 11.26 (br s, 1H, NH), 10.30 (br s, 1H, NH), 8.26 (d, 1H), 7.79 (s, 1H, H-vinyl), 7.51-7.57 (m, 2H), 7.22 (t, J=8.1 Hz, 1H), 7.15 (m, H), 7.07 (m, 1H), 7.0 (m, 2H), 3.44 (m, 2H, CH$_2$), 2.57 (t, J=7.0 Hz, 2H, CH$_2$), 2.49 (m, 4H, 2×CH$_2$), 2.44 (s, 3H, CH$_3$), 2.43 (s, 3H, CH$_3$), 1.68 (m, 4H, 2×CH$_2$). MS m/z 568 [M$^+$].

Example 84

2,4-Dimethyl-5-[2-oxo-5-(pyridin-3-ylsulfamoyl)-1,2-dihydroindol-3-ylidenemethyl]-1H-pyrrole-3-carboxylic acid (2-pyrrolidin-1-ylethyl)amide 2-Oxo-2,3-dihydro-1H-indole-5-sulfonic acid pyridin-3-ylamide (110 mg, 0.38 mmol) was condensed with 5-formyl-2,4-dimethyl-1H-pyrrole-3-carboxylic acid (2-pyrrolidin-1-ylethyl)amide (100 mg) to give 150 mg (74%) of the title compound as an orange solid.

$^1$HNMR (360 MHz, DMSO-d6) δ 13.58 (s, 1H, NH), 8.21 (d, J=2.0 Hz, 2H), 8.04 (m, 1H), 7.76 (s, 1H, H-vinyl), 7.49-7.54 (m, 2H), 7.41 (m, 1H), 7.14 (m, 1H), 6.94 (d, J=8.5 Hz, 1H), 3.33 (m, 2H, CH$_2$), 2.56 (t, J=7.06 Hz, 2H, CH$_2$), 2.49 (m, 4H, 2×CH$_2$), 2.43 (s, 6H, 2×CH$_3$), 1.68 (m, 4H, 2×CH$_2$). MS m/z 535 [M$^+$].

Example 85

3-[3,5-Dimethyl-4-(4-methylpiperazine-1-carbonyl)-1H-pyrrol-2-ylmethylene]-4-(2-hydroxyethyl)-1,3-dihydroindol-2-one 4-(2-Hydroxyethyl)-1,3-dihydroindol-2-one (71 mg, 0.4 mmol) was condensed with 3,5-dimethyl-4-(4-methyl-piperazine-1-carbonyl)-1H-pyrrole-2-carbaldehyde to give 90 mg (55%) of the title compound as an orange solid.

$^1$HNMR (300 MHz, DMSO-d6) δ 14.25(s, 1H, NH), 10.88 (s, 1H, NH), 7.57 (s, 1H, H-vinyl), 7.03 (m, 1H), 6.75-6.82 (m, 2H), 4.86 (m, 1H, OH), 3.70 (m, 2H, CH$_2$), 3.04 (m, 2H, CH$_2$), 2.48 (m, 4H, 2×CH$_2$), 2.28 (br s, 7H), 2.19 (s, 3H, CH$_3$), 2.18 (s, 3H, CH$_3$) MS m/z (+ve) 4.09.3 [M$^+$].

Example 86

3-[3,5-Dimethyl-4-(4-methylpiperazine-1-carbonyl)-1H-pyrrol-2-ylmethylene]-2-oxo-2,3-dihydro-1H-indole-5-sulfonic acid phenylamide 2-Oxo-2,3-dihydro-1H-indole-5-sulfonic acid phenylamide (110 mg, 0.4 mmol) was condensed with 3,5-dimethyl-4-(4-methylpiperazine-1-carbonyl)-1H-pyrrole-2-carbaldehyde (100 mg) to give 50 mg (24%) of the title compound as a yellow solid.

$^1$HNMR (300 MHz, DMSO-d6) δ 13.52(s, 1H, NH), 11.26 (s, 1H, NH), 10.08 (s, 1H, NH), 8.21 (d, J=1.6 Hz, 1H), 7.75 (s, 1H, H-vinyl), 7.50 (dd, J=1.6 & 8.3 Hz, 1H), 7.19 (m, 2H), 7.10 (m, 2H), 6.97 (m, 2H), 2.49 (m, 4H, 2×CH$_2$), 2.28 (m, 10H, 2×CH$_3$ & 2×CH$_2$), 2.18 (s, 3H, CH$_3$). MS-EI m/z 519 [M$^+$].

Example 87

5-(5-Dimethylsulfamoyl-2-oxo-1,2-dihydroindol-3-ylidenemethyl)-2,4-dimethyl-1H-pyrrole-3-carboxylic acid (2-diethylaminoethyl)amide 2-Oxo-2,3-dihydro-1H-indole-5-sulfonic acid dimethylamide (90 mg, 0.38 mmol) was condensed with 5-formyl-2,4-dimethyl-1H-pyrrole-3-carboxylic acid (2-diethylaminoethyl)amide (100 mg) to give 80 mg (43%) of the title compound as a yellow solid.

$^1$HNMR (300 MHz, DMSO-d6) δ 11.30 (s, 1H, NH), 8.27 (d, J=1.7 Hz, 1H), 7.94 (s, 1H, H-vinyl), 7.49 (dd, J=1.7 & 8.0 Hz, 1H), 7.44 (m, 1H, CONHCH$_2$CH$_2$), 7.07 (d, J=8.0 Hz, 1H), 3.26 (m, 2H, CH$_2$), 2.60 (s, 6H, N(CH$_3$)$_2$), 2.53 (m, 2H, CH$_2$), 2.45-2.50 (m, 10H, 2×CH$_3$ & N(CH$_2$CH$_3$)$_2$), 0.96 (t, J=7.2 Hz, 6H, N(CH$_2$CH$_3$)$_2$), MS-EI m/z 487 [M$^+$].

Example 88

5-[5-(3-Chlorophenylsulfamoyl)-2-oxo-1,2-dihydroindol-3-ylidenemethyl]-2,4-dimethyl-1H-pyrrole-3-carboxylic acid (2-diethylaminoethyl)amide 2-Oxo-2,3-dihydro-1H-indole-5-sulfonic acid (3-chlorophenyl)amide (120 mg, 3.8 mmol) was condensed with 5-formyl-2,4-dimethyl-1H-pyrrole-3-carboxylic acid (2-diethylaminoethyl)amide (100 mg) to give 80 mg (37%) of the title compound as a yellow solid.

$^1$HNMR (360 MHz, DMSO-d6) δ 13.55 (s, 1H, NH), 11.24 (s, 1H, NH), 10.29 (s, 1H, NH), 8.25 (d, J=1.87 Hz, 1H), 7.79 (s, 1H, H-vinyl), 7.52 (dd, J=1.87 & 8.3 Hz, 1H), 7.42 (m, 1H, CONHCH$_2$CH$_2$), 7.22 (t, J=8.02 Hz, 1H), 7.15 (t, J=2 Hz, 1H), 7.08 (m, 1H), 7.0 (m, 2H), 3.27 (m, 2H, CH$_2$), 2.48-2.57 (m, 6H, 3×CH$_2$), 2.45 (s, 3H, CH$_3$), 2.44 (s, 3H, CH$_3$), 0.97 (t, J=7.0 Hz, 6H, N(CH$_2$CH$_3$)$_2$). MS m/z 570.1 [M$^+$].

Example 95

3-(2-oxo-5-phenyl-1,2-dihydroindol-3-ylidenemethyl)-4,5,6,7-tetrahydro-2H-isoindole-1-carboxylic acid ethyl ester $^1$HNMR (360 MHz, DMSO-d6) δ 13.74 (s, 1H, NH), 11.00 (s, 1H, NH), 8.13 (d, J=1.7 Hz, 1H), 7.74 (s, 1H, H-vinyl), 7.70 (d, J=7.7 Hz, 2H), 7.49 (dd, J=1.7 & 8.0 Hz, 1H), 7.44 (t, J=7.7 Hz, 2H), 7.32 (m, 1H), 6.96 (d, J=8.0 Hz, 1H), 4.26 (q, J=7.0 Hz, 2H, —OCH$_2$CH$_3$), 2.79 (m, 2H, CH$_2$), 2.72 (m, 2H, CH$_2$), 1.73 (m, 4H, 2×CH$_2$), 1.30 (t, J=7.0 Hz, 3H, OCH$_2$CH$_3$). MS-EI m/z 412 [M$^+$].

Example 99

3-(2-Oxo-5-phenylsulfamoyl-1,2-dihydroindol-3-ylidenemethyl)-4,5,6,7-tetrahydro-2H-isoindole-1-carboxylic acid ethyl ester $^1$HNMR (360 MHz, DMSO-d6) δ 13.64 (s, 1H, NH), 11.33 (s, 1H, NH), 10.07 (s, 1H, NH), 8.24 (d, J=1.8 Hz, 1H), 7.74 (s, 1H, H-vinyl), 7.57 (dd, J=1.8 & 8.0 Hz, 1H), 7.21 (t, J=7.6 Hz, 2H), 7.11 (d, J=7.6 Hz, 2H), 6.99 (d, J=8.0 Hz, 1H), 6.98 (d, J=7.6 Hz, 1H), 4.27 (q, J=7.0 Hz, 2H, OCH$_2$CH$_3$), 2.80 (m, 2H, CH$_2$), 2.73 (m, 2H, CH$_2$), 1.73 (m, 4H, 2×CH$_2$), 1.30 (t, J=7.0 Hz, 3H, OCH$_2$CH$_3$). MS-EI m/z 491 [M$^+$].

Example 109

3-[3-(Morpholine-4-carbonyl)-4,5,6,7-tetrahydro-2H-isoindol-1-ylmethylene]-2-oxo-2,3-dihydro-1H-indole-6-carboxylic acid $^1$HNMR (360 MHz, DMSO-d6) δ 13.60 (s, 1H, NH), 12.75 (br s, 1H, COOH), 11.08 (s, 1H, NH), 7.85 (d, J=7.8 Hz, 1H), 7.71 (s, 1H, H-vinyl), 7.62 (dd, J=1.4 & 7.8 Hz, 1H), 7.41 (d, J=1.4 Hz, 1H), 3.65 (m, 4H, 2×CH$_2$), 3.55 (m, 4H, 2×CH$_2$), 2.81 (m, 2H, CH$_2$), 2.54 (m, 2H, CH$_2$). 1.73 (m, 4H, 2×CH$_2$). MS-EI m/z 421 [M$^+$].

Example 112

5-Bromo-3-[3-(pyrrolidine-1-carbonyl)-4,5,6,7-tetrahydro-2H-isoindol-1-ylmethylene]-1,3-dihydroindol-2-one $^1$HNMR (360 MHz, DMSO-d6) δ 13.56 (s, 1H, NH), 11.00 (s, 1H, NH), 8.05 (d, J=1.8 Hz, 1H), 7.74 (s, 1H, H-vinyl), 7.28 (dd, J=1.3 & 8.3 Hz, 1H), 6.83 (d, J=8.3 Hz, 1H), 3.57 (m, 4H, 2×CH$_2$), 2.79 (m, 2H, CH$_2$), 2.65 (m, 2H, CH$_2$), 1.88 (m, 4H, 2×CH$_2$), 1.71 (m, 4H, 2×CH$_2$). MS-EI m/z 439 & 441 [M$^+$−1] & [M$^+$+1].

Example 114

3-(3-Dimethylcarbamoyl-4,5,6,7-tetrahydro-2H-isoindol-1-ylmethylene)-2-oxo-2,3-dihydro-1H-indole-6-carboxylic acid $^1$HNMR (360 MHz, DMSO-d6) δ 13.60 (s, 1H, NH), 12.72 (br s, 1H, COOH), 11.05 (s, 1H, NH), 7.85 (d, J=7.9 Hz, 1H), 7.72 (s, 1H, H-vinyl), 7.62 (dd, J=1.3 & 7.9 Hz, 1H), 7.42 (d, J=1.3 Hz, 1H), 3.03 (s, 6H, N(CH$_3$)$_2$), 2.81 (m, 2H, CH$_2$), 2.55 (m, 2H, CH$_2$), 1.73 (m, 4H, 2×CH$_2$). MS-EI m/z 379 [M$^+$].

Exapmle 115

4-Methyl-5-(5-methylsulfamoyl-2-oxo-1,2-dihydroindol-3-ylidenemethyl)-1H-pyrrole-3-carboxylic acid $^1$HNMR (300 MHz, DMSO-d6) □ 13.56 (br s, 1H, NH), 8.24 (d, J=1.5 Hz, 1H), 7.86 (s, 1H, H-vinyl), 7.74 (d, J=2.96 Hz, 1H), 7.56 (dd, J=1.5 & 8.1 Hz, 1H), 7.20 (br m, 1H, NHCH$_3$), 7.03 (d, J=8.1 Hz, 1H), 2.57 (s, 3H, CH$_3$), 2.41 (s, 3H, CH$_3$). MS-EI m/z 361 [M$^+$].

Example 116

{[4-Methyl-5-(4-methyl-5-methylsulfamoyl-2-oxo-1,2-dihydroindol-3-ylidenemethyl)-1H-pyrrole-3-carbonyl]-amino}-acetic acid ethyl ester 4-Methyl-1H-pyrrole-3-carboxylic acid ethyl ester (lit. ref. D. O. Cheng, T. L. Bowman and E. LeGoff; J. Heterocyclic Chem.; 1976; 13; 1145-1147) was formylated using method A, hydrolysed using method B followed by amidation (method C) to give [(5-formyl-4-methyl-1H-pyrrole-3-carbonyl)-amino]-acetic acid ethyl ester.

4-Methyl-5-methylaminosulfonyl-2-oxindole (50 mg, 0.21 mmol) was condensed with [(5-formyl-4-methyl-1H-pyrrole-3-carbonyl)-amino]-acetic acid ethyl ester (100 mg, 0.42 mmol) and piperidine (0.1 mL) in ethanol (2 mL) to give 50 mg (52%) of the title compound.

$^1$HNMR (360 MHz, DMSO-d6) δ 13.59 (s, 1H, NH), 11.29 (v.br. s, 1H, NH—CO), 8.33 (t, J=5.8 Hz, 1H, CONHCH$_2$), 7.83 (d, J=3.11 Hz, 1H), 7.80 (s, 1H, H-vinyl), 7.71 (d, J=8.5 Hz, 1H), 7.34 (br m, 1H, NHCH$_3$), 6.89 (d, J=8.5 Hz, 1H), 4.11 q, J=7.1 Hz, 2H, OCH$_2$CH$_3$), 3.92 (d, J=5.8 Hz, 2H, GlyCH$_2$), 2.86 (s, 3H, CH$_3$), 2.48 (s, 3H, CH$_3$), 2.42 (d, J=4.71 Hz, 3H, HNCH$_3$), 1.20 (t, J=7.1 Hz, 3H, OCH$_2$CH$_3$). MS-EI m/z 460 [M$^+$].

Example 117

{[4-Methyl-5-(5-methylsulfamoyl-2-oxo-1,2-dihydro-indol-3-ylidenemethyl)-1H-pyrrole-3-carbonyl]-amino}-acetic acid ethyl ester A mixture of 5-methylaminosulfonyl-2-oxindole (0.06 g, 0.22 mmol), [(5-formyl-4-methyl-1H-pyrrole-3-carbonyl)-amino]-acetic acid ethyl ester (0.075 g, 0.27 mmol) and piperidine (2 drops) in ethanol (5 mL) was heated in a sealed tube at 90° C. for 12 hrs. After cooling, the precipitate was collected by vacuum filtration, washed with ethanol, triturated with dichloromethane/ether and dried to give 0.035 g (36%) of the title compound as a yellowish brown solid.

$^1$H NMR (360 MHz, DMSO-d6) δ 13.6 (s, 1H, NH), 11 (v.br. s, 1H, NH—CO), 8.30 (t, J=5.7 Hz, 1H, CONHCH$_2$), 8.25 (d, J=1.2 Hz, 1H), 7.88 (s, 1H, H-vinyl), 7.84 (d, J=3.3 Hz, 1H), 7.57 (dd, J=1.9 & 8.5 Hz, 1H), 7.14 (br m, 1H, NHCH$_3$), 7.04 (d, J=8.5 Hz, 1H), 4.11 (q, J=6.7 Hz, 2H, OCH$_2$CH$_3$), 3.92 (d, J=5.7 Hz, 2H, GlyCH$_2$), 2.55 (s, 3H, CH$_3$), 2.41 (m, 3H, NCH$_3$), 1.20 (t, J=6.7, Hz, 3H, OCH$_2$CH$_3$). MS m/z 446 [M+].

Example 118

{[4-Methyl-5-(5-methylsulfamoyl-2-oxo-1,2-dihydro-indol-3-ylidenemethyl)-1H-pyrrole-3-carbonyl]-amino}-acetic acid A mixture of [(5-formyl-4-methyl-1H-pyrrole-3-carbonyl)-amino]-acetic acid ethyl ester (0.142 g, 0.59 mmol) and 1N NaOH (1.2 mL) in methanol (10 mL) was stirred at room temperature for 1 hr. The reaction was concentrated and the residue was condensed with 5-methylaminosulfonyl-2-oxindole (0.13 g, 0.48 mmol) and piperidine (0.12 mL) in ethanol (12 mL) to give 0.11 g (52%) of the title compound.

$^1$HNMR (300 MHz, DMSO-d6) δ 13.98 (br s, 1H, NH), 8.17 (s, 1H), 7.80 (s, 1H), 7.75 (d, J=3.1 Hz, 1H), 7.51 (dd, J=2 & 8.2 Hz, 1H), 7.21 (m on br s, 2H), 6.97 (d, J=8.1 Hz, 1H), 3.41 (d, J=4.2 Hz, 2H, CH$_2$NH), 2.54 (s, 3H, pyrrole-CH$_3$), 2.39 (s, 3H, ArCH$_3$). MS m/z 417 [M−1]+.

Example 120

5-Methyl-2-(2-oxo-1,2-dihydro-indol-3-ylidenemethyl)-1H-pyrrole-3-carboxylic acid $^1$HNMR (300 MHz, DMSO-d6) δ 13.77 (br s, 1H, NH), 12.49 (s, 1H, COOH), 11.07 (s, 1H, NH), 8.39 (s, 1H, H-vinyl), 7.43 (d, J=7.47 Hz, 1H), 7.20 (t, J=7.47 Hz, 1H), 7.03 (t, J=7.47 Hz, 1H), 6.91 (d, J=7.47 Hz, 1H), 6.49 (d, J=1.53 Hz, 1H), 2.34 (s, 3H, CH$_3$). MS m/z 269 [M+H]+.

Example 121

5-Methyl-2-(2-oxo-1,2-dihydro-indol-3-ylidenemethyl)-1H-pyrrole-3-carboxylic acid ethyl ester $^1$HNMR (300 MHz, DMSO-d6) δ 13.79 (s, 1H, NH), 11.08 (s, 1H, NH), 8.31 (s, 1H, H-vinyl), 7.45 (d, J=7.52 Hz, 1H), 7.20 (t, J=7.52 Hz, 1H), 7.03 (t, J=7.52 Hz, 1H), 6.91 (d, J=7.52 Hz, 1H), 6.50 (d, J=2.1 Hz, 1H), 4.26 (q, J=7.2 Hz, 2H, OCH$_2$CH$_3$), 2.33 (s, 3H, CH$_3$), 1.32 (t, J=7.2 Hz, 3H, OCH$_2$CH$_3$). MS m/z 297.1 [M+H]+.

Example 122

2-(5-Bromo-2-oxo-1,2-dihydroindol-3-ylidenemethyl)-5-methyl-1H-pyrrole-3-carboxylic acid ethyl ester $^1$HNMR (360 MHz, DMSO-d6) δ 13.72(s, 1H, NH), 11.16 (s, 1H, NH), 8.29 (s, 1H, H-vinyl), 7.53 (d, J=2.0 Hz, 1H), 7.35 (dd, J=2.0 & 8.05 Hz, 1H), 6.87 (t, J=8.05 Hz, 1H), 6.53 (d, J=2.4 Hz, 1H), 4.28 (q, J=7.03 Hz, 2H, OCH$_2$CH$_3$), 2.35 (s, 3H, CH$_3$), 1.33 (t, J=, 7.03 Hz, 3H, OCH$_2$CH$_3$). MS m/z 375 & 377 [M+H]+.

Example 123

2-(5-Bromo-2-oxo-1,2-dihydroindol-3-ylidenemethyl)-5-methyl-1H-pyrrole-3-carboxylic acid $^1$HNMR (300 MHz, DMSO-d6) δ 13.72(s, 1H, NH), 12.57 (s, 1H, COOH), 11.19 (s, 1H, NH), 8.36 (s, 1H, H-vinyl), 7.51 (d, J=1.4 Hz, 1H), 7.34 (dd, J=1.4 & 8.17 Hz, 1H), 6.87 (t, J=8.17 Hz, 1H), 6.52 (d, J=2.5 Hz, 1H), 2.35 (s, 3H, CH$_3$). MS m/z 347 & 349 [M+H]+.

Example 124

2-(5-Bromo-2-oxo-1,2-dihydroindol-3-ylidenemethyl)-5-methyl-1H-pyrrole-3-carboxylic acid (2-pyrrolidin-1-ylethyl)-amide To a solution of 2-formyl-5-methyl-1H-pyrrole-3-carboxylic acid (250 mg, 1.63 mmol) in dimethylformamide (3 mL) was added 1-ethyl-3-(3-dimethylaminopropyl)carbodiimide (376 mg, 1.2 equiv.), 1-hydroxybenzotriazole (265 mg, 1.2 equiv.), triethylamine (0.45 mL, 2 equiv.) and 1-(2-aminoethyl)pyrrolidine (0.23 mL. 1.1 equiv.). After stirring at room temperature overnight, the reaction was diluted with saturated sodium bicarbonate and brine (with extra salt) and extracted with 10% methanol in dichloromethane. The combined organic layers were washed with brine, dried over anhydrous sodium sulfate and concentrated to give 130 mg of 2-formyl-5-methyl-1H-pyrrole-3-carboxylic acid (2-pyrrolidin-1-yl-ethyl)amide.

A mixture of 5-bromo-2-oxindole (106 mg, 0.5 mmol), 2-formyl-5-methyl-1H-pyrrole-3-carboxylic acid (2-pyrrolidin-1-yl-ethyl)-amide (125 mg, 1 equiv.) and piperidine (0.2 mL) in ethanol (2 mL) was heated in a sealed tube at 80° C. for 1 hr and then cooled. The precipitate which formed was collected by vacuum filtration, washed with ethanol and ethyl acetate and dried to give the title compound as an orange solid.

$^1$HNMR (300 MHz, DMSO-d6) δ 13.62 (s, 1H, NH), 11.06 (br s, 1H, NH), 8.56 (s, 1H, H-vinyl), 8.15 (m, 1H, CONHCH$_2$), 7.48 (d, J=1.8 Hz, 1H), 7.31 (dd, J=1.8 & 7.9 Hz, 1H), 6.86 (d, J=7.9 Hz, 1H), 6.60 (d, J=2.3 Hz, 1H), 3.35 (m, 2H, HNCH$_2$CH$_2$), 2.56 (t, J=6.91 Hz, 2H, HNCH$_2$CH$_2$), 2.35 (s, 3H, CH$_3$), 1.67 (m, 4H, 2×CH$_2$). MS m/z 443/445 [M+ and M++2].

Example 125

2-(5-Bromo-2-oxo-1,2-dihydroindol-3-ylidenemethyl)-5-methyl-1H-pyrrole-3-carboxylic acid (2-diethylaminoethyl)-amide To a solution of 2-formyl-5-methyl-1H-pyrrole-3-carboxylic acid (320 mg, 2.1 mmol) in dimethylformamide (3 mL) was added 1-ethyl-3-(3-dimethylaminopropyl)carbodiimide (483 mg, 1.2 equiv.), 1-hydroxybenzotriazole (340 mg, 1.2 equiv.), triethylamine (0.59 mL, 2 equiv.) and N,N-diethylethylenediamine (0.32 mL, 1.1 equiv.). After stirring at room temperature overnight, the reaction was diluted with saturated sodium bicarbonate and brine (with extra salt) and extracted with 10% methanol in dichloromethane. The combined organic layers were washed with brine, dried over anhydrous sodium sulfate and concentrated to give 2-formyl-5-methyl-1H-pyrrole-3-carboxylic acid (2-diethylaminoethyl)-amide.

A mixture of 5-bromo-2-oxindole (106 mg, 0.5 mmol), 2-formyl-5-methyl-1H-pyrrole-3-carboxylic acid (2-diethylaminoethyl)-amide (126 mg, 1 equiv.) and piperidine (0.2 mL) in ethanol (2 mL) was heated in a sealed tube at 80° C. for 1 hr and then cooled. The precipitate was collected by vacuum filtration, washed with ethanol and ethyl acetate and dried to give the title compound as an orange solid.

$^1$HNMR (360 MHz, DMSO-d6) δ 13.62 (s, 1H, NH), 11.11 (br s, 1H, NH), 8.54 (s, 1H, H-vinyl), 8.1 (m, 1H, CONHCH$_2$), 7.49 (d, J=2.2 Hz, 1H), 7.31 (dd, J=2.2 & 8.3 Hz, 1H), 6.86 (d, J=8.3 Hz, 1H), 6.58 (d, J=2.24 Hz, 1H), 3.31 (m, 2H, HNCH$_2$CH$_2$), 2.59 (m, 6H, 3×CH$_2$), 2.36 (s, 3H, CH$_3$), 0.99 (t, J=6.8 Hz, 6H, N(CH$_2$CH$_3$)$_2$). MS m/z 445/447 [M$^+$ and M$^+$+2].

Example 126

2,4-Dimethyl-5-(2-oxo-1,2-dihydro-indol-3-ylidenemethyl)-1H-pyrrole-3-carboxylic acid (2-diethylamino-ethyl)-amide A mixture of 1,3-dihydro-indol-2-one (266 mg, 2 mmol), 5-formyl-2,4-dimethyl-1H-pyrrole-3-carboxylic acid (2-diethylamino-ethyl)-amide (530 mg, 2 mmol) and piperidine (1 drop) in ethanol was heated at 90° C. for 2 hours. The reaction was cooled to room temperature, the resulting precipitate was collected by vacuum filtration, washed with ethanol and dried to give 422 mg (55%) of the title compound as a light yellow solid.

$^1$H NMR (400 MHz, DMSO-d6) δ 13.7 (s, 1H, NH), 10.9 (s, 1H, NH), 7.88 (d, J=7.6 Hz, 1H), 7.64 (s, 1H, H-vinyl), 7.41 (t, J=5.4 Hz, 1H, NH), 7.13 (dt, J=1.2 & 7.6 Hz, 1H), 6.99 (dt, J=1.2 & 7.6 Hz, 1H), 6.88 (d, J=7.6 Hz, 1H), 3.28 (m, 2H), 2.48-2.55 (m, 6H), 2.44 (s, 3H, CH$_3$), 2.41 (s, 3H, CH$_3$), 0.97 (t, J=7.2 Hz, 6H, N(CH$_2$CH$_3$)$_2$).

MS+ve APCI 381 [M$^+$+1].

Example 127

5-(5-Chloro-2-oxo-1,2-dihydro-indol-3-ylidenemethyl)-2,4-dimethyl-1H-pyrrole-3-carboxylic acid (2-diethylamino-ethyl)amide A mixture of 5-Chloro-1,3-dihydro-indol-2-one (335 mg, 2 mmol), 5-formyl-2,4-dimethyl-1H-pyrrole-3-carboxylic acid (2-diethylamino-ethyl)-amide (530 mg, 2 mmol) and piperidine (1 drop) in ethanol was heated at 90° C. for 2 hours. The reaction was cooled to room temperature, the resulting precipitate was collected by vacuum filtration, washed with ethanol and dried to give 565 mg (68%) of the title compound as an orange solid.

$^1$H NMR (400 MHz, DMSO-d6) δ 13.65 (s, 1H, NH), 11.0 (s, 1H, NH), 7.98 (d, J=2.1 Hz, 1H) 7.77 (s, 1H H-vinyl), 7.44 (t, NH), 7.13 (dd, J=2.1 & 8.4 Hz, 1H) 6.87 (d, J=8.4 Hz, 1H), 3.28 (g, 2H), 2.48-2.53 (m, 6H), 2.44 (s, 3H, CH$_3$), 2.43 (s, 3H, CH$_3$), 0.97 (t, J=7.0 Hz, 6H, N(CH$_2$CH$_3$)$_2$)

MS+ve APCI 415 [M$^+$+1].

Example 128

2,4-Dimethyl-5-(2-oxo-1,2-dihydro-indol-3-ylidenemethyl)-1H-pyrrole-3-carboxylic acid (2-pyrrolidin-1-ethyl)-amide 1,3-Dihydro-indol-2-one was condensed with 5-formyl-2,4-dimethyl-1H-pyrrole-3-carboxylic acid (2-pyrrolidin-1-yl-ethyl)-amide to give the title compound.

MS+ve APCI 379 [M$^+$+1].

Example 129

5-(5-Fluoro-2-oxo-1,2-dihydro-indol-3-ylidenemethyl)-2,4-dimethyl-1H-pyrrole-3-carboxylic acid (2-pyrrolidin-1-ylethyl)-amide 5-Fluoro-1,3-dihydro-indol-2-one was condensed with 5-formyl-2,4-dimethyl-1H-pyrrole-3-carboxylic acid (2-pyrrolidin-1-yl-ethyl)-amide to give the title compound.

MS+ve APCI 397 [M$^+$+1].

Scale-Up Procedure:

5-Formyl-2,4-dimethyl-1H-pyrrole-3-carboxylic acid (61 g), 5-fluoro-1,3-dihydro-indol-2-one (79 g), ethanol (300 mL) and pyrrolidine (32 mL) were refluxed for 4.5 hours. Acetic acid (24 mL) was added to the mixture and refluxing was continued for 30 minutes. The mixture was cooled to room temperature and the solids collected by vacuum filtration and washed twice with ethanol. The solids were stirred for 130 minutes in 40% acetone in water (400 mL) containing 12 N hydrochloric acid (6.5 mL). The solids were collected by vacuum filtration and washed twice with 40% acetone in water. The solids were dried under vacuum to give 5-[5-fluoro-2-oxo-1,2-dihydro-indol-(3Z)-ylidenemethyl]-2,4-dimethyl-1H-pyrrole-3-carboxylic acid (86 g, 79% yield) as an orange solid. $^1$H-NMR (dimethylsulfoxide-d$_6$) δ 2.48, 2.50 (2×s, 6H, 2×CH$_3$), 6.80, 6.88, 7.68, 7.72 (4×m, 4H, aromatic and vinyl), 10.88 (s, 1H, CONH), 12.12 (s, 1H, COOH), 13.82 (s, 1H, pyrrole NH). MS m/z 299 [M−1].

5-[5-Fluoro-2-oxo-1,2-dihydro-indol-(3Z)-ylidenemethyl]-2,4-dimethyl-1H-pyrrole-3-carboxylic acid (100 g) and dimethylformamide (500 mL) were stirred and benzotriazol-1-yloxytris(dimethylamino)phosphonium hexafluorophosphate (221 g), 1-(2-aminoethyl)pyrrolidine (45.6 g) and triethylamine (93 mL) were added. The mixture was stirred for 2 hours at ambient temperature. The solid product was collected by vacuum filtration and washed with ethanol. The solids were slurry-washed by stirring in ethanol (500 mL) for one hour at 64° C. and cooled to room temperature. The solids were collected by vacuum filtration, washed with ethanol, and dried under vacuum to give 5-[5-fluoro-2-oxo-1,2-dihydro-indol-(3Z)-ylidenemethyl]-2,4-dimethyl-1H-pyrrole-3-carboxylic acid (2-pyrrolidin-1-yl-ethyl)-amide (101.5 g, 77% yield). $^1$H-NMR (dimethylsulfoxide-d$_6$) δ 1.60 (m, 4H, 2×CH$_2$), 2.40, 2.44 (2×s, 6H, 2×CH$_3$), 2.50 (m, 4H, 2×CH$_2$), 2.57, 3.35 (2×m, 4H, 2×CH$_2$), 7.53, 7.70, 7.73, 7.76 (4×m, 4H, aromatic and vinyl), 10.88 (s, 1H, CONH), 13.67 (s, 1H, pyrrole NH). MS m/z 396 [M+1].

Example 130

5-(5-Chloro-2-oxo-1,2-dihydro-indol-3-ylidenemethyl)-2,4-dimethyl-1H-pyrrole-3-carboxylic acid (2-pyrrolidin-1-ylethyl)-amide 5-Chloro-1,3-dihydro-indol-2-one was condensed with 5-formyl-2,4-dimethyl-1H-pyrrole-3-carboxylic acid (2-pyrrolidin-1-yl-ethyl)-amide to give the title compound.
MS+ve APCI 413 [M$^+$+1].

Example 131

2,4-Dimethyl-5-(2-oxo-1,2-dihydro-indol-3-ylidenemethyl)-1H-pyrrole-3-carboxylic acid (2-dimethylaminoethyl)-amide 1,3-Dihydro-indol-2-one was condensed with 5-formyl-2,4-dimethyl-1H-pyrrole-3-carboxylic acid (2-dimethylaminoethyl)amide to give the title compound.
$^1$H NMR (400 MHz, DMSO-d6) δ 13.63 (s, 1H, NH), 10.90 (s, 1H, NH), 7.78 (d, J=7.8 Hz, 1H), 7.63 (s, 1H H-vinyl), 7.48 (t, 1H, NH), 7.13 (dt, 1H), 6.98 (dt, 1H), 6.88 (d, J=7.7 Hz, 1H), 3.31 (q, J=6.6 Hz, 2H), 2.43 (s, 3H, CH$_3$), 2.40 (s, 3H, CH$_3$), 2.38 (t, J=6.6 Hz, 2H), 2.19 (s, 6H, N(CH$_2$CH$_3$)$_2$) MS+ve APCI 353 [M$^+$+1].

Example 132

5-(5-Fluoro-2-oxo-1,2-dihydro-indol-3-ylidenemethyl)-2,4-dimethyl-1H-pyrrole-3-carboxylic acid (2-dimethylaminoethyl)amide 5-Fluoro-1,3-dihydro-indol-2-one was condensed with 5-formyl-2,4-dimethyl-1H-pyrrole-3-carboxylic acid (2-dimethylaminoethyl)amide to give the title compound.
$^1$H NMR (400 MHz, DMSO-d6) δ 13.68 (s, 1H, NH), 10.90 (s, 1H, NH), 7.76 (dd, J=2.4 & 9.4 Hz, 1H), 7.71 (s, 1H H-vinyl), 7.51 (t, 1H, NH), 6.93 (m, 1H), 6.84 (dd, J=4.6 & 8.4 Hz, 1H), 3.31 (q, J=6.6 Hz, 2H), 2.43 (s, 3H, CH$_3$), 2.41 (s, 3H, CH$_3$), 2.38 (t, J=6.6 Hz, 2H), 2.19 (s, 6H, N(CH$_2$CH$_3$)$_2$) MS+ve APCI 371 [M$^+$+1].

Example 193

5-[5-Fluoro-2-oxo-1,2-dihydro-indol-(3Z)-ylidenemethyl]-2,4-dimethyl-1H-pyrrole-3-carboxylic acid (2-ethylamino-ethyl)amide 5-Formyl-2,4-dimethyl-1H-pyrrole-3-carboxylic acid (2-ethylamino-ethyl)-amide (99 g), ethanol (400 mL), 5-fluoro-2-oxindole (32 g) and pyrrolidine (1.5 g) were refluxed for 3 hours with stirring. The mixture was cooled to room temperature and the solids collected by vacuum filtration. The solids were stirred in ethanol at 60° C., cooled to room temperature and collected by vacuum filtration. The product was dried under vacuum to give 5-[5-fluoro-2-oxo-1,2-dihydroindol-(3Z)-ylidenemethyl]-2,4-dimethyl-1H-pyrrole-3-carboxylic acid (2-ethylamino-ethyl)-amide (75 g, 95% yield). $^1$H-NMR (dimethylsulfoxide-d$_6$) δ 1.03 (t, 3H, CH$_3$), 2.42, 2.44 (2×s, 6H, 2×CH$_3$), 2.56 (q, 2H, CH$_2$), 2.70, 3.30 (2×t, 4H, 2×CH$_2$), 6.85, 6.92, 7.58, 7.72, 7.76 (5×m, 5H, aromatic, vinyl and CONH), 10.90 (br s, 1H, CONH), 13.65 (br s, 1H, pyrrole NH). MS m/z 369 [M−1].

Example 195

5-[5-Fluoro-2-oxo-1,2-dihydro-indol-(3Z)-ylidenemethyl]-2,4-dimethyl-1H-pyrrole-3-carboxylic acid (2-diethyl-N-oxoaminoethyl)-amide Method A:
5-[5-Fluoro-2-oxo-1,2-dihydro-indol-(3Z)-ylidenemethyl]-2,4-dimethyl-1H-pyrrole-3-carboxylic acid (2-diethylaminoethyl)-amide (598 mg) and dichloromethane (60 mL) in an ice bath were treated with 3-chloroperbenzoic acid (336 mg) and the mixture stirred at room temperature overnight. The solvent was rotary evaporated and the residue suspended in methanol (20 mL). Water (20 mL) containing sodium hydroxide (240 mg) was added and the mixture stirred for one hour. The precipitate was collected by vacuum filtration, washed with 5 mL of water and dried under a vacuum to give 5-[5-fluoro-2-oxo-1,2-dihydro-indol-(3Z)-ylidenemethyl]-2,4-dimethyl-1H-pyrrole-3-carboxylic acid (2-diethyl-N-oxoamino-ethyl)-amide (510 mg, 82% yield) as an orange solid. $^1$H-NMR (DMSO-d6) δ 13.72 (br s, 1H, NH), 11.02 (br s, 1H, CONH), 9.81 (br s, 1H, CONH), 7.75 (dd, 1H, aromatic), 7.70 (s, 1H, aromatic), 6.93 (td, 1H, aromatic), 6.84 (m, 1H, aromatic), 3.63 (m, 2H, CH$_2$), 3.29 (m, 2H, CH$_2$), 3.14 (m, 4H, 2×CH$_2$), 2.47 (s, 1H, CH$_3$), 2.45 (s, 3H, CH$_3$), 1.64 (t, 6H, 2×CH$_3$). MS m/z 415 [M+1].

Method B:
5-Formyl-2,4-dimethyl-1H-pyrrole-3-carboxylic acid (2-diethylamino-ethyl)-amide (10 g) was suspended in dichloromethane (100 mL) and cooled in an ice bath. 3-Chloro-peroxybenzoic acid (13.1 g) was added with stirring and the mixture allowed to warm to room temperature and then stirred ovenight. The mixture was rotary evaporated to dryness and chromatographed on a column of silica gel eluting with 20% methanol in dichloromethane. Fractions containing product were combined and rotary evaporated to dryness to give 5-formyl-2,4-dimethyl-1H-pyrrole-3-carboxylic acid (2-diethyl-N-oxoamino-ethyl)-amide (9 g, 83% yield).

5-Formyl-2,4-dimethyl-1H-pyrrole-3-carboxylic acid (2-diethyl-N-oxoamino-ethyl)-amide (9 g), 5-fluoro-1,3-dihydroindol-2-one ((9 g, 83% yield)), and pyrrolidine ((9 g, 83% yield (0.1 g) were refluxed in ethanol (30 mL) for 4 hours. The mixture was cooled in an ice bath and the precipitate collected by vacuum filtration and washed with ethanol. The solids were stirred in ethyl acetate (30 mL), collected by vacuum filtration, washed with ethyl acetate and dried under vacuum to give 5-[5-fluoro-2-oxo-1,2-dihydro-indol-(3Z)-ylidenemethyl]-2,4-dimethyl-1H-pyrrole-3-carboxylic acid (2-diethyl-N-oxoamino-ethyl)-amide (10.3 g 80% yield) as an orange solid. $^1$H-NMR (DMSO-d6) δ 13.72 (br s, 1H, NH), 11.02 (br s, 1H, CONH), 9.81 (br s, 1H, CONH), 7.75 (dd, 1H, aromatic), 7.70 (s, 1H, aromatic), 6.93 (td, 1H, aromatic), 6.84 (m, 1H, aromatic), 3.63 (m, 2H, CH$_2$), 3.29 (m, 2H, CH$_2$), 3.14 (m, 4H, 2×CH$_2$), 2.47 (s, 1H, CH$_3$), 2.45 (s, 3H, CH$_3$), 1.64 (t, 6H, 2×CH$_3$). MS m/z 415 [M+1].

Example 190

5-[5-fluoro-2-oxo-1,2-dihydro-indol-(3Z)-ylidenemethyl]-2,4-dimethyl-1H-pyrrole-3-carboxylic acid [2-(pyridin-1-yl)ethyl]-amide 5-[5-Fluoro-2-oxo-1,2-dihydro-indol-(3Z)-ylidenemethyl]-2,4-dimethyl-1H-pyrrole-3-carboxylic acid (120 mg, 0.4 mmol) was shaken with EDC, HCl (96 mg, 0.5 mmol), anhydrous 1-hydroxy-benztriazole (68 mg, 0.5 mmol), and 2-(2-aminoethylpyridine purchased from Aldrich in anhydrous DMF (3 mL) for 2-3 days at room temperature. The reaction mixture was diluted with 1M NaHCO3 (1.5 ml), then with 8 ml of water. The precipitated crude product was collected by filtration, washed with water, dried and purified by crystallization or chromatography to give 5-[5-fluoro-2-oxo-1,2-dihydro-indol-(3Z)-ylidenemethyl]-2,4-dimethyl-1H-pyrrole-3-carboxylic acid [2-(pyridin-1-yl)-ethyl]amide.

Example 189

5-[5-Chloro-2-oxo-1,2-dihydro-indol-(3Z)-ylidenemethyl]-2,4-dimethyl-1H-pyrrole-3-carboxylic acid [2-(pyridin-1-yl)ethyl]amide Proceeding as described in previous example but substituting 5-[5-fluoro-2-oxo-1,2-dihydro-indol-(3Z)-ylidenemethyl]-2,4-dimethyl-1H-pyrrole-3-carboxylic acid with 5-[5-chloro-2-oxo-1,2-dihydro-indol-(3Z)-ylidenemethyl]-2,4-dimethyl-1H-pyrrole-3-carboxylic acid (127 mg) provided 5-[5-chloro-2-oxo-1,2-dihydro-indol-(3Z)-ylidenemethyl]-2,4-dimethyl-1H-pyrrole-3-carboxylic acid [2-(pyridin-1-yl)ethyl]amide.

Example 192

5-[5-Bromo-2-oxo-1,2-dihydro-indol-(3Z)-ylidenemethyl]-2,4-dimethyl-1H-pyrrole-3-carboxylic acid [2-(pyridin-1-yl)ethyl]amide Proceeding as described in Example 190 above but substituting 5-[5-fluoro-2-oxo-1,2-dihydro-indol-(3Z)-ylidenemethyl]-2,4-dimethyl-1H-pyrrole-3-carboxylic acid with 5-[5-bromo-2-oxo-1,2-dihydro-indol-(3Z)-ylidenemethyl]-2,4-dimethyl-1H-pyrrole-3-carboxylic acid (145 mg) provided 5-[5-bromo-2-oxo-1,2-dihydro-indol-(3Z)-ylidenemethyl]-2,4-dimethyl-1H-pyrrole-3-carboxylic acid [2-(pyridin-1-yl) ethyl]amide.

Example 191

5-[2-Oxo-1,2-dihydro-indol-(3Z)-ylidenemethyl]-2,4-dimethyl-1H-pyrrole-3-carboxylic acid [2-(pyridin-1-yl)ethyl]amide Proceeding as described in Example 190 above but substituting 5-[5-fluoro-2-oxo-1,2-dihydro-indol-(3Z)-ylidenemethyl]-2,4-dimethyl-1H-pyrrole-3-carboxylic acid with 5-[2-oxo-1,2-dihydro-indol-(3Z)-ylidenemethyl]-2,4-dimethyl-1H-pyrrole-3-carboxylic acid (113 mg) provided 5-[2-oxo-1,2-dihydro-indol-(3Z)-ylidenemethyl]-2,4-dimethyl-1H-pyrrole-3-carboxylic acid [2-(pyridin-1-yl)ethyl]amide.

Example 203

5-[5-Cyano-2-oxo-1,2-dihydro-indol-(3Z)-ylidenemethyl]-2,4-dimethyl-1H-pyrrole-3-carboxylic acid (2-(pyridin-1-yl)ethyl]amide Proceeding as described in Example 190 above but substituting 5-[5-fluoro-2-oxo-1,2-dihydro-indol-(3Z)-ylidenemethyl]-2,4-dimethyl-1H-pyrrole-3-carboxylic acid with 5-[5-cyano-2-oxo-1,2-dihydro-indol-(3Z)-ylidenemethyl]-2,4-dimethyl-1H-pyrrole-3-carboxylic acid (123 mg) provided 5-[5-cyano-2-oxo-1,2-dihydro-indol-(3Z)-ylidenemethyl]-2,4-dimethyl-1H-pyrrole-3-carboxylic acid [2-(pyridin-1-yl) ethyl]amide.

Examples 142, 186, 187, 188 and 204

Proceeding as described in Examples 190, 189, 191, 192, and 203 above but substituting 2-(2-aminoethyl)pyridine with 1-(2-aminoethyl)pyrrolidine, purchased from Aldrich Chemical Company, Inc. provided the desired compounds.

Examples 143-147

Proceeding as described in Examples 190, 189, 191, 192, and 203 above but substituting 2-(2-aminoethyl)pyridine with 1-(2-aminoethyl)imidazolin-2-one (prepared by heating dimethyl carbonate with bis(2-aminoethyl)amine (2 equivalents) in a sealed flask to 150° C. for 30 min., following the procedure described in U.S. Pat. No. 2,613,212 (1950), to Rohm & Haas Co. The crude product was purified on silica using an eluent mixture chloroform-methanol-aqueous ammonia 80:25:2) provided the desired compounds.

Examples 148-151 and 184

Proceeding as described in Examples 190, 189, 191, 192, and 203 above but substituting 2-(2-aminoethyl)pyridine with 4-(2-aminoethyl)piperazine-1-acetic acid ethyl ester (prepared as follows: piperazine-1-acetic acid ethyl ester (11.22 g) was treated with iodoacetonitrile (5.0 mL) in the presence of potassium carbonate (6.9 g) in ethyl acetate (260 mL) at 0° C. After complete iodoacetonitrile addition (45 min), the reaction mixture was subsequently stirred at room temperature for 11 hours. The reaction mixture was filtered and the filtrates evaporated. The residue was hydrogenated in a presence of cobalt boride (prepared from CoCl2 and sodium borohydride) at room temperature at 50 psi for 2 days in ethanol. Filtration, evaporation and chromatographic purification using an eluent mixture chloroform-methanol-aqueous ammonia 80:25:2 provided the desired amine (3.306 g) as a pale yellow oil) provided the desired compounds.

Example 152-153

Proceeding as described in Examples 190, 189, 191, 192, and 203 above but substituting 2-(2-aminoethyl)pyridine with 2-[(2-aminoethylamino)]acetonitrile (prepared as follows: A solution of iodoacetonitrile (50 mmol) in ethyl alcohol (80 ml) was added to a solution of ethylene diamine (150 ml) in ethyl alcohol (60 ml) at 0° C. over a period of 30 minutes. The stirring was continued for another 1 hr at 0° C., then at room temperature for 14 hours. 55 mmol of potassium carbonate was added, stirred for 30 minutes, filtered and the filtrate was concentrated at room temperature. The residue was purified on silica using an eluent mixture chloroform-methanol-aqueous ammonia 80:15:1.5 to give 2-[(2-aminoethylamino)]-acetonitrile (3.550 g) which was used immediately) provided the desired compounds.

Example 154-158

Proceeding as described in Examples 190, 189, 191, 192, and 203 above but substituting 2-(2-aminoethyl)pyridine with 1-(3-aminopropyl)-azepin-2-one (prepared according to the procedure in Kraft A.: J. Chem. Soc. Perkin Trans. 1, 6, 1999, 705-14, except that the hydrolysis of DBU was performed at 145° C. neat in a presence of lithium hydroxide (1 hr, 5 ml of DBU, 2 ml of water, 420 mg of lithium hydroxyde hydrate). Purification of the crude product on silica using an eluent mixture chloroform-methanol-aqueous ammonia 80:40:4 provided 1-(3-aminopropyl)azepin-2-one (4.973 g, 87. % yield)) provide the desired compounds.

Examples 133-135, 159 and 200

Proceeding as described in Examples 190, 189, 191, 192, and 203 above but substituting 2-(2-aminoethyl)pyridine with N-acetyl ethylene diamine, (prepared by heating a mixture of ethyl acetate with ethylene diamine (1.5 equivalents) to 160° C. for 1 hr in a sealed vessel. The vacuum distillation provided the desired product in 56% yield. N-acetylethylene diamine is also available from Aldrich) provide the desired compounds.

Examples 146-140

Proceeding as described in Examples 190, 189, 191, 192, and 203 above but substituting 2-(2-aminoethyl)pyridine with 1-(3-aminopropyl)-tetrahydro-pyrimidin-2-one (prepared in the same way as 1-(3-aminopropyl)-azepin-2-one according to the procedure in Kraft A.: J. Chem. Soc. Perkin Trans. 1, 6, 1999, 705-14: Briefly, 1,3,4,6,7,8-hexahydro-2H-pyrimido[1,2-a]pyrimidine (4.939 g), lithium hydroxyde hydrate (918 mg) and 2 ml of water was heated without a solvent in a sealed vessel to 145° C. for 1 hr. The crude product was purified on a column of silica in chloroform-methanol-aqueous ammonia 80:40:4 to give pure amine (5.265 g, 94% yield).

Examples 141, 160-162 and 185

Proceeding as described in Examples 190, 189, 191, 192, and 203 above but substituting 2-(2-aminoethyl)pyridine with 1-(2-aminoethyl)-piperazine-2-one (prepared as follows: Neat tert-butyldiphenylsilyl chloride (25 mL, 97.7 mmol) was added dropwise into a solution of DBU (19.5 ml, 130 mmol) and bis(2-aminoethyl)amine (4.32 mL, 40 mmol) in anhydrous dimethyl acetamide (80 mL) at room temperature upon cooling on water bath within 5 minutes. The mixture was stirred for 5 hours. Bromoacetic acid ethyl ester (6.70 mL, 60 mmol) was added neat upon cooling to room temperature. The reaction was stirred for 25 minutes, then evaporated on high vacuum. The residue was dissolved in methanol (200 ml), KHCO$_3$ (10 g) and KF (12 g, 200 mmol) were added and the mixture was stirred at 60° C. for 5 hours. 10 g of Na$_2$CO$_3$ was added, stirred for 10 minutes, cooled and filtered. The filtrates were evaporated. The residue was extracted with hexanes (2 times 250 ml). The hexane-insoluble material was dissolved in ethanol (60 ml), filtered and evaporated. The residue was purified on a column of silica in chloroform-methanol-aqueous ammonia 80:40:4 to give pure amine (4.245 g, 74% yield)) provided the desired compounds.

Examples 163-167

Proceeding as described in Examples 190, 189, 191, 192, and 203 above but substituting 2-(2-aminoethyl)pyridine with 3-[(2-aminoethyl)amino]propionitrile (prepared from ethylene diamine (150 mmol) and acrylonitrile (50 mmol) in THF at room temperature, as described in Israel, M. et al: *J. Med. Chem.* 7, 1964, 710-16., provided the desired amine (4.294 g)) provided the desired compounds.

Example 168

5-(5-Fluoro-2-oxo-1,2-dihydro-indol-3-ylidenemethyl)-2,4-dimethyl-1H-pyrrole-3-carboxylic acid [2-(4-methylpiperazin-1-yl)-ethyl]-amide To a stirred yellow muddy mixture of 5-[5-fluoro-2-oxo-1,2-dihydro-indol-(3Z)-ylidenemethyl]-2,4-dimethyl-1H-pyrrole-3-carboxylic acid (90 mg), DMF (0.8 mL) and TEA (0.084 mL) in a 20 mL reaction tube, was added BOP reagent (199 mg). The mixture became clear in 5 min. 2-(4-Methylpiperazin-1-yl)ethylamine[1] (51 mg) was added into the clear mixture. The resulting solution was stirred at room temperature over night. Yellow solid products precipitated from the reaction system. Thin layer chromatography (10% methanol in methylene chloride) showed that all the starting material had been converted into the product. The solid was isolated by vacuum filtration and washed once with ethanol (1 mL). The solid was sonicated in diethyl ether (2 mL) for 20 min and collected by vacuum filtration. After drying under vacuum, 5-(5-Fluoro-2-oxo-1,2-dihydro-indol-3-ylidenemethyl)-2,4-dimethyl-1H-pyrrole-3-carboxylic acid (4-methylpiperazin-1-yl-ethyl)-amide (79 mg, 62% yield) was obtained.

$^1$H NMR (DMSO-d6) δ 2.13 (s, 3H, CH$_3$), 2.40, 2.42 (2×s, 6H, 2×CH$_3$), 2.41 (m, 2H, CH$_2$), 2.47 (m, 8H, 4×CH$_2$), 3.30 (m, 2H, CH$_2$), 6.82 (dd, J=4.5, 8.7 Hz, 1H), 6.91(td, $^2$J=2.4, $^3$J=8.8 Hz, 1H), 7.43 (t, J=5.6 Hz, 1H), 7.70 (s, 1H), 7.75 (dd, J=2.8, 9.6 Hz, 1H) (aromatic and vinyl), 10.88 (s, 1H, CONH), 13.67 (s, 1H, NH). LC-MS (m/z) 424.4 (M−1).

Example 169

5-(5-Chloro-2-oxo-1,2-dihydro-indol-3-ylidenemethyl)-2,4-dimethyl-1H-pyrrole-3-carboxylic acid (4-methylpiperazin-1-ylethyl)-amide Following the procedure in Example 168 above but substituting 5-[5-fluoro-2-oxo-1,2-dihydro-indol-(3Z)-ylidenemethyl]-2,4-dimethyl-1H-pyrrole-3-carboxylic acid with 5-[5-chloro-2-oxo-1,2-dihydro-indol-(3Z)-ylidenemethyl]-2,4-dimethyl-1H-pyrrole-3-carboxylic acid (95 mg, 0.3 mmol) gave 5-(5-chloro-2-oxo-1,2-dihydro-indol-3-ylidenemethyl)-2,4-dimethyl-1H-pyrrole-3-carboxylic acid (4-methylpiperazin-1-ylethyl)-amide (76 mg, 58%).

$^1$H NMR (DMSO-d6) δ 2.13 (s, 3H, CH$_3$), 2.41, 2.42 (2×s, 6H, 2×CH$_3$), 2.42 (m, 2H, CH$_2$), 2.48 (m, 8H, 4×CH$_2$), 3.30 (m, 2H, CH$_2$), 6.84 (d, J=8.0 Hz, 1H), 7.11 (dd, J=2.0, 8.0 Hz,1H), 7.44 (t, J=5.6 Hz, 1H), 7.76 (s, 1H), 7.97 (d, J=2.0 Hz, 1H) (aromatic and vinyl), 10.98 (s, 1H, CONH), 13.62 (s, 1H, NH). LC-MS (m/z) 440.2 (M−1).

Example 170

5-(5-Bromo-2-oxo-1,2-dihydro-indol-3-ylidenemethyl)-2,4-dimethyl-1H-pyrrole-3-carboxylic acid (4-methylpiperazin-1-ylethyl)-amide Following the procedure described in Example 168, but substituting 5-(5-chloro-2-oxo-1,2-dihydro-indol-3-ylidenemethyl)-2,4-dimethyl-1H-pyrrole-3-carboxylic acid with 5-(5-bromo-2-oxo-1,2-dihydro-indol-3-ylidenemethyl)-2,4-dimethyl-1H-pyrrole-3-carboxylic acid gave 5-(5-bromo-2-oxo-1,2-dihydro-indol-3-ylidenemethyl)-2,4-dimethyl-1H-pyrrole-3-carboxylic acid (4-methylpiperazin-1-yl-ethyl)-amide (39 mg, 54%) was obtained from SU011670 (54 mg, 0.15 mmol).

$^1$H NMR (DMSO-d6) δ 2.14 (s, 3H, CH$_3$), 2.41, 2.42 (2×s, 6H, 2×CH$_3$), 2.42 (m, 2H, CH$_2$), 2.48 (m, 8H, 4×CH$_2$), 3.31 (m, 2H, CH$_2$), 6.80 (d, J=8.0 Hz, 1H), 7.23 (dd, J=2.0, 8.0 Hz, 1H), 7.44 (t, J=5.6 Hz, 1H), 7.76 (s, 1H), 8.09 (d, J=2.0 Hz, 1H) (aromatic and vinyl), 10.99 (s, 1H, CONH), 13.61 (s, 1H, NH). LC-MS (m/z) 486.6 (M).

Example 172

5-(2-Oxo-1,2-dihydro-indol-3-ylidenemethyl)-2,4-dimethyl-1H-pyrrole-3-carboxylic acid (4-methylpiperazin-1-yl-ethyl)-amide Following the procedure described in Example 168 above but substituting 5-(5-fluoro-2-oxo-1,2-dihydro-indol-3-ylidenemethyl)-2,4-dimethyl-1H-pyrrole-3-carboxylic acid SU014900 with 5-(2-oxo-1,2-dihydro-indol-3-ylidenemethyl)-2,4-dimethyl-1H-pyrrole-3-carboxylic acid gave 5-(2-oxo-1,2-dihydro-indol-3-ylidenemethyl)-2,4-dimethyl-1H-pyrrole-3-carboxylic acid (4-methylpiperazin-1-yl-ethyl)-amide, SU014903 (136 mg, 84%) was obtained from SU012120 (112.8 mg, 0.4 mmol).

$^1$H-NMR (DMSO-d6) δ 2.13 (s, 3H, —CH$_3$), 2.39, 2.42 (2×s, 6H, 2×CH$_3$), 2.42 (m, 2H, CH$_2$), 2.48 (m, 8H, 4×CH$_2$), 3.30 (t, 2H, CH$_2$), 6.86 (d, J=8.0 Hz, 1H), 6.96 (t, J=7.4 Hz, 1H), 7.10 (t, J=7.8 Hz, 1H), 7.41 (t, J=5.4 Hz, 1H), 7.62 (s, 1H), 7.76 (d, J=7.6 Hz, 1H) (aromatic and vinyl), 10.88 (s, 1H, CONH), 13.61 (s, 1H, NH). LC-MS (m/z) 406.6 (M−1).

Example 171

5-[2-Oxo-1,2-dihydro-indol-(3Z)-ylidenemethyl]-2,4-dimethyl-1H-pyrrole-3-carboxylic acid (2-(3,5-dimethylpiperazin-1-yl)ethyl)amide To a stirred yellow muddy mixture of 5-[2-oxo-1,2-dihydro-indol-(3Z)-ylidenemethyl]-2,4-dimethyl-1H-pyrrole-3-carboxylic acid (112.8 mg, 0.4 mmol), DMF (0.5 mL) and triethylamine (0.111 mL) in a 20 mL reaction tube, was added BOP reagent (265 mg). The mixture became clear in 5 min. 2-(2,6-dimethylpiperazin-1-yl)ethylamine (68.6 mg) (see., Tapia, L. Alonso-Cires, P. Lopez-Tudanca, R. Mosquera, L. Labeaga, A. Innerarity, A. Orjales, *J. Med. Chem.*, 1999, 42, 2870-2880) was added into the clear mixture. The resulting solution was stirred at room temperature over night. Thin layer chromatography (10% methanol in methylene chloride) showed that all the starting material had been converted into the product. The reaction mixture was evaporated to dryness and then purified by flash chromatography (CH$_2$Cl$_2$/CH$_3$OH=20/1-15/1) followed by recrystalization to give 5-[2-oxo-1,2-dihydroindol-(3Z)-ylidenemethyl]-2,4-dimethyl-1H-pyrrole-3-carboxylic acid [2-(3,5-dimethylpiperazin-1-yl)ethyl)amide (83 mg, 50% yield).

$^1$H NMR (DMSO-d6) δ 1.15, 1.16 (2×s, 6H, 2×CH$_3$), 1.95 (t, J=11.6 Hz, 2H, CH$_2$), 2.41, 2.47 (2×s, 6H, 2×CH$_3$), 2.50 (m, 2H, CH$_2$), 3.03 (d, J=10 Hz, 2H), 3.19 (m, 2H), 3.30 (m, 2H, CH$_2$), 6.86 (d, J=8.0 Hz, 1H), 6.97 (t, J=7.2 Hz, 1H), 7.11 (t, J=7.8 Hz, 1H), 7.48 (t, J=5.6 Hz, 1H), 7.61 (s, 1H), 7.75 (d, J=7.6 Hz, 1H) (aromatic and vinyl), 10.88 (s, 1H, CONH), 13.62 (s, 1H, NH). LC-MS (m/z) 422.2 (M+1).

Example 173

5-[5-Fluoro-2-oxo-1,2-dihydro-indol-(3Z)-ylidenemethyl]-2,4-dimethyl-1H-pyrrole-3-carboxylic acid [2-(3,5-dimethylpiperazin-1-yl)ethyl)amide Following the procedure described in Example 168 above the desired compound was obtained (60 mg, 0.2 mmol).

$^1$H NMR (DMSO-d6) δ 0.891, 0.907 (2×s, 6H, 2×CH$_3$), 1.49 (t, J=10.4 Hz, 2H), 2.40, 2.42 (2×s, 6H, 2×CH$_3$), 2.41 (m, 2H, CH$_2$), 2.74 (m, 4H), 3.30 (m, 2H), 6.82 (dd, J=4.5, 8.7 Hz, 1H), 6.90 (td, $^2$J=2.4, $^3$J=8.4 Hz, 1H), 7.42 (t, J=5.6 Hz, 1H), 7.70 (s, 1H), 7.74 (dd, J=4.6, 8.4 Hz, 1H) (aromatic and vinyl), 10.88 (s, 1H, CONH), 13.65 (s, 1H, NH). LC-MS (m/z) 438.4 (M−1).

Example 174

5-[5-Chloro-2-oxo-1,2-dihydro-indol-(3Z)-ylidenemethyl]-2,4-dimethyl-1H-pyrrole-3-carboxylic acid [2-(3,5-dimethylpiperazin-1-yl)ethyl)amide Following the procedure for Example 171 above the desired compound (31.2 mg, 34%) was obtained from 5-[5-chloro-2-oxo-1,2-dihydro-indol-(3Z)-ylidenemethyl]-2,4-dimethyl-1H-pyrrole-3-carboxylic acid (63 mg, 0.2 mmol).

$^1$H NMR (DMSO-d6) δ 1.15, 1.16 (2×s, 6H, 2×CH$_3$), 1.95 (t, J=11.6 Hz, 2H, CH$_2$), 2.40, 2.42 (2×s, 6H, 2×CH$_3$), 2.50 (m, 2H, CH$_2$), 3.03 (d, J=11.2 Hz, 2H), 3.19 (m, 2H), 3.30 (m, 2H, CH$_2$), 6.85 (d, J=8.4 Hz, 1H), 7.11 (dd, J=2.0, 8.0 Hz,1H), 7.52 (t, J=5.6 Hz, 1H), 7.76 (s, 1H), 7.97 (d, J=2.0 Hz, 1H) (aromatic and vinyl), 10.99 (s, 1H, CONH), 13.63 (s, 1H, NH). LC-MS (m/z) 456.2 (M+1).

Example 175

5-[5-Bromo-2-oxo-1,2-dihydro-indol-(3Z)-ylidenemethyl]-2,4-dimethyl-1H-pyrrole-3-carboxylic acid [2-(3,5-dimethylpiperazin-1-yl)ethyl)amide Following the procedure described in Example 171 the desired compound (40 mg, 40%) was obtained from 5-[5-bromo-2-oxo-1,2-dihydro-indol-(3Z)-ylidenemethyl]-2,4-dimethyl-1H-pyrrole-3-carboxylic acid (74 mg, 0.2 mmol).

$^1$H NMR (DMSO-d6) δ 1.15, 1.16 (2×s, 6H, 2×CH$_3$), 1.95 (t, J=11.6 Hz, 2H, CH$_2$), 2.40, 2.42 (2×s, 6H, 2×CH$_3$), 2.50 (m, 2H, CH$_2$), 3.03 (d, J=10.4 Hz, 2H), 3.19 (m, 2H), 3.30 (m, 2H, CH$_2$), 6.81 (d, J=8.4 Hz, 1H), 7.24 (dd, J=2.0, 8.4 Hz, 1H), 7.51 (t, J=5.6 Hz, 1H), 7.76 (s, 1H), 8.10 (d, J=2.0 Hz, 1H) (aromatic and vinyl), 10.99 (s, 1H, CONH), 13.62 (s, 1H, NH). LC-MS (m/z) 498.4 (M−1).

Biological Examples

The following assays are employed to find those compounds demonstrating the optimal degree of the desired activity.

A. Assay Procedures.

The following assays may be used to determine the level of activity and effect of the different compounds of the present invention on one or more of the PKs. Similar assays can be designed along the same lines for any PK using techniques well known in the art.

Several of the assays described herein are performed in an ELISA (Enzyme-Linked Immunosorbent Sandwich Assay) format (Voller, et al., 1980, "Enzyme-Linked Immunosorbent Assay," Manual of Clinical Immunology, 2d ed., Rose and Friedman, Am. Soc. Of Microbiology, Washington, D.C., pp. 359-371). The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The presently preferred protocols for conducting the ELISA experiments for specific PKs is provided below. However, adaptation of these protocols for determining the activity of compounds against other RTKs, as well as for CTKs and STKs, is well within the scope of knowledge of those skilled in the art. Other assays described herein measure the amount of DNA made in response to activation of a test kinase, which is a general measure of a proliferative response. The general procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as 5-bromodeoxyuridine (BrdU) or $H^3$-thymidine is added. The amount of labeled DNA is detected with either an anti-BrdU antibody or by measuring radioactivity and is compared to control cells not contacted with a test compound.

GST-FLK-1 Bioassay

This assay analyzes the tyrosine kinase activity of GST-Flk1 on poly(glu,tyr) peptides.

Materials and Reagents:
1. Corning 96-well ELISA plates (Corning Catalog No. 5805-96).
2. poly(glu,tyr) 4:1, lyophilizate (Sigma Catalog # P0275).
3. Preparation of poly(glu,tyr)(pEY) coated assay plates: Coat 2 ug/well of poly(glu,tyr)(pEY) in 100 ul PBS, hold at room temperature for 2 hours or at 4° C. overnight. Cover plates well to prevent evaporation.
4. PBS Buffer: for 1 L, mix 0.2 g $KH_2PO_4$, 1.15 g $Na_2HPO_4$, 0.2 g KCl and 8 g NaCl in approx. 900 ml $dH_2O$. When all reagents have dissolved, adjust the pH to 7.2 with HCl. Bring total volume to 1 L with $dH_2O$.
5. PBS Buffer: to 1 L of PBS Buffer, add 1.0 ml Tween-20.
6. TBB—Blocking Buffer: for 1 L, mix 1.21 g TRIS, 8.77 g NaCl, 1 ml TWEEN-20 in approximately 900 ml $dH_2O$. Adjust pH to 7.2 with HCl. Add 10 g BSA, stir to dissolve. Bring total volume to 1 L with $dH_2O$. Filter to remove particulate matter.
7. 1% BSA in PBS: To make a 1× working solution, add 10 g BSA to approx. 990 ml PBS buffer, stir to dissolve. Adjust total volume to 1 L with PBS buffer, filter to remove particulate matter.
8. 50 mM Hepes pH 7.5.
9. GST-Flk1cd purified from sf9 recombinant baculovirus transformation (SUGEN, Inc.).
10. 4% DMSO in $dH_2O$.
11. 10 mM ATP in $dH_2O$.
12. 40 mM $MnCl_2$
13. Kinase Dilution Buffer (KDB): mix 10 ml Hepes (pH 7.5), 1 ml 5M NaCl, 40 µL 100 mM sodium orthovanadate and 0.4 ml of 5% BSA in $dH_2O$ with 88.56 ml $dH_2O$.
14. NUNC 96-well V bottom polypropylene plates, Applied Scientific Catalog # AS-72092
15. EDTA: mix 14.12 g ethylenediaminetetraacetic acid (EDTA) to approx. 70 ml $dH_2O$. Add 10 N NaOH until EDTA dissolves. Adjust pH to 8.0. Adjust total volume to 100 ml with $dH_2O$.
16. 1° Antibody Dilution Buffer: mix 10 ml of 5% BSA in PBS buffer with 89.5 ml TBST.
17. Anti-phosphotyrosine monoclonal antibody conjugated to horseradish peroxidase (PY99 HRP, Santa Cruz Biotech).
18. 2,2'-Azinobis(3-ethylbenzthiazoline-6-sulfonic acid (ABTS, Moss, Cat. No. ABST).
19. 10% SDS.

Procedure:
1. Coat Corning 96-well ELISA plates with 2 µg of polyEY peptide in sterile PBS as described in step 3 of Materials and Reagents.
2. Remove unbound liquid from wells by inverting plate. Wash once with TBST. Pat the plate on a paper towel to remove excess liquid.
3. Add 100 µl of 1% BSA in PBS to each well. Incubate, with shaking, for 1 hr. at room temperature.
4. Repeat step 2.
5. Soak wells with 50 mM HEPES (pH7.5) (150 µl/well).
6. Dilute test compound with $dH_2O$/4% DMSO to 4 times the desired final assay concentration in 96-well polypropylene plates.
7. Add 25 µl diluted test compound to ELISA plate. In control wells, place 25 µl of $dH_2O$/4% DMSO.
8. Add 25 µl of 40 mM $MnCl_2$ with 4×ATP (2 µM) to each well.
9. Add 25 µl 0.5M EDTA to negative control wells.
10. Dilute GST-Flk1 to 0.005 µg (5 ng)/well with KDB.
11. Add 50 µl of diluted enzyme to each well.
12. Incubate, with shaking, for 15 minutes at room temperature.
13. Stop reaction by adding 50 µl of 250 mM EDTA (pH 8.0).
14. Wash 3× with TBST and pat plate on paper towel to remove excess liquid.
15. Add 100 µl per well anti-phosphotyrosine HRP conjugate, 1:5,000 dilution in antibody dilution buffer. Incubate, with shaking, for 90 min. at room temperature.
16. Wash as in step 14.
17. Add 100 µl of room temperature ABTS solution to each well.
18. Incubate, with shaking, for 10 to 15 minutes. Remove any bubbles.
19. Stop reaction by adding 20 µl of 10% SDS to each well.
20. Read results on Dynatech MR7000 ELISA reader with test filter at 410 nM and reference filter at 630 nM.

PYK2 Bioassay

This assay is used to measure the in vitro kinase activity of HA epitope-tagged full length pyk2 (FL.pyk2-HA) in an ELISA assay.

Materials and Reagents:
1. Corning 96-well Elisa plates.
2. 12CA5 monoclonal anti-HA antibody (SUGEN, Inc.)
3. PBS (Dulbecco's Phosphate-Buffered Saline (Gibco Catalog # 450-1300EB)

4. TBST Buffer: for 1 L, mix 8.766 g NaCl, 6.057 g TRIS and 1 ml of 0.1% Triton X-100 in approx. 900 ml dH$_2$O. Adjust pH to 7.2, bring volume to 1 L.
5. Blocking Buffer: for 1 L, mix 100 g 10% BSA, 12.1 g 100 mM TRIS, 58.44 g 1M NaCl and 10 mL of 1% TWEEN-20.
6. FL.pyk2-HA from sf9 cell lysates (SUGEN, Inc.).
7. 4% DMSO in MilliQue H$_2$O.
8. 10 mM ATP in dH$_2$O.
9. 1M MnCl$_2$.
10. 1M MgCl$_2$.
11. 1M Dithiothreitol (DTT).
12. 10× Kinase buffer phosphorylation: mix 5.0 ml 1M Hepes (pH 7.5), 0.2 ml 1M MnCl$_2$, 1.0 ml 1 M MgCl$_2$, 1.0 ml 10% Triton X-100 in 2.8 ml dH$_2$O. Just prior to use, add 0.1 ml 1M DTT.
13. NUNC 96-well V bottom polypropylene plates.
14. 500 mM. EDTA in dH$_2$O.
15. Antibody dilution buffer: for 100 mL, 1 mL 5% BSA/PBS and 1 mL 10% Tween-20 in 88 mL TBS.
16. HRP-conjugated anti-Ptyr PY99), Santa Cruz Biotech Cat. No. SC-7020.
17. ABTS, Moss, Cat. No. ABST-2000.
18. 10% SDS.

Procedure:
1. Coat Corning 96 well ELISA plates with 0.5 µg per well 12CA5 anti-HA antibody in 100 µl PBS. Store overnight at 4° C.
2. Remove unbound HA antibody from wells by inverting plate. Wash plate with dH$_2$O. Pat the plate on a paper towel to remove excess liquid.
3. Add 150 µl Blocking Buffer to each well. Incubate, with shaking, for 30 min at room temperature.
4. Wash plate 4× with TBS-T.
5. Dilute lysate in PBS (1.5 µg lysate/100 µl PBS).
6. Add 100 µl of diluted lysate to each well. Shake at room temperature for 1 hr.
7. Wash as in step 4.
8. Add 50 µl of 2× kinase Buffer to ELISA plate containing captured pyk2-HA.
9. Add 25 µL of 400 µM test compound in 4% DMSO to each well. For control wells use 4% DMSO alone.
10. Add 25 µL of 0.5 M EDTA to negative control wells.
11. Add 25 µl of 20 µM ATP to all wells. Incubate, with shaking, for 10 minutes.
12. Stop reaction by adding 25 µl 500 mM EDTA (pH 8.0) to all wells.
13. Wash as in step 4.
14. Add 100 µL HRP conjugated anti-Ptyr diluted 1:6000 in Antibody Dilution Buffer to each well. Incubate, with shaking, for 1 hr. at room temperature.
15. Wash plate 3× with TBST and 1× with PBS.
16. Add 100 µL of ABST solution to each well.
17. If necessary, stop the development reaction by adding 20 µL 10% SDS to each well.
18. Read plate on ELISA reader with test filter at 410 nM and reference filter at 630 nM.

FGFR1 Bioassay

This assay is used to measure the in vitro kinase activity of FGF1-R in an ELISA assay.

Materials and Reagents:
1. Costar 96-well Elisa plates (Corning Catalog # 3369).
2. Poly(Glu-Tyr) (Sigma Catalog # P0275).
3. PBS (Gibco Catalog # 450-1300EB)
4. 50 mM Hepes Buffer Solution.
5. Blocking Buffer (5% BSA/PBS).
6. Purified GST-FGFR1 (SUGEN, Inc.)
7. Kinase Dilution Buffer.
  Mix 500 µl 1M Hepes (GIBCO), 20 µl 5% BSA/PBS, 10 µl 100 mM sodium orthovanadate and 50 µl 5M NaCl.
8. 10 mM ATP
9. ATP/MnCl$_2$ phosphorylation mix: mix 20 µL ATP, 400 µL 1M MnCl$_2$ and 9.56 ml dH$_2$O.
10. NUNC 96-well V bottom polypropylene plates (Applied Scientific Catalog # AS-72092).
11. 0.5M EDTA.
12. 0.05% TBST Add 500 µL TWEEN to 1 liter TBS.
13. Rabbit polyclonal anti-phosphotyrosine serum (SUGEN, Inc.).
14. Goat anti-rabbit IgG peroxidase conjugate (Biosource, Catalog # ALI0404).
15. ABTS Solution.
16. ABTS/H$_2$O$_2$ solution.

Procedure:
1. Coat Costar 96 well ELISA plates with 1 µg per well Poly(Glu,Tyr) in 100 µl PBS. Store overnight at 4° C.
2. Wash coated plates once with PBS.
3. Add 150 µL of 5% BSA/PBS Blocking Buffer to each well. Incubate, with shaking, for 1 hr. room temperature.
4. Wash plate 2× with PBS, then once with 50 mM Hepes. Pat plates on a paper towel to remove excess liquid and bubbles.
5. Add 25 µL of 0.4 mM test compound in 4% DMSO or 4% DMSO alone (controls) to plate.
6. Dilute purified GST-FGFR1 in Kinase Dilution Buffer (5 ng kinase/50 ul KDB/well).
7. Add 50 µL of diluted kinase to each well.
8. Start kinase reaction by adding 25 µl/well of freshly prepared ATP/Mn++ (0.4 ml 1M MnCl$_2$, 40 µL 10 mM ATP, 9.56 ml dH$_2$O), freshly prepared).
9. This is a fast kinase reaction and must be stopped with 25 µL of 0.5M EDTA in a manner similar to the addition of ATP.
10. Wash plate 4× with fresh TBST.
11. Make up Antibody Dilution Buffer: Per 50 ml:
  Mix 5 ml of 5% BSA, 250 µl of 5% milk and 50 µl of 100 mM sodium vanadate, bring to final volume with 0.05% TBST.
12. Add 100 µl per well of anti-phosphotyrosine (1:10000 dilution in ADB). Incubate, with shaking for 1 hr. at room temperature.
13. Wash as in step 10.
14. Add 100 µl per well of Biosource Goat anti-rabbit IgG peroxidase conjugate (1:6000 dilution in ADB). Incubate, with shaking for 1 hr. at room temperature.
15. Wash as in step 10 and then with PBS to remove bubbles and excess TWEEN.
16. Add 100 µl of ABTS/H$_2$O$_2$ solution to each well.
17. Incubate, with shaking, for 10 to 20 minutes. Remove any bubbles.
18. Read assay on Dynatech MR7000 elisa reader: test filter at 410 nM, reference filtrate 630 nM.

EGFR Bioassay

This assay is used to the in vitro kinase activity of FGF1-R in an ELISA assay.

Materials and Reagents:
1. Corning 96-well Elisa plates.
2. SUMO1 monoclonal anti-EGFR antibody (SUGEN, Inc.).
4. TBST Buffer 5. Blocking Buffer: for 100 ml, mix 5.0 g Carnation Instant Non-fat Milk® with 100 ml of PBS.
6. A431 cell lysate (SUGEN, Inc.).
7. TBS Buffer:
8. TBS+10% DMSO: for 1 L, mix 1.514 g TRIS, 2.192 g NaCl and 25-ml DMSO; bring to 1 liter total volume with $dH_2O$.
9. ATP (Adenosine-5'-triphosphate, from Equine muscle, Sigma Cat. No. A-5394), 1.0 mM solution in $dH_2O$. This reagent should be made up immediately prior to use and kept on ice.
10. 1.0 mM $MnCl_2$.
11. ATP/$MnCl_2$ phosphorylation mix: to make 10 ml, mix 300 µl of 1 mM ATP, 500 µl $MnCl_2$ and 9.2 ml $dH_2O$. Prepare just prior to use, keep on ice.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. 30% Hydrogen peroxide.
18. ABTS/$H_2O_2$.
19. 0.2 M HCl.

Procedure:
1. Coat Corning 96 well ELISA plates with 0.5 µg SUMO1 in 100 µl PBS per well, store overnight at 4° C.
2. Remove unbound SUMO1 from wells by inverting plate to remove liquid. Wash 1× with $dH_2O$. Pat the plate on a paper towel to remove excess liquid.
3. Add 150 µl of Blocking Buffer to each well. Incubate, with shaking, for 30 min. at room temperature.
4. Wash plate 3× with deionized water, then once with TBST. Pat plate on a paper towel to remove excess liquid and bubbles.
5. Dilute lysate in PBS (7 µg lysate/100 µl PBS).
6. Add 100 µl of diluted lysate to each well. Shake at room temperature for 1 hr.
7. Wash plates as in 4, above.
8. Add 120 µl TBS to ELISA plate containing captured EGFR.
9. Dilute test compound 1:10 in TBS, place in well
10. Add 13.5 µl diluted test compound to ELISA plate. To control wells, add 13.5 µl TBS in 10% DMSO.
11. Incubate, with shaking, for 30 minutes at room temperature.
12. Add 15 µl phosphorylation mix to all wells except negative control well. Final well volume should be approximately 150 µl with 3 µM ATP/5 mM $MnCl_2$ final concentration in each well. Incubate with shaking for 5 minutes.
13. Stop reaction by adding 16.5 µl of EDTA solution while shaking. Shake for additional 1 min.
14. Wash 4× with deionized water, 2× with TBST.
15. Add 100 µl anti-phosphotyrosine (1:3000 dilution in TBST) per well. Incubate, with shaking, for 30-45 min. at room temperature.
16. Wash as in 4, above.
17. Add 100 µl Biosource Goat anti-rabbit IgG peroxidase conjugate (1:2000 dilution in TBST) to each well. Incubate with shaking for 30 min. at room temperature.
18. Wash as in 4, above.
19. Add 100 µl of ABTS/$H_2O_2$ solution to each well.
20. Incubate 5 to 10 minutes with shaking. Remove any bubbles.
21. If necessary, stop reaction by adding 100 µl 0.2 M HCl per well.
22. Read assay on Dynatech MR7000 ELISA reader: test filter at 410 nM, reference filter at 630 nM.

PDGFR Bioassay

This assay is used to the in vitro kinase activity of FGF1-R in an ELISA assay.

Materials and Reagents:
1. Corning 96-well Elisa plates
2. 28D4C10 monoclonal anti-PDGFR antibody (SUGEN, Inc.).
3. PBS.
4. TBST Buffer.
5. Blocking Buffer (same as for EGFR bioassay).
6. PDGFR-β expressing NIH 3T3 cell lysate (SUGEN, Inc.).
7. TBS Buffer.
8. TBS+10% DMSO.
9. ATP.
10. $MnCl_2$.
11. Kinase buffer phosphorylation mix: for 10 ml, mix 250 µl 1M TRIS, 200 µl 5M NaCl, 100 µl 1M $MnCl_2$ and 50 µl 100 mM Triton X-100 in enough $dH_2O$ to make 10 ml.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. Hydrogen peroxide, 30% solution.
18. ABTS/$H_2O_2$.
19. 0.2 M HCl.

Procedure:
1. Coat Corning 96 well ELISA plates with 0.5 µg 28D4C10 in 100 µl PBS per well, store overnight at 4° C.
2. Remove unbound 28D4C10 from wells by inverting plate to remove liquid. Wash 1× with $dH_2O$. Pat the plate on a paper towel to remove excess liquid.
3. Add 150 µl of Blocking Buffer to each well. Incubate for 30 min. at room temperature with shaking.
4. Wash plate 3× with deionized water, then once with TBST. Pat plate on a paper towel to remove excess liquid and bubbles.
5. Dilute lysate in HNTG (10 µg lysate/100 µl HNTG).
6. Add 100 µl of diluted lysate to each well. Shake at room temperature for 60 min.
7. Wash plates as described in Step 4.
8. Add 80 µl working kinase buffer mix to ELISA plate containing captured PDGFR.
9. Dilute test compound 1:10 in TBS in 96-well polypropylene plates.
10. Add 10 µl diluted test compound to ELISA plate. To control wells, add 10 µl TBS+10% DMSO. Incubate with shaking for 30 minutes at room temperature.
11. Add 10 µL ATP directly to all wells except negative control well (final well volume should be approximately 100 µl with 20 µM ATP in each well.) Incubate 30 minutes with shaking.
12. Stop reaction by adding 10 µl of EDTA solution to each well.
13. Wash 4× with deionized water, twice with TBST.
14. Add 100 µl anti-phosphotyrosine (1:3000 dilution in TBST) per well. Incubate with shaking for 30-45 min. at room temperature.

15. Wash as in Step 4.
16. Add 100 μl Biosource Goat anti-rabbit IgG peroxidase conjugate (1:2000 dilution in TBST) to each well. Incubate with shaking for 30 min. at room temperature.
17. Wash as in Step 4.
18. Add 100 μl of ABTS/$H_2O_2$ solution to each well.
19. Incubate 10 to 30 minutes with shaking. Remove any bubbles.
20. If necessary stop reaction with the addition of 100 μl 0.2 M HCl per well.
21. Read assay on Dynatech MR7000 ELISA reader with test filter at 410 nM and reference filter at 630 nM.

Cellular HER-2 Kinase Assay

This assay is used to measure HER-2 kinase activity in whole cells in an ELISA format.

Materials and Reagents:
1. DMEM (GIBCO Catalog #11965-092).
2. Fetal Bovine Serum (FBS, GIBCO Catalog #16000-044), heat inactivated in a water bath for 30 min. at 56° C.
3. Trypsin (GIBCO Catalog #25200-056).
4. L-Glutamine (GIBCO Catalog #25030-081)
5. HEPES (GIBCO Catalog #15630-080).
6. Growth Media
   Mix 500 ml DMEM, 55 ml heat inactivated FBS, 10 ml HEPES and 5.5 ml L-Glutamine.
7. Starve Media
   Mix 500 ml DMEM, 2.5 ml heat inactivated FBS, 10 ml HEPES and 5.5 ml L-Glutamine.
8. PBS.
9. Flat Bottom 96-well Tissue Culture Micro Titer Plates (Corning Catalog # 25860).
10. 15 cm Tissue Culture Dishes (Corning Catalog #08757148).
11. Corning 96-well ELISA Plates.
12. NUNC 96-well V bottom polypropylene plates.
13. Costar Transfer Cartridges for the Transtar 96 (Costar Catalog #7610).
14. SUMO 1: monoclonal anti-EGFR antibody (SUGEN, Inc.).
15. TBST Buffer.
16. Blocking Buffer: 5% Carnation Instant Milk® in PBS.
17. EGF Ligand: EGF-201, Shinko American, Japan. Suspend powder in 100 uL of 10 mM HCl. Add 100 uL 10 mM NaOH. Add 800 uL PBS and transfer to an Eppendorf tube, store at −20° C. until ready to use.
18. HNTG Lysis Buffer
   For Stock 5×HNTG, mix 23.83 g Hepes, 43.83 g NaCl, 500 ml glycerol and 100 ml Triton X-100 and enough $dH_2O$ to make 1 L of total solution.
   For 1×HNTG*, mix 2 ml HNTG, 100 μL 0.1M $Na_3VO_4$, 250 μL 0.2M $Na_4P_2O_7$ and 100 μL EDTA.
19. EDTA.
20. $Na_3VO_4$. To make stock solution, mix 1.84 g $Na_3VO_4$ with 90 ml $dH_2O$. Adjust pH to 10. Boil in microwave for one minute (solution becomes clear). Cool to room temperature. Adjust pH to 10. Repeat heating/cooling cycle until pH remains at 10.
21. 200 mM $Na_4P_2O_7$.
22. Rabbit polyclonal antiserum specific for phosphotyrosine (anti-Ptyr antibody, SUGEN, Inc.).
23. Affinity purified antiserum, goat anti-rabbit IgG antibody, peroxidase conjugate (Biosource Cat # ALI0404).
24. ABTS Solution.
25. 30% Hydrogen peroxide solution.
26. ABTS/$H_2O_2$.
27. 0.2 M HCl.

Procedure:
1. Coat Corning 96 well ELISA plates with SUMO1 at 1.0 ug per well in PBS, 100 ul final volume/well. Store overnight at 4° C.
2. On day of use, remove coating buffer and wash plate 3 times with $dH_2O$ and once with TBST buffer. All washes in this assay should be done in this manner, unless otherwise specified.
3. Add 100 ul of Blocking Buffer to each well. Incubate plate, with shaking, for 30 min. at room temperature. Just prior to use, wash plate.
4. Use EGFr/HER-2 chimera/3T3-C7 cell line for this assay.
5. Choose dishes having 80-90% confluence. Collect cells by trypsinization and centrifuge at 1000 rpm at room temperature for 5 min.
6. Resuspend cells in starve medium and count with trypan blue. Viability above 90% is required. Seed cells in starve medium at a density of 2,500 cells per well, 90 ul per well, in a 96 well microtiter plate. Incubate seeded cells overnight at 37° under 5% $CO_2$.
7. Start the assay two days after seeding.
8. Test compounds are dissolved in 4% DMSO. Samples are then further diluted directly on plates with starve-DMEM. Typically, this dilution will be 1:10 or greater. All wells are then transferred to the cell plate at a further 1:10 dilution (10 μl sample and media into 90 μl of starve media. The final DMSO concentration should be 1% or lower. A standard serial dilution may also be used.
9. Incubate under 5% $CO_2$ at 37° C. for 2 hours.
10. Prepare EGF ligand by diluting stock EGF (16.5 uM) in warm DMEM to 150 nM.
11. Prepare fresh HNTG* sufficient for 100 ul per well; place on ice.
12. After 2 hour incubation with test compound, add prepared EGF ligand to cells, 50 ul per well, for a final concentration of 50 nM. Positive control wells receive the same amount of EGF. Negative controls do not receive EGF. Incubate at 37° C. for 10 min.
13. Remove test compound, EGF, and DMEM. Wash cells once with PBS.
14. Transfer HNTG* to cells, 100 ul per well. Place on ice for 5 minutes. Meanwhile, remove blocking buffer from ELISA plate and wash.
15. Scrape cells from plate with a micropipettor and homogenize cell material by repeatedly aspirating and dispensing the HNTG* lysis buffer. Transfer lysate to a coated, blocked, washed ELISA plate. Or, use a Costar transfer cartridge to transfer lysate to the plate.
16. Incubate, with shaking, at room temperature for 1 hr.
17. Remove lysate, wash. Transfer freshly diluted anti-Ptyr antibody (1:3000 in TBST) to ELISA plate, 100 ul per well.
18. Incubate, with shaking, at room temperature, for 30 min.
19. Remove anti-Ptyr antibody, wash. Transfer freshly diluted BIOSOURCE antibody to ELISA plate (1:8000 in TBST, 100 ul per well).
20. Incubate, with shaking, at room temperature for 30 min.
21. Remove BIOSOURCE antibody, wash. Transfer freshly prepared ABTS/$H_2O_2$ solution to ELISA plate, 100 ul per well.

22. Incubate, with shaking, for 5-10 minutes. Remove any bubbles.
23. Stop reaction with the addition of 100 ul of 0.2M HCl per well.
24. Read assay on Dynatech MR7000 ELISA reader with test filter set at 410 nM and reference filter at 630 nM.

CDK2/Cyclin A Assay

This assay is used to measure the in vitro serine/threonine kinase activity of human cdk2/cyclin A in a Scintillation Proximity Assay (SPA).

Materials and Reagents.
1. Wallac 96-well polyethylene terephthalate (flexi) plates (Wallac Catalog # 1450-401).
2. Amersham Redivue [$\gamma^{33}$P] ATP (Amersham catalog #AH 9968).
3. Amersham streptavidin coated polyvinyltoluene SPA beads (Amersham catalog #RPNQ0007). The beads should be reconstituted in PBS without magnesium or calcium, at 20 mg/ml.
4. Activated cdk2/cyclin A enzyme complex purified from Sf9 cells (SUGEN, Inc.).
5. Biotinylated peptide substrate (Debtide). Peptide biotin-X-PKTPKKAKKL is dissolved in dH$_2$O at a concentration of 5 mg/ml.
6. Peptide/ATP Mixture: for 10 ml, mix 9.979 ml dH$_2$O, 0.00125 ml "cold" ATP, 0.010 ml Debtide and 0.010 ml $\gamma^{33}$P ATP. The ultimate concentration per well will be 0.5 µM "cold" ATP, 0.1 µg Debtide and 0.2 µCi $\gamma^{33}$P ATP.
7. Kinase buffer: for 10 ml, mix 8.85 ml dH$_2$O, 0.625 ml TRIS (pH 7.4), 0.25 ml 1M MgCl$_2$, 0.25 ml 10% NP40 and 0.025 ml 1M DTT, added fresh just prior to use.
8. 10 mM ATP in dH$_2$O.
9. 1M Tris, pH adjusted to 7.4 with HCl.
10. 1M MgCl$_2$.
11. 1M DTT.
12. PBS (Gibco Catalog # 14190-144).
13. 0.5M EDTA.
14. Stop solution: For 10 ml, mix 9.25 ml PBS, 0.005 ml 100 mM ATP, 0.1 ml 0.5 M EDTA, 0.1 ml 10% Triton X-100 and 1.25 ml of 20 mg/ml SPA beads.

Procedure:
1. Prepare solutions of test compounds at 5× the desired final concentration in 5% DMSO. Add 10 ul to each well. For negative controls, use 10 ul 5% DMSO alone in wells.
2. Dilute 5 µof cdk2/cyclin A solution with 2.1 ml 2× kinase buffer.
3. Add 20 ul enzyme to each well.
4. Add 10 µL of 0.5 M EDTA to the negative control wells.
5. To start kinase reaction, add 20 µL of peptide/ATP mixture to each well. Incubate for 1 hr. without shaking.
6. Add 200 µl stop solution to each well.
7. Hold at least 10 min.
8. Spin plate at approx. 2300 rpm for 3-5 min.
9. Count plate using Trilux or similar reader.

Met Transphosphorylation Assay

This assay is used to measure phosphotyrosine levels on a poly(glutamic acid:tyrosine (4:1)) substrate as a means for identifying agonists/antagonists of met transphosphorylation of the substrate.

Materials and Reagents:
1. Corning 96-well Elisa plates, Corning Catalog # 25805-96.
2. Poly(glu, tyr) 4:1, Sigma, Cat. No; P 0275.
3. PBS, Gibco Catalog # 450-1300EB
4. 50 mM HEPES
5. Blocking Buffer: Dissolve 25 g Bovine Serum Albumin, Sigma Cat. No A-7888, in 500 ml PBS, filter through a 4 µm filter.
6. Purified GST fusion protein containing the Met kinase domain, Sugen, Inc.
7. TBST Buffer.
8. 10% aqueous (MilliQue H$_2$O) DMSO.
9. 10 mM aqueous (dH$_2$O) Adenosine-5'-triphosphate, Sigma Cat. No. A-5394.
10. 2× Kinase Dilution Buffer: for 100 ml, mix 10 mL 1M HEPES at pH 7.5 with 0.4 mL 5% BSA/PBS, 0.2 mL 0.1 M sodium orthovanadate and 1 mL 5M sodium chloride in 88.4 mL dH$_2$O.
11. 4×ATP Reaction Mixture: for 10 mL, mix 0.4 mL 1 M manganese chloride and 0.02 mL 0.1 M ATP in 9.56 mL dH$_2$O.
12. 4× Negative Controls Mixture: for 10 mL, mix 0.4 mL 1 M manganese chloride in 9.6 mL dH$_2$O.
13. NUNC 96-well V bottom polypropylene plates, Applied Scientific Catalog # S-72092
14. 500 mM EDTA.
15. Antibody Dilution Buffer: for 100 mL, mix 10 mL 5% BSA/PBS, 0.5 mL 5% Carnation Instant Milk® in PBS and 0.1 mL 0.1 M sodium orthovanadate in 88.4 mL TBST.
16. Rabbit polyclonal antophosphotyrosine antibody, Sugen, Inc.
17. Goat anti-rabbit horseradish peroxidase conjugated antibody, Biosource, Inc.
18. ABTS Solution: for 1 L, mix 19.21 g citric acid, 35.49 g Na$_2$HPO$_4$ and 500 mg ABTS with sufficient dH$_2$O to make 1 L.
19. ABTS/H$_2$O$_2$: mix 15 mL ABST solution with 2 µL H$_2$O$_2$ five minutes before use.
20. 0.2 M HCl Procedure:
1. Coat ELISA plates with 2 µg Poly(Glu-Tyr) in 100 µL PBS, store overnight at 4° C.
2. Block plate with 150 µL of 5% BSA/PBS for 60 min.
3. Wash plate twice with PBS, once with 50 mM Hepes buffer pH 7.4.
4. Add 50 µl of the diluted kinase to all wells. (Purified kinase is diluted with Kinase Dilution Buffer. Final concentration should be 10 ng/well.)
5. Add 25 µL of the test compound (in 4% DMSO) or DMSO alone (4% in dH$_2$O) for controls to plate.
6. Incubate the kinase/compound mixture for 15 minutes.
7. Add 25 µL of 40 mM MnCl$_2$ to the negative control wells.
8. Add 25 µL ATP/MnCl$_2$ mixture to the all other wells (except the negative controls). Incubate for 5 min.
9. Add 25 µL 500 mM EDTA to stop reaction.
10. Wash plate 3× with TBST.
11. Add 100 µL rabbit polyclonal anti-Ptyr diluted 1:10,000 in Antibody Dilution Buffer to each well. Incubate, with shaking, at room temperature for one hour.
12. Wash plate 3× with TBST.
13. Dilute Biosource HRP conjugated anti-rabbit antibody 1: 6,000 in Antibody Dilution buffer. Add 100 µL per well and incubate at room temperature, with shaking, for one hour.
14. Wash plate 1× with PBS.
15. Add 100 µl of ABTS/H$_2$O$_2$ solution to each well.

16. If necessary, stop the development reaction with the addition of 100 µl of 0.2M HCl per well.
17. Read plate on Dynatech MR7000 elisa reader with the test filter at 410 nM and the reference filter at 630 nM.

IGF-1 Transphosphorylation Assay

This assay is used to measure the phosphotyrosine level in poly(glutamic acid:tyrosine)(4:1) for the identification of agonists/antagonists of gst-IGF-1 transphosphorylation of a substrate.

Materials and Reagents:
1. Corning 96-well Elisa plates.
2. Poly (Glu-tyr) (4:1), Sigma Cat. No. P 0275.
3. PBS, Gibco Catalog # 450-1300EB.
4. 50 mM HEPES
5. TBB Blocking Buffer: for 1 L, mix 100 g BSA, 12.1 gTRIS (pH 7.5), 58.44 g sodium chloride and 10 mL 1% TWEEN-20.
6. Purified GST fusion protein containing the IGF-1 kinase domain (Sugen, Inc.)
7. TBST Buffer: for 1 L, mix 6.057 g Tris, 8.766 g sodium chloride and 0.5 ml TWEEN-20 with enough $dH_2O$ to make 1 liter.
8. 4% DMSO in Milli-Q $H_2O$.
9. 10 mM ATP in $dH_2O$.
10. 2× Kinase Dilution Buffer: for 100 mL, mix 10 mL 1 M HEPES (pH 7.5), 0.4 mL 5% BSA in $dH_2O$, 0.2 mL 0.1 M sodium orthovanadate and 1 mL 5 M sodium chloride with enough $dH_2O$ to make 100 mL.
11. 4×ATP Reaction Mixture: for 10 mL, mix 0.4 mL 1 M $MnCl_2$ and 0.008 mL 0.01 M ATP and 9.56 mL $dH_2O$.
12. 4× Negative Controls Mixture: mix 0.4 mL 1 M manganese chloride in 9.60 mL $dH_2O$.
13. NUNC 96-well V bottom polypropylene plates.
14. 500 mM EDTA in $dH_2O$.
15. Antibody Dilution Buffer: for 100 mL, mix 10 mL 5% BSA in PBS, 0.5 mL 5% Carnation Instant Non-fat Milk® in PBS and 0.1 mL 0.1 M sodium orthovanadate in 88.4 mL TBST.
16. Rabbit Polyclonal antiphosphotyrosine antibody, Sugen, Inc.
17. Goat anti-rabbit HRP conjugated antibody, Biosource.
18. ABTS Solution.
20. $ABTS/H_2O_2$: mix 15 mL ABTS with 2 µL $H_2O_2$ 5 minutes before using.
21. 0.2 M HCl in $dH_2O$.

Procedure:
1. Coat ELISA plate with 2.0 µg/well Poly(Glu, Tyr) 4:1 (Sigma P0275) in 100 µl PBS. Store plate overnight at 4° C.
2. ash plate once with PBS.
3. Add 100 µl of TBB Blocking Buffer to each well. Incubate plate for 1 hour with shaking at room temperature.
4. Wash plate once with PBS, then twice with 50 mM Hepes buffer pH 7.5.
5. Add 25 µL of test compound in 4% DMSO (obtained by diluting a stock solution of 10 mM test compound in 100% DMSO with $dH_2O$) to plate.
6. Add 10.0 ng of gst-IGF-1 kinase in 50 µl Kinase Dilution Buffer) to all wells.
7. Start kinase reaction by adding 25 µl 4×ATP Reaction Mixture to all test wells and positive control wells. Add 25 µl 4× Negative Controls Mixture to all negative control wells. Incubates for 10 minutes with shaking at room temperature.
8. Add 25 µl 0.5M EDTA (pH 8.0) to all wells.
9. Wash plate 4× with TBST Buffer.
10. Add rabbit polyclonal anti-phosphotyrosine antisera at a dilution of 1:10,000 in 10011 Antibody Dilution Buffer to all wells. Incubate, with shaking, at room temperature for 1 hour.
11. Wash plate as in step 9.
12. Add 100 µL Biosource anti-rabbit HRP at a dilution of 1:10,000 in Antibody dilution buffer to all wells. Incubate, with shaking, at room-temperature for 1 hour.
13. Wash plate as in step 9, follow with one wash with PBS to reduce bubbles and excess Tween-20.
14. Develop by adding 100 µl/well $ABTS/H_2O_2$ to each well
15. After about 5 minutes, read on ELISA reader with test filter at 410 nm and referenced filter at 630 nm.

BRDU Incorporation Assays

The following assays use cells engineered to express a selected receptor and then evaluate the effect of a compound of interest on the activity of ligand-induced DNA synthesis by determining BrdU incorporation into the DNA.

The following materials, reagents and procedure are general to each of the following BrdU incorporation assays. Variances in specific assays are noted.

Materials and Reagents:
1. The appropriate ligand.
2. The appropriate engineered cells.
3. BrdU Labeling Reagent: 10 mM, in PBS (pH 7.4) (Boehringer-Mannheim, Germany).
4. FixDenat: fixation solution (ready to use)(Boehringer Mannheim, Germany).
5. Anti-BrdU-POD: mouse monoclonal antibody conjugated with peroxidase (Boehringer Mannheim, Germany).
6. TMB Substrate Solution: tetramethylbenzidine (TMB, Boehgringer Mannheim, Germany).
7. PBS Washing Solution: 1×PBS, pH 7.4.
8. Albumin, Bovine (BSA), fraction V powder (Sigma Chemical Co., USA).

General Procedure:
1. Cells are seeded at 8000 cells/well in 10% CS, 2 mM Gln in DMEM, in a 96 well plate. Cells are incubated overnight at 37° C. in 5% $CO_2$.
2. After 24 hours, the cells are washed with PBS, and then are serum-starved in serum free medium (0% CS DMEM with 0.1% BSA) for 24 hours.
3. On day 3, the appropriate ligand and the test compound are added to the cells simultaneously. The negative control wells receive serum free DMEM with 0.1% BSA only; the positive control cells receive the ligand but no test compound. Test compounds are prepared in serum free DMEM with ligand in a 96 well plate, and serially diluted for 7 test concentrations.
4. After 18 hours of ligand activation, diluted BrdU labeling reagent (1:100 in DMEM, 0.1% BSA) is added and the cells are incubated with BrdU (final concentration=10 µM) for 1.5 hours.
5. After incubation with labeling reagent, the medium is removed by decanting and tapping the inverted plate on a paper towel. FixDenat solution is added (50 µl/well) and the plates are incubated at room temperature for 45 minutes on a plate shaker.
6. The FixDenat solution is thoroughly removed by decanting and tapping the inverted plate on a paper towel. Milk is added (5% dehydrated milk in PBS, 200 µl/well) as a blocking solution and the plate is incubated for 30 minutes at room temperature on a plate shaker.
7. The blocking solution is removed by decanting and the wells are washed once with PBS. Anti-BrdU-POD solution (1:200 dilution in PBS, 1% BSA) is added (50 µl/well) and the plate is incubated for 90 minutes at room temperature on a plate shaker.
8. The antibody conjugate is thoroughly removed by decanting and rinsing the wells 5 times with PBS, and the plate is dried by inverting and tapping on a paper towel.
9. TMB substrate solution is added (100 µl/well) and incubated for 20 minutes at room temperature on a plate shaker until color development is sufficient for photometric detection.
10. The absorbance of the samples are measured at 410 nm (in "dual wavelength" mode with a filter reading at 490 nm, as a reference wavelength) on a Dynatech ELISA plate reader.

EGF-Induced BrdU Incorporation Assay

Materials and Reagents:
1. Mouse EGF, 201-(Toyobo Co., Ltd., Japan).
2. 3T3/EGFRc7.

EGF-Induced Her-2-driven BrdU Incorporation Assay

Materials and Reagents:
1. Mouse EGF, 201 (Toyobo Co., Ltd., Japan).
2. 3T3/EGFr/Her2/EGFr (EGFr with a Her-2 kinase domain).

EGF-Induced Her-4-Driven BrdU Incorporation Assay

Materials and Reagents:
1. Mouse EGF, 201 (Toyobo Co., Ltd., Japan).
2. 3T3/EGFr/Her4/EGFr (EGFr with a Her-4 kinase domain).

PDGF-Induced BrdU Incorporation Assay

Materials and Reagents:
1. Human PDGF B/B (Boehringer Mannheim, Germany).
2. 3T3/EGFRc7.

FGF-Induced BrdU Incorporation Assay

Materials and Reagents:
1. Human FGF2/bFGF (Gibco BRL, USA).
2. 3T3c7/EGFr

IGF1-Induced BrdU Incorporation Assay

Materials and Reagents:
1. Human, recombinant (Gibco, Promega Corp., USA)
2. 3T3c7/EGFr.

Insulin-Induced BrdU Incorporation Assay

Materials and Reagents:
1. Insulin, crystalline, bovine, Zinc (13007, Gibco BRL, USA).
2. 3T3/H25.

EGF-Induced BrdU Incorporation Assay

Materials and Reagents:
1. Recombinant human HGF (Cat. No. 249-HG, R&D Systems, Inc. USA).
2. BxPC-3 cells (ATCC CRL-1687).

Procedure:
1. Cells are seeded at 9000 cells/well in RPMI 10% FBS in a 96 well plate. Cells are incubated overnight at 37° C. in 5% $CO_2$.
2. After 24 hours, the cells are washed with PBS, and then are serum starved in 100 µl serum-free medium (RPMI with 0.1% BSA) for 24 hours.
3. On day 3, 25 µl containing ligand (prepared at 1 µg/ml in RPMI with 0.1% BSA; final HGF conc. is 200 ng/ml) and test compounds are added to the cells. The negative control wells receive 25 µl serum-free RPMI with 0.1% BSA only; the positive control cells receive the ligand (HGF) but no test compound. Test compounds are prepared at 5 times their final concentration in serum-free RPMI with ligand in a 96 well plate, and serially diluted to give 7 test concentrations. Typically, the highest final concentration of test compound is 100 µM, and 1:3 dilutions are used (i.e. final test compound concentration range is 0.137-100 µM).
4. After 18 hours of ligand activation, 12.5 µl of diluted BrdU labeling reagent (1:100 in RPMI, 0.1% BSA) is added to each well and the cells are incubated with BrdU (final concentration is 10 µM) for 1 hour.
5. Same as General Procedure.
6. Same as General Procedure.
7. The blocking solution is removed by decanting and the wells are washed once with PBS. Anti-BrdU-POD solution (1:100 dilution in PBS, 1% BSA) is added (100 µl/well) and the plate is incubated for 90 minutes at room temperature on a plate shaker.
8. Same as General Procedure.
9. Same as General Procedure.
10. Same as General Procedure.

HUV-EC-C Assay

This assay is used to measure a compound's activity against PDGF-R, FGF-R, VEGF, aFGF or Flk-1/KDR, all of which are naturally expressed by HUV-EC cells.

Day 0

1. Wash and trypsinize HUV-EC-C cells (human umbilical vein endothelial cells, (American Type Culture Collection, catalogue no. 1730 CRL). Wash with Dulbecco's phosphate-buffered saline (D-PBS, obtained from Gibco BRL, catalogue no. 14190-029) 2 times at about 1 ml/10 $cm^2$ of tissue culture flask. Trypsinize with 0.05% trypsin-EDTA in non-enzymatic cell dissociation solution (Sigma Chemical Company, catalogue no. C-1544). The 0.05% trypsin is made by diluting 0.25% trypsin/1 mM EDTA (Gibco, catalogue no. 25200-049) in the cell dissociation solution. Trypsinize with about 1 ml/25-30 $cm^2$ of tissue culture flask for about 5 minutes at 37° C. After cells have detached from the flask, add an equal volume of assay medium and transfer to a 50 ml sterile centrifuge tube (Fisher Scientific, catalogue no. 05-539-6).

2. Wash the cells with about 35 ml assay medium in the 50 ml sterile centrifuge tube by adding the assay medium, centrifuge for 10 minutes at approximately 200×g, aspirate the supernatant, and resuspend with 35 ml D-PBS. Repeat the wash two more times with D-PBS, resuspend the cells in about 1 ml assay medium/15 $cm^2$ of tissue culture flask. Assay medium consists of F12K medium (Gibco BRL, catalogue no. 21127-014) and 0.5% heat-inactivated fetal bovine serum. Count the cells with a Coulter Counter® (Coulter Electronics, Inc.) and add assay medium to the cells to obtain a concentration of 0.8-1.0×$10^5$ cells/ml.

3. Add cells to 96-well flat-bottom plates at 100 µl/well or 0.8-1.0×10⁴ cells/well, incubate ~24 h at 37° C., 5% $CO_2$.

Day 1

1. Make up two-fold test compound titrations in separate 96-well plates, generally 50 µM on down to 0 µM. Use the same assay medium as mentioned in day 0, step 2 above. Titrations are made by adding 90 µl/well of test compound at 200 µM (4× the final well concentration) to the top well of a particular plate column. Since the stock test compound is usually 20 mM in DMSO, the 200 µM drug concentration contains 2% DMSO.

A diluent made up to 2% DMSO in assay medium (F12K+ 0.5% fetal bovine serum) is used as diluent for the test compound titrations in order to dilute the test compound but keep the DMSO concentration constant. Add this diluent to the remaining wells in the column at 60 µl/well. Take 60 µl from the 120 µl of 200 µM test compound dilution in the top well of the column and mix with the 60 µl in the second well of the column. Take 60 µl from this well and mix with the 60 µl in the third well of the column, and so on until two-fold titrations are completed. When the next-to-the-last well is mixed, take 60 µl of the 120 µl in this well and discard it. Leave the last well with 60 µl of DMSO/media diluent as a non-test compound-containing control. Make 9 columns of titrated test compound, enough for triplicate wells each for: (1) VEGF (obtained from Pepro Tech Inc., catalogue no. 100-200, (2) endothelial cell growth factor (ECGF) (also known as acidic fibroblast growth factor, or aFGF) (obtained from Boehringer Mannheim Biochemica, catalogue no. 1439 600), or, (3) human PDGF B/B (1276-956, Boehringer Mannheim, Germany) and assay media control. ECGF comes as a preparation with sodium heparin.

2. Transfer 50 µl/well of the test compound dilutions to the 96-well assay plates containing the 0.8-10×10⁴ cells/100 µl/well of the HUV-EC-C cells from day 0 and incubate ~2 h at 37° C., 5% $CO_2$.

3. In triplicate, add 50 µl/well of 80 µg/ml VEGF, 20 ng/ml ECGF, or media control to each test compound condition. As with the test compounds, the growth factor concentrations are 4× the desired final concentration. Use the assay media from day 0 step 2 to make the concentrations of growth factors. Incubate approximately 24 hours at 37° C., 5% $CO_2$. Each well will have 50 µl test compound dilution, 50 µl growth factor or media, and 100 µl cells, which calculates to 200 µl/well total. Thus the 4× concentrations of test compound and growth factors become 1× once everything has been added to the wells.

Day 2

1. Add ³H-thymidine (Amersham, catalogue no. TRK-686) at 1 µCi/well (10 µl/well of 100 µCi/ml solution made up in RPMI media+10% heat-inactivated fetal bovine serum) and incubate ~24 h at 37° C., 5% $CO_2$. RPMI is obtained from Gibco BRL, catalogue no. 11875-051.

Day 3

1. Freeze plates overnight at −20° C.

Day 4

Thaw plates and harvest with a 96-well plate harvester (Tomtec Harvester 96®) onto filter mats (Wallac, catalogue no. 1205-401), read counts on a Wallac Betaplate® liquid scintillation counter.

TABLE 3 shows the results of biological testing of some exemplary compounds of this invention. The results are reported in terms of $IC_{50}$, the micromolar (µM) concentration of the compound being tested which causes a 50% change in the activity of the target PKT compared to the activity of the PTK in a control to which no test compound has been added. Specifically, the results shown indicate the concentration of a test compound needed to cause a 50% reduction of the activity of the target PTK. Bioassays which have been or can be used to evaluate compounds are described in detail below.

TABLE 3

| Example | bio flkGST IC50 (µM) | bio FGFR1 IC50 (µM) | bio PDGF IC50 (µM) | bio EGF IC50 (µM) | cell EGF IC50 (µM) | Her2 Kinase IC50 (µM) | cdk2spa C50 (µM) | bio pyk2 IC50 (µM) |
|---|---|---|---|---|---|---|---|---|
| 1 | 57.68 | 15.16 | >100 | >100 | >100 | | | >100 |
| 2 | >100 | | >100 | >100 | >100 | | | |
| 3 | 9.85 | 9.62 | >100 | >100 | >100 | | | >100 |
| 4 | 3.57 | >20 | >100 | >100 | >100 | >100 | | |
| 5 | 8.3 | 16.06 | >100 | >100 | >100 | >100 | | |
| 6 | 4.04 | | >100 | 3.26 | 7.82 | 2.43 | | |
| 7 | 7.74 | | >100 | 5.07 | 9.8 | 4.24 | | |
| 8 | 12.1 | | >100 | 51.34 | 20.08 | 5.5 | | |
| 9 | 0.96 | | >100 | >100 | >100 | 16.38 | | |
| 10 | 5.72 | | >100 | 94.04 | 15.86 | 8.06 | | |
| 11 | 9.77 | | >100 | >100 | >100 | >100 | | |
| 12 | >20 | | 21.46 | >100 | | 27.73 | | |
| 13 | >20 | | 81.92 | 8.17 | | 2.66 | | |
| 14 | 13.01 | | 42.41 | >100 | | 66.02 | | |
| 15 | >20 | | >100 | >100 | | 98.61 | | |
| 16 | >20 | | 98.06 | >100 | | 23.32 | | |
| 17 | 8.25 | 2.47 | 94.35 | 0.83 | 11.47 | 15.94 | >10 | |
| 18 | 2.67 | | | 2.57 | 9.23 | 4.99 | | |
| 19 | 7.5 | | | 6.86 | 34.18 | 8.37 | | |
| 20 | 11.53 | | | >100 | 41.16 | 8 | | |
| 21 | 7.18 | | >100 | 40.34 | | 27.69 | | |
| 22 | >20 | | >100 | >100 | | 87.67 | | |
| 23 | >20 | | >100 | 36.64 | | 4.05 | | |
| 24 | | | >100 | 16.84 | | 5.31 | | |
| 25 | 12.55 | | >100 | 23.48 | | 7.9 | | |
| 26 | 16.03 | | 66.87 | 34.67 | | 10.04 | | |
| 27 | | | >100 | 26.5 | | 3.91 | | |
| 28 | 4.5 | | 71.27 | 53.66 | | 2.67 | | |

TABLE 3-continued

| Example | bio flkGST IC50 (µM) | bio FGFR1 IC50 (µM) | bio PDGF IC50 (µM) | bio EGF IC50 (µM) | cell EGF IC50 (µM) | Her2 Kinase IC50 (µM) | cdk2spa C50 (µM) | bio pyk2 IC50 (µM) |
|---|---|---|---|---|---|---|---|---|
| 29 | 10.12 | | >100 | 26.72 | | 3.98 | | |
| 30 | 9.4 | | >100 | 18.69 | | 4.1 | | |
| 31 | >50 | | >100 | 9.83 | | 47.19 | | |
| 32 | 45.74 | | 5.94 | >100 | | >100 | | |
| 34 | >50 | | >100 | >100 | | >100 | | |
| 35 | >20 | | >100 | 80.4 | | 54.14 | | |
| 36 | >20 | | >100 | >100 | | >100 | | |
| 37 | 0.22 | | 3.06 | 10.78 | 9.84 | 1.4 | | |
| 38 | 4.17 | | 3.06 | 6.04 | 8.97 | 2.16 | | |
| 39 | 3.38 | | 4.69 | 3.67 | 14.54 | 3.53 | | |
| 40 | 4.5 | | 7.9 | 6.52 | | 6.27 | | |
| 42 | 0.1 | | 0.12 | 11.95 | 74.55 | 20.43 | | |
| 43 | 1.12 | | 8.38 | >100 | 37.33 | 53.37 | | |
| 44 | <0.05 | | 0.02 | 20.73 | 67.46 | 6.99 | | |
| 45 | 1.71 | | >100 | >100 | 29.95 | >100 | | |
| 46 | 30.62 | | 6.18 | >100 | >100 | >100 | | |
| 47 | 0.08 | 1.56 | 0.06 | 11.42 | 41.54 | 8.4 | >20 | 1.05 |
| 48 | 0.006 | 0.3 | <0.78 | 17.88 | 21.58 | 7.93 | | 0.09 |
| 49 | | | <0.78 | >100 | 43.86 | >100 | | |
| 50 | | | <0.78 | >100 | 20.34 | >100 | | |
| 51 | 0.006 | 1.66 | 0.01 | 18.1 | 21.61 | 23.24 | 16.69 | 0.35 |
| 52 | 0.08 | 1.26 | <0.78 | 12.53 | >100 | >100 | 10.66 | 0.45 |
| 53 | | | <0.78 | >100 | >100 | >100 | | |
| 54 | 1.98 | | <0.78 | 23.88 | 9.76 | 7.02 | | |
| 55 | 0.27 | | 0.53 | 6.03 | 35.99 | 77.82 | | |
| 56 | 2.32 | | 3.19 | >100 | 10.03 | 7.11 | | |
| 57 | 0.06 | | 7.98 | >100 | 9.97 | 6.94 | | |
| 58 | | | 21.14 | >100 | >100 | >100 | | |
| 59 | | | <0.78 | >100 | >100 | >100 | | |
| 60 | | | <0.78 | >100 | >100 | >100 | | |
| 61 | | | <0.78 | >100 | >100 | >100 | | |
| 62 | 8.00 | | 8.32 | >100 | >100 | >100 | | |
| 63 | 0.21 | | <0.78 | 8.59 | >100 | >100 | | |
| 64 | 0.55 | | <0.78 | 30.49 | >100 | >100 | | |
| 65 | 0.37 | | <0.05 | >100 | 74.36 | 15.97 | | |
| 66 | <0.05 | | | >100 | 11.84 | 2.76 | | |
| 67 | 0.39 | | 24.77 | 31.38 | 19.79 | 2.56 | | |
| 68 | 1.16 | | 0.03 | >100 | 23.52 | 34.13 | | |
| 69 | 0.3 | | 56.55 | >100 | 97.54 | >100 | | |
| 70 | 0.09 | 1.50 | 0.0030 | 10.57 | 6.42 | 7.99 | 12.62 | 0.63 |
| 71 | 15.21 | | 22.5 | >100 | | 9.91 | | |
| 72 | 6.06 | | 10.54 | >100 | 39.94 | 9.65 | | |
| 73 | 5.95 | | 14.12 | >100 | 39.5 | 8.59 | | |
| 74 | 1.2 | | 0.09 | 46.75 | | >100 | | |
| 75 | 2.7 | | 61.55 | >100 | | >100 | | |
| 76 | 3.33 | | 19.18 | 5.11 | | 3.01 | | |
| 77 | 0.49 | | 25.01 | >100 | | >100 | | |
| 78 | 1.94 | | 70.62 | 9.33 | | 4.25 | | |
| 79 | 1.49 | | >100 | 27.39 | | >100 | | |
| 80 | 0.13 | 4.29 | 0.001 | >100 | | 50.19 | 17.19 | 0.28 |
| 81 | 0.21 | | 0.18 | >100 | | >100 | | |
| 82 | 2.03 | 7.69 | 6.88 | >100 | | >100 | | 0.31 |
| 83 | 0.34 | 0.41 | 9.46 | 2.18 | | 86.9 | | 0.008 |
| 84 | 1.38 | | 12.51 | 67.2 | | 5.86 | | 0.006 |
| 85 | 0.2 | 0.8 | 2.59 | >100 | | 3.76 | | |
| 86 | 1.45 | 1.3 | 19.6 | 41.8 | | >100 | | 3.58 |
| 87 | 3.27 | 7.56 | 6.46 | >100 | | 9.1 | | 0.17 |
| 88 | 0.35 | 1.18 | 8.06 | 2.36 | | >100 | | 0.09 |
| 89 | 7.84 | | 47.58 | 8.53 | 9.67 | 15.97 | | |
| 115 | 7.3 | | 7.48 | >100 | | >100 | 0.006 | |
| 116 | >20 | | >100 | >100 | | >100 | <0.0005 | |
| 117 | 0.91 | | 12.9 | >100 | | >100 | 0.006 | |
| 118 | 1.93 | | 1.2 | >100 | | >100 | 0.002 | |
| 119 | 1.38 | | 61.63 | >100 | | >100 | <0.0005 | |

In Vivo Animal Models

Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, *Acta Pathol. Microbial. Scand.* 77:758-760), many different human tumor cell lines (e.g., mammary, lung, genitourinary, gastrointestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC # CCL 107), A375 cells (melanoma, ATCC # CRL 1619), A431 cells (epidermoid carcinoma, ATCC # CRL 1555), Calu 6 cells (lung, ATCC.# HTB 56), PC3 cells (prostate, ATCC # CRL 1435), SKOV3TP5 cells and NIH 3T3 fibroblasts genetically engineered to overexpress EGFR, PDGFR, IGF-1R or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%-10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90-95% air and 5-10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8-10 mice per group, 2-10×$10^6$ cells/animal). Tumor growth is measured over 3 to 6 weeks using venier calipers. Tumor volumes are calculated as a product of length×width×height unless otherwise indicated. P values are calculated using the Students t-test. Test compounds in 50-100 μL excipient (DMSO, or VPD:D5W) can be delivered by IP injection at different concentrations generally starting at day one after implantation.

Tumor Invasion Model

The following tumor invasion model has been developed and may be used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells can be performed in a laminar flow hood. For anesthesia, Xylazine/Ketamine Cocktail (100 mg/kg ketamine and 5 mg/kg Xylazine) are administered intraperitoneally. A midline incision is done to expose the abdominal cavity (approximately 1.5 cm in length) to inject $10^7$ tumor cells in a volume of 100 μl medium. The cells are injected either into the duodenal lobe of the pancreas or under the serosa of the colon. The peritoneum and muscles are closed with a 6-0 silk continuous suture and the skin is closed by using wound clips. Animals are observed daily.

Analysis

After 2-6 weeks, depending on gross observations of the animals, the mice are sacrificed, and the local tumor metastases to various organs (lung, liver, brain, stomach, spleen, heart, muscle) are excised and analyzed (measurement of tumor size, grade of invasion, immunochemistry, in situ hybridization determination, etc.).

C-Kit Assay

This assay is used to detect the level of c-kit tyrosine phosphorylation.

MO7E (human acute myeloid leukemia) cells were serum starved overnight in 0.1% serum. Cells were pre-treated with the compound (concurrent with serum starvation), prior to ligand stimulation. Cells were stimulated with 250 ng/ml rh-SCF for 1.5 minutes. Following stimulation, cells were lysed and immunoprecipitated with an anti-c-kit antibody. Phosphotyrosine and protein levels were determined by Western blotting.

MTT Proliferation Assay

MO7E cells were serum starved and pre-treated with compound as described for the phosphorylation experiments. Cells were plated @ 4×$10^5$ cells/well in a 96 well dish, in 100 μl RPMI+10% serum. rh-SCF (100 ng/mL) was added and the plate was incubated for 48 hours. After 48 hours, 10 μl of 5 mg/ml MTT [3-(4,5-dimethythiazol-2-yl)-2,5-diphenyl tetrazolium bromide) was added and allowed to incubate for 4 hours. Acid isopropanol (100 μl of 0.04N HCl in isopropanol) was added and the optical density was measured at a wavelength of 550 nm.

Apoptosis Assay

MO7E cells were incubated +/− SCF and +/− compound in 10% FBS with rh-GM-CSF (long/mL) and rh-IL-3 (10 ng/mL). Samples were assayed at 24 and 48 hours. To measure activated caspase-3, samples were washed with PBS and permeabilized with ice-cold 70% ethanol. The cells were then stained with PE-conjugated polyclonal rabbit anti-active caspase-3 and analyzed by FACS. To measure cleaved PARP, samples were lysed and analyzed by western blotting with an anti-PARP antibody.

Additional Assays

Additional assays which may be used to evaluate the compounds of this invention include, without limitation, a bio-flk-1 assay, an EGF receptor-HER2 chimeric receptor assay in whole cells, a bio-src assay, a bio-lck assay and an assay measuring the phosphorylation function of raf. The protocols for each of these assays may be found in U.S. application Ser. No. 09/099,842, which is incorporated by reference, including any drawings, herein.

Measurement of Call Toxicity

Therapeutic compounds should be more potent in inhibiting receptor tyrosine kinase activity than in exerting a cytotoxic effect. A measure of the effectiveness and cell toxicity of a compound can be obtained by determining the therapeutic index, i.e., $IC_{50}/LD_{50}$. $IC_{50}$, the dose required to achieve 50% inhibition, can be measured using standard techniques such as those described herein. $LD_{50}$, the dosage which results in 50% toxicity, can also be measured by standard techniques as well (Mossman, 1983, *J. Immunol. Methods,* 65:55-63), by measuring the amount of LDH released (Korzeniewski and Callewaert, 1983, *J. Immunol. Methods,* 64:313, Decker and Lohmann-Matthes, 1988, *J. Immunol. Methods,* 115:61), or by measuring the lethal dose in animal models. Compounds with a large therapeutic index are preferred. The therapeutic index should be greater than 2, preferably at least 10, more preferably at least 50.

B. Example of Cellular Assay Results Using 5-(5-Fluoro-2-oxo-1,2-dihydroindol-3-ylidenemethyl)-2, 4-dimethyl-1H-pyrrole-3-carboxylic acid (2-diethylamino-ethyl)amide To confirm the potency of 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) detected in biochemical assays (vide infra), the ability of said compound to inhibit ligand-dependent RTK phosphorylation was evaluated in cell-based assays using NIH-3T3 mouse cells engineered to overexpress Flk-1 or human PDGFRβ. 5-(5-Fluoro-2-oxo-1,2-dihydroindol-3-ylidenemethyl)-2,4-dimethyl-1H-pyrrole-3-carboxylic acid (2-diethylamino-ethyl)amide (Compound 80) inhibited VEGF-dependent Flk-1 tyrosine phosphorylation with an $IC_{50}$ value of approximately 0.03 µM. This value is similar to the 0.009 µM $K_i$ value determined for inhibition of Flk-1 by 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) determined in biochemical assays. This indicates that 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) readily penetrates into cells. Consistent with the biochemical data (vide infra) indicating that 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) had comparable activity against Flk-1 and PDGFRβ, it was also found that it inhibited PDGF-dependent receptor phosphorylation in cells with an $IC_{50}$ value of approximately 0.03 µM. The ability of 5-(5-fluoro-2-oxo-1,2-dihydroindol-3-ylidenemethyl)-2,4-dimethyl-1H-pyrrole-3-carboxylic acid (2-diethylamino-ethyl) amide (Compound 80) to inhibit c-kit, a closely related RTK that binds stem cell factor (SCF), was determined using MO7E cells that express this receptor. In these cells, 5-(5-fluoro-2-oxo-1,2-dihydroindol-3-ylidenemethyl)-2,4-dimethyl-1H-pyrrole-3-carboxylic acid (2-diethylamino-ethyl) amide (Compound 80) inhibited SCF-dependent c-kit phosphorylation with an $IC_{50}$ value of 0.01-0.1 µM. This compound also inhibited SCF-stimulated c-kit phosphorylation in acute myeloid leukemia (AML) blasts isolated from the peripheral blood of patients.

In addition to testing the ability of 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) to inhibit ligand-dependent receptor phosphorylation in cells, its effect on ligand-dependent proliferative response of cells was also examined in vitro (see Table 4). In these studies, cells quiesced by overnight serum starvation were induced to undergo DNA synthesis upon addition of the appropriate mitogenic ligand. As shown in Table 4, 5-(5-fluoro-2-oxo-1, 2-dihydroindol-3-ylidenemethyl)-2,4-dimethyl-1H-pyrrole-3-carboxylic acid (2-diethylamino-ethyl)amide (Compound 80) inhibited the PDGF-induced proliferation of NIH-3T3 cells overexpressing PDGFRβ or PDGFRα with $IC_{50}$ values 0.031 and 0.069 µM, respectively, and the SCF-induced proliferation of MO7E cells with an $IC_{50}$ value of 0.007 µM.

TABLE 4

| Receptor | Biochemical $K_i$[1] (µM) | Cellular $IC_{50}$ | |
|---|---|---|---|
| | | Receptor Phosphorylation (µM) | Ligand-dependent Proliferation (µM) |
| Flk-1/KDR | 0.009 | 0.03[2] | 0.004[3] |
| PDGFRα | 0.008 | 0.03[4] | 0.031[4] |
| PDGFRβ | ND | ND | 0.069[5] |
| FGFR | 0.83 | ND | 0.7[3] |
| c-kit | ND | 0.01-0.1[6] | 0.007[6] |

ND = Not Determined
[1] Determined using recombinant enzyme
[2] Determined using serum-starved NIH-3T3 cells expressing Flk-1
[3] Determined using serum-starved HUVECs
[4] Determined using serum-starved NIH-3T3 cells expressing PDGFR☐
[5] Determined using serum-starved NIH-3T3 cells expressing PDGFR☐
[6] Determined using serum-starved MO7E cells As shown in Table 4, there is a general agreement between the biochemical and cellular activities of 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) supporting the conclusion that this compound crosses cellular membranes. Further, it can be concluded that the cellular responses are a result of the activity of compound 80 against the indicated target. In contrast, when tested in the presence of complete growth medium in vitro, substantially higher concentrations of 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) (>10 µM) were required to inhibit the growth of a variety of human tumor cells (see Table 5). This indicates that the compound did not directly inhibit the growth of these cells at concentrations required to inhibit ligand-dependent receptor phosphorylation and cell proliferation.

TABLE 5

| Cell Line | Origin | $IC_{50}$ (µM) | $LD_{50}$ (µM) |
|---|---|---|---|
| HT29 | Colon carcinoma | 10 | 22 |
| A549 | Lung carcinoma | 9.5 | 22 |
| NCI-H460 | NSC lung carcinoma | 8.9 | 20 |
| SF767T | Glioma | 7.9 | 14 |
| A431 | Epidermoid carcinoma | 6.0 | 18 |

Briefly, the results shown in Table 5 were obtained by incubating cells for 48 hr in complete growth medium in the presence of serial dilutions 5-(5-Fluoro-2-oxo-1,2-dihydroindol-3-ylidenemethyl)-2,4-dimethyl-1H-pyrrole-3-carboxylic acid (2-diethylamino-ethyl)amide. At the end of the growth period, the relative number of cells was determined. $IC_{50}$ values were calculated as the concentration of compound that inhibited the growth of cells by 50% relative to untreated cells. $LD_{50}$ values were calculated as the concentration of compound that caused a 50% reduction in the number of cells relative to those at the start of the experiment.

A more relevant cell-based assay in which to evaluate the anti-angiogenic potential of 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) is the in vitro mitogenesis assay using human umbilical vein endothelial cells (HUVECs) as a model system for the endothelial cell proliferation critical to the angiogenic process. In this assay, a mitogenic response, measured as an increase in DNA synthesis, is induced in serum-starved HUVECs upon addition of VEGF or FGF. In these cells, 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) inhibited the VEGF- and FGF-induced mitogenic response in a dose-dependent manner with $IC_{50}$ values of 0.004 µM and 0.7 µM, respectively, when compound was present throughout the 48-hr assay.

Briefly, the aforementioned results were obtained using Serum-starved HUVECs that were incubated with mitogenic concentrations of VEGF (100 ng/ml) or FGF (30 ng/ml) in the presence of serial dilutions of 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) for 24 hrs. The mitogenic response during the following 24 hrs. in the presence of ligand and inhibitor was quantitated by measurement of DNA synthesis based on incorporation of bromodeoxyuridine into cellular DNA.

In separate experiments, compound 80 inhibited the VEGF-dependent phosphorylation of ERK 1/2 (p42/44MAP kinase), an early downstream target of Flk-1/KDR, in a dose-dependent manner. The inhibitory activity of compound 80 was also shown to be long-lasting in this system; inhibiting VEGF-dependent phosphorylation of ERK 1/2 for as long as 48 hours after removal of 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) from the medium following a short (2 hr) exposure to micromolar concentrations of the compound.

VEGF has been recognized to be an important survival factor for endothelial cells. Since 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) inhibits the VEGF-dependent mitogenic response of HUVECs, the effect of the compound on HUVEC survival was investigated. In these experiments, cleavage of the caspase 3 substrate poly-ADP-ribosyl polymerase (PARP) was used as a readout for apoptosis. HUVECs cultured in serum-free conditions for 24 hours exhibited substantial levels of PARP cleavage, as detected by the accumulation of the 23 kDa PARP cleavage fragment. This was largely prevented by the addition of VEGF to the cell medium, indicating that VEGF acts as a survival factor in this assay. 5-(5-Fluoro-2-oxo-1,2-dihydroindol-3-ylidenemethyl)-2,4-dimethyl-1H-pyrrole-3-carboxylic acid (2-diethylamino-ethyl)amide (Compound 80) has been shown to inhibit KDR signaling. Accordingly, 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) inhibited VEGF-mediated HUVEC survival in a dose-dependent manner. Thus, these data indicate that compound 80 induced apoptosis in endothelial cells in culture in the presence of VEGF.

C. In Vivo Efficacy Studies i. Efficacy Against Established Tumor Xenografts

The in vivo efficacy of 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) was studied in subcutaneous (SC) xenograft models using human tumor cells implanted into the hindflank region of athymic mice. Following implantation, tumors were allowed to become established to a size of 100-550 $mm^3$ prior to starting oral treatment with the compound.

Daily oral administration of compound 80 caused a dose-dependent inhibition of A431 tumor growth when treatment was initiated after tumors had grown to a size of 400 $mm^3$. Statistically significant (P<0.05) inhibition of tumor growth was seen at doses of 40 mg/kg/day (74% inhibition) and 80 mg/kg/day (84% inhibition) (see Table 6). In preliminary experiments, a higher (160 mg/kg/day) dose of the compound was not more efficacious against established A431 tumors than the 80 mg/kg/day dose. In addition, mice treated at the 160 mg/kg/day dose of the compound lost body weight, indicating that the higher dose was not as well tolerated. Similar results were obtained in an experiment in which A431 tumors were only allowed to reach 100 $mm^3$ in size (see Table 5). In this second experiment, complete regression of the tumors occurred in six of the eight animals treated at the 80 mg/kg/day for 21-days. In these six animals, the tumors did not regrow during a 110-day observation period following the end of treatment. In the two animals in which the tumors regrew to a large size (2000-3000 $mm^3$), the tumors regressed in response to a second round of treatment with compound 80. Importantly, in all efficacy experiments, 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) at 80 mg/kg/day has been well tolerated, even when dosed continuously for more than 100 days.

TABLE 6

| Initial Tumor Volume ($mm^3$) | Compound[1] (mg/kg/day) | % Inhibition (day) | P-Value |
|---|---|---|---|
| 400 | 80 | 84 (36) | 0.001 |
| | 40 | 74 (36) | 0.003 |
| | 20 | 51 (36) | 0.130 |
| 100 | 80 | 93 (40) | 0.002 |
| | 40 | 75 (40) | 0.015 |
| | 10 | 61 (40) | 0.059 |

[1]Compound 80.

Briefly, the results shown in Table 6 were obtained using A431 cells (0.5×106 cells/mouse) which were implanted SC into the hindflank region of athymic mice. Daily oral administration of 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) in a Cremophore-based vehicle or vehicle control began when tumors reached the indicated average volume. Tumors were measured using vernier calipers and tumor volume was calculated as the product of length×width×height. P-values were calculated by comparing the size of the tumors for animals that were treated with compound 80 (n=8) to those of animals that were treated with a vehicle (n=16) on the last day of the experiment, using the two-tailed Student's t-test.

The efficacy compound 80 against established human tumors of different origins was determined using Colo205 (colon carcinoma), SF763T (glioma), and NCI-H460 (non-small cell lung carcinoma) xenografts (see Table 7). These experiments were conducted using 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) administered orally at 80 mg/kg/day; a dose that was effective and well tolerated.

TABLE 7

| Tumor Type | | Initial Tumor Volume (mm³) | % Inhibition (day) | P-Value |
|---|---|---|---|---|
| A431[1] | Epidermoid | 100 | 93 (40) | 0.002 |
| A431[1] | Epidermoid | 400 | 84 (36) | 0.001 |
| Colo205 | Colon | 370 | 77 (54) | 0.028 |
| NCI-H460 | Lung | 300 | 61 (54) | 0.003 |
| SF763T | Glioma | 550 | 53 (30) | 0.001 |

[1]Data are from experiment reported in Table 5.

In the abovementioned experiments, compound 80 was administered once daily at 80 mg/kg in a Cremophor-based vehicle once tumors reached the indicated size. Percent inhibition compared to the vehicle-treated control group was calculated at termination of the experiments. P-values were calculated by comparing tumor sizes of the animals that had been treated with the compound to tumor sizes of those animals that had been treated with the vehicle, using the two-tailed Student's t-test.

Although 5-(5-fluoro-2-oxo-1,2-dihydroindol-3-ylidenemethyl)-2,4-dimethyl-1H-pyrrole-3-carboxylic acid (2-diethylamino-ethyl)amide (Compound 80) inhibited the growth of all the tumor types shown in Table 7, there was a difference in the response of the different xenograft models. Specifically, the growth of NCI-H460 and SF763T tumors was arrested or greatly slowed whereas the Colo205 tumors, like A431 tumors, regressed when treated with 5-(5-Fluoro-2-oxo-1,2-dihydroindol-3-ylidenemethyl)-2,4-dimethyl-1H-pyrrole-3-carboxylic acid (2-diethylamino-ethyl)amide.

In order to determine the molecular basis for the difference in response between xenograft models, the SF763T tumors were studied. Therefore, SF763T tumors, which were less responsive to treatment with 5-(5-Fluoro-2-oxo-1,2-dihydroindol-3-ylidenemethyl)-2,4-dimethyl-1H-pyrrole-3-carboxylic acid (2-diethylamino-ethyl)amide, have been evaluated at the molecular level using immunohistological techniques to determine the effect of treatment with the compound. These studies were initially conducted in this tumor type because SF763T tumors are highly vascularized with microvessels that strongly express the endothelial cell marker CD31 and are hence well suited for studies of tumor microvessel density (MVD). Immunohistological evaluation of SF763T tumors indicated that tumors from treated animals had reduced MVD relative to vehicle-treated controls, consistent with an anti-angiogenic mechanism of action for compound 80; MVD was 24.2±4.1 in animals treated with compound 80, compared to 39.3±5.7 for those that were treated with just the vehicle. As anticipated from the associated tumor growth arrest, a pronounced inhibition of tumor cell proliferation was evident in tumors that were treated with compound 80. These tumors had half the mitotic index of those in vehicle-treated tumors (data not shown). The effect compound 80 on MVD and tumor cell proliferation indicates that the compound has profound anti-angiogenic and anti-tumor effects, even under conditions in which tumors do not regress.

The ability of compound 80 to inhibit PDGFR phosphorylation and subsequent signaling in vivo was also evaluated in the SF763T tumors, which express high levels of PDGFRβ. Treatment of the SF763T tumors with compound 80 strongly inhibited PDGFRβ tyrosine phosphorylation in established SF763T tumors. Compound 80 also reduced the levels of phosphorylated (activated) phospholipase C gamma (PLC-γ), an immediate downstream indicator of PDGFR activation. These data demonstrate that oral administration of compound 80 causes a direct effect on target (PDGFR) activity in tumors in vivo.

Based on the demonstration that the ability of compound 80 to inhibit VEGF-dependent signaling in HUVECs in vitro was long-lasting (vide supra), the efficacy of the compound was evaluated when the compound was administered infrequently in the Colo205 tumor model. As shown in Table 8, 80 mg/kg (91% inhibition) and 40 mg/kg (84% inhibition) were efficacious when administered daily, but not when administered twice weekly. In contrast, a higher dose of compound 80 (160 mg/kg) did inhibit (52% inhibition) the growth of established Colo205 tumors when administered twice weekly, suggesting that this compound can demonstrate efficacy when administered infrequently at a higher dose. It should be noted that dosing regimens may be determined by those with ordinary skill in the art without undue experimentation.

TABLE 8

| Dose (mg/kg) | Frequency | % Inhibition | P-Value |
|---|---|---|---|
| 160 | Twice weekly | 52 | 0.085 |
|  | Once weekly | 17 | NS |
| 80 | Daily | 91 | 0.039 |
|  | Twice weekly | 19 | NS |
|  | Once weekly | 0 | NS |
| 40 | Daily | 84 | 0.028 |
|  | Twice weekly | 36 | NS |

NS: not significant ($P > 0.05$)

Briefly, the results shown in Table 8 were obtained using Colo205 cells ($0.5 \times 10^6$ cells/mouse) that had been implanted SC into the hindflank region of athymic mice. Oral administration of compound 80 according to the indicated schedule began when tumors reached 400 mm³. Tumors were measured using vernier calipers and tumor volume was calculated as the product of length×width×height. P-values were calculated by comparing the size of the tumors for animals that were treated with compound 80 to those of animals that were treated with a vehicle on the last day of the experiment, using the two-tailed Student's t-test.

ii. Efficacy of Compound 80 in a Model of Disseminated Disease

In addition to supporting the sustained growth of solid primary tumors, angiogenesis is also an essential component supporting the development of disseminated disease due to metastasis from the primary tumor. The effect of compound 80 on the development of disseminated disease was examined in the B16-F1 mouse melanoma lung colonization model. In this model, B16-F1 cells inoculated intravenously via the tail vein of athymic mice colonize the lungs and form tumors. As shown in Table 8, oral administration of compound 80 at 80 mg/kg/day effectively reduced the burden of B16-F1 cells in the lung as evaluated by measurements of total lung weight. These data suggest that compound 80 can inhibit disseminated disease in vivo.

TABLE 9

|  | Lung Weight (g) | % Inhibition | P-Value |
|---|---|---|---|
| Vehicle | 0.83 ± 0.07 | — | — |
| Compound[1] | 0.41 ± 0.04 | 50 | <0.001 |

[1]Compound 80

Briefly, the results shown in Table 9 were obtained using athymic mice that had been inoculated with B16-F1 tumor cells ($5 \times 10^5$ cells/mouse) via the tail vein. Mice were treated daily with orally administered compound 80 at 80 mg/kg/day (n=10) or vehicle (n=18) for 24 days after tumor cell inoculation. At the end of the treatment period, the mice were sacrificed and their lungs removed and weighed. Percent inhibition was calculated by comparing the lung weight of those animals that had been treated with compound 80, with the lung weight of the animals that had only been treated with vehicle. P-values were determined using the two-tailed Student's t-test.

D. Examples of Biological Activity

Examples of the in vitro potency of compounds of this invention are shown in Table 2.

CONCLUSION

In studies to investigate the pharmacokinetic characteristics of the compounds of the preferred embodiments of the present invention it has been demonstrated that oral administration of a single dose of said compounds resulted in high oral bioavailability in mice. The good oral bioavailability and linear pharmacokinetics indicate that the compounds of the preferred embodiments of the present have favorable pharmacokinetic characteristics.

In addition, the compounds of the preferred embodiments of the present invention are potent inhibitor of the tyrosine kinase activity of the split-kinase domain RTKs Flk-1/KDR and PDGFR, which are involved in angiogenesis, and the RTK c-kit, a receptor for stem cell factor (SCF), that is involved in certain hematologic cancers. At higher concentrations, the compounds of the preferred embodiments of the present invention also inhibit the tyrosine kinase activity of FGFR-1, a third RTK involved in angiogenesis. Consistent with their biochemical activity, the compounds of the preferred embodiments of the present invention inhibit the ligand-dependent tyrosine phosphorylation of target RTKs and the in vitro mitogenic response of human umbilical vein endothelial cells (HUVECs) stimulated with VEGF or FGF, of PDGFR-expressing NIH-3T3 cells stimulated with PDGF, and of MO7E acute myeloid leukemia cells stimulated with SCF. In contrast, the compounds of the preferred embodiments of the present invention do not directly inhibit the proliferation of tumor cells in complete growth medium except at concentrations 2 to 3 orders of magnitude higher than those required to inhibit the ligand-dependent mitogenic responses. In mouse xenograft studies, the compounds of the prefered embodiments of the present invention inhibited the growth of established human tumors of various origins in a dose-dependent manner and at concentrations that were well tolerated even upon extended (>100 days) dosing. At 80 mg/kg/day, the compounds of the preferred embodiments of the present invention induced regression of large established A431 and Colo205 tumors, and caused substantial growth inhibition or stasis of SF763T and NCI-H460 tumors. In mice bearing SF763T tumors, the compounds of the preferred embodiments of the present invention caused reductions in microvessel density, phosphorylation of PDGFR in the tumors, and mitotic index in the tumor cells. At this dose, the compounds of the preferred embodiments of the present invention also inhibited lung colonization by B16-F1 tumor cells in a model of tumor metastasis. Regimen studies demonstrated that the compounds of the preferred embodiments of the present invention are most efficacious when administered daily. Direct evidence of the anti-angiogenic activity of the compounds of the preferred embodiments of the present invention was detected in SF763T tumors in which microvessel density was reduced. Direct evidence that the compounds of the preferred embodiments of the present invention inhibit PDGFR phosphorylation and signaling in vivo was also obtained in SF763T tumors.

Taken together, these data support the notion that orally administered compounds of the preferred embodiments of the present invention are anti-angiogenic agents for the treatment of cancers, including solid tumors and hematological malignancies in which angiogenesis and/or signaling through c-kit are important in the disease pathology.

It will be appreciated that the compounds, methods and pharmaceutical compositions of the present invention are effective in modulating PK activity and therefore are expected to be effective as therapeutic agents against RTK, CTK-, and STK-related disorders.

One skilled in the art would also readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which Have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

What is claimed is:

1. A compound of Formula (I):

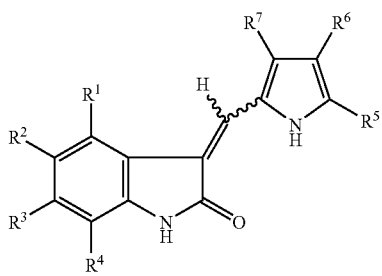

(I)

wherein:
R$^1$ is hydrogen;
R$^2$ is halo;
R$^3$ is hydrogen;
R$^4$ is hydrogen;
R$^5$ is alkyl;
R$^6$ is —C(O)R$^{10}$;
R$^7$ is alkyl;
R$^{10}$ is —N(R$^{11}$)(CH$_2$)$_n$R$^{12}$;
R$^{11}$ is selected from the group consisting of hydrogen and alkyl;
R$^{12}$ is —NR$^{13}$R$^{14}$;
R$^{13}$ and R$^{14}$ combine to form a group selected from the group consisting of —(CH$_2$)$_4$—, —(CH$_2$)$_5$—, —(CH$_2$)$_2$O(CH$_2$)$_2$—, and —(CH$_2$)$_2$N(CH$_3$)(CH$_2$)$_2$—; and
n is 1, 2, 3, or 4;
or a pharmaceutically acceptable salt thereof.

2. A compound of formula

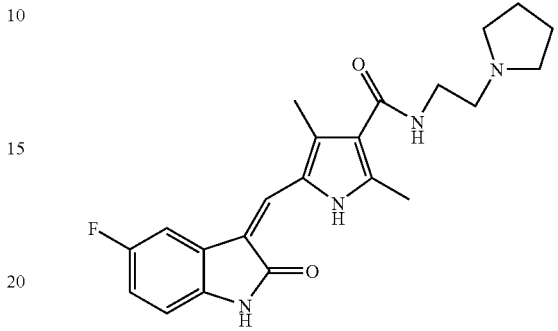

or a pharmaceutically acceptable salt thereof.

3. A pharmaceutical composition comprising the compound or salt of claim 2 and a pharmaceutically accepatable carrier or excipient.

* * * * *